US011845778B2

(12) United States Patent
Zhang et al.

(10) Patent No.: US 11,845,778 B2

(45) Date of Patent: Dec. 19, 2023

(54) PREFUSION PIV F IMMUNOGENS AND THEIR USE

(71) Applicants: The United States of America, as represented by the Secretary, Department of Health and Human Services, Bethesda, MD (US); Institute for Research in Biomedicine, Bellinzona (CH)

(72) Inventors: Baoshan Zhang, Bethesda, MD (US); Guillaume Stewart-Jones, Bethesda, MD (US); John Mascola, Rockville, MD (US); Kai Xu, Bethesda, MD (US); Gwo-Yu Chuang, Rockville, MD (US); Li Ou, Bethesda, MD (US); Peter Kwong, Washington, DC (US); Yaroslav Tsybovsky, Jefferson, MD (US); Wing-Pui Kong, Germantown, MD (US); Aliaksandr Druz, Germantown, MD (US); Davide Corti, Bellinzona (CH); Antonio Lanzavecchia, Bellinzona (CH)

(73) Assignees: The United States of America, as represented by the Secretary, Department of Health and Human Services, Bethesda, MD (US); Institute for Research in Biomedicine, Bellinzona (CH)

( * ) Notice: Subject to any disclaimer, the term of this patent is extended or adjusted under 35 U.S.C. 154(b) by 153 days.

(21) Appl. No.: 17/378,587

(22) Filed: Jul. 16, 2021

(65) Prior Publication Data

US 2022/0024987 A1 Jan. 27, 2022

Related U.S. Application Data

(62) Division of application No. 16/344,772, filed as application No. PCT/US2017/058322 on Oct. 25, 2017, now Pat. No. 11,078,239.

(Continued)

(51) Int. Cl.

*A61K 39/155* (2006.01)

*C07K 14/005* (2006.01)

(Continued)

(52) U.S. Cl.

CPC .......... *C07K 14/005* (2013.01); *A61K 39/155* (2013.01); *A61P 31/14* (2018.01);

(Continued)

(58) Field of Classification Search

None

See application file for complete search history.

(56) References Cited

U.S. PATENT DOCUMENTS

2011/0318355 A1 12/2011 Rosa Calatrava et al.

2012/0135028 A1 5/2012 Blais et al.

FOREIGN PATENT DOCUMENTS

WO WO/2016/118642 7/2016

OTHER PUBLICATIONS

Ambrose, et al. "Evaluation of the immunogenicity and protective efficacy of a candidate parainfluenza virus type 3 subunit vaccine in cotton rats." *Vaccine* 9, No. 7 (1991): 505-511.

(Continued)

*Primary Examiner* — M Franco G Salvoza

(74) *Attorney, Agent, or Firm* — Klarquist Sparkman, LLP

(57) ABSTRACT

Embodiments of a recombinant human Parainfluenza Virus (hPIV) F ectodomain trimer stabilized in a prefusion con- (Continued)

formation are provided. Also disclosed are nucleic acids encoding the hPIV F ectodomain trimer and methods of producing the hPIV F ectodomain trimer. Methods for inducing an immune response in a subject are also disclosed. In some embodiments, the method can be a method for treating or inhibiting a hPIV infection in a subject by administering a effective amount of the recombinant hPIV F ectodomain trimer to the subject.

23 Claims, 59 Drawing Sheets

Specification includes a Sequence Listing.

Related U.S. Application Data

(60) Provisional application No. 62/412,699, filed on Oct. 25, 2016.

(51) Int. Cl.
*A61P 31/14* (2006.01)
*C12N 7/00* (2006.01)

(52) U.S. Cl.
CPC ............ *C12N 7/00* (2013.01); *C07K 2319/50* (2013.01); *C12N 2760/18634* (2013.01); *C12N 2760/18734* (2013.01)

(56) References Cited

OTHER PUBLICATIONS

Bose, et al. "Mutations in the parainfluenza virus 5 fusion protein reveal domains important for fusion triggering and metastability." *Journal of Virology* 87, No. 24 (2013): 13520-13531.

Durbin, Anna P., and Ruth A. Karron. "Progress in the development of respiratory syncytial virus and parainfluenza virus vaccines." *Clinical Infectious Diseases* 37, No. 12 (2003): 1668-1677.

Garg, et al. "Vaccination with a human parainfluenza virus type 3 chimeric FHN glycoprotein formulated with a combination adjuvant induces protective immunity." *Vaccine* 35, No. 51 (2017): 7139-7146.

Henrickson, Kelly J. "Parainfluenza viruses." *Clinical Microbiology Reviews* 16, No. 2 (2003): 242-264.

International Search Report and Written Opinion, ISA European Patent Office, Issued in Application No. PCT/US2017/058322, dated May 29, 2018, WIPO, 18 pages.

Karron, et al. "A live human parainfluenza type 3 virus vaccine is attenuated and immunogenic in young infants." *The Pediatric Infectious Disease Journal* 22, No. 5 (2003): 394-405.

McLellan, et al. "Structure-based design of a fusion glycoprotein vaccine for respiratory syncytial virus." *Science* 342, No. 6158 (2013): 592-598.

Schmidt, et al. "Progress in the development of human parainfluenza virus vaccines." *Expert Review of Respiratory Medicine* 5, No. 4 (2011): 515-526.

Stewart-Jones et al., "Structure-Based Design of a Quadrivalent Fusion Glycoprotein Vaccine for Human Parainfluenza Virus Types 1-4," *Proc Natl Acad Sci USA* 115.48: 12265-12270, Nov. 2018.

Welch, et al. "Structure of the cleavage-activated prefusion form of the parainfluenza virus 5 fusion protein." *Proceedings of the National Academy of Sciences* 109, No. 41 (2012): 16672-16677.

Widjaja, et al. "Recombinant soluble respiratory syncytial virus F protein that lacks heptad repeat B, contains a GCN4 trimerization motif and is not cleaved displays prefusion-like characteristics." *PloS One* 10, No. 6 (2015): e0130829.

Yin, et al. "Structure of the parainfluenza virus 5 F protein in its metastable, prefusion conformation." *Nature* 439, No. 7072 (2006): 38.

Pre-fusion F specific antibodies

FIG. 4A

| Name | Prefusion Stabilizing Mutations | | 0 week | | | 1 week 4°C | | |
|---|---|---|---|---|---|---|---|---|
| | | | PIA3, 15ug/ml | PIA56, 15ug/ml | Strep, 1.0μg/ml | PIA3, 15μg/ml | PIA56, 15μg/ml | Strep, 1.0μg/ml |
| hpiv3NO-GCN4 backbone | none | | 2.5958 | 0.6361 | 1.0234 | 1.6178 | 0.5563 | 1.7138 |
| hPIV3NO-GCN4 scfp G191P | proline stabilization | G191P | 0.0754 | 0.111 | 0.1397 | 0.0605 | 0.1374 | 0.5542 |
| hPIV3NO-GCN4 scfp N155P | proline stabilization | N155P | 1.2645 | 1.7792 | 1.6517 | 0.2064 | 0.202 | 2.2658 |
| hPIV3NO-GCN4 scfp A140P | proline stabilization | A140P | 0.235 | 0.26 | 0.6774 | 0.086 | 0.1692 | 1.4865 |
| hPIV3NO-GCN4 scfp K141P | proline stabilization | K141P | 0.0615 | 0.1045 | 0.4864 | 0.0542 | 0.1339 | 1.1604 |
| hPIV3NO-GCN4 scfp S142P | proline stabilization | S142P | 3.0898 | 2.4339 | 1.8564 | 1.3133 | 1.0833 | 2.1614 |
| hPIV3NO-GCN4 A194P | proline stabilization | A194P | 1.1207 | 0.3669 | 0.5623 | 0.4413 | 0.2606 | 0.9259 |
| hPIV3NO-GCN4 A195P | proline stabilization | A195P | 0.0735 | 0.1101 | 0.2713 | 0.057 | 0.1384 | 0.7547 |
| hPIV3NO-GCN4 G191P | proline stabilization | G191P | 0.0773 | 0.1318 | 0.4008 | 0.0548 | 0.1331 | 1.0556 |
| hPIV3NO-GCN4 G196P | proline stabilization | G196P | 0.067 | 0.0926 | 0.3707 | 0.062 | 0.1349 | 0.759 |
| hPIV3NO-GCN4 E193P | proline stabilization | E193P | 2.0437 | 0.6037 | 0.52 | 0.9261 | 0.1455 | 1.6221 |
| hPIV3NO-GCN4_cav1_gyc_pk | cavity filling | K173L | 0.0601 | 0.097 | 0.3785 | 0.053 | 0.1106 | 0.7859 |
| hPIV3NO-GCN4_cav2_gyc_pk | cavity filling | E145L | 2.8346 | 0.9029 | 0.8029 | 1.5424 | 0.3844 | 1.6984 |
| hPIV3NO-GCN4_cav3_gyc_pk | cavity filling | A131L | 0.0583 | 0.1035 | 0.2252 | 0.0561 | 0.1243 | 0.6803 |
| hPIV3NO-GCN4_cav4_gyc_pk | cavity filling | V179L | 0.0696 | 0.1023 | 0.2386 | 0.0634 | 0.1207 | 1.0559 |
| hPIV3NO-GCN4_cav5_gyc_pk | cavity filling | V170I | 2.7103 | 0.4931 | 0.8365 | 1.434 | 0.4892 | 1.5562 |
| hPIV3NO-GCN4_cav6_gyc_pk | cavity filling | V175I | 2.9962 | 1.0232 | 1.0641 | 2.326 | 0.6998 | 1.8955 |
| hPIV3NO-GCN4_cav7_gyc_pk | cavity filling | Q127W | 0.07 | 0.1157 | 0.2126 | 0.0578 | 0.1401 | 0.3503 |
| hPIV3NO-GCN4_cav8_gyc_pk | cavity filling | I187F | 0.0747 | 0.1039 | 0.289 | 0.056 | 0.1142 | 1.0397 |
| hPIV3NO-GCN4_cav9_gyc_pk | cavity filling | Q127W/A131L | 0.0564 | 0.0846 | 0.1623 | 0.0544 | 0.1109 | 0.2068 |

FIG. 4B

| Name | Prefusion Stabilizing Mutations | | 0 week | | | 1 week 4 C | | |
|---|---|---|---|---|---|---|---|---|
| | | | PIA3, 15ug/ml | PIA56, 15ug/ml | Strep, 1.0µg/ml | PIA3, 15µg/ml | PIA56, 15µg/ml | Strep, 1.0µg/ml |
| hPIV3NO-GCN4_cav10_gyc_pk | cavity filling | V170I/V175I/V179L | 0.0594 | 0.0973 | 0.137 | 0.0782 | 0.1078 | 0.3441 |
| hPIV3NO-GCN4_cav11_gyc_pk | cavity filling | K173L/E145L | 0.0546 | 0.1136 | 0.2616 | 0.0576 | 0.1231 | 1.1391 |
| hPIV3NO-GCN4_cav12_gyc_pk | cavity filling | Q127W/A131L/V170I/V175I/V179L | 0.0642 | 0.1027 | 0.1353 | 0.0626 | 0.1188 | 0.204 |
| hPIV3NO-GCN4_cav13_gyc_pk | cavity filling | Q127W/A131L/K173L/E145L | 0.0619 | 0.0964 | 0.1985 | 0.0611 | 0.1208 | 0.3464 |
| hPIV3NO-GCN4_cav14_gyc_pk | cavity filling | V170I/V175I/V179L/K173L/E145L | 0.0985 | 0.0972 | 0.588 | 0.1217 | 0.198 | 1.3534 |
| hPIV3NO-GCN4_cav15_gyc_pk | cavity filling | I187F/Q127W/A131L | 0.0642 | 0.1014 | 0.1133 | 0.0599 | 0.1223 | 0.1852 |
| hPIV3NO-GCN4_cav16_gyc_pk | cavity filling | I187F/V170I/V175I/V179L | 0.0675 | 0.0908 | 0.3112 | 0.0748 | 0.1295 | 0.7623 |
| hPIV3NO-GCN4_cav17_gyc_pk | cavity filling | I187F/K173L/E145L | 0.0611 | 0.1143 | 0.4676 | 0.0593 | 0.1248 | 1.2559 |
| hPIV3NO-GCN4_cav18_gyc_pk | cavity filling | I187F/V170I/V175I/V179L/Q127W/ A131L/K173L/E145L | 0.0799 | 0.0701 | 0.2807 | 0.1506 | 0.107 | 0.6168 |
| hPIV3NO-GCN4_cav19_gyc_pk | cavity filling | S470L | 2.9031 | 0.9592 | 1.0141 | 1.7704 | 0.4632 | 1.7484 |
| hPIV3NO-GCN4_cav20_gyc_pk | cavity filling | A463I | 2.771 | 1.6293 | 0.8732 | 1.8252 | 0.9304 | 1.4743 |
| hPIV3NO-GCN4_cav21_gyc_pk | cavity filling | S477L | 2.6103 | 0.6117 | 0.8309 | 1.2761 | 0.3608 | 1.1602 |
| hPIV3NO-GCN4_cav22_gyc_pk | cavity filling | I474Y | 3.1381 | 0.9344 | 1.8912 | 2.9542 | 0.6424 | 2.3417 |
| hPIV3NO-GCN4_cav23_gyc_pk | cavity filling | V170I/I172V/I242F | 3.2082 | 1.8057 | 1.1379 | 2.9099 | 1.2184 | 1.9497 |
| hPIV3NO-GCN4_cav24_gyc_pk | cavity filling | L49F/V170I/I172V/I242L | 0.4383 | 0.2274 | 0.4977 | 0.1873 | 0.16 | 1.0516 |
| hPIV3NO-GCN4_cav25_gyc_pk | cavity filling | L49F/V170L/I172G/I242Y | 0.0681 | 0.1034 | 0.4031 | 0.0621 | 0.1328 | 1.2618 |
| hPIV3NO-GCN4_cav26_gyc_pk | cavity filling | D59Y/N61M/D65F/I187F | 0.0739 | 0.0907 | 0.4006 | 0.0563 | 0.1263 | 0.5342 |
| hPIV3NO-GCN4_cav27_gyc_pk | cavity filling | D59A/N61V/D65F/I187F | 0.0839 | 0.1322 | 0.2276 | 0.0651 | 0.132 | 0.6788 |
| hPIV3NO-GCN4_cav28_gyc_pk | cavity filling | A130F/E223M/R265W/R281M | 0.1735 | 0.2102 | 0.5417 | 0.1608 | 0.313 | 1.1927 |
| hPIV3NO-GCN4_cav29_gyc_pk | cavity filling | A130F/E223L/R265W/R281I | 0.0946 | 0.1393 | 0.3881 | 0.1109 | 0.2743 | 1.3185 |
| hPIV3NO-GCN4_cav30_gyc_pk | cavity filling | S52M/I151L | 3.118 | 2.299 | 1.2147 | 2.8451 | 1.3728 | 2.1612 |
| hPIV3NO-GCN4_cav31_gyc_pk | cavity filling | S52F/I151L/A171G | 0.2701 | 1.129 | 1.1104 | 0.1929 | 0.4255 | 2.0026 |
| hPIV3NO-GCN4_cav32_gyc_pk | cavity filling | S52G/I151L/A171F | 0.0992 | 0.1191 | 0.3607 | 0.0699 | 0.1099 | 1.0457 |
| hPIV3NO-GCN4_cav33_gyc_pk | cavity filling | S174F/V175I/H206M | 0.0663 | 0.1067 | 0.2383 | 0.0645 | 0.1222 | 0.6425 |
| hPIV3NO-GCN4_cav34_gyc_pk | cavity filling | S174F/H206L | 0.095 | 0.1157 | 0.4962 | 0.1175 | 0.2558 | 0.9833 |
| hPIV3NO-GCN4_cav35_gyc_pk | cavity filling | S174G/V175I/H206F | 0.1406 | 0.2279 | 0.328 | 0.0837 | 0.1703 | 0.9944 |
| hPIV3NO-GCN4_cav36_gyc_pk | cavity filling | E145L/D268L/T277L | 0.0674 | 0.0996 | 0.2781 | 0.0598 | 0.1221 | 0.8873 |

FIG. 4C

| Name | Prefusion Stabilizing Mutations | | 0 week | | | 1 week 4 C | | |
|---|---|---|---|---|---|---|---|---|
| | | | PIA3, 15ug/ml | PIA56, 15ug/ml | Strep, 1.0μg/ml | PIA3, 15μg/ml | PIA56, 15μg/ml | Strep, 1.0μg/ml |
| hPIV3NO-GCN4_cav37_gyc_pk | cavity filling | E145M/D268A/T277L | 0.0767 | 0.1116 | 0.2439 | 0.0603 | 0.1292 | 0.5604 |
| hPIV3NO-GCN4_cav38_gyc_pk | cavity filling | I50M/E145F/D268G/T277L | 0.0626 | 0.0953 | 0.3562 | 0.0574 | 0.1151 | 0.6865 |
| hPIV3NO-GCN4_cav39_gyc_pk | cavity filling | Q89F/V94I/A131F/E223L | 0.098 | 0.1466 | 0.3871 | 0.1166 | 0.2547 | 0.617 |
| hPIV3NO-GCN4_cav40_gyc_pk | cavity filling | Q89F/V94F/E223F | 2.619 | 0.9076 | 1.3274 | 1.4658 | 0.4787 | 1.1967 |
| hPIV3NO-GCN4_cav41_gyc_pk | cavity filling | Q89F/V94I/A131F/E223F | 0.0865 | 0.0922 | 0.2829 | 0.1036 | 0.132 | 0.6926 |
| hPIV3NO-GCN4_cav42_gyc_pk | cavity filling | D59F/Q127W/S220L/E223F | 0.0606 | 0.1082 | 0.0818 | 0.0535 | 0.1106 | 0.1473 |
| hPIV3NO-GCN4_cav43_gyc_pk | cavity filling | D59A/N61V/D65F/I187F/S174G/V175I/H206F | 0.0805 | 0.0841 | 0.3401 | 0.0839 | 0.1329 | 0.8339 |
| hPIV3NO-GCN4_cav44_gyc_pk | cavity filling | E145L/D268L/T277L/Q89F/V94I/A131F/E223L | 0.0795 | 0.074 | 0.3274 | 0.0963 | 0.1301 | 0.6815 |
| hPIV3NO-GCN4_cav45_gyc_pk | cavity filling | A130F/E223L/R265W/R281I/S52G/I151L/A171F | 0.0967 | 0.088 | 0.7681 | 0.0894 | 0.5427 | 1.3693 |
| hPIV3NO-GCN4_cav46_gyc_pk | cavity filling | D59F/Q127W/S220L/E223F/V170I/I172V/I242F | 2.8701 | 1.5228 | 0.9089 | 1.8133 | 1.1997 | 1.4102 |
| hPIV3NO-GCN4_cav47_gyc_pk | cavity filling | D59Y/N61M/D65F/I187F/Q89F/V94F/E223F | 0.079 | 0.0899 | 0.3682 | 0.1021 | 0.1144 | 0.5436 |
| hPIV3NO-GCN4_cav48_gyc_pk | cavity filling | D59F/Q127W/S220L/E223F/I50M/E145F/D268G/T277L | 0.075 | 0.0932 | 0.308 | 0.0848 | 0.2242 | 0.4231 |
| hPIV3NO-GCN4_cav49_gyc_pk | cavity filling | L49F/V170I/I172V/I242L/S52F/I151L/A171G | 0.0839 | 0.1412 | 0.8834 | 0.0907 | 0.2923 | 1.7589 |
| hPIV3NO-GCN4_cav50_gyc_pk | cavity filling | S174F/H206L/A130F/E223M/R265W/R281M | 0.0807 | 0.118 | 0.3978 | 0.11 | 0.2353 | 0.9253 |
| hPIV3NO-GCN4_A157P_gyc | proline to break postfusion helix | A157P | 3.1117 | 3.4184 | 2.3811 | 3.3532 | 2.8071 | 2.333 |
| hPIV3NO-GCN4_R189P_gyc | proline to break postfusion helix | R189P | 0.074 | 0.1058 | 0.3713 | 0.0649 | 0.12 | 0.8259 |
| hPIV3NO-GCN4_L190P_gyc | proline to break postfusion helix | L190P | 0.0641 | 0.0951 | 0.3925 | 0.0556 | 0.1116 | 0.7423 |
| hPIV3NO-GCN4_G191P_gyc | proline to break postfusion helix | G191P | 0.0959 | 0.0784 | 0.5563 | 0.1039 | 0.1276 | 1.444 |

FIG. 4D

| Name | Prefusion Stabilizing Mutations | | 0 week | | | 1 week 4 C | | |
|---|---|---|---|---|---|---|---|---|
| | | | **PIA3, 15ug/ml** | **PIA56, 15ug/ml** | **Strep, 1.0μg/ml** | **PIA3, 15μg/ml** | **PIA56, 15μg/ml** | **Strep, 1.0μg/ml** |
| hPIV3NO-GCN4_E182C_Q198C_gyc | Disulfide | E182C/Q198C | 0.0747 | 0.1063 | 0.1729 | 0.0685 | 0.1346 | 0.5359 |
| hPIV3NO-GCN4_I187C_N61C_gyc | Disulfide | I187C/N61C | 1.1421 | 0.4023 | 0.5695 | 0.3538 | 0.2407 | 1.0448 |
| hPIV3NO-GCN4_D268C_K141C_gyc | Disulfide | D268C/K141C | 0.0789 | 0.0973 | 0.165 | 0.0848 | 0.1116 | 0.7451 |
| hPIV3NO-GCN4_Y48C_I169C_gyc | Disulfide | Y48C/I169C | 0.0556 | 0.1094 | 0.2969 | 0.0543 | 0.1062 | 0.83 |
| hPIV3NO-GCN4_I50C_A171C_gyc | Disulfide | I50C/A171C | 0.0582 | 0.0989 | 0.3393 | 0.0552 | 0.1156 | 0.9372 |
| KX_T154D | Cav | T154D | 0.0859 | 3.1018 | 2.3558 | 0.2246 | 0.9978 | 2.5064 |
| KX_T154R | Cav | T154R | 0.0746 | 0.2607 | 0.5451 | 0.0718 | 0.1714 | 1.1082 |
| KX_V165T | Cav | V165T | 3.184 | 3.0921 | 2.0657 | 3.2061 | 2.3404 | 2.2814 |
| KX_V165R | Cav | V165R | 3.162 | 3.0259 | 2.0392 | 3.1442 | 2.2721 | 2.2698 |
| KX_A464I | Cav | A464I | 0.8077 | 0.382 | 0.3538 | 0.5735 | 0.1761 | 0.7732 |
| KX_A464V | Cav | A464V | 1.91 | 0.3652 | 0.4427 | 1.6194 | 0.1805 | 1.3257 |
| KX_S470I | Cav | S470I | 1.222 | 0.2832 | 0.367 | 0.7037 | 0.2872 | 0.6859 |
| KX_S470V | Cav | S470V | 2.9613 | 0.6959 | 1.0594 | 2.0363 | 0.4884 | 1.6702 |
| KX_S477I | Cav | S477I | 2.8181 | 0.5073 | 0.7682 | 1.5909 | 0.3783 | 1.2491 |
| KX_S477V | Cav | S477V | 2.9801 | 0.7299 | 0.9844 | 2.24 | 0.6792 | 1.6129 |
| KX_stem1 | | | 0.0804 | 0.2681 | 0.6521 | 0.0668 | 0.2008 | 1.4614 |
| KX_stem2 | | | 0.0787 | 0.1729 | 0.4159 | 0.0699 | 0.1755 | 1.6992 |
| KX_stem3 | | | 0.5019 | 0.1942 | 0.2763 | 0.3356 | 0.1449 | 0.8699 |
| KX_stem4 | | | 3.014 | 2.3086 | 1.5437 | 2.0136 | 1.317 | 2.3662 |
| KX_stem5 | | | 1.1053 | 0.2401 | 0.2801 | 0.6467 | 0.1073 | 0.6957 |
| KX_stem6 | | | 3.1941 | 3.0845 | 2.1224 | 3.2032 | 2.5975 | 2.4872 |
| MP-1 | Disulfide | A139C-V268C | 0.061 | 0.0879 | 0.3044 | 0.0562 | 0.1084 | 0.8705 |
| MP-2 | Disulfide | A139C-D270C | 0.0653 | 0.1079 | 0.2851 | 0.0618 | 0.1058 | 0.7563 |
| MP-3 | Disulfide | K140C-I269C | 0.5298 | 0.5285 | 0.3628 | 0.3214 | 0.6781 | 0.866 |
| MP-4 | Disulfide | K140C-D270C | 0.0651 | 0.0984 | 0.2495 | 0.0723 | 0.117 | 0.8042 |
| MP-5 | Disulfide | K143C-D270C | 0.0599 | 0.0894 | 0.1709 | 0.0663 | 0.1185 | 0.6382 |
| MP-6 | Disulfide | K143C-I269C | 0.0754 | 0.0956 | 0.5207 | 0.0791 | 0.1424 | 1.4477 |
| MP-7 | Disulfide | K143C-V271C | 0.058 | 0.0863 | 0.1966 | 0.0549 | 0.1041 | 0.5212 |

FIG. 4E

| Name | Prefusion Stabilizing Mutations | | 0 week | | | 1 week 4 C | | |
|---|---|---|---|---|---|---|---|---|
| | | | PIA3, 15ug/ml | PIA56, 15ug/ml | Strep, 1.0μg/ml | PIA3, 15μg/ml | PIA56, 15μg/ml | Strep, 1.0μg/ml |
| MP-8 | Disulfide | I146C-D272C | 0.0555 | 0.0979 | 0.1585 | 0.0521 | 0.0982 | 0.4492 |
| MP-9 | Disulfide | I146C-V271C | 0.0559 | 0.0942 | 0.2662 | 0.0585 | 0.1027 | 0.7975 |
| MP-10 | Disulfide | E147C-D272C | 0.05 | 0.1002 | 0.313 | 0.0567 | 0.1038 | 0.7629 |
| MP-11 | Disulfide | L149C-L273C | 0.0695 | 0.1891 | 0.3771 | 0.0669 | 0.561 | 0.8904 |
| MP-12 | Disulfide | L149C-N274C | 0.0639 | 0.1048 | 0.306 | 0.0573 | 0.2037 | 0.971 |
| MP-13 | Disulfide | L149C-D275C | 0.0666 | 0.1008 | 0.4129 | 0.0587 | 0.1271 | 1.2266 |
| hPIV3-tz2-S52C-K173C | inter SS | S52C-K173C | 0.0588 | 0.1046 | 0.2795 | 0.0622 | 0.1296 | 1.0338 |
| hPIV3-tz3-I172C-N238C | inter SS | I172C-N238C | 3.0986 | 2.1065 | 2.0637 | 3.1526 | 1.8119 | 2.4926 |
| hPIV3-tz4-K141C-D258C | inter SS | K141C-D258C | 0.0979 | 0.0843 | 0.2548 | 0.0576 | 0.1018 | 0.5917 |
| hPIV3-tz5-R365C-S448C | inter SS | R365C-S448C | 0.0673 | 0.0931 | 0.1872 | 0.0607 | 0.1412 | 0.3967 |
| hPIV3-tz6-D452W | Cav | D452W | 0.4048 | 0.3229 | 0.4896 | 0.1677 | 0.2455 | 1.056 |
| hPIV3-tz7-D452R | Cav | D452R | 2.217 | 0.6562 | 0.9229 | 1.2529 | 0.5031 | 1.4839 |
| hPIV3-tz8-Q205W | Cav | Q205W | 0.0716 | 0.0803 | 0.6028 | 0.0788 | 0.1684 | 1.3155 |
| hPIV3-tz9-S60-I187C | replace S60 stretch, intra SS | S60-I187C | 0.9971 | 0.2571 | 0.5538 | 0.3326 | 0.162 | 0.9854 |
| hPIV3-tz10inter-K181C-Q198C | inter SS | K181C-Q198C | 0.064 | 0.1049 | 0.3865 | 0.0622 | 0.1197 | 0.9049 |
| hPIV3-tz11-A188P-I172C-N238C | disrupt, intra SS | A188P-I172C-N238C | 3.0707 | 1.6104 | 2.1298 | 3.0538 | 1.7553 | 2.4203 |
| hPIV3-tz268 | Combine tz2,6,8 | S52C-K173C, D452W, Q205W | 0.0875 | 0.0789 | 0.4608 | 0.0806 | 0.2523 | 1.3104 |
| hPIV3-tz2568 | Combo | S52C-K173C, R365C-S448C, D452W | 0.0845 | 0.0689 | 0.538 | 0.0789 | 0.1212 | 1.0029 |
| hPIV3-tz367 | Combo | I172C-N238C, D452W, D452R | 3.3042 | 3.2658 | 3.1371 | 3.3855 | 2.9675 | 2.0438 |
| hPIV3-tz368 | Combo | I172C-N238C, D452W, Q205W | 3.2959 | 3.1384 | 2.4192 | 3.3373 | 2.3805 | 1.8494 |
| hPIV3-tz48 | Combo | K141C-D258C, Q205W | 0.0683 | 0.0802 | 0.4626 | 0.0997 | 0.166 | 0.7086 |
| hPIV3-tz568 | Combo | R365C-S448C, D452W,Q205W | 0.0824 | 0.0823 | 0.2089 | 0.0971 | 0.1243 | 0.4889 |
| hPIV3-tz811 | Combo | Q205W, A188P-I172C-N238C | 3.1453 | 1.9227 | 2.7574 | 3.2241 | 2.1027 | 2.4746 |
| hPIV3-tz19-Y48C-I169C-V170L-I187F | Intra Ss, cav | Y48C-I169C-V170L-I187F | 0.0781 | 0.0711 | 0.6277 | 0.0987 | 0.1282 | 1.484 |
| hPIV3-tz20-S52C-K173C-V170L-I187F | Intra Ss, cav | S52C-K173C-V170L-I187F | 0.0953 | 0.0772 | 0.8702 | 0.0821 | 0.2277 | 1.892 |

FIG. 4F

| Name | Prefusion Stabilizing Mutations | | 0 week | | | 1 week 4 C | | |
|---|---|---|---|---|---|---|---|---|
| | | | **PIA3, 15ug/ml** | **PIA56, 15ug/ml** | **Strep, 1.0μg/ml** | **PIA3, 15μg/ml** | **PIA56, 15μg/ml** | **Strep, 1.0μg/ml** |
| hPIV3-tz21-I172C-N238C-V170L-I187F | Intra Ss, cav | I172C-N238C-V170L-I187F | 2.5555 | 0.1576 | 1.376 | 1.8752 | 0.2509 | 2.1117 |
| hPIV3-tz22-K141C-D258C-V170L-I187F | Intra Ss, cav | K141C-D258C-V170L-I187F | 0.1528 | 0.0859 | 0.6575 | 0.0864 | 0.1478 | 1.3575 |
| hPIV3-tz23-Y48C-I169C-I57VI183FL199V | Intra Ss, cav | Y48C-I169C-I57VI183FL199V | 0.0826 | 0.0823 | 0.7758 | 0.0801 | 0.1522 | 1.7806 |
| hPIV3-tz24-Y48C-I169C-D177C-S201C | Intra Ss, inter SS | Y48C-I169C-D177C-S201C | 0.0736 | 0.077 | 0.7705 | 0.0924 | 0.237 | 1.7129 |
| hPIV3-tz25-Y48C-I169C-Y178W | Intra Ss, cav | Y48C-I169C-Y178W | 0.0765 | 0.0949 | 0.5918 | 0.0935 | 0.1657 | 1.2745 |
| hPIV3-tz26-S52C-K173C-Y178W | Intra Ss, cav | S52C-K173C-Y178W | 0.0733 | 0.1048 | 0.3309 | 0.0586 | 0.1326 | 1.4404 |
| hPIV3-tz27-I172C-N238C-Y178W | Intra Ss, cav | I172C-N238C-Y178W | 3.0967 | 0.9397 | 1.496 | 2.9639 | 1.1992 | 2.1728 |
| hPIV3-tz28-K141C-D258C-Y178W | Intra Ss, cav | K141C-D258C-Y178W | 0.0663 | 0.0973 | 0.3328 | 0.0584 | 0.11 | 0.92 |

FIG. 5

| Construct | Oligomeric state | Elution volume (mL) | Yield (mg/L) | Antibody $K_D$ value (nM) | | Physical stability (fractional PIA174 reactivity) | | | | | | |
|---|---|---|---|---|---|---|---|---|---|---|---|---|
| | | | | | | Temp (°C) | | pH | | Freeze/ | Osmolality (mM) | |
| | | | | PIA3 (1:3) | PIA174 (1:1) | 50 | 70 | 3.5 | 10.0 | Thaw | 10 | 3000 |
| hPIV3 GCN4 | Trimer | 16.07 | 0.2 | 74.4 | <0.001 | 0.9 | 0.0 | 0.0 | 0.4 | 0.8 | 0.5 | 0.6 |
| hPIV3 GCN4, 172C-238C | Trimer | 16.19 | 2.2 | 23.6 | 20.5 | 1.2 | 0.0 | 1.2 | 1.2 | 0.6 | 1.2 | 1.4 |
| hPIV3 GCN4, A464V | Trimer | 16.01 | 0.6 | 92.8 | <0.001 | 0.3 | 0.1 | 0.1 | 0.0 | 0.1 | 0.1 | 0.5 |
| hPIV3 GCN4, A473V, I474Y | Trimer | 16.18 | 1.6 | 29.8 | <0.001 | 0.9 | 0.0 | 0.0 | 0.4 | 0.9 | 0.6 | 0.6 |
| hPIV3 GCN4, Y178W | Trimer | 16.01 | <0.1 | N.B. | N.B. | N/A | N/A | N/A | N/A | N/A | N/A | N/A |
| hPIV3 GCN4, Y178W A473V, I474Y | Trimer | 15.51 | 0.2 | N.B. | N.B. | N/A | N/A | N/A | N/A | N/A | N/A | N/A |
| hPIV3 GCN4, 172C-238C, Y178W | Trimer | 16.23 | 0.5 | 43.2 | 33.9 | 1.0 | 0.1 | 1.2 | 0.7 | 0.8 | 0.7 | 1.0 |
| hPIV3 GCN4, 172C-238C, I474Y | Trimer | 16.48 | 3.2 | 31.7 | 9.75 | 0.8 | 0.0 | 1.3 | 0.8 | 0.6 | 0.8 | 0.6 |
| hPIV3 GCN4, 172C-238C, A473V, I474Y | Trimer | 16.34 | 2.9 | 29.8 | 10.6 | 1.0 | 0.3 | 1.0 | 0.7 | 1.0 | 0.9 | 0.5 |
| hPIV3 postfusion | Trimer | 15.74 | 2.6 | N.B. | N.B. | N/A | N/A | N/A | N/A | N/A | N/A | N/A |

PIV3 F GCN4
Week 1 — Prefusion: 91%
Week 2 — 69%
Week 3 — 32%
Week 4 — 0%

PIV3 F GCN4 I172C-N238C/A464V
Week 1 — Prefusion: 100%
Week 2 — 100%
Week 3 — 100%
Week 4 — 100% hPIV1_880_preF4 hPIV1_880_preF2 hPIV1_880_preF1

FIG. 13
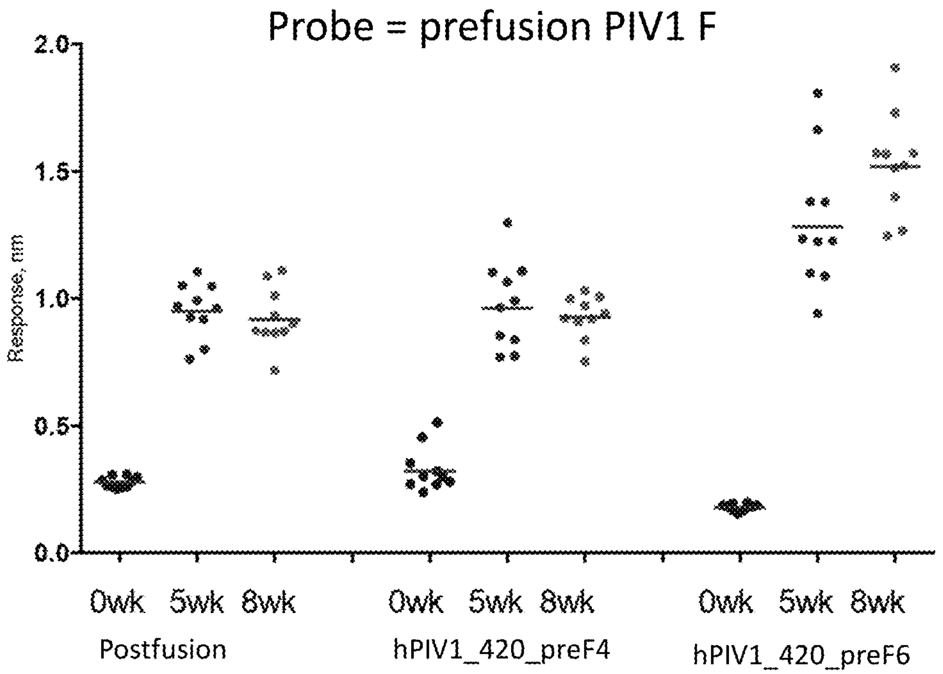
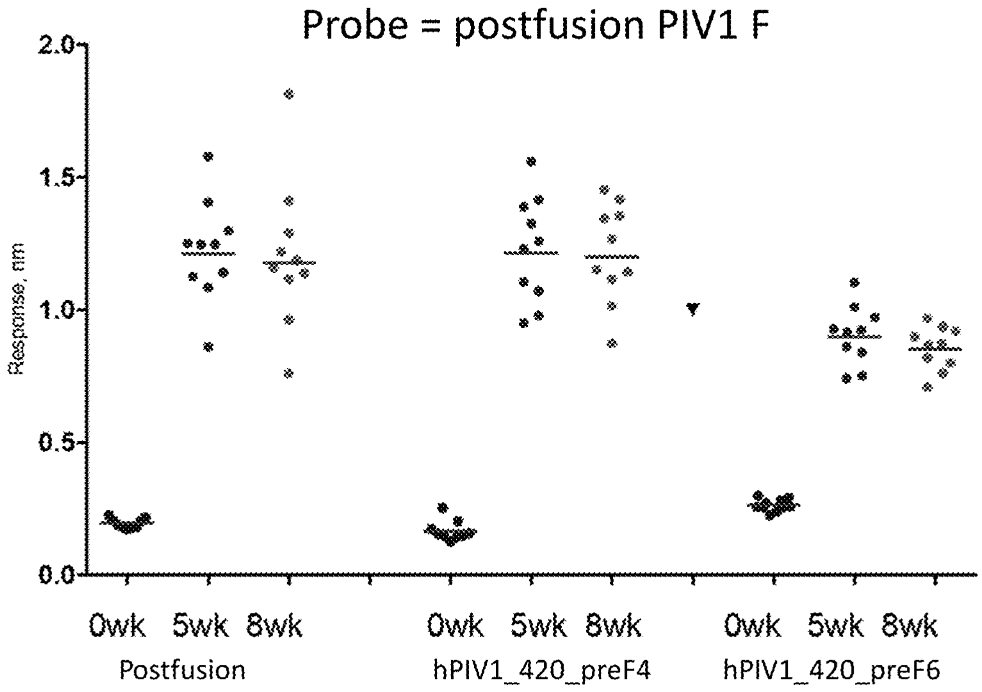

hPIV2_preF6 hPIV2 F Postfusion hPIV2_preF6-v4 hPIV2_preF6-v3 hPIV2_preF6-V2 hPIV4_PreF5 hPIV4_PreF4

FIG. 19A
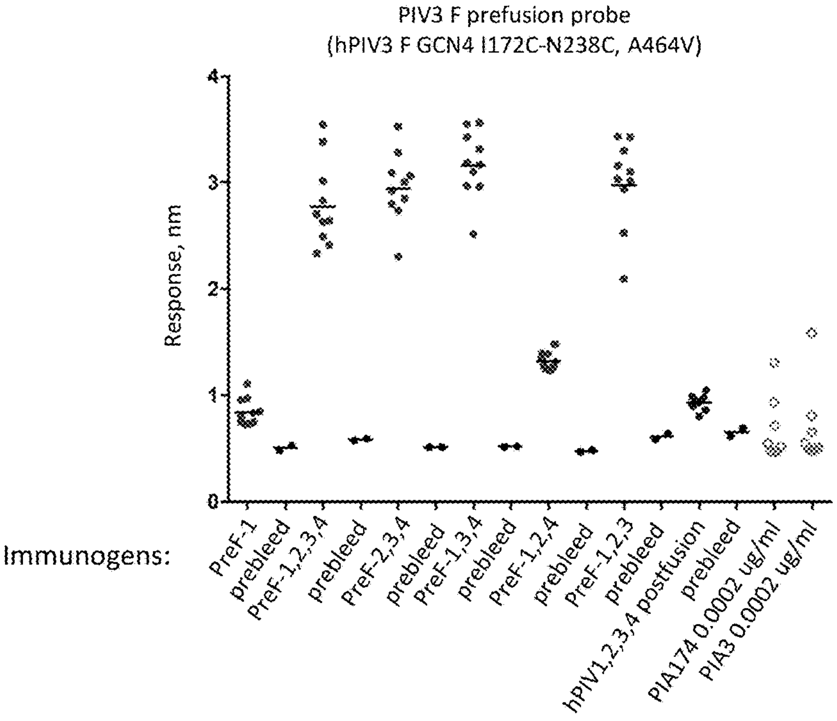
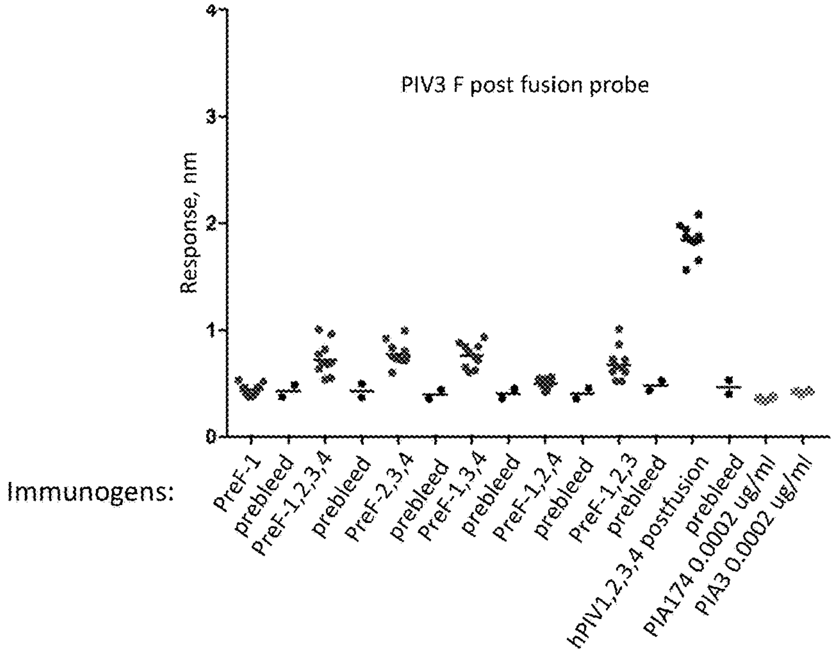
Immunogens:
PreF-1: hPIV1_880_preF2
PreF-2: hPIV2_preF6
PreF-3: hPIV3 F GCN4 I172C-N238C, A463V
PreF-4: hPIV4_preF4

FIG. 19B
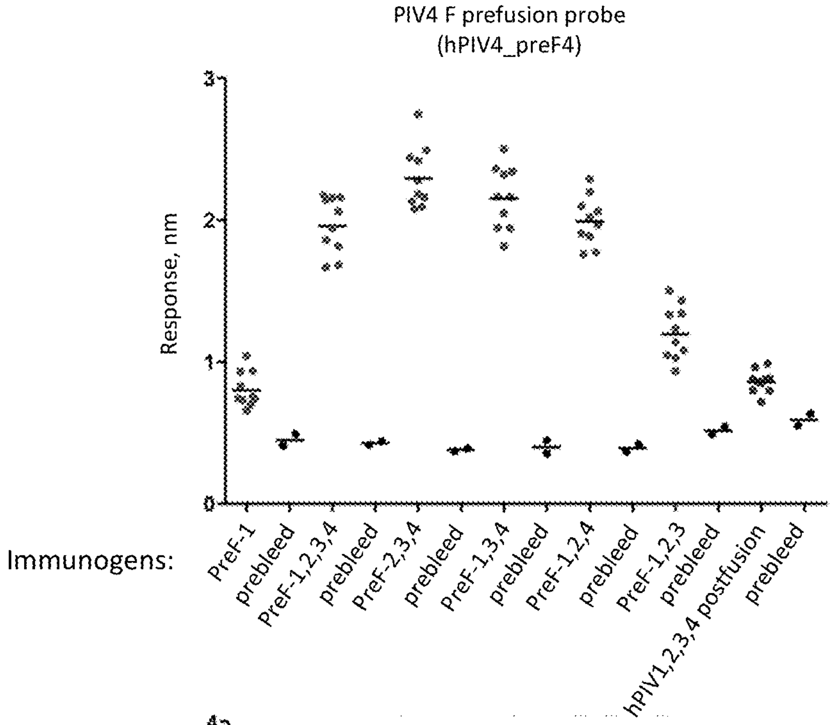
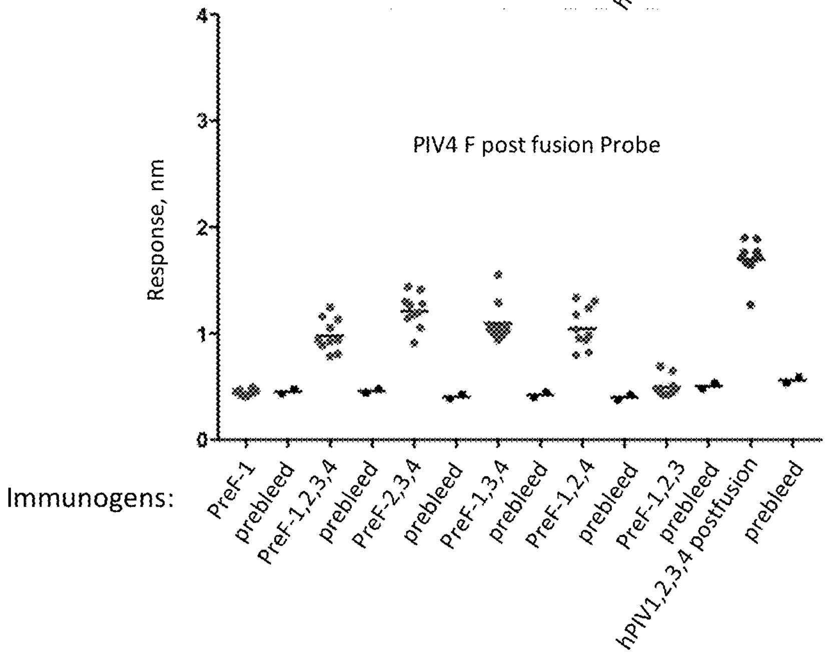
Immunogens:
PreF-1: hPIV1_880_preF2
PreF-2: hPIV2_preF6
PreF-3: hPIV3 F GCN4 I172C-N238C, A463V
PreF-4: hPIV4_preF4

FIG. 20A

NHP Immunization Scheme hPIV Immunization study 5 x 2 groups

| Group | Immunogen |
|---|---|
| 1 (5 animals) | Prefusion hPIV-1, 2, 3, 4, 25ug each with PolyIC:LC |
| 2 (5 animals) | Postfusion hPIV-1, 2, 3, 4, 25ug each with PolyIC:LC |

Time (week)

| | Pre-4 | Pre-2 | 0 | 2 | 4 | 6 | 10 | 14 | 16 | 18 | 22 | 26 | 32 | 34 | 38 | 44 |
|---|---|---|---|---|---|---|---|---|---|---|---|---|---|---|---|---|
| Immunization | | | ✓ | | ✓ | | | | ✓ | | | | *hPIV-3 BOOST* | | | *hPIV-3 BOOST* |
| Blood collection | ✓ | ✓ | ✓ | ✓ | ✓ | ✓ | ✓ | ✓ | ✓ | ✓ | ✓ | ✓ | ✓ | ✓ | ✓ | ✓ |

Immunogens:
PreF-1: hPIV1_880_preF2
PreF-2: hPIV2_preF6
PreF-3: hPIV3 F GCN4 I172C-N238C/A463V
PreF-4: hPIV4_preF4

Broad and Potent Neutralization of hPIVs from NHPs Immunized with Combined hPIV-1, 2, 3, 4 Prefusion F Glycoproteins PostF = Postfusion hPIV1, 2, 3, 4 F combination
PreF = Prefusion hPIV1, 2, 3, 4 F combination Unpaired nonparametric Mann-Whitney test
* <0.05
** <0.01

Broad and Potent Neutralization of hPIVs from NHPs Immunized with Combined hPIV-1, 2, 3, 4 Prefusion F Glycoproteins PostF = Postfusion hPIV1, 2, 3, 4 F combination
PreF = Prefusion hPIV1, 2, 3, 4 F combination Unpaired nonparametric Mann-Whitney test
* <0.05
** <0.01

Broad and Potent Neutralization of hPIVs from NHPs Immunized with Combined hPIV-1, 2, 3, 4 Prefusion F Glycoproteins PostF = Postfusion hPIV1, 2, 3, 4 F combination
PreF = Prefusion hPIV1, 2, 3, 4 F combination Unpaired nonparametric Mann-Whitney test
* <0.05
** <0.01

Immunizations:
Week0 PreF: PreF-1, 2, 3, 4
Week0 PostF: PostF-1, 2, 3, 4
Week4 PreF: PreF-1, 2, 3, 4
Week4 PostF: PostF-1, 2, 3, 4
Week16 PreF: PreF-1, 2, 3, 4
Week16 PostF: PostF-1, 2, 3, 4
Week32 PreF: PreF-3
Week32 PostF: PostF-3
Week44 PreF: PreF-3
Week44 PostF: PostF-3

Immunogens:
PreF-1: hPIV1_880_preF2
PreF-2: hPIV2_preF6
PreF-3: hPIV3 F GCN4 I172C-N238C/A463V
PreF-4: hPIV4_preF4

FIG. 21 hPIV-3 F 172C-238C Mutation Increases Koff rate of PIA174 Binding

| | | | | Antibody $K_D$ value (nM) | | | | | |
|---|---|---|---|---|---|---|---|---|---|
| Construct | Oligomeric state | Elution volume (mL)† | Yield (mg/L) | PIA3 $k_{on}$ | PIA3 $k_{off}$ | PIA3 (1:3) | PIA174 $k_{on}$ | PIA174 $k_{off}$ | PIA174 (1:1) |
| hPIV3 GCN4 | Trimer | 16.07 | 0.2 | 1.18E+05 | 8.79E-03 | 74.4 | 7.19E+04 | <1.0E-07 | <0.001 |
| hPIV3 GCN4, 172C-238C | Trimer | 16.19 | 2.2 | 1.77E+05 | 4.19E-03 | 23.6 | 3.72E+04 | 7.62E-04 | 20.5 |
| hPIV3 GCN4, A463V | Trimer | 16.01 | 0.6 | 9.00E+04 | 8.35E-03 | 92.8 | 1.73E+06 | <1.0E-07 | <0.001 |
| hPIV3 GCN4, A463V, I474Y | Trimer | 16.18 | 1.6 | 2.48E+05 | 7.48E-03 | 29.8 | 3.19E+05 | <1.0E-07 | <0.001 |
| hPIV3 GCN4, Y178W | Trimer | 16.01 | <0.1 | | | N.B. | | | N.B. |
| hPIV3 GCN4, Y178W ,A463V, I474Y | Trimer | 15.51 | 0.2 | | | N.B. | | | N.B. |
| hPIV3 GCN4, 172C-238C, Y178W | Trimer | 16.23 | 0.5 | 2.06E+05 | 5.18E+03 | 43.2 | 7.34E+04 | 2.49E-03 | 33.9 |
| hPIV3 GCN4, 172C-238C, I474Y | Trimer | 16.48 | 3.2 | 1.55E+05 | 4.91E-03 | 31.7 | 9.78E+04 | 9.54E-04 | 9.75 |
| hPIV3 GCN4, 172C-238C, A463V, I474Y | Trimer | 16.34 | 2.9 | 1.51E+05 | 4.49E-03 | 29.8 | 9.10E+04 | 9.66E-04 | 10.6 |
| hPIV3 postFusion | Trimer | 15.74 | 2.6 | | | N.B. | | | N.B. |

SDS-PAGE for prefusion stabilized hPIV-3 F Glycoprotein Variants (Non-reduced and Reduced gels showing PIV3 F GCN4, I172C-N238C/I474Y, G85C-Q222C/A463V/I474Y, D216C-L221C/A463V/I474Y, Q162C-L168C/A463V/I474Y, L228C-I262C/A463V/I474Y, V170C-I242C/A463V/I474Y, I213C-G230C/A463V/I474Y variants)

Structures of prefusion stabilized hPIV-3 F Glycoprotein Variants

| hPIV3 F<br>V170C-I242C<br>A463V, I474Y | hPIV3 F<br>Q162C-L168C<br>A463V, I474Y | hPIV3 F<br>I213C-G230C<br>A463V, I474Y | hPIV3 F<br>D216C-L221C<br>A463V, I474Y | hPIV3 F<br>G85C-Q222C<br>A463V, I474Y |
|---|---|---|---|---|
| PreF particles: 99.46% | PreF particles: 98.49% | PreF particles: : 93% | PreF particles: 99.68% | PreF particles: 99.49% |
| PostF particles: 0.54% | PostF particles: 1.51% | PostF particles: 7% | PostF particles: 0.32% | PostF particles: 0.51% |

FIG. 22C

Antigenic and physical stability of prefusion hPIV3 F variants

| Construct | Antibody $K_D$ value (nM) | | | | | |
|---|---|---|---|---|---|---|
| | PIA3 (1:3) | PIA3 on | PIA3 off | PIA174 (1:1) | PIA174 on | PIA174 off |
| PIV3 F GNC4 V170C-I242C, A463V, I474Y | 247.3 | 7.29E+04 | 1.80E-02 | 0.3 | 2.27E+05 | 8.20E-05 |
| PIV3 F GNC4 I213C-G230C, A463V, I474Y | 269.1 | 3.51E+04 | 9.45E-03 | 0.2 | 3.22E+05 | 7.23E-05 |
| PIV3 F GNC4 D216C-L221C, A463V, I474Y | 235.2 | 5.18E+04 | 1.22E-02 | <0.001 | 1.55E+04 | <1.0E-07 |
| PIV3 F GNC4 Q162C-L168C, A463V, I474Y | 79.1 | 7.74E+04 | 6.12E-03 | <0.001 | 1.35E+04 | <1.0E-07 |
| PIV3 F GNC4 G85C-Q222C, A463V, I474Y | 414.7 | 3.46E+04 | 1.44E-02 | <0.001 | 1.22E+04 | <1.0E-07 |
| PIV3 F GNC4 I172C-N238C, I474Y | 29.8 | 1.55E+05 | 4.91E-3 | 10.6 | 9.10E+04 | 9.66E-4 |

FIG. 22D

Double-Disulfide + Stem-Stabilized hPIV-3 F Glycoprotein Variants

| Prefusion hPIV3 F construct | SEQ ID NO | Yield mg/L |
|---|---|---|
| hPIV3 F GNC4 A463V, I474Y | 20 | 3.1 |
| hPIV3 F GNC4 V170C-I242C, A463V, I474Y | 39 | 11.9 |
| hPIV3 F GNC4 I213C-G230C, A463V, I474Y | 40 | 15.2 |
| hPIV3 F GNC4 G85C-Q222C, A463V, I474Y | 41 | 8.2 |
| hPIV3 F GNC4 D216C-L221C, A463V, I474Y | 42 | 5.7 |
| hPIV3 F GNC4 Q162C-L168C, A463V, I474Y | 43 | 10.3 |
| hPIV3 F GNC4 Q162C-L168C, V170C-I242C, A463V, I474Y | 44 | 12.5 |
| hPIV3 F GNC4 Q162C-L168C, I213C-G230C, A463V, I474Y | 45 | 23.0 |
| hPIV3 F GNC4 Q162C-L168C, D216C-L221C, A463V, I474Y | 46 | 15.8 |
| hPIV3 F GNC4 Q162C-L168C, G85C-Q222C, A463V, I474Y | 47 | 10.2 |
| hPIV3 F GNC4 I213C-G230C, V170C-I242C, A463V, I474Y | 48 | 13.3 |
| hPIV3 F GNC4 I213C-G230C, D216C-L221C, A463V, I474Y | 49 | 11.9 |
| hPIV3 F GNC4 I213C-G230C, G85C-Q222C, A463V, I474Y | 50 | 3.5 |
| hPIV3 F GNC4 I172C-N238C, A463V, I474Y | 51 | 3.7 |

FIG. 22E

Double-Disulfide + Stem-Stabilized hPIV-3 F Glycoprotein Variants

Antigenic and physical stability of engineered hPIV3 F glycoproteins

| Construct | Antibody $K_D$ value (nM) | | | | | |
|---|---|---|---|---|---|---|
| | PIA3 (1:3) | PIA3 on | PIA3 off | PIA174 (1:1) | PIA174 on | PIA174 off |
| hPIV3 F GNC4 Q162C-L168C, V170C-I242C, A463V, I474Y | 661.2 | 2.00E+04 | 1.32E-02 | <0.001 | 6.51E+05 | <1.0E-07 |
| hPIV3 F GNC4 Q162C-L168C, I213C-G230C, A463V, I474Y | 229.4 | 1.91E+04 | 4.38E-03 | <0.001 | 1.08E+05 | <1.0E-07 |
| hPIV3 F GNC4 Q162C-L168C/D216C-L221C, A463V, I474Y | 200.4 | 2.24E+04 | 4.49E-03 | <0.001 | 1.04E+05 | <1.0E-07 |
| hPIV3 F GNC4 Q162C-L168C/G85C-Q222C, A463V, I474Y | 186.5 | 2.13E+04 | 3.96E-03 | <0.001 | 1.04E+05 | <1.0E-07 |
| hPIV3 F GNC4 I213C-G230C/V170C-I242C, A463V, I474Y | 1058.0 | 2.74E+04 | 2.90E-02 | <0.001 | 3.40E+04 | <1.0E-07 |
| hPIV3 F GNC4 I213C-G230C/D216C-L221C, A463V, I474Y | 500.0 | 2.06E+04 | 1.03E-02 | 0.18 | 8.16E+04 | 1.50E-05 |
| hPIV3 F GNC4 I213C-G230C/G85C-Q222C, A463V, I474Y | 676.1 | 2.09E+04 | 1.41E-02 | <0.001 | 4.44E+04 | <1.0E-07 |

FIG. 22F

Double-Disulfide + Stem-Stabilized hPIV-3 F Glycoprotein Variants

Physical stability of hPIV3 F glycoproteins stabilized in the pre-fusion state

| | Physical stability (fractional PIA3 reactivity) | | | | | | |
|---|---|---|---|---|---|---|---|
| | Temp (ºC) | | pH | | Freeze-Thaw | Osmolality (mM) | |
| Construct | 50 | 70 | 3.5 | 10.0 | | 10 | 3000 |
| hPIV3 F GNC4 Q162C-L168C, V170C-I242C, A463V, I474Y | 0.94 | 0 | 1.26 | 0.57 | 0 | 0.83 | 0 |
| hPIV3 F GNC4 Q162C-L168C, I213C-G230C, A463V, I474Y | 0.90 | 0 | 1.76 | 1.32 | 0 | 1.30 | 0 |
| hPIV3 F GNC4 Q162C-L168C, D216C-L221C, A463V, I474Y | 0.92 | 0 | 1.10 | 0.64 | 0 | 0.75 | 0 |
| hPIV3 F GNC4 Q162C-L168C, G85C-Q222C, A463V, I474Y | 0.93 | 0 | 1.04 | 0.63 | 0 | 0.63 | 0 |
| hPIV3 F GNC4 I213C-G230C, V170C-I242C, A463V, 474Y | 0.90 | 0 | 0.97 | 0.65 | 0 | 0.56 | 0 |
| hPIV3 F GNC4 I213C-G230C, D216C-L221C, A463V, I474Y | 0.97 | 0 | 1.21 | 0.12 | 0 | 0.69 | 0 |
| hPIV3 F GNC4 I213C-G230C, G85C-Q222C, A463V, I474Y | 0.97 | 0 | 1.23 | 0.56 | 0 | 0.84 | 0 |

hPIV3 F GCN4 A463V, I474Y

The sample contains a mixture of prefusion and postfusion molecules.

61% of the molecules are in the prefusion state.

hPIV3 F GCN4 V170C-I242C, A463V, I474Y

The sample contains prefusion molecules only.

FIG. 22I
hPIV3 F GCN4 I213C-G230C, A463V, I474Y
Representative Image at 100,000x
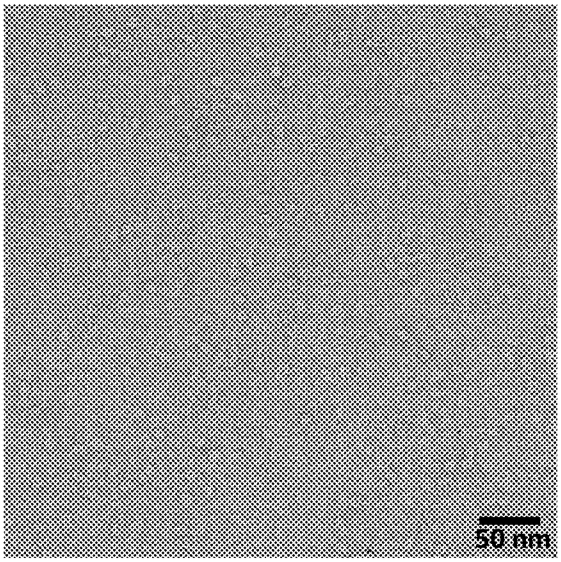
2D Class Averages
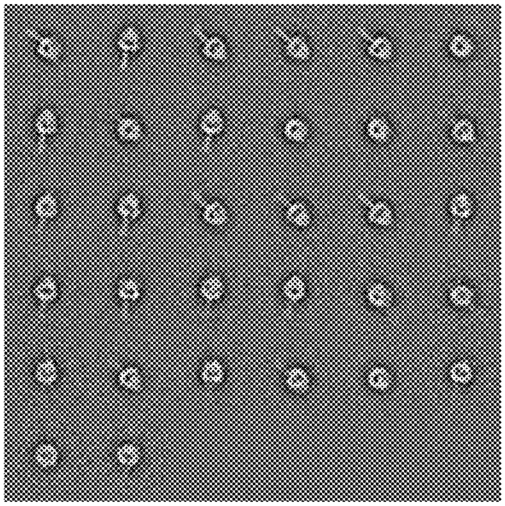
The sample contains prefusion molecules only.
FIG. 22J
hPIV3 F GCN4 G85C-Q222C, A463V, I474Y
Representative Image at 100,000x
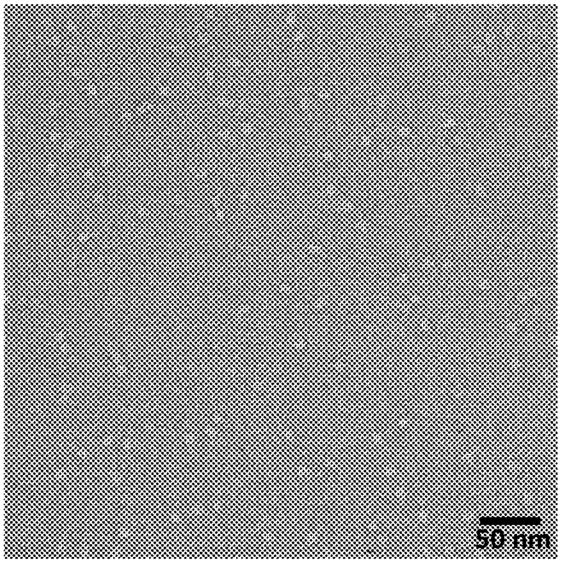
2D Class Averages
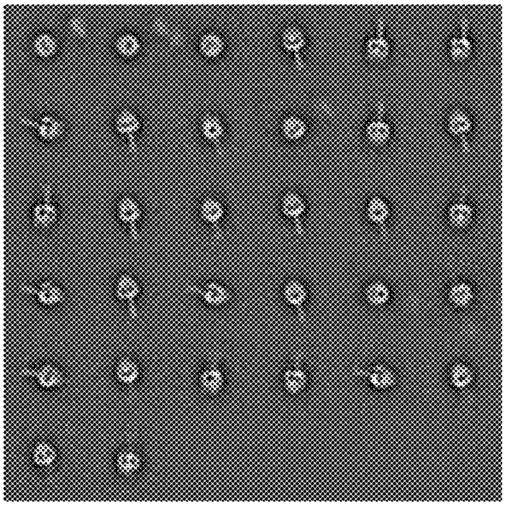
The sample contains prefusion molecules only.

FIG. 22K
hPIV3 F GCN4 D216C-L221C, A463V, I474Y
Representative Image at 100,000x
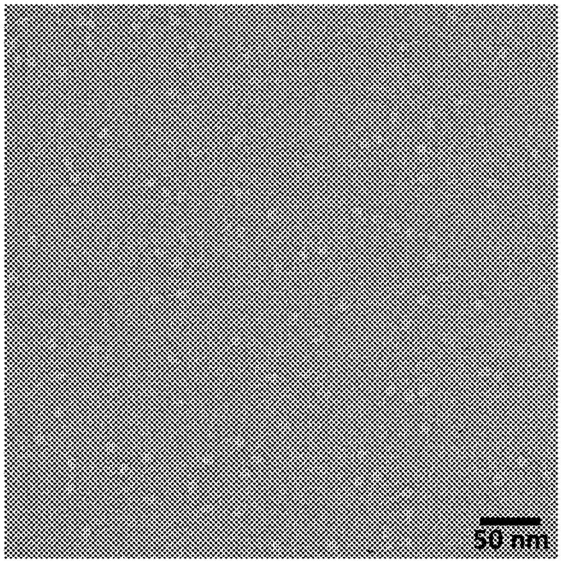
2D Class Averages
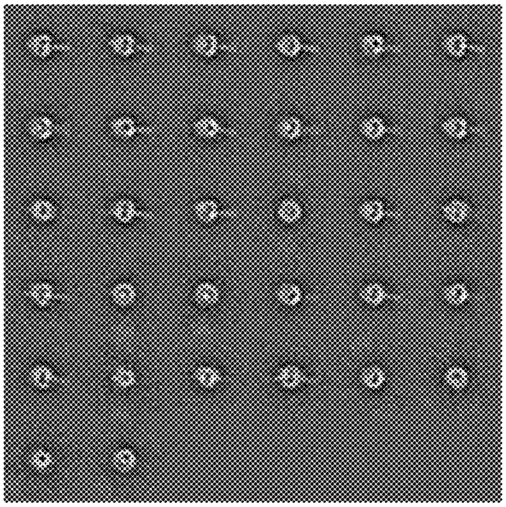
The sample contains prefusion molecules only.
FIG. 22L
hPIV3 F GCN4 Q162C-L168C, A463V, I474Y
Representative Image at 100,000x
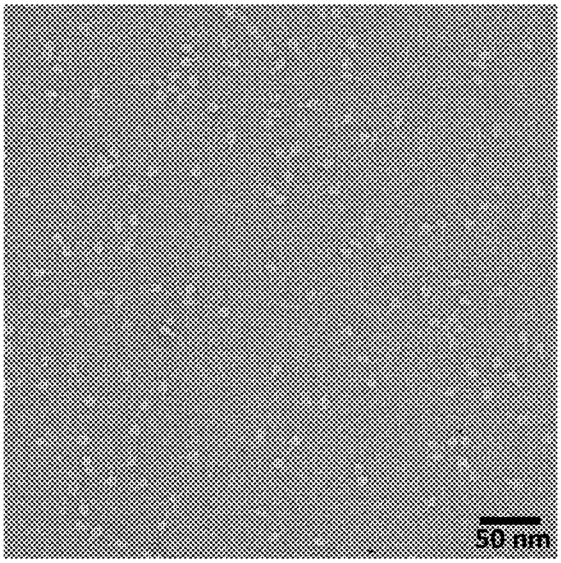
2D Class Averages
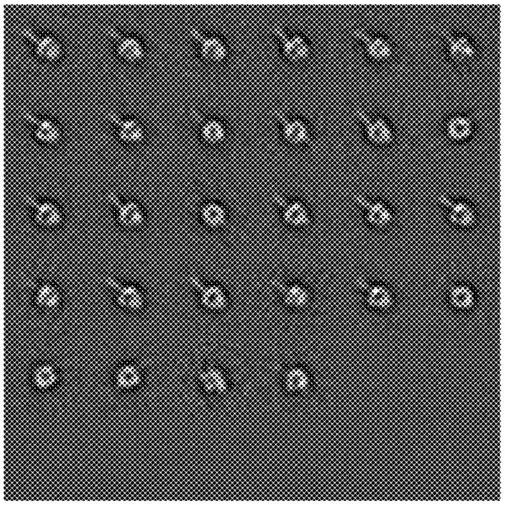
The sample contains prefusion molecules only.

FIG. 22M
hPIV3 F GCN4 Q162C-L168C, V170C-I242C, A463V, I474Y
Representative Image at 100,000x
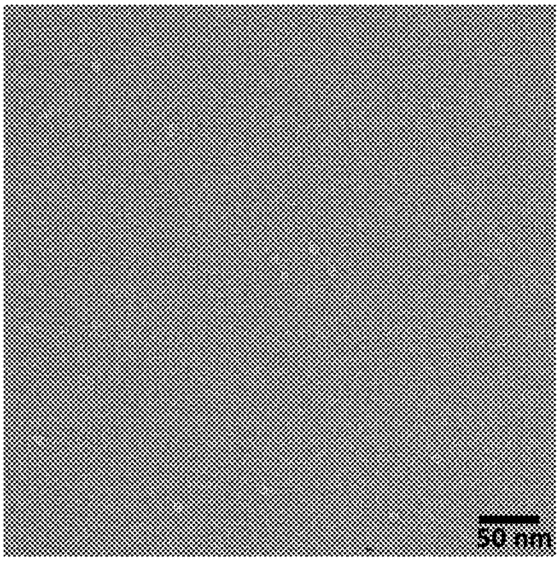
2D Class Averages
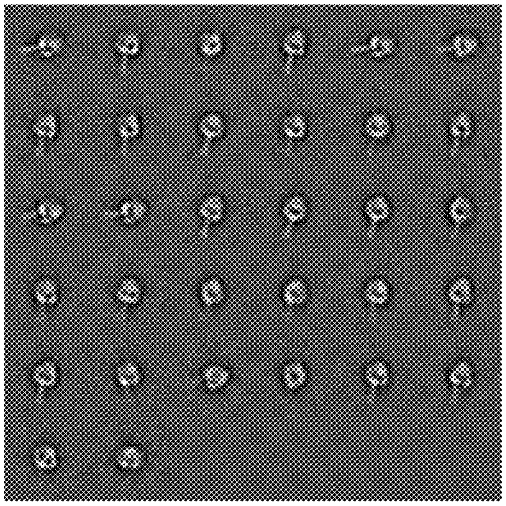
The sample contains prefusion molecules only.
FIG. 22N
hPIV3 F GCN4 Q162C-L168C, I213C-G230C, A463V, I474Y
Representative Image at 100,000x
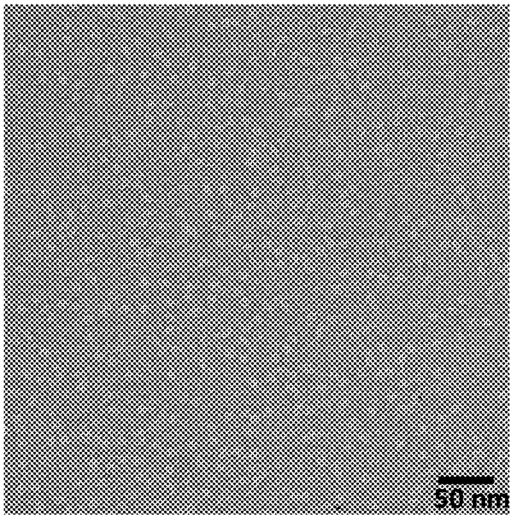
2D Class Average
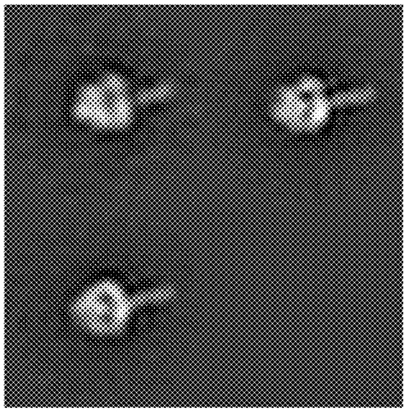
The sample contains prefusion molecules only.

hPIV3 F GCN4 Q162C-L168C, D216C-L221C, A463V, I474Y

Representative Image at 100,000x

2D Class Averages

The sample contains prefusion molecules only.

hPIV3 F GCN4 Q162C-L168C, G85C-Q222C, A463V, I474Y

Representative Image at 100,000x

2D Class Averages

The sample contains prefusion molecules only.

FIG. 22Q
hPIV3 F GCN4 I213C-G230C, V170C-I242C, A463V, I474Y
Representative Image at 100,000x
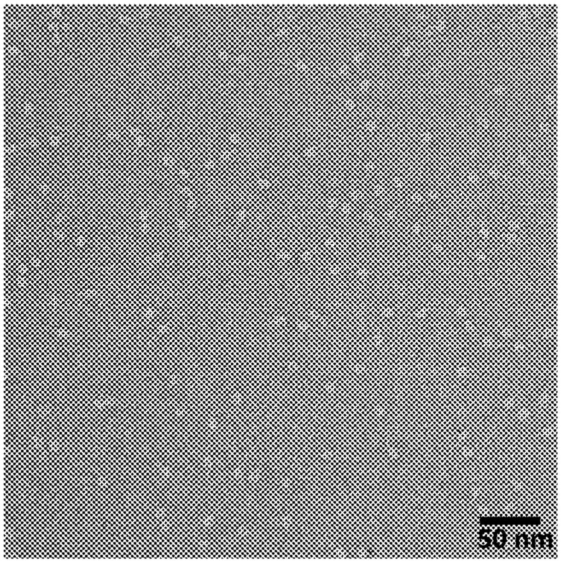
2D Class Averages
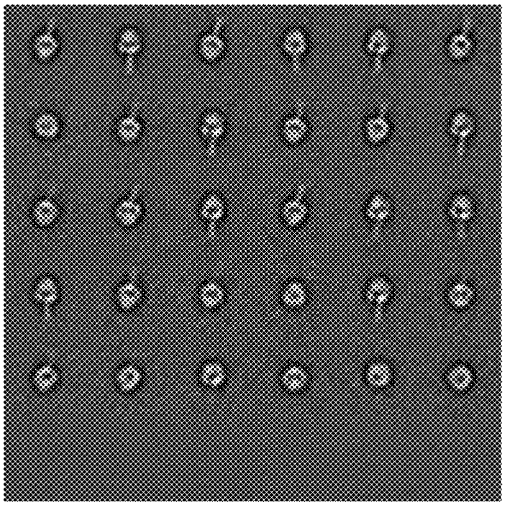
The sample contains prefusion molecules only.
FIG. 22R
hPIV3 F GCN4 I213C-G230C, D216C-L221C, A463V, I474Y
Representative Image at 100,000x
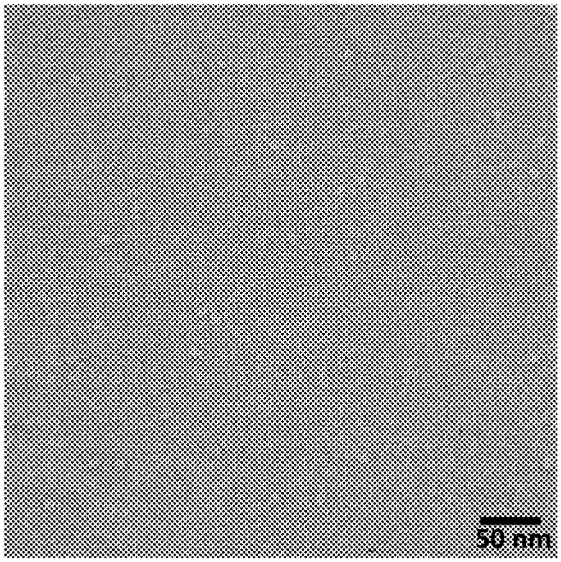
2D Class Averages
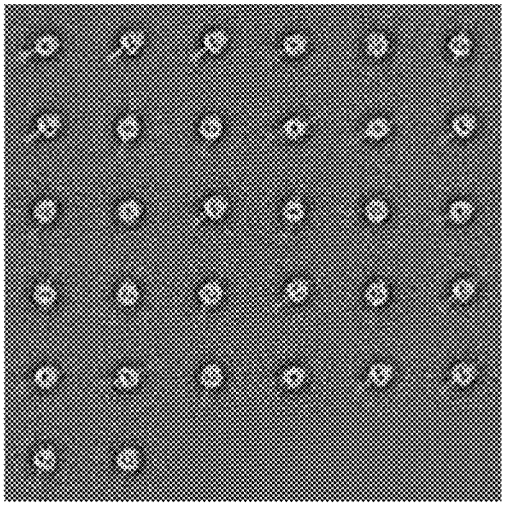
The sample contains prefusion molecules only.

FIG. 22S
hPIV3 F GCN4 I213C-G230C, G85C-Q222C, A463V, I474Y
Representative Image at 100,000x
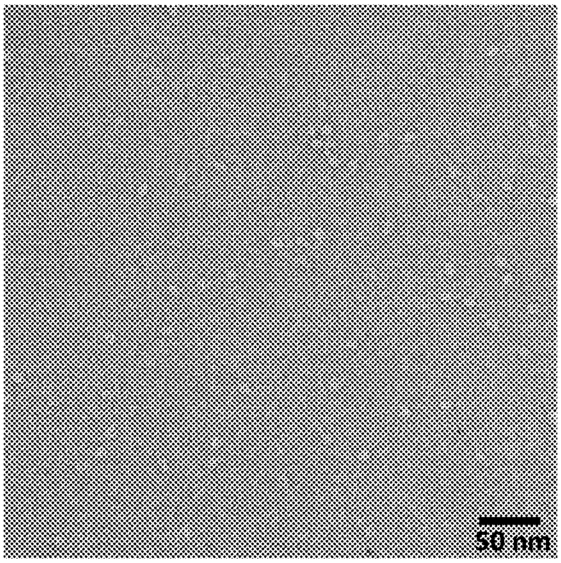
2D Class Averages
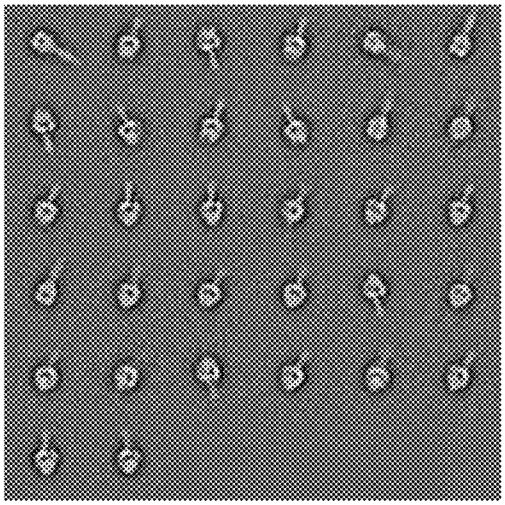
The sample contains primarily prefusion molecules.
88% of the molecules are in the prefusion state.
FIG. 22T
hPIV3 F GCN4 I171C-N238C, A463V, I474Y
Representative Image at 100,000x
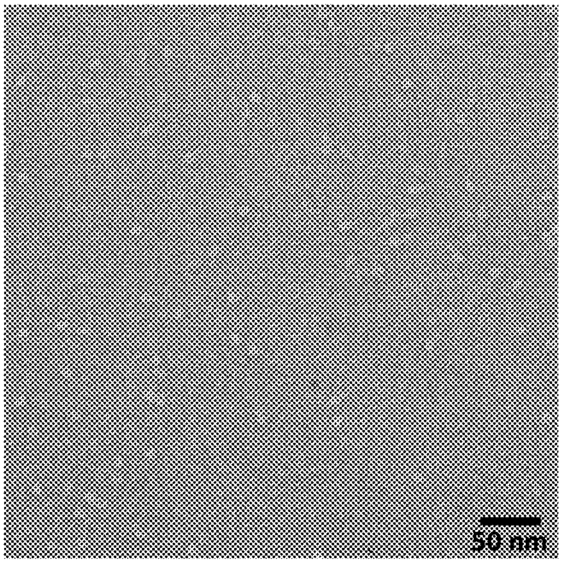
2D Class Averages
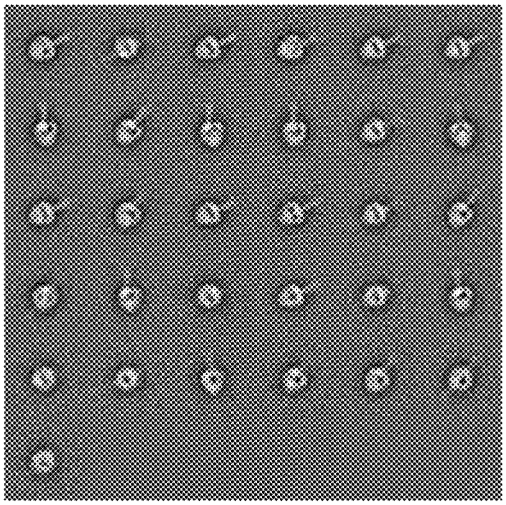
The sample contains prefusion molecules only.

| Group | 10 µg protein immunogen/PolyIC per immunization |
|---|---|
| 101 | hPIV3 F GNC4 A463V, I474Y |
| 102 | hPIV3 F GNC4 V170C/I242C, A463V, I474Y |
| 103 | hPIV3 F GNC4 I213C/G230C, A463V, I474Y |
| 104 | hPIV3 F GNC4 G85C/Q222C, A463V, I474Y |
| 105 | hPIV3 F GNC4 D216C/L221C, A463V, I474Y |
| 106 | hPIV3 F GNC4 Q162C/L168C, A463V, I474Y |
| 107 | hPIV3 F GNC4 Q162C/L168C/I213C/G230C, A463V, I474Y |
| 108 | hPIV3 F GNC4 I213C/G230C/D216C/L221C, A463V, I474Y |
| 109 | hPIV3 F GNC4 I172C/N238C ,A463V, I474Y |
| 110 | Postfusion hPIV3 F GNC4 |

Mouse Sera Octet Binding Analysis

| Group | 10 µg protein immunogen/PolyIC per immunization |
|---|---|
| 101 | hPIV3 F GNC4 A463V, I474Y |
| 102 | hPIV3 F GNC4 V170C/I242C, A463V, I474Y |
| 103 | hPIV3 F GNC4 I213C/G230C, A463V, I474Y |
| 104 | hPIV3 F GNC4 G85C/Q222C, A463V, I474Y |
| 105 | hPIV3 F GNC4 D216C/L221C, A463V, I474Y |
| 106 | hPIV3 F GNC4 Q162C/L168C, A463V, I474Y |
| 107 | hPIV3 F GNC4 Q162C/L168C/I213C/G230C, A463V, I474Y |
| 108 | hPIV3 F GNC4 I213C/G230C/D216C/L221C, A463V, I474Y |
| 109 | hPIV3 F GNC4 I172C/N238C ,A463V, I474Y |
| 110 | Postfusion hPIV3 F GNC4 |

Mouse Sera Octet Binding Analysis

| Group | 10 µg protein immunogen/PolyIC per immunization |
|---|---|
| 101 | hPIV3 F GNC4 A463V, I474Y |
| 102 | hPIV3 F GNC4 V170C/I242C, A463V, I474Y |
| 103 | hPIV3 F GNC4 I213C/G230C, A463V, I474Y |
| 104 | hPIV3 F GNC4 G85C/Q222C, A463V, I474Y |
| 105 | hPIV3 F GNC4 D216C/L221C, A463V, I474Y |
| 106 | hPIV3 F GNC4 Q162C/L168C, A463V, I474Y |
| 107 | hPIV3 F GNC4 Q162C/L168C/I213C/G230C, A463V, I474Y |
| 108 | hPIV3 F GNC4 I213C/G230C/D216C/L221C, A463V, I474Y |
| 109 | hPIV3 F GNC4 I172C/N238C ,A463V, I474Y |
| 110 | Postfusion hPIV3 F GNC4 |

| Group | Immunogen | Geometrc mean $IC_{50}$ |
|---|---|---|
| 101 | hPIV3 F GNC4 A463V, I474Y | 486019 |
| 102 | hPIV3 F GNC4 V170C/I242C, A463V, I474Y | 407911 |
| 103 | hPIV3 F GNC4 I213C/G230C, A463V, I474Y | 334250 |
| 104 | hPIV3 F GNC4 G85C/Q222C, A463V, I474Y | 592742 |
| 105 | hPIV3 F GNC4 D216C/L221C, A463V, I474Y | 497310 |
| 106 | hPIV3 F GNC4 Q162C/L168C, A463V, I474Y | 239636 |
| 107 | hPIV3 F GNC4 Q162C/L168C/I213C/G230C, A463V, I474Y | 474987 |
| 108 | hPIV3 F GNC4 I213C/G230C/D216C/L221C, A463V, I474Y | 427839 |
| 109 | hPIV3 F GNC4 I172C/N238C ,A463V, I474Y | 531007 |
| 110 | Postfusion hPIV3 F GNC4 | 1295 |

| Lane | PIV3 strain (Genbank number)/design | Yield mg/L 293F |
|---|---|---|
| 1 | ABZ85923.1 (Bovine PIV3) F GCN4 I172C-N238C/I474Y-GCN4 | 12.1 |
| 2 | AHZ90086.1 (Bovine PIV3) F GCN4 I172C-N238C/I474Y-GCN4 | 14.6 |
| 3 | AIW42876.1 (Caprine PIV3) F GCN4 I172C-N238C/I474Y-GCN4 | 20.3 |
| 4 | ABZ85923.1 (Bovine PIV3) F GCN4 I172C-N238C/A463V-GCN4 | 13.4 |
| 5 | AHZ90086.1 (Bovine PIV3) F GCN4 I172C-N238C/A463V-GCN4 | 14.2 |
| 6 | AIW42876.1 (Caprine PIV3) F GCN4 I172C-N238C/A463V-GCN4 | 18.8 |
| 7 | ABZ85923.1 (BovinePIV3) F GCN4 | 0.1 |
| 8 | AHZ90086.1 (BovinePIV3) F GCN4 | 0.1 |
| 9 | AIW42876.1 (CaprinePIV3) F GCN4 | 0.2 |

PREFUSION PIV F IMMUNOGENS AND THEIR USE

CROSS REFERENCE TO RELATED APPLICATIONS

This application is a divisional of U.S. patent application Ser. No. 16/344,772, filed Apr. 24, 2019, which is the U.S. National Stage of International Application No. PCT/US2017/058322, filed Oct. 25, 2017, which was published in English under PCT Article 21(2), which in turn claims the benefit of U.S. Provisional Application No. 62/412,699, filed Oct. 25, 2016, each of which applications are herein incorporated by reference in their entirety.

FIELD

This disclosure relates to polypeptides, polynucleotides, compositions, and methods of their use, for elicitation and detection of an immune response to parainfluenza virus.

BACKGROUND

Human parainfluenza viruses (hPIVs) are significant causes of childhood illness and hospitalization worldwide. hPIVs are enveloped non-segmented negative-strand RNA virus in the family paramyxovirus, subfamily Paramyxovirinae. There are four common types: hPIV1, hPIV2, hPIV3, and hPIV4.

The hPIV envelope protein, F, is initially expressed as a single polypeptide precursor, designated $F_0$. $F_0$ trimerizes in the endoplasmic reticulum and, for many strains of hPIV, is processed by a cellular protease at a conserved site, generating, $F_1$ and $F_2$ polypeptides. The $F_2$ polypeptide originates from the N-terminal portion of the $F_0$ precursor and links to the $F_1$ polypeptide via disulfide bonds. The $F_1$ polypeptide anchors the mature F protein in the membrane via a transmembrane domain, which is linked to a cytoplasmic tail. Three protomers of the $F_2$-$F_1$ heterodimer assemble to form a mature F protein, which adopts a metastable "prefusion" conformation that is triggered to undergo a conformational change that fuses the viral and target-cell membranes.

Although hPIV1, hPIV2, hPIV3, and hPIV are known to contribute to human illness and disease burden, vaccines for these viruses are not available.

SUMMARY

Disclosed herein are recombinant hPIV1, hPIV2, hPIV3, and hPIV4 F ectodomain trimers comprising protomers comprising one or more modifications (such as amino acid substitutions) that stabilize the F ectodomain trimer in its prefusion conformation. Embodiments of such prefusion-stabilized hPIV1, hPIV2, hPIV3, and hPIV4 F ectodomain trimers are demonstrated to produce a superior immune response in animal models compared to corresponding hPIV1, hPIV2, hPIV3, and hPIV4 F ectodomain trimers that are not stabilized in the prefusion conformation.

In some embodiments, the recombinant hPIV3 F ectodomain trimer comprises protomers comprising one or more amino acid substitutions or deletions that stabilize the hPIV3 ectodomain trimer in a prefusion conformation, wherein the one or more amino acid substitutions or deletions comprise one or more of the following sets of substitutions to form a disulfide bond to stabilize the hPIV3 ectodomain trimer in a prefusion conformation: 162C and 168C; 170C and 242C; 213C and 230C; 216C and 221C; 85C and 222C; and 172C and 238C.

In some embodiments, the recombinant hPIV1 F ectodomain trimer comprises protomers comprising one or more amino acid substitutions that stabilize the hPIV1 ectodomain trimer in a prefusion conformation, wherein the one or more amino acid substitutions comprise A466I and 54731 cavity filling substitutions.

In some embodiments, the recombinant hPIV2 F ectodomain trimer comprises protomers comprising one or more amino acid substitutions or deletions that stabilize the hPIV2 ectodomain trimer in a prefusion conformation, wherein the one or more amino acid substitutions or deletions comprise deletion of hPIV2 residues 101-108 and wherein residues 100 and 109 are linked by a heterologous peptide linker.

In some embodiments, the recombinant hPIV4 F ectodomain trimer comprises protomers comprising one or more amino acid substitutions or deletions that stabilize the hPIV4 ectodomain trimer in a prefusion conformation, wherein the one or more amino acid substitutions comprise a non-native disulfide bond between I166C and T232C substitutions and/or Y457F and S471I cavity filling substitutions.

In some embodiments, the protomers of the recombinant hPIV1, hPIV2, hPIV3, or hPIV4 F ectodomain trimer further comprise one or more additional mutations, such as amino acid substitutions that stabilize the recombinant hPIV1, hPIV2, hPIV3, or hPIV4 F ectodomain trimer in the prefusion conformation, or amino acid substitutions to inhibit or prevent protease cleavage at a $F_1$/$F_2$ protease cleavage site of the F ectodomain.

In some embodiments, a C-terminal residue of the protomers of the recombinant hPIV1, hPIV2, hPIV3, or hPIV4 F ectodomain trimer (such as a residue of the stem region of the trimer) is linked to a trimerization domain (such as GCN4 trimerization domain) to promote trimerization of the ectodomain. In some embodiments, a C-terminal residue of the protomers of the recombinant hPIV1, hPIV2, hPIV3, or hPIV4 F ectodomain trimer (such as a residue of the stem region of the trimer) is linked to a transmembrane domain for membrane bound forms of the hPIV F ectodomain trimer.

In some embodiments, the recombinant hPIV1, hPIV2, hPIV3, or hPIV4 F ectodomain trimer can be included on a protein nanoparticle, such as a ferritin protein nanoparticle. Nucleic acid molecules encoding a protomer of the disclosed recombinant hPIV1, hPIV2, hPIV3, or hPIV4 F ectodomain trimers are also provided, as are vectors including the nucleic acid molecules, and methods of producing the disclosed recombinant hPIV1, hPIV2, hPIV3, or hPIV4 F ectodomain trimers.

Immunogenic compositions including the recombinant hPIV1, hPIV2, hPIV3, or hPIV4 F ectodomain trimer that are suitable for administration to a subject are also provided, and may also be contained in a unit dosage form. In some embodiments, the immunogenic compositions can comprise two or more (such as all four) of the recombinant hPIV1, hPIV2, hPIV3, and hPIV4 F ectodomain trimers. The compositions can further include an adjuvant. The recombinant hPIV1, hPIV2, hPIV3, or hPIV4 F ectodomain trimers may also be conjugated to a carrier to facilitate presentation to the immune system.

Methods of inducing an immune response in a subject are disclosed, as are methods of treating, inhibiting or preventing a hPIV1, hPIV2, hPIV3, and/or hPIV4 infection in a subject, by administering to the subject an effective amount of a disclosed recombinant hPIV1, hPIV2, hPIV3, and/or hPIV4 F ectodomain trimer, nucleic acid molecule, or vector.

Due to the high sequence identity between human PIV3 F sequences and non-human PIV3 F sequences, the amino acid substitutions disclosed herein for stabilizing hPIV3 F ectodomain trimers in a prefusion conformation can also be used to stabilize non-human (such as bovine or caprine) PIV3 F ectodomain trimers in a prefusion conformation. The non-human PIV3 F ectodomain trimers can be included in an immunogenic composition immunogenic that is suitable for administration to a subject (such as a bovine or caprine subject). The compositions can further include an adjuvant. The non-human PIV3 F ectodomain trimers may also be conjugated to a carrier to facilitate presentation to the immune system. Methods of inducing an immune response in a subject (such as bovine or caprine subject) using the non-human PIV3 F ectodomain trimers are also provided.

The foregoing and other features and advantages of this disclosure will become more apparent from the following detailed description of several embodiments which proceeds with reference to the accompanying figures.

BRIEF DESCRIPTION OF THE FIGURES

FIGS. 4A-4F show a set of tables of antigenicity of hPIV3 F variants for prefusion (PIA3) and postfusion (PIA56) specific antibodies immediately following expression and purification (0 week) and after one week incubation at 4° C. (1 week). Over 100 hPIV3 F variants were constructed, expressed in a 96-well transfection format, and tested by ELISA of the culture supernatants for binding to pre- and post-fusion hPIV3 antibodies, or a control antibody that binds to the strep tag present on each purified hPIV3 F variant.

FIG. 5 shows a table of expression and purification yields, antigenicity and biophysical characteristics for various hPIV3 F variants. Combinations of optimal mutations were made and expressed at the one liter scale and biophysical characteristics were assessed with purified proteins.

FIG. 13 shows a set of graphs of results from Octet binding assays using the serum from mice immunized with prefusion-stabilized hPIV1 F ectodomain trimers. Octet binding titers for week 0, 5, and 8 sera from CB6F1/J mice immunized with 2×10 μg of the indicated hPIV1 F trimers in poly I:C were probed with prefusion hPIV1 F or postfusion hPIV1 F linked to the sensor.

FIGS. 19A-19D show a set of graphs of results from immunization assays in mice using combination of prefusion-stabilized hPIV1, hPIV2, hPIV3, and hPIV4 F ectodomain trimers. The F ectodomain trimers used for immunization included the hPIV1_880_preF2, hPIV2_preF6, hPIV3 F GCN4 I172C-N238C/A463V, and hPIV4_preF4 ectodomain timers. (A) Octet binding readout of sera at week 5 from CB6F1/J mice immunized with 2×10 μg of various combinations of hPIV1-4 F in poly I:C at weeks 0 and 3 using a prefusion hPIV3 F probe (left) and postfusion hPIV3 F. (B) Same as in (A) but using pre/postfusion F from hPIV4 (C and D) Neutralization titers at week 5 for CB6F1/J mice immunized with 2×10 μg of various combinations of hPIV1-4 F in poly I:C at weeks 0 and 3, readout for hPIV1 (left) and hPIV3 (right) viruses.

FIGS. 20A-20E show results from non-human primate (NHP) immunization assays using the prefusion stabilized hPIV F ectodomain trimers. The immunization scheme is shown in FIG. 20A. Immunization with the prefusion-stabilized forms of hPIV1, 2, 3 and 4 F ectodomain trimers induced a potent neutralizing immune response to hPIV1 and hPIV2 (FIG. 20B), hPIV3 (FIG. 20C and FIG. 20E), and hPIV4 (FIG. 20D) that is superior to the response induced by corresponding forms of postfusion-stabilized hPIV F ectodomain trimers.

FIG. 21 is a table showing antigenic characteristics of prefusion stabilized hPIV3 F ectodomain trimers.

(FIGS. 23B and 23C) Octet binding titers for week 5 sera binding to prefusion hPIV3 F probe and postfusion hPIV3 F probe. (FIG. 23D) Neutralization titers at week 5 in CB6F1/J mice immunized with 2×10 μg of the indicated hPIV3 F immunogen in poly I:C at weeks 0 and 3.

SEQUENCES

Figure 1:
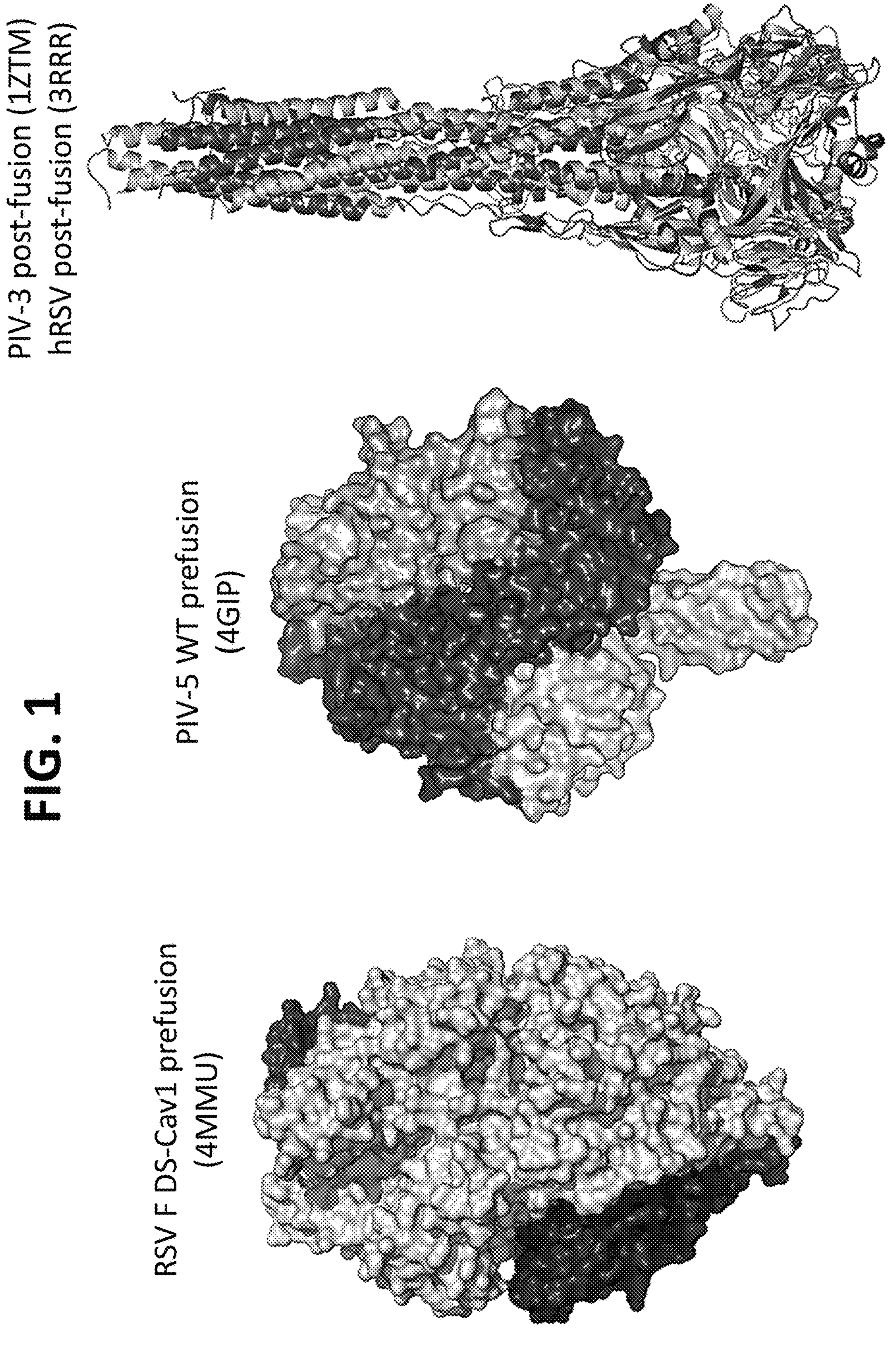
FIG. 1 shows diagrams of the structure of the RSV F ectodomain trimer stabilized in a prefusion conformation by the "DS-Cav1" substitutions (PDB No. 4MMU), the PIV5 F ectodomain timer in its prefusion conformation (PDB No. 4GIP), and structures of the hPIV3 F and RSV F proteins in their postfusion conformations (PDB Nos. 1ZTM and 3RRR, respectively).

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~368 kb), which was created on Jul. 16, 2021, which is incorporated by reference herein.

DETAILED DESCRIPTION

Disclosed herein are recombinant hPIV1, hPIV2, hPIV3, and hPIV4 F ectodomain trimers comprising protomers comprising one or more modifications (such as amino acid substitutions) that stabilize the F ectodomain trimer in its prefusion conformation. Due to the sequence diversity between the F glycoproteins of hPIV1-4, RSV and PIVS, it was not possible to use a sequence alignment to identify relevant prefusion-stabilizing mutations for hPIV1-4 F based on the known prefusion structures of F glycoproteins from RSV and PIVS, for which atomic-level structures have been determined. Accordingly, as discussed in the Examples, a multi-step iterative approach was undertaken to identify prefusion stabilized mutants of each of hPIV1-4 F. Embodiments of such pre-fusion-stabilized F ectodomain trimers are demonstrated to produce a superior immune response in an animal model compared to corresponding hPIV1, hPIV2, hPIV3, or hPIV4 F ectodomain trimers that are not stabilized in the prefusion conformation.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references. As used herein, the singular forms "a," "an," and "the," refer to both the singular as well as plural, unless the context indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. In some embodiments, an adjuvant includes a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJUPLEX™ adjuvant available from Advanced BioAdjuvants, LLC, see also Wegmann, Clin Vaccine Immunol, 22(9): 1004-1012, 2015). Additional adjuvants for use in the disclosed immunogenic compositions include the QS21 purified plant extract, Matrix M, ASO1, MF59, and ALFQ adjuvants Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. (See, e.g., Singh (ed.) Vaccine Adjuvants and Delivery Systems. Wiley-Interscience, 2007).

Administration: The introduction of a composition into a subject by a chosen route. Administration can be local or systemic. For example, if the chosen route is intranasal, the composition (such as a composition including a disclosed recombinant hPIV F ectodomain) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of an amino acid in a polypeptide with one or more different amino acids. In the context of a protein sequence, an amino acid substitution is also referred to as a mutation.

Antibody: An immunoglobulin, antigen-binding fragment, or derivative thereof, that specifically binds and recognizes an analyte (antigen) such as hPIV F protein, an antigenic fragment thereof, or a dimer or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

Carrier: An immunogenic molecule to which an antigen can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Cavity-filling amino acid substitution: An amino acid substitution that fills a cavity within the protein core of a protein, such as a hPIV F ectodomain. Cavities are essentially voids within a folded protein where amino acids or amino acid side chains are not present. In several embodiments, a cavity filling amino acid substitution is introduced to fill a cavity present in the prefusion conformation of the hPIV F ectodomain core that collapses (e.g., has reduced volume) after transition to the postfusion conformation.

Conservative variants: "Conservative" amino acid substitutions are those substitutions that do not substantially affect or decrease a function of a protein, such as the ability of the protein to induce an immune response when administered to a subject. The term conservative variation also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the recombinant hPIV F ectodomain trimer, such as the ability to induce an immune response when administered to a subject. For instance, if an amino acid residue is essential for a function of the protein, even an otherwise conservative substitution may disrupt that activity. Thus, a conservative substitution does not alter the basic function of a protein of interest.

Control: A reference standard. In some embodiments, the control is a negative control sample obtained from a healthy patient. In other embodiments, the control is a positive control sample obtained from a patient diagnosed with hPIV infection. In still other embodiments, the control is a historical control or standard reference value or range of values (such as a previously tested control sample, such as a group of hPIV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Effective amount: An amount of agent, such as an immunogen, that is sufficient to elicit a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to inhibit or reduce or prevent hPIV infection. The hPIV infection does not need to be completely eliminated or reduced or prevented for the method to be effective. For example, administration of an effective amount of the agent can decrease the hPIV infection (for example, as measured by infection of cells, or by number or percentage of subjects infected by hPIV) by a desired amount, for example by at least 50%, at least 60%, at least 70%, at least 80%, at least 90%, at least 95%, at least 98%, or even at least 100% (elimination or prevention of detectable hPIV infection), as compared to a suitable control.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on hPIV3 F protein. Epitopes can be formed both from contiguous amino acids or noncontiguous amino acids juxtaposed by tertiary folding of a protein.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

GCN4 trimerization domain: A trimerization domain from the GCN4 protein that comprises a leucine zipper amino acid sequence that naturally forms a trimeric structure. Embodiments of the GCN4 trimerization domain is described, for example, Harbury et al. (1993 *Science* 262: 1401-1407). In some examples, a GCN4 trimerization domain can be included in the amino acid sequence of a disclosed recombinant protein so that the recombinant protein will trimerize. Non-limiting examples of GCN4 trimerization domain sequences for use with the disclosed embodiments include:

```
            (residues 464-496 of SEQ ID NO: 7)
MKQIEDKIEEILSKIYHIENEIARIKKLIGEAP,

            (residues 467-496 of SEQ ID NO: 7)
IEDKIEEILSKIYHIENEIARIKKLIGEAP,

                             (SEQ ID NO: 31)
MKQVEDKIEEILSKIYHIENEIARIKKLIGEAP,
and

               (residues 4-33 of SEQ ID NO: 31)
VEDKIEEILSKIYHIENEIARIKKLIGEAP.
```

Glycosylation site: An amino acid sequence on the surface of a polypeptide, such as a protein, which accommodates the attachment of a glycan. An N-linked glycosylation site is triplet sequence of NX(S/T) in which N is asparagine, X is any residues except proline, and (S/T) is a serine or threonine residue. A glycan is a polysaccharide or oligosaccharide. Glycan may also be used to refer to the carbohydrate portion of a glycoconjugate, such as a glycoprotein, glycolipid, or a proteoglycan.

Heterologous: Originating from a different genetic source.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Parainfluenza Virus (hPIV): An enveloped non-segmented negative-sense single-stranded RNA viruses from family Paramyxoviridae. hPIV includes hPIV1 and hPIV3 from the genus respirovirus and hPIV2 and hPIV4 from the genus rubulavirus. hPIV1, hPIV2, and hPIV3 are second only to respiratory syncytial virus in causing severe respiratory infections in infants and children worldwide, with hPIV3 having the greatest disease impact of the hPIVs. hPIVs are made up of two structural modules: (1) an internal ribonucleoprotein core, or nucleocapsid, containing the viral genome, and (2) an outer, roughly spherical lipoprotein envelope. The hPIV viral genome is approximately 15,000 nucleotides in length and encodes at least eight polypeptides. These proteins include the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins. The P gene contains one or more additional open reading frames (ORFs) encoding accessory proteins. The gene order is 3'-N-P-M-F-HN-L-5', and each gene encodes a separate protein encoding mRNA.

hPIV F protein: An envelope glycoprotein of hPIV1, hPIV2, hPIV3, or hPIV4 that facilitates fusion of viral and cellular membranes. In nature, the F protein from hPIV1, hPIV2, hPIV3, and hPIV4 is initially synthesized as a single polypeptide precursor approximately 550 amino acids in length, designated $F_0$. $F_0$ includes an N-terminal signal peptide that directs localization to the endoplasmic reticulum, where the signal peptide is proteolytically cleaved. The remaining $F_0$ residues oligomerize to form a trimer and may be proteolytically processed by a cellular protease to generate two disulfide-linked fragments, $F_1$ and F2. In hPIV1 F the cleavage site is located approximately between residues 112/113, in hPIV2 F the cleavage site is located approximately between residues 106/107, in hPIV3 F the cleavage site is located approximately between residues 109/110, and in hPIV4 F the cleavage site is located approximately between residues 103/104. The smaller of these fragments, $F_2$, originates from the N-terminal portion of the $F_0$ precursor (hPIV1, approximately residues 22-113; hPIV2, approximately residues 22-106; hPIV3, approximately residues 19-109; hPIV4, approximately residues 21-103). The larger of these fragments, $F_1$, includes the C-terminal portion of the $F_0$ precursor (hPIV1, approximately residues 114-555; hPIV2, approximately residues 107-551; hPIV3, approximately residues 110-539; hPIV4, approximately residues 104-544) including an extracellular/lumenal region (hPIV1, approximately residues 114-497; hPIV2, approximately residues 107-493; hPIV3, approximately residues 110-493; hPIV4, approximately residues 104-486), a transmembrane domain (hPIV1, approximately residues 498-518; hPIV2, approximately residues 494-514; hPIV3, approximately residues 494-514; hPIV4, approximately residues 487-507), and a cytoplasmic tail at the C-terminus. The extracellular portion of the hPIV F protein is the hPIV F ectodomain, which includes the $F_2$ protein and the $F_1$ ectodomain.

The hPIV F protein exhibits remarkable sequence conservation within hPIV subtypes. In view of this conservation, the person of ordinary skill in the art can easily compare amino acid positions of different hPIV F proteins of the same subtype. Unless context indicates otherwise, the numbering of amino acid substitutions disclosed herein is made with reference to SEQ ID NO: 2 (GenBank BAS30410.1) for hPIV1 F, SEQ ID NO: 6 (GenBank AAA46842.1) for hPIV2 F, SEQ ID NO: 9 (GenBank AGW51052.1) for hPIV3 F, and SEQ ID NO: 28 (GenBank AGU90035.1) for hPIV4 F, unless context indicates otherwise.

Three hPIV F protomers oligomerize in the mature F protein, which adopts a metastable prefusion conformation that is triggered to undergo a conformational change to a postfusion conformation upon contact with a target cell membrane. This conformational change exposes a hydrophobic sequence, known as the fusion peptide, which is located at the N-terminus of the $F_1$ ectodomain, and which associates with the host cell membrane and promotes fusion of the membrane of the virus, or an infected cell, with the target cell membrane.

An hPIV F ectodomain trimer "stabilized in a prefusion conformation" comprises one or more amino acid substitutions, deletions, or insertions compared to a corresponding native hPIV F sequence that provide for increased retention of the prefusion conformation compared to hPIV F ectodomain trimers formed from a corresponding native hPIV F sequence. The "stabilization" of the prefusion conformation can be, for example, energetic stabilization (for example, reducing the energy of the prefusion conformation relative to the post-fusion open conformation) and/or kinetic stabilization (for example, reducing the rate of transition from the prefusion conformation to the postfusion conformation). Additionally, stabilization of the hPIV F ectodomain trimer in the prefusion conformation can include an increase in resistance to denaturation compared to a corresponding native hPIV F sequence. Methods of determining if a hPIV F ectodomain trimer is in the prefusion conformation are provided herein, and include (but are not limited to) negative stain electron microscopy and antibody binding assays using a prefusion conformation specific antibody, such as the PIA3 or PIA174 antibody in the case of hPIV3.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance (for example, a recombinant hPIV F ectodomain trimer) that can elicit an immune response in an animal, including compositions that are injected or absorbed into an animal Administration of an immunogen to a subject can lead to protective immunity against a pathogen of interest.

Immunogenic composition: A composition comprising a disclosed recombinant PIV F ectodomain trimer that induces a measurable CTL response against the PIV, or induces a measurable B cell response (such as production of antibodies) against the PIV, when administered to a subject. It further refers to isolated nucleic acid molecules and vectors encoding a protomer of a disclosed recombinant PIV F ectodomain trimer that can be used to express the protomer (and thus be used to elicit an immune response against recombinant PIV F ectodomain trimer). For in vivo use, the immunogenic composition will typically include the recombinant PIV F ectodomain trimer or a nucleic acid molecule encoding a protomer of the recombinant PIV F ectodomain trimer in a pharmaceutically acceptable carrier and may also include other agents, such as an adjuvant.

Inhibiting or treating a disease: Inhibiting the full development of a disease or condition, for example, in a subject who is at risk for a disease such as hPIV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of viral infection. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linker and Linked: A bi-functional molecule that can be used to link two molecules into one contiguous molecule. Non-limiting examples of peptide linkers include glycine-serine peptide linkers. Unless context indicates otherwise, reference to "linking" a first polypeptide and a second polypeptide, or to two polypeptides "linked" together, or to a first polypeptide having a "linkage" to a second polypeptide, refers to covalent linkage by peptide bond (for example via a peptide linker) such that the first and second polypeptides form a contiguous polypeptide chain. If a peptide linker is involved, the covalent linkage of the first and second polypeptides can be to the N- and C-termini of the peptide linker. Typically, such linkage is accomplished using molecular biology techniques to genetically manipulate DNA encoding the first polypeptide linked to the second polypeptide by the peptide linker.

Native protein, sequence, or disulfide bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Prefusion specific antibody: An antibody that specifically binds to the hPIV F protein in a prefusion conformation, but does not specifically bind to the hPIV F protein in a post-fusion conformation.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as immunogenic compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic.

A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost vaccination: An immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is administered to the subject after the primer vaccine; a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein subunit or protein nanoparticle based vaccine.

Protein nanoparticle: A multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. *Int. J. Mol. Sci.,* 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.,* 306: 1099-1114, 2001) or pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a recombinant hPIV F ectodomain and self-assemble into a protein nanoparticle presenting the recombinant hPIV F ectodomain on its surface, which can be administered to a subject to stimulate an immune response to the antigen.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-25 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). An exemplary signal peptide sequence is set forth as residues 1-18 of SEQ ID NO: 9 (hPIV3 F signal peptide)

Single chain PIV F ectodomain: A recombinant hPIV F ectodomain (such as a hPIV1, hPIV2, hPIV3, bPIV3, cPIV3, or hPIV4 F ectodomain) including the PIV F2 polypeptide and the PIV $F_1$ ectodomain in a single contiguous polypeptide chain. A single chain PIV F ectodomain does not include a protease cleavage site separating the F2 polypeptide and $F_1$ ectodomain; therefore, when produced in cells, the $F_0$ polypeptide is not cleaved into separate $F_1$ and F2 polypeptide chains.

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example, an antigenic site at the membrane distal apex of the hPIV3 F ectodomain timer) and does not bind in a significant amount to other proteins or polysaccharides present in the sample or subject. Specific binding can be determined by methods known in the art. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{10}$ Molar.

Soluble protein: A protein capable of dissolving in aqueous liquid at room temperature and remaining dissolved. The solubility of a protein may change depending on the concentration of the protein in the water-based liquid, the buffering condition of the liquid, the concentration of other solutes in the liquid, for example salt and protein concentrations, and the heat of the liquid. In several embodiments, a soluble protein is one that dissolves to a concentration of at least 0.5 mg/ml in phosphate buffered saline (pH 7.4) at room temperature and remains dissolved for at least 48 hours.

Subject: Living multi-cellular vertebrate organisms, a category that includes human and non-human mammals. In an example, a subject is a human. In a particular example, the subject is a newborn infant. In an additional example, a subject is selected that is in need of inhibiting of a hPIV infection. For example, the subject is either uninfected and at risk of hPIV infection or is infected in need of treatment.

Transmembrane domain: An amino acid sequence that inserts into a lipid bilayer, such as the lipid bilayer of a cell or virus or virus-like particle. A transmembrane domain can be used to anchor an antigen to a membrane. In some examples a transmembrane domain is a hPIV F transmembrane domain.

Under conditions sufficient for: A phrase that is used to describe any environment that permits a desired activity.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides, or DNA derived from them. A vaccine may include a disclosed immunogen (such as a recombinant hPIV F ectodomain trimer or nucleic acid molecule encoding same), a virus, a cell or one or more cellular constituents. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response. In one specific, non-limiting example, a vaccine prevents and/or reduces the severity of the symptoms associated with hPIV infection and/or decreases the viral load compared to a control.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.,* 2011; Schneider-Ohrum and Ross, *Curr. Top. Microbiol. Immunol.,* 354: 53073, 2012).

II. Immunogens

Recombinant hPIV1, hPIV2, hPIV3, and hPIV4 F ectodomain trimers are disclosed herein that are modified from a native form (e.g., by introduction of one or more amino acid substitutions) to be stabilized in a prefusion conformation. As described in the Examples, the disclosed hPIV1, hPIV2, hPIV3, and hPIV4 F ectodomain trimers have been selected through multiple rounds of structure based design for optimized solubility, stability, expression, and immunogenicity. The recombinant hPIV1, hPIV2, hPIV3, and hPIV4 F ectodomain trimers are useful to induce an immune response in a vertebrate animal (such humans) to hPIV1, hPIV2, hPIV3, and/or hPIV4. Exemplary embodiments are shown to produce a superior immune response in an animal model compared to corresponding hPIV F ectodomain trimers that are not stabilized in the prefusion conformation.

Due to the high sequence identity between human PIV3 F sequences and non-human PIV3 F sequences, the amino acid substitutions disclosed herein for stabilizing hPIV3 F ectodomain trimers in a prefusion conformation can also be used to stabilize non-human (such as bovine or caprine) PIV3 F ectodomain trimers in a prefusion conformation.

A. hPIV1 F

In some embodiments, the immunogen comprises a recombinant hPIV1 F ectodomain trimer comprising protomers comprising one or more amino acid substitutions or deletions that stabilize the hPIV1 F ectodomain trimer in the prefusion conformation.

In several embodiments, the protomers of the recombinant hPIV1 F ectodomain trimer comprise A466I and/or 54731 substitutions for stabilization in the prefusion conformation.

In some embodiments, the recombinant hPIV1 F ectodomain trimer comprises protomers that are "single chain"

proteins wherein the $F_2$ polypeptide and the $F_1$ ectodomain of each protomer are directly linked or linked via a peptide linker to form a contiguous polypeptide chain. In some embodiments, the recombinant $F_2$-$F_1$ ectodomain protomers in the disclosed recombinant hPIV1 F ectodomain trimers comprise a deletion of hPIV1 F positions 113-114, and a glycine-serine peptide linker between hPIV1 F positions 112 and 115; for example, the protomers of the hPIV1 F protein can each comprise a FF113-114GS substitution.

In several embodiments, the N-terminal position of the recombinant F2 polypeptide in the protomer can be one of hPIV1 F positions 20-30 (such as position 22), and the C-terminal position of the $F_1$ ectodomain can be from the stem region of the ectodomain (residues 462-487). In several embodiments, the N-terminal position of the recombinant F2 polypeptide in the protomer can be one of hPIV1 F positions 20-30 (such as position 22), and the C-terminal position of the $F_1$ ectodomain can be one of hPIV1 F positions 473-497 (such as positions 475-482, for example, position 479).

In some embodiments, the protomers of the recombinant hPIV1 F ectodomain trimer include hPIV1 F positions 22-479, deletion of positions 113-114, insertion of a glycine serine (GS) linker between position 112 and 115, A466I and 54731 cavity filling substitutions, and linkage to a C-terminal GCN4 trimerization domain.

In some embodiments, the recombinant hPIV1 F ectodomain trimer can be a soluble protein complex, for example, for use as a recombinant subunit vaccine. In several such embodiments, the protomers of the recombinant hPIV1 F ectodomain trimer can each comprise a C-terminal linkage to a trimerization domain, such as a GCN4 trimerization domain. The trimerization domain promotes trimerization and stabilization of the membrane proximal aspect of the recombinant hPIV1 F ectodomain trimer. For example, a C-terminal residue of the protomers of the recombinant hPIV1 F ectodomain trimer (such as a residue of the stem region of the trimer) can be directly linked to the trimerization domain, or indirectly linked to the trimerization domain via a peptide linker. Exemplary linkers include glycine and glycine-serine linkers. Non-limiting examples of exogenous multimerization domains that promote stable trimers of soluble recombinant proteins include: the GCN4 leucine zipper, the trimerization motif from the lung surfactant protein (Hoppe et al. 1994 *FEBS Lett* 344:191-195), collagen (McAlinden et al. 2003 *J Biol Chem* 278:42200-42207) any of which can be linked to the C-terminus of the protomers of a recombinant hPIV1 F ectodomain to promote trimerization, as long as the recombinant hPIV1 F ectodomain trimer retains the prefusion conformation. In some examples, the protomers of the recombinant hPIV1 F ectodomain trimer can be linked to a GCN4 trimerization domain, for example, each protomer in the trimer can include a C-terminal linkage to the GCN4 trimerization domain, such as a linkage to any one of hPIV1 F positions 475-485, such as hPIV1 F position 479. In specific examples, the GCN4 fibritin trimerization domain can comprise the amino acid sequence IEDKIEEILSKIYHIENE-IARIKKLIGEAP (residues 467-496 of SEQ ID NO: 7).

In other embodiments, the recombinant hPIV1 F ectodomain trimer can be a membrane anchored protein complex, for example, for use in an attenuated virus or virus like particle vaccine. Membrane anchoring can be accomplished, for example, by C-terminal linkage of the protomers of the recombinant hPIV1 F ectodomain trimer to a transmembrane domain and optionally a cytoplasmic tail, such as an hPIV1 F transmembrane domain and cytoplasmic tail. In some embodiments, one or more peptide linkers (such as a gly-ser linker, for example, a 10 amino acid glycine-serine peptide linker can be used to link the protomers of the recombinant hPIV1 F ectodomain trimer to the transmembrane domain A non-limiting example of a transmembrane domain for use with the disclosed embodiments is a hPIV1 F transmembrane domain, such as IIIIIIVCVLIIIICSILYYL (residues 498-518 of SEQ ID NO: 2).

Native hPIV1 F proteins from different hPIV1 strains, as well as nucleic acid sequences encoding such proteins and methods, are known. The disclosed recombinant hPIV1 F ectodomain trimers can be derived from any strain of hPIV1. Exemplary sequences of native hPIV1 F proteins include:

```
SWISS-PROT: P12605.1 (incorporated by
reference herein)
                                    (SEQ ID NO: 1)
MQKSEILFLIYSSLLLSSSLCQIPVDKLSNVGVIINEGKLLKIAGSYE

SRYIVLSLVPSIDLEDGCGTTQIIQYKNLLNRLLIPLKDALDLQESLI

TITNDTTVTNDNPQSRFFGAVIGTIALGVATAAQITAGIALAEAREAR

KDIALIKDSIIKTHNSVELIQRGIGEQIIALKTLQDFVNNEIRPAIGE

LRCETTALKLGIKLTQHYSELATAFSSNLGTIGEKSLTLQALSSLYSA

NITEILSTIKKDKSDIYDIIYTEQVKGTVIDVDLEKYMVTLLVKIPIL

SEIPGVLIYRASSISYNIEGEEWHVAIPNYIINKASSLGGADVTNCIE

SRLAYICPRDPTQLIPDNQQKCILGDVSKCPVTKVINNLVPKFAFING

GVVANCIASTCTCGTNRIPVNQDRSRGVTFLTYTNCGLIGINGIELYA

NKRGRDTTWGNQIIKVGPAVSIRPVDISLNLASATNFLEESKIELMKA

KAIISAVGGWHNTESTQIIIIIIVCILIIIICGILYYLYRVRRLLVMI

NSTHNSPVNTYTLESRMRNPYIGNNSN

GenBank No. BAS30410.1 (incorporated by
reference herein)
                                    (SEQ ID NO: 2)
MQSSEVLLLVYSSLLLSSSLCQIPVDKLSNVGVIINEGKLLKIAGSYE

SRYIVLSLVPSIDLQDGCGTTQIIQYKNLLNRLLIPLKDALDLQESLI

TITNDTTVTNDNPQTRFFGAVIGTIALGVATAAQITAGIALAEAREAR

KDIALIKDSIVKTHNSVEFIQRGIGEQIIALKTLQDFVNDEIRPAIGE

LRCETTALKLGIKLTQHYSELATAFSSNLGTIGEKSLTLQALSSLYSA

NITEILSTIKKDKSDIYDIIYTEQVKGTVIDVDLEKYMVTLLVKIPIL

SEIPGVLIYRASSISYNIEGEEWHVAIPNYIINKASSLGGADVTNCIE

SKLAYICPRDPTQLIPDNQQKCILGDVSKCPVTKVINNLVPKFAFING

GVVANCIASTCTCGTNRIPVNQDRSKGVTFLTYTNCGLIGINGIELYA

NKRGRDTTWGNQIIKVGPAVSIRPVDISLNLASATNFLEESKTELMKA

RAIISAVGGWHNKESTQIIIIIIVCVLIIIICSILYYLYRVRRLLIMI

NSTNNSPINAYTLESRMKNPYMGNHSNKIRSSILHTYNNQIYPQLLSD

VVRK

GenBank No. AFP49418.1 (incorporated by
reference herein)
                                    (SEQ ID NO: 3)
MQSSEILILVYSSLLLSSSLCQIPVDKLSNVGVIINEGKLLKIAGSYE

SRYIVLSLVPSIDLQDGCGTTQIIQYKNLLNRLLIPLKDALDLQESLI

TITNDTTVTNDNPQTRFFGAVIGTIALGVATAAQITAGIALAEAREAR
```

-continued

KDIALIKDSIVKTHNSVEFIQRGIGEQIIALKTLQDFVNDEIPPAIGE

LRCETTAMKLGIKLTQHYSELATAFSSNLGTIGEKSLTLQALSSLYSA

NITEILSTIKKDKSDIYDIIYTEQVKGTVIDVDLEKYMVTLLVKIPIL

SEIPGVLIYRASSISYNIEGEEWHVAIPNYIISKASSLGGADVTNCIE

SKLAYICPRDPTQLIPDNQQKCILGDVSKCPVTKVINNLVPKFAFING

GVVANCIASTCTCGTNRIPVNQDRSKGVTFLTYTNCGLIGINGIELYG

NKRGRDTTWGNQIIKEGPAVSIRPVDISLNLASATNFLEESKTELMKA

RAIISAVGGWHNTESTQIIIIIIVCILIIIICGILYYLYRVRRLLVMI

NSTNNSPINAYTLESRMRNPYMGNHSN

Unless context indicates otherwise, reference to amino acid substitutions or deletions in hPIV1 F is made with reference to SEQ ID NO: 2. An exemplary sequence of a protomer of an hPIV1 F ectodomain trimer stabilized in a prefusion conformation is provided as the hPIV1_880_preF2 protein:

hPIV1_880_preF2

(SEQ ID NO: 4)

QIPVDKLSNVGVIINEGKLLKIAGSYESRYIVLSLVPSIDLQDGCGTT

QIIQYKNLLNRLLIPLKDALDLQESLITITNDTTVTNDNPQTRGSGAV

IGTIALGVATAAQITAGIALAEAREARKDIALIKDSIVKTHNSVEFIQ

RGIGEQIIALKTLQDFVNDEIRPAIGELRCETTALKLGIKLTQHYSEL

ATAFSSNLGTIGEKSLTLQALSSLYSANITEILSTIKKDKSDIYDIIY

TEQVKGTVIDVDLEKYMVTLLVKIPILSEIPGVLIYRASSISYNIEGE

EWHVAIPNYIINKASSLGGADVTNCIESKLAYICPRDPTQLIPDNQQK

CILGDVSKCPVTKVINNLVPKFAFINGGVVANCIASTCTCGTNRIPVN

QDRSKGVTFLTYTNCGLIGINGIELYANKRGRDTTWGNQIIKVGPAVS

IRPVDISLNLASITNFLEEIKTELMKIEDKIEEILSKIYHIENEIARI

KKLIGEAP hPIV1_880_preF2 includes a $F_1$-$F_2$ linker (FF113-114GS), A466I and S473I cavity filling substitutions, a C-term truncation at position 479, and C-terminal GCN4 trimerization domain.

In some embodiments, the protomers of the hPIV1 F ectodomain trimer include an amino acid sequence set forth as residues 1-458 of SEQ ID NO: 4, or an amino acid sequence at least 90% identical thereto, wherein the C-terminus of the ectodomain trimer is linked to a trimerization domain (such as a GCN4 trimerization domain, for soluble ectodomain trimers) or a transmembrane domain (for membrane anchored embodiments). In some embodiments, the protomers of the hPIV1 F ectodomain trimer include an amino acid sequence set forth as SEQ ID NO: 4, or an amino acid sequence at least 90% identical thereto.

In some embodiments, the immunogen comprises a recombinant hPIV1 F ectodomain trimer comprising protomers comprising the one or more amino acid substitutions or deletions noted below for stabilizing the hPIV3 F ectodomain trimer in its prefusion conformation. For example, in some embodiments, the protomers of the recombinant hPIV1 F ectodomain trimer comprise a non-native disulfide bond between one of 172C-238C, 170C-242C, 213C-230C, 85C-222C, or 216C-221C substitutions for stabilization in the prefusion conformation. The residue numbering for these substitutions is made with reference to the PIV3 F sequence set forth as SEQ ID NO: 9, and the substitutions are introduced into hPIV1 F at residues corresponding to the hPIV3 F SEQ ID NO: 9 sequence. In some embodiments, the protomers of the recombinant hPIV3 F ectodomain trimer comprise two or more non-native disulfide bonds between sets of substitutions selected from 172C-238C, 170C-242C, 213C-230C, 85C-222C, or 216C-221C substitutions for stabilization in the prefusion conformation. Exemplary combinations for prefusion stabilization include: 162C-168C and 213C-230C; 162C-168 and 216C-221C; 162C-168C and 85C-222C; 213C-230C and 170C-242C; 213C-230C and 216C-221C; and 213C-230C and 85C-222C. In some embodiments, the hPIV1 F protomers further comprise cavinty filling substitutions corresponding to the hPIV3 F 463V and 474Y cavity filling substitutions for stabilization in the prefusion conformation. In several embodiments, the hPIV1 F ectodomain trimers can be soluble (e.g., can include a GCN4 trimerization domain as discussed above) or can be membrane anchored (e.g., the full-length hPIV1 F sequence is modified with the prefusion stabilizing amino acid substitutions).

B. hPIV2 F

In some embodiments, the immunogen comprises a recombinant hPIV2 F ectodomain trimer comprising protomers comprising one or more amino acid substitutions or deletions that stabilize the F ectodomain trimer in the prefusion conformation.

In several embodiments, the N-terminal position of the recombinant F2 polypeptide in the protomer can be one of hPIV2 F positions 20-30 (such as position 22), and the C-terminal position of the $F_1$ ectodomain can be from the stem region of the ectodomain (residues 456-481).

In several embodiments, the N-terminal position of the recombinant F2 polypeptide in the protomer can be one of hPIV2 F positions 20-30 (such as position 22), and the C-terminal position of the $F_1$ ectodomain can be one of hPIV2 F positions 473-493 (such as positions 475-485, for example, position 484).

In some embodiments, the recombinant hPIV2 F ectodomain trimer comprises protomers that are "single chain" proteins wherein the F2 polypeptide and the $F_1$ ectodomain of each protomer are directly linked or linked via a peptide linker to form a contiguous polypeptide chain. In some embodiments, the protomers in the disclosed recombinant hPIV2 F ectodomain trimers comprise a deletion of hPIV2 F positions 101-108, and a glycine-serine peptide linker between hPIV2 F positions 100 and 109; for example, the protomers of the hPIV2 F protein can each comprise a KTRQKRFA101-108GGGSGGGS (SEQ ID NO: 33 to SEQ ID NO: 32) substitution.

In some embodiments, the protomers of the recombinant hPIV2 F ectodomain trimer include hPIV2 F positions 22-484, deletion of positions 101-108, insertion of a GGGSGGGS (SEQ ID NO: 32) peptide linker between position 100 and 109, and linkage to a C-terminal GCN4 trimerization domain.

In some embodiments, the recombinant hPIV2 F ectodomain trimer can be a soluble protein complex, for example, for use as a recombinant subunit vaccine. In several such embodiments, the protomers of the recombinant hPIV2 F ectodomain trimer can each comprise a C-terminal linkage to a trimerization domain, such as a GCN4 trimerization domain. The trimerization domain promotes trimerization and stabilization of the membrane proximal aspect of the recombinant hPIV2 F ectodomain trimer. For example, a C-terminal residue of the protomers of the recombinant hPIV2 F ectodomain trimer (such as a residue of the stem region of the trimer) can be directly linked to the trimerization domain, or indirectly linked to the trimerization domain via a peptide linker. Exemplary linkers include glycine and glycine-serine linkers. Non-limiting examples of exogenous multimerization domains that promote stable trimers of soluble recombinant proteins include: the GCN4 leucine zipper, the trimerization motif from the lung surfactant protein (Hoppe et al. 1994 *FEBS Lett* 344:191-195), collagen (McAlinden et al. 2003 *J Biol Chem* 278:42200-42207) any of which can be linked to the C-terminus of the protomers of a recombinant hPIV2 F ectodomain to promote trimerization, as long as the recombinant hPIV2 F ectodomain trimer retains the prefusion conformation. In some examples, the protomers of the recombinant hPIV2 F ectodomain trimer can be linked to a GCN4 trimerization domain, for example, each protomer in the trimer can include a C-terminal linkage to the GCN4 trimerization domain, such as a linkage to any one of hPIV2 F positions 475-485, such as hPIV2 F position 484. In specific examples, the GCN4 fibritin trimerization domain can comprise the amino acid sequence MKQIEDKIEEILSKIYHIENEIARIKKLIGEAP (residues 464-496 of SEQ ID NO: 7).

In other embodiments, the recombinant hPIV2 F ectodomain trimer can be a membrane anchored protein complex, for example, for use in an attenuated virus or virus like particle vaccine. Membrane anchoring can be accomplished, for example, by C-terminal linkage of the protomers of the recombinant hPIV2 F ectodomain trimer to a transmembrane domain and optionally a cytoplasmic tail, such as an hPIV2 F transmembrane domain and cytoplasmic tail. In some embodiments, one or more peptide linkers (such as a gly-ser linker, for example, a 10 amino acid glycine-serine peptide linker can be used to link the protomers of the recombinant hPIV2 F ectodomain trimer to the transmembrane domain A non-limiting example of a transmembrane domain for use with the disclosed embodiments is a hPIV2 F transmembrane domain, such as ALILSVITLVVVGLLIAYIIK (residues 494-514 of SEQ ID NO: 6).

Native hPIV2 F proteins from different hPIV2 strains, as well as nucleic acid sequences encoding such proteins and methods, are known. The disclosed recombinant hPIV2 F ectodomain trimers can be derived from any strain of hPIV2. Exemplary sequences of native hPIV2 F proteins include:

```
SWISS-PROT: P27286.1 (incorporated by
reference herein)
                                    (SEQ ID NO: 5)
MHHLHPMIVCIFVMYTGIVGSDAIAGDQLLNIGVIQSKIRSLMYYTDG

GASFIVVKLLPNLPPSNGTCNITSLDAYNVTLFKLLTPLIENLSKIST

VTDTKTRQKRFAGVVVGLAALGVATAAQITAAVAIVKANANAAAINNL

ASSIQSTNKAVSDVIDASRTIATAVQAIQDHINGAIVNGITSASCRAH

DALIGSILNLYLTELTTIFHNQITNPALTPLSIQALRILLGSTLPIVI

ESKLNTNLNTAELLSSGLLTGQIISISPMYMQMLIQINVPTFIMQPGA

KVIDLIAISANHKLQEVVVQVPNRILEYANELQNYPANDCVVTPNSVC

CRYNEGSPIPESQYQCLRGNLNSCTFTPIIGNFLKRFAFANGVLYANC

KSLLCRCADPPHVVSQDDTQGISIIDIKRCSEMMLDTFSFRITSTFNA

TYVTDFSMINANIVHLSPLDLSNQINSINKSLKSAEDWIADSNFFANQ
```

-continued

```
ARTAKTLYSLSAIALILSVITLVVVGLLIAYIIKLVSQIHQFRSLAAT

TMFHRENPAFFSKNNHGNIYGIS

GenBank No. AAA46842.1 (incorporated by
reference herein)
                                    (SEQ ID NO: 6)
MHHLHPMIVCIFVMYTGIVGSDAIAGDQLLNIGVIQSKIRSLMYYTDG

GASFIVVKLLPNLPPSNGTCNITSLDAYNVTLFKLLTPLIENLSKIST

VTDTKTRQKRFAGVVVGLAALGVATAAQITAAVAIVKANANAAAINNL

ASSIQSTNKAVSDVIDASRTIATAVQAIQDRINGAIVNGITSASCRAH

DALIGSILNLYLTELTTIFHNQITNPALTPLSIQALRILLGSTLPIVI

ESKLNTNFNTAELLSSGLLTGQIISISPMYMQMLIQINVPTFIMQPGA

KVIDLIAISANHKLQEVVVQVPNRILEYANELQNYPANDCVVTPNSVF

CRYNEGSPIPESQYQCLRGNLNSCTFTPIIGNFLKRFAFANGVLYANC

KSLLCRCADPPHVVSQDDTQGISIIDIKRCSEMMLDTFSFRITSTFNA

TYVTDFSMINANIVHLSPLDLSNQINSINKSLKSAEDWIADSNFFANQ

ARTAKTLYSLSAIALILSVITLVVVGLLIAYIIKLVSQIHQFRSLAAT

TMFHRENPAFFSKNNHGNIYGIS
```

Unless context indicates otherwise, reference to amino acid substitutions or deletions in hPIV2 F is made with reference to SEQ ID NO: 6. An exemplary sequence of a protomer of an hPIV2 F ectodomain trimer stabilized in a prefusion conformation is provided as the hPIV2_preF6 protein:

hPIV2_preF6

(SEQ ID NO: 7)

DAIAGDQLLNIGVIQSKIRSLMYYTDGGASFIVVKLLPNLPPSNGTCN

ITSLDAYNVTLFKLLTPLIENLSKISTVTDTGGGSGGGSGVVVGLAAL

GVATAAQITAAVAIVKANANAAAINNLASSIQSTNKAVSDVIDASRTI

ATAVQAIQDRINGAIVNGITSASCRAHDALIGSILNLYLTELTTIFHN

QITNPALTPLSIQALRILLGSTLPIVIESKLNTNFNTAELLSSGLLTG

QIISISPMYMQMLIQINVPTFIMQPGAKVIDLIAISANHKLQEVVVQV

PNRILEYANELQNYPANDCVVTPNSVFCRYNEGSPIPESQYQCLRGNL

NSCTFTPIIGNFLKRFAFANGVLYANCKSLLCRCADPPHVVSQDDTQG

ISIIDIKRCSEMMLDTFSFRITSTFNATYVTDFSMINANIVHLSPLDL

SNQINSINKSLKSAEDWIADSNFFANQARTAMKQIEDKIEEILSKIYH

IENEIARIKKLIGEAP hPIV2_preF6 includes deletion of hPIV2 F positions 101-108, linkage of positions 100-109 by a GGGSGGGS (SEQ ID NO: 32) peptide linker, C-term truncation at position 484, and C-terminal linkage to a GCN4 trimerization domain.

In some embodiments, the protomers of the hPIV2 F ectodomain trimer include an amino acid sequence set forth as residues 1-463 of SEQ ID NO: 7, or an amino acid sequence at least 90% identical thereto, wherein the C-terminus of the ectodomain trimer is linked to a trimerization domain (such as a GCN4 trimerization domain, for soluble ectodomain trimers) or a transmembrane domain (for membrane anchored embodiments). In some embodiments, the protomers of the hPIV2 F ectodomain trimer include an amino acid sequence set forth as SEQ ID NO: 7, or an amino acid sequence at least 90% identical thereto.

In some embodiments, the immunogen comprises a recombinant hPIV2 F ectodomain trimer comprising protomers comprising the one or more amino acid substitutions or deletions noted below for stabilizing the hPIV3 F ectodomain trimer in its prefusion conformation. For example, in some embodiments, the protomers of the recombinant hPIV2 F ectodomain trimer comprise a non-native disulfide bond between one of 172C-238C, 170C-242C, 213C-230C, 85C-222C, or 216C-221C substitutions for stabilization in the prefusion conformation. The residue numbering for these substitutions is made with reference to the PIV3 F sequence set forth as SEQ ID NO: 9, and the substitutions are introduced into hPIV2 F at residues corresponding to the hPIV3 F SEQ ID NO: 9 sequence. In some embodiments, the protomers of the recombinant hPIV3 F ectodomain trimer comprise two or more non-native disulfide bonds between sets of substitutions selected from 172C-238C, 170C-242C, 213C-230C, 85C-222C, or 216C-221C substitutions for stabilization in the prefusion conformation. Exemplary combinations for prefusion stabilization include: 162C-168C and 213C-230C; 162C-168 and 216C-221C; 162C-168C and 85C-222C; 213C-230C and 170C-242C; 213C-230C and 216C-221C; and 213C-230C and 85C-222C. In some embodiments, the hPIV2 F protomers further comprise cavinty filling substitutions corresponding to the hPIV3 F 463V and 474Y cavity filling substitutions for stabilization in the prefusion conformation. In several embodiments, the hPIV2 F ectodomain trimers can be soluble (e.g., can include a GCN4 trimerization domain as discussed above) or can be membrane anchored (e.g., the full-length hPIV2 F sequence is modified with the prefusion stabilizing amino acid substitutions).

C. hPIV3 F

In some embodiments, the immunogen comprises a recombinant hPIV3 F ectodomain trimer comprising protomers comprising one or more amino acid substitutions or deletions that stabilize the F ectodomain trimer in the prefusion conformation.

In some embodiments, the protomers of the recombinant hPIV3 F ectodomain trimer comprise Y457F and/or S471V substitutions for stabilization in the prefusion conformation. In some embodiments, the protomers of the recombinant hPIV3 F ectodomain trimer comprise one of E145L, V170I, V1751, Y178W, I187F, E193P, A463V, S470L, S470V, I474Y, or S477V substitutions, or a combination of two or more thereof, such as A463V and I474Y; Y178W, A463V, and I474Y; or V170L and I187F substitutions, for stabilization in the prefusion conformation. A protomer of an hPIV3 F ectodomain trimer including any of the above mutations can include a non-native disulfide bond between I172C and N238C substitutions to stabilize the F ectodomain in the prefusion conformation. Combinations of the above mutations can also be used to stabilize the hPIV3 F ectodomain in its prefusion conformation. Exemplary combinations include I172C-N238C, V170L, and I187F; 172C-238C, and Y178W; 172C-238C, and I474Y; and 172C-238C, A463V, and I474Y.

In some embodiments, the protomers of the recombinant hPIV3 F ectodomain trimer comprise a non-native disulfide bond between one of 172C-238C, 170C-242C, 213C-230C, 85C-222C, or 216C-221C substitutions (such as I172C-N238C, V170C-1242C, 1213C-G230C, G85C-Q222C, or D216C-L221C substitutions) for stabilization in the prefusion conformation. In some embodiments, the protomers of the recombinant hPIV3 F ectodomain trimer comprise two or more non-native disulfide bonds between sets of substitutions selected from 172C-238C, 170C-242C, 213C-230C, 85C-222C, or 216C-221C substitutions (such as I172C-N238C, V170C-1242C, 1213C-G230C, G85C-Q222C, or D216C-L221C substitutions) for stabilization in the prefusion conformation. Exemplary combinations of substitutions for introducing disulfide bonds for prefusion stabilization include: Q162C-L168C and 1213C-G230C; Q162C-L168 and D216C-L221C; Q162C-L168C and G85C-Q222C; I213C-G230C and V170C-1242C; I213C-G230C and D216C-L221C; and I213C-G230C and G85C-Q222C.

The above non-native disulfide bonds stabilize the membrane-distal portion of the hPIV3 F ectodomain in its prefusion conformation. Any of these mutations can be combined with modifications to the membrane proximal portion (such as the stem) of the hPIV3 F ectodomain. For example, any of the above non-native disulfide bonds can be combined with 463V and/or 474Y cavity filling substitutions (such as A463V and I474Y substitutions) in the prefusion-stabilized hPIV3 F ectodomain trimer. In other embodiments, the 463V and/or 474Y cavity filling substitutions (such as A463V and I474Y substitutions) can be used on their own to stabilize the hPIV3 F ectodomain trimer in the prefusion conformation.

In some embodiments, the recombinant hPIV3 F ectodomain trimer comprises protomers that are "single chain" proteins wherein the $F_2$ polypeptide and the $F_1$ ectodomain of each protomer are directly linked or linked via a peptide linker to form a contiguous polypeptide chain. Some examples of native hPIV3 F proteins (such as GENBANK: AGW51052.1) do not include a consensus furin cleavage site between the $F_1$ and $F_2$ proteins; hPIV3 F immunogens based on such native hPIV3 F proteins generally do not need to be modified to produce single chain F proteins. However, other native hPIV3 F proteins (such as SWISS-PROT: P06828.2) do include a consensus furin cleavage site between the $F_1$ and $F_2$ proteins; hPIV3 F immunogens based on such native hPIV3 F proteins can be modified to produce single chain F proteins. Exemplary modifications include amino acid substitutions to remove the consensus furin cleavage site, such as a K108E substitution.

In several embodiments, the N-terminal position of the recombinant F2 polypeptide in the protomer can be one of hPIV3 F positions 15-25 (such as position 19), and the C-terminal position of the $F_1$ ectodomain can be from the stem region of the ectodomain, such as one of hPIV3 F positions 475-493 (such as positions 475-485, for example, position 481).

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 145L (such as E145L) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 170I (such as V170I) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 175I (such as V175I) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 178W (such as Y178W) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 187F (such as I187F) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 193P (such as E193P) substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 463V (such as A463V) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 470L (such as S470L) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 470V (such as S470V) substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 474Y (such as I474Y) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a 477V (such as S477V) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), 463V and 474Y (such as A463V and I474Y) cavity filling substitutions, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), 178W, 463V, and 474Y (such as Y178W, A463V, and I474Y) cavity filling substitutions, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), 170L and 187F (such as V170L and I187F) cavity filling substitutions, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 172C and 238C (such as I172C and N238C) substitutions, 170L and 187F (such as V170L and I187F) cavity filling substitutions, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 172C and 238C (such as I172C and N238C) substitutions, 178W (such as Y178W) cavity filling substitutions, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 172C and 238C (such as I172C and N238C) substitutions, 474Y (such as I474Y) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 172C and 238C (such as I172C and N238C) substitutions, 463V (such as A463V) cavity filling substitution, and linkage to a C-terminal GCN4 trimerization domain (for example, via an SA peptide linker), that stabilize the hPIV3 F ectodomain trimer in a prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 172C and 238C (such as I172C and N238C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 170C and 242C (such as V170C and I242C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 213C and 230C (such as I213C and G230C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 85C and 222C (such as G85C and Q222C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 216C and 221C (such as D216C and L221C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 170C and 242C (such as V170C and I242C) substitutions, a non-native disulfide bond between 162C and 168C (such as Q162C and L168C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, a non-native disulfide bond between 213C and 230C (such as I213C and G230C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, a non-native disulfide bond between 216C and 221C (such as D216C and L221C)

substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, a non-native disulfide bond between 85C and 222C (such as G85C and Q222C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 213C and 230C (such as I213C and G230C) substitutions, a non-native disulfide bond between 216C and 221C (such as D216C and L221C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include hPIV3 F positions 19-481, an amino acid substitution (such as K108E) to remove the consensus furin cleavage site between $F_2$ and $F_1$ (if the consensus site is present in the native sequence), a non-native disulfide bond between 213C and 230C (such as I213C and G230C) substitutions, a non-native disulfide bond between 85C and 222C (such as G85C and Q222C) substitutions, and linkage to a C-terminal GCN4 trimerization domain (for example, via an SA peptide linker), that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the recombinant hPIV3 F ectodomain trimer can be a soluble protein complex, for example, for use as a recombinant subunit vaccine. In several such embodiments, the protomers of the recombinant hPIV3 F ectodomain trimer can each comprise a C-terminal linkage to a trimerization domain, such as a GCN4 trimerization domain. The trimerization domain promotes trimerization and stabilization of the membrane proximal aspect of the recombinant hPIV3 F ectodomain trimer. For example, a C-terminal residue of the protomers of the recombinant hPIV3 F ectodomain trimer (such as a residue of the stem region of the trimer) can be directly linked to the trimerization domain, or indirectly linked to the trimerization domain via a peptide linker. Exemplary linkers include glycine and glycine-serine linkers. Non-limiting examples of exogenous multimerization domains that promote stable trimers of soluble recombinant proteins include: the GCN4 leucine zipper, the trimerization motif from the lung surfactant protein (Hoppe et al. 1994 *FEBS Lett* 344:191-195), collagen (McAlinden et al. 2003 *J Biol Chem* 278:42200-42207) any of which can be linked to the C-terminus of the protomers of a recombinant hPIV3 F ectodomain to promote trimerization, as long as the recombinant hPIV3 F ectodomain trimer retains the prefusion conformation. In some examples, the protomers of the recombinant hPIV3 F ectodomain trimer can be linked to a GCN4 trimerization domain, for example, each protomer in the trimer can include a C-terminal linkage to the GCN4 trimerization domain, such as a linkage to any one of hPIV3 F positions 475-485, such as hPIV3 F position 481. In specific examples, the GCN4 fibritin trimerization domain can comprise the amino acid sequence IEDKIEEILSKIYHIENEIARIKKLIGEAP (residues 467-496 of SEQ ID NO: 7).

In other embodiments, the recombinant hPIV3 F ectodomain trimer can be a membrane anchored protein complex, for example, for use in an attenuated virus or virus like particle vaccine. Membrane anchoring can be accomplished, for example, by C-terminal linkage of the protomers of the recombinant hPIV3 F ectodomain trimer to a transmembrane domain and optionally a cytoplasmic tail, such as an hPIV3 F transmembrane domain and cytoplasmic tail. In some embodiments, one or more peptide linkers (such as a gly-ser linker, for example, a 10 amino acid glycine-serine peptide linker can be used to link the protomers of the recombinant hPIV3 F ectodomain trimer to the transmembrane domain A non-limiting example of a transmembrane domain for use with the disclosed embodiments includes an hPIV3 F transmembrane domain, such as IIIILIMMIILFIINITIITI (residues 494-514 of SEQ ID NO: 9).

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), and 463V (such as A463V) and 474Y (such as I474Y) cavity filling substitutions that stabilizes the hPIV3 F ectodomain trimer in a prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), and a non-native disulfide bond between 172C and 238C (such as I172C and N238C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), and a non-native disulfide bond between 170C and 242C (such as V170C and I242C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), and a non-native disulfide bond between 213C and 230C (such as I213C and G230C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), and a non-native disulfide bond between 85C and 222C (such as G85C and Q222C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), and a non-native disulfide bond between 216C and 221C (such as D216C and L221C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), and a non-native disulfide bond between 162C and 168C (such as Q162C and L168C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), a non-native disulfide bond between 170C and 242C (such as V170C and I242C) substitutions, and a non-native disulfide bond between 162C and 168C (such as Q162C and L168C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, and a non-native disulfide bond between 213C and 230C (such as I213C and G230C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, and a non-native disulfide bond between 216C and 221C (such as D216C and L221C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, and a non-native disulfide bond between 85C and 222C (such as G85C and Q222C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), a non-native disulfide bond between 213C and 230C (such as I213C and G230C) substitutions, and a non-native disulfide bond between 216C and 221C (such as D216C and L221C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

In some embodiments, the protomers of the recombinant hPIV3 F ectodomain trimer include a full-length hPIV3 F protein (minus the signal peptide) comprising an amino acid substitution (such as K108E) to remove the consensus furin cleavage site between $F_2$ and $F_1$ (if the consensus site is present in the native sequence), a non-native disulfide bond between 213C and 230C (such as I213C and G230C) substitutions, and a non-native disulfide bond between 85C and 222C (such as G85C and Q222C) substitutions that stabilize the hPIV3 F ectodomain trimer in a prefusion conformation. In some such embodiments, protomers further comprise 463V and 474Y (such as A463V and I474Y) cavity filling substitutions for stabilization in the prefusion conformation.

Native hPIV3 F proteins from different hPIV3 strains, as well as nucleic acid sequences encoding such proteins and methods, are known. The disclosed recombinant hPIV3 F ectodomain trimers can be derived from any strain of hPIV3. Exemplary sequences of native hPIV3 F proteins that can be modified to generate a prefusion-stabilized hPIV3 F protein include:

SWISS-PROT: P06828.2 (incorporated by reference herein)

(SEQ ID NO: 8)

MPTSILLIITTMIMASFCQIDITKLQHVGVLVNSPKGMKISQNFETRYLILSLIPKIEDSNSCGDQQIKQYKRLLDRLII

PLYDGLRLQKDVIVSNQESNENTDPRTKRFFGGVIGTIALGVATSAQITAAVALVEAKQARSDIEKLKEAIRDTNKAVQS

VQSSIGNLIVAIKSVQDYVNKEIVPSIARLGCEAAGLQLGIALTQHYSELTNIFGDNIGSLQEKGIKLQGIASLYRTNIT

EIFTTSTVDKYDIYDLLFTESIKVRVIDVDLNDYSITLQVRLPLLTRLLNTQIYRVDSISYNIQNREWYIPLPSHIMTKG

AFLGGADVKECIEAFSSYICPSDPGFVLNHEMESCLSGNISQCPRTVVKSDIVPRYAFVNGGVVANCITTTCTCNGIGNR

INQPPDQGVKIITHKECNTIGINGMLFNTNKEGTLAFYTPNDITLNNSVALDPIDISIELNKAKSDLEESKEWIRRSNQK

LDSIGNWHQSSTTIIIVLIMIIILFIINVTIIIIAVKYYRIQKRNRVDQNDKPYVLTNK

GENBANK: AGW51052.1 (incorporated by reference herein)

(SEQ ID NO: 9)

MLISILSIITTMIMASHCQIDITKLQHVGVLVNSPKGMKISQNFETRYLILSLIPKIEDSNSCGDQQIKQYKRLLDRLII

PLYDGLKLQKDVIVTNQESNENTDPRTERFFGGVIGTIALGVATSAQITAAVALVEAKQAKSDIEKLKEAIRDTNKAVQS

VQSSVGNLIVAIKSVQDYVNKEIVPSIARLGCEAAGLQLGIALTQHYSELTNIFGDNIGSLQEKGIKLQGIASLYRTNIT

EIFTTSTVDKYDIYDLLFTESIKVRVIDVDLNDYSITLQVRLPLLTRLLNTQIYKVDSISYNIQNREWYIPLPSHIMTKG

AFLGGADVKECIEAFSSYICPSDPGFVLNHEMESCLSGNISQCPRTTVTSDIVPRYAFVNGGVVANCITTTCTCNGIGNR

INQPPDQGVKIITHKECNTIGINGMLFNTNKEGTLAFYTPDDITLNNSVALDPIDISIELNKAKSDLEESKEWIRRSNQK

LDSIGSWHQSSTTIIIILIMMIILFIINITIITIAIKYYRIQKRNRVDQNDKPYVLTNK

Unless context indicates otherwise, reference to amino acid substitutions or deletions in hPIV3 F is made with reference to SEQ ID NO: 9. Exemplary sequences of protomers of an hPIV3 F ectodomain trimer stabilized in a prefusion conformation and including a C-terminal GCN4 domain are provided as follows:

hPIV3 F GCN4, E145L (SEQ ID NO: 10)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDILKLKEAIRDTNKAVQSVQSSVGNLIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLSAIEDKIEEILSKIYHI

ENEIARIKKLIGEAP hPIV3 F GCN4, V170I (SEQ ID NO: 11)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIIAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLSAIEDKIEEILSKIYHI

ENEIARIKKLIGEAP hPIV3 F GCN4, V175I (SEQ ID NO: 12)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSIQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

-continued

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLSAIEDKIEEILSKIYHI

ENEIARIKKLIGEAP hPIV3 F GCN4, Y178W (SEQ ID NO: 13)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDW

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLSAIEDKIEEILSKIYHI

ENEIARIKKLIGEAP hPIV3 F GCN4, E193P (SEQ ID NO: 14)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCPAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLSAIEDKIEEILSKIYHI

ENEIARIKKLIGEAP hPIV3 F GCN4, A463V (SEQ ID NO: 15)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWIRRSNQKLSAIEDKIEEILSKIYHI

ENEIARIKKLIGEAP hPIV3 F GCN4, S470L (SEQ ID NO: 16)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEELKEWIRRSNQKLSAIEDKIEEILSKIYHI

ENEIARIKKLIGEAP hPIV3 F GCN4, S470V (SEQ ID NO: 17)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

-continued

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEEVKEWIRRSNQKLSAIEDKIEEILSKIYHI

ENEIARIKKLIGEAP hPIV3 F GCN4, I474Y (SEQ ID NO: 18)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWYRRSNQKLSAIEDKIEEILSKIYHI

ENEIARIKKLIGEAP hPIV3 F GCN4, S477V (SEQ ID NO: 19)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRVNQKLSAIEDKIEEILSKIYHI

ENEIARIKKLIGEAP hPIV3 F GCN4, A463V, I474Y (SEQ ID NO: 20)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GCN4, Y178W, A463V, I474Y (SEQ ID NO: 21)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDW

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GCN4, I172C-N238C (SEQ ID NO: 22)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVACKSVQDY

VNKEIVPSIARLGCEAAGLQLGIALTQHYSELTNIFGDNIGSLQEKGIKLQGIASLYRTCITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

-continued

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLSAIEDKIEEILSKIYHI

ENEIARIKKLIGEAP hPIV3 F GCN4, I172C-N238C, V170L, I187F (SEQ ID NO: 23)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLILACKSVQDY

VNKEIVPSFARLGCEAAGLQLGIALTQHYSELTNIFGDNIGSLQEKGIKLQGIASLYRTCITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLSAIEDKIEEILSKIYHI

ENEIARIKKLIGEAP hPIV3 F GCN4, 172C-238C, Y178W (SEQ ID NO: 24)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDW

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLSAIEDKIEEILSKIYHI

ENEIARIKKLIGEAP hPIV3 F GCN4, 172C-238C, I474Y (SEQ ID NO: 25)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVACKSVQDY

VNKEIVPSIARLGCEAAGLQLGIALTQHYSELTNIFGDNIGSLQEKGIKLQGIASLYRTCITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWYRRSNQKLSAIEDKIEEILSKIYHI

ENEIARIKKLIGEAP hPIV3 F GCN4, 172C-238C, A463V, I474Y (SEQ ID NO: 26)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVACKSVQDY

VNKEIVPSIARLGCEAAGLQLGIALTQHYSELTNIFGDNIGSLQEKGIKLQGIASLYRTCITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GNC4 V170C-I242C, A463V, I474Y (SEQ ID NO: 39)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIcAIKSVQDY

VNKEIVPSIARLGCEAAGLQLGIALTQHYSELTNIFGDNIGSLQEKGIKLQGIASLYRTNITEcFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

-continued

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLSAIEDKIEEILSKIYHI

ENEIARIKKLIGEAP hPIV3 F GNC4 I213C-G230C, A463V, I474Y (SEQ ID NO: 40)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNcFGDNIGSLQEKGIKLQcIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLSAIEDKIEEILSKIYHI

ENEIARIKKLIGEAP hPIV3 F GNC4 G85C-Q222C, A463V, I474Y (SEQ ID NO: 41)

QIDITKLQHVGVLVNSPKGMKISQNFETRYLILSLIPKIEDSNSCGDQQIKQYKRLLDRLIIPLYDCLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLCEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GNC4 D216C-L221C, A463V, I474Y (SEQ ID NO: 42)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGCNIGSCQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GNC4 Q162C-L168C, A463V, I474Y (SEQ ID NO: 43)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVCSSVGNCIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GNC4 Q162C-L168C, V170C-I242C, A463V, I474Y (SEQ ID NO: 44)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVCSSVGNCIcAIKSVQDY

VNKEIVPSIARLGCEAAGLQLGIALTQHYSELTNIFGDNIGSLQEKGIKLQGIASLYRTNITEcFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

-continued

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLSAIEDKIEEILSKIYHI

ENEIARIKKLIGEAP hPIV3 F GNC4 Q162C-L168C, I213C-G230C, A463V, I474Y (SEQ ID NO: 45)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVCSSVGNCIVAIKSVQDY

VNKEIVPSIARLGCEAAGLQLGIALTQHYSELTNcFGDNIGSLQEKGIKLQcIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLSAIEDKIEEILSKIYHI

ENEIARIKKLIGEAP hPIV3 F GNC4 Q162C-L168C, D216C-L221C, A463V, I474Y (SEQ ID NO: 46)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVCSSVGNCIVAIKSVQDY

VNKEIVPSIARLGCEAAGLQLGIALTQHYSELTNIFGCNIGSCQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GNC4 Q162C-L168C, G85C-Q222C, A463V, I474Y (SEQ ID NO: 47)

QIDITKLQHVGVLVNSPKGMKISQNFETRYLILSLIPKIEDSNSCGDQQIKQYKRLLDRLIIPLYDCLKLQKDVIVTNQE

SNENTDPRTERFFGGVIGTIALGVATSAQITAAVALVEAKQAKSDIEKLKEAIRDTNKAVQSVCSSVGNCIVAIKSVQDY

VNKEIVPSIARLGCEAAGLQLGIALTQHYSELTNIFGDNIGSLCEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GNC4 I213C-G230C, V170C-I242C, A463V, I474Y (SEQ ID NO: 48)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIcAIKSVQDY

VNKEIVPSIARLGCEAAGLQLGIALTQHYSELTNcFGDNIGSLQEKGIKLQcIASLYRTNITEcFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLSAIEDKIEEILSKIYHI

ENEIARIKKLIGEAP hPIV3 F GNC4 I213C-G230C, D216C-L221C, A463V, I474Y (SEQ ID NO: 49)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNcFGcNIGScQEKGIKLQcIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

-continued

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP hPIV3 F GNC4 I213C-G230C, G85C-Q222C, A463V, I474Y (SEQ ID NO: 50)

QIDITKLQHVGVLVNSPKGMKISQNFETRYLILSLIPKIEDSNSCGDQQIKQYKRLLDRLIIPLYDCLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNcFGDNIGSLcEKGIKLQcIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLSAIEDKIEEILSKIYHI

ENEIARIKKLIGEAP

In some embodiments, the protomers of the hPIV3 F ectodomain trimer include an amino acid sequence set forth as residues 1-463 of any one of SEQ ID NOs: 10-26 or 39-50, or an amino acid sequence at least 90% identical thereto, wherein the C-terminus of the ectodomain trimer is linked to a trimerization domain (such as a GCN4 trimerization domain, for soluble ectodomain trimers) or a transmembrane domain (for membrane anchored embodiments). In some embodiments, the protomers of the hPIV3 F ectodomain trimer include an amino acid sequence set forth as SEQ ID NO: 10-26 or 39-50, or an amino acid sequence at least 90% identical thereto.

Exemplary sequences of protomers of an hPIV3 F ectodomain trimer stabilized in a prefusion conformation and linked to hPIV3 TM and CT regions (for example, for use in an attenuated virus immunogen, or for DNA or RNA immunization) are provided as follows:

hPIV3 F A463V, I474Y (SEQ ID NO: 51)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK hPIV3 F I172C-N238C (SEQ ID NO: 52)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVACKSVQDY

VNKEIVPSIARLGCEAAGLQLGIALTQHYSELTNIFGDNIGSLQEKGIKLQGIASLYRTCITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKAKSDLEESKEWIRRSNQKLDSIGSWHQSSTTIIIIL

IMMIILFIINITIITIAIKYYRIQKRNRVDQNDKPYVLTNK hPIV3 F 172C-238C, A463V, I474Y (SEQ ID NO: 53)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVACKSVQDY

VNKEIVPSIARLGCEAAGLQLGIALTQHYSELTNIFGDNIGSLQEKGIKLQGIASLYRTCITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

-continued

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK hPIV3 F V170C-I242C, A463V, I474Y (SEQ ID NO: 54)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIcAIKSVQDY

VNKEIVPSIARLGCEAAGLQLGIALTQHYSELTNIFGDNIGSLQEKGIKLQGIASLYRTNITEcFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLDSIGSWHQSSTTIIIIL

IMMIILFIINITIITIAIKYYRIQKRNRVDQNDKPYVLTNK hPIV3 F I213C-G230C, A463V, I474Y (SEQ ID NO: 55)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNcFGDNIGSLQEKGIKLQcIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLDSIGSWHQSSTTIIIIL

IMMIILFIINITIITIAIKYYRIQKRNRVDQNDKPYVLTNK hPIV3 F G85C-Q222C, A463V, I474Y (SEQ ID NO: 56)

QIDITKLQHVGVLVNSPKGMKISQNFETRYLILSLIPKIEDSNSCGDQQIKQYKRLLDRLIIPLYDCLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGDNIGSLCEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK hPIV3 F D216C-L221C, A463V, I474Y (SEQ ID NO: 57)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNIFGCNIGSCQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK hPIV3 F Q162C-L168C, A463V, I474Y (SEQ ID NO: 58)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVCSSVGNCIVAIKSVQDY

VNKEIVPSIARLGCEAAGLQLGIALTQHYSELTNIFGDNIGSLQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

-continued

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK hPIV3 F Q162C-L168C, V170C-I242C, A463V, I474Y (SEQ ID NO: 59)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVCSSVGNCIcAIKSVQDY

VNKEIVPSIARLGCEAAGLQLGIALTQHYSELTNIFGDNIGSLQEKGIKLQGIASLYRTNITEcFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLDSIGSWHQSSTTIIIIL

IMMIILFIINITIITIAIKYYRIQKRNRVDQNDKPYVLTNK hPIV3 F Q162C-L168C, I213C-G230C, A463V, I474Y (SEQ ID NO: 60)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVCSSVGNCIVAIKSVQDY

VNKEIVPSIARLGCEAAGLQLGIALTQHYSELTNcFGDNIGSLQEKGIKLQcIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKyKSDLEESKEWyRRSNQKLDSIGSWHQSSTTIIIIL

IMMIILFIINITIITIAIKYYRIQKRNRVDQNDKPYVLTNK hPIV3 F Q162C-L168C, D216C-L221C, A463V, I474Y (SEQ ID NO: 61)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVCSSVGNCIVAIKSVQDY

VNKEIVPSIARLGCEAAGLQLGIALTQHYSELTNIFGCNIGSCQEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK hPIV3 F Q162C-L168C, G85C-Q222C, A463V, I474Y (SEQ ID NO: 62)

QIDITKLQHVGVLVNSPKGMKISQNFETRYLILSLIPKIEDSNSCGDQQIKQYKRLLDRLIIPLYDCLKLQKDVIVTNQE

SNENTDPRTERFFGGVIGTIALGVATSAQITAAVALVEAKQAKSDIEKLKEAIRDTNKAVQSVCSSVGNCIVAIKSVQDY

VNKEIVPSIARLGCEAAGLQLGIALTQHYSELTNIFGDNIGSLCEKGIKLQGIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK hPIV3 F I213C-G230C, V170C-I242C, A463V,I474Y (SEQ ID NO: 63)

QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIcAIKSVQDY

VNKEIVPSIARLGCEAAGLQLGIALTQHYSELTNcFGDNIGSLQEKGIKLQcIASLYRTNITEcFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

-continued

```
TIGINGMLFNTNKEGTLAFYTPDDITLNNSVALDPIDISIELNKyKSDLEESKEWyRRSNQKLDSIGSWHQSSTTIIIIL

IMMIILFIINITIITIAIKYYRIQKRNRVDQNDKPYVLTNK

hPIV3 F I213C-G230C, D216C-L221C, A463V, I474Y
                                                                  (SEQ ID NO: 64)
QIDITKLQHVGVLVNSPKGMKISQNFETRYLILSLIPKIEDSNSCGDQQIKQYKRLLDRLIIPLYDGLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNcFGcNIGScQEKGIKLQcIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK

hPIV3 F I213C-G230C, G85C-Q222C, A463V, I474Y
                                                                  (SEQ ID NO: 65)
QIDITKLQHVGVLVNSPKGMKISQNFETRYLILSLIPKIEDSNSCGDQQIKQYKRLLDRLIIPLYDCLKLQKDVIVTNQE

SNENTDPRTERFFGGVIGTIALGVATSAQITAAVALVEAKQAKSDIEKLKEAIRDTNKAVQSVQSSVGNLIVAIKSVQDY

VNKEIVPSIARLGCEAAGLQLGIALTQHYSELTNcFGDNIGSLcEKGIKLQcIASLYRTNITEIFTTSTVDKYDIYDLLF

TESIKVRVIDVDLNDYSITLQVRLPLLTRLLNTQIYKVDSISYNIQNREWYIPLPSHIMTKGAFLGGADVKECIEAFSSY

ICPSDPGFVLNHEMESCLSGNISQCPRTTVTSDIVPRYAFVNGGVVANCITTTCTCNGIGNRINQPPDQGVKIITHKECN

TIGINGMLFNTNKEGTLAFYTPDDITLNNSVALDPIDISIELNKVKSDLEESKEWYRRSNQKLDSIGSWHQSSTTIIIIL

IMMIILFIINITIITIAIKYYRIQKRNRVDQNDKPYVLTNK
```

In some embodiments, the protomers of the hPIV3 F ectodomain trimer include an amino acid sequence set forth as any one of SEQ ID NOs: 51-65, or an amino acid sequence at least 90% identical thereto.

D. Non-Human PIV3 F Ectodomain Trimers

In some embodiments, the immunogen comprises a recombinant PIV3 F ectodomain trimer from a strain of PIV3 other than hPIV3, such as a bovine or caprine strain of PIV3. The recombinant PIV3 F ectodomain trimer comprises protomers comprising one or more amino acid substitutions or deletions that stabilize the F ectodomain trimer in the prefusion conformation. Based on the high sequence identity between hPIV3 F sequences and non-human PIV3 F sequences, the residues of the non-human PIV3 F sequence corresponding to those of hPIV3 are readily attainable. Accordingly, the amino acid substitutions for stabilizing non-human PIV3 F proteins in a prefusion conformation noted below are referenced in the context of SEQ ID NO: 9.

Any of the amino acid substitutions (or combinations of substitutions) noted above for stabilizing hPIV3 F in its prefusion conformation can be introduced into a non-human PIV3 F sequence for prefusion stabilization.

In some embodiments, the protomers of the recombinant PIV3 F ectodomain trimer comprise a non-native disulfide bond between one of 170C-242C, 213C-230C, 85C-222C, or 216C-221C substitutions (such as V170C-I242C, I213C-G230C, G85C-Q222C, or D216C-L221C substitutions) for stabilization in the prefusion conformation. In some embodiments, the protomers of the recombinant PIV3 F ectodomain trimer comprise two or more non-native disulfide bonds between sets of substitutions selected from 170C-242C, 213C-230C, 85C-222C, or 216C-221C substitutions (such as V170C-I242C, I213C-G230C, G85C-Q222C, or D216C-L221C substitutions) for stabilization in the prefusion conformation. Exemplary combinations of substitutions for introducing disulfide bonds for prefusion stabilization include: Q162C-L168C and I213C-G230C; Q162C-L168 and D216C-L221C; Q162C-L168C and G85C-Q222C; I213C-G230C and V170C-I242C; I213C-G230C and D216C-L221C; and I213C-G230C and G85C-Q222C.

The above non-native disulfide bonds stabilize the membrane-distal portion of the PIV3 F ectodomain in its prefusion conformation. Any of these mutations can be combined with modifications to the membrane proximal portion (such as the stem) of the PIV3 F ectodomain. For example, any of the above non-native disulfide bonds can be combined with 463V and/or 474Y cavity filling substitutions (such as A463V and I474Y substitutions) in the prefusion-stabilized PIV3 F ectodomain trimer. In other embodiments, the 463V and/or 474Y cavity filling substitutions (such as A463V and I474Y substitutions) can be used on their own to stabilize the PIV3 F ectodomain trimer in the prefusion conformation.

In some embodiments, the recombinant PIV3 F ectodomain trimer comprises protomers that are "single chain" proteins wherein the $F_2$ polypeptide and the $F_1$ ectodomain of each protomer are directly linked or linked via a peptide linker to form a contiguous polypeptide chain. For example, many native PIV3 F proteins include a consensus furin cleavage site between the $F_1$ and $F_2$ proteins; PIV3 F immunogens based on such native PIV3 F proteins can be modified to produce single chain F proteins. Exemplary modifications include amino acid substitutions to remove the consensus furin cleavage site, such as a K108E substitution.

In several embodiments, the N-terminal position of the recombinant $F_2$ polypeptide in the protomer can be one of PIV3 F positions 15-25 (such as position 19), and the C-terminal position of the $F_1$ ectodomain can be from the stem region of the ectodomain, such as one of PIV3 F positions 475-493 (such as positions 475-485, for example, position 481).

In some embodiments, the protomers of the recombinant PIV3 F ectodomain trimer include PIV3 F positions 19-481, an amino acid substitution (such as K108E) to remove the consensus furin cleavage site between $F_2$ and $F_1$ (if the consensus site is present in the native sequence), 463V and 474Y (such as A463V and I474Y) cavity filling substitutions, and linkage to a C-terminal GCN4 trimerization domain (for example, via an SA peptide linker), that stabilize the PIV3 F ectodomain trimer in a prefusion conformation.

In some embodiments, the protomers of the recombinant PIV3 F ectodomain trimer include PIV3 F positions 19-481, an amino acid substitution (such as K108E) to remove the consensus furin cleavage site between $F_2$ and $F_1$ (if the consensus site is present in the native sequence), a non-native disulfide bond between 172C and 238C (such as I172C and N238C) substitutions, and linkage to a C-terminal GCN4 trimerization domain (for example, via an SA peptide linker), that stabilize the PIV3 F ectodomain trimer in a prefusion conformation. In some such embodiments, protomers further comprise 463V and/or 474Y (such as A463V and/or I474Y) cavity filling substitutions for stabilization in the prefusion conformation.

In some embodiments, the protomers of the recombinant PIV3 F ectodomain trimer include PIV3 F positions 19-481, an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, a non-native disulfide bond between 213C and 230C (such as I213C and G230C) substitutions, and linkage to a C-terminal GCN4 trimerization domain (for example, via an SA peptide linker), that stabilize the PIV3 F ectodomain trimer in a prefusion conformation. In some such embodiments, protomers further comprise 463V and/or 474Y (such as A463V and/or I474Y) cavity filling substitutions for stabilization in the prefusion conformation.

In some embodiments, the recombinant PIV3 F ectodomain trimer can be a soluble protein complex, for example, for use as a recombinant subunit vaccine. In several such embodiments, the protomers of the recombinant PIV3 F ectodomain trimer can each comprise a C-terminal linkage to a trimerization domain, such as a GCN4 trimerization domain. The trimerization domain promotes trimerization and stabilization of the membrane proximal aspect of the recombinant PIV3 F ectodomain trimer. For example, a C-terminal residue of the protomers of the recombinant PIV3 F ectodomain trimer (such as a residue of the stem region of the trimer) can be directly linked to the trimerization domain, or indirectly linked to the trimerization domain via a peptide linker. Exemplary linkers include glycine and glycine-serine linkers. Non-limiting examples of exogenous multimerization domains that promote stable trimers of soluble recombinant proteins include: the GCN4 leucine zipper, the trimerization motif from the lung surfactant protein (Hoppe et al. 1994 *FEBS Lett* 344:191-195), collagen (McAlinden et al. 2003 *J Biol Chem* 278:42200-42207) any of which can be linked to the C-terminus of the protomers of a recombinant PIV3 F ectodomain to promote trimerization, as long as the recombinant PIV3 F ectodomain trimer retains the prefusion conformation. In some examples, the protomers of the recombinant PIV3 F ectodomain trimer can be linked to a GCN4 trimerization domain, for example, each protomer in the trimer can include a C-terminal linkage to the GCN4 trimerization domain, such as a linkage to any one of PIV3 F positions 475-485, such as PIV3 F position 481. In specific examples, the GCN4 fibritin trimerization domain can comprise the amino acid sequence IEDKIEEILSKIYHIENEIARIKKLIGEAP (residues 467-496 of SEQ ID NO: 7).

In other embodiments, the recombinant PIV3 F ectodomain trimer can be a membrane anchored protein complex, for example, for use in an attenuated virus or virus like particle vaccine. Membrane anchoring can be accomplished, for example, by C-terminal linkage of the protomers of the recombinant PIV3 F ectodomain trimer to a transmembrane domain and optionally a cytoplasmic tail, such as an PIV3 F transmembrane domain and cytoplasmic tail. In some embodiments, one or more peptide linkers (such as a gly-ser linker, for example, a 10 amino acid glycine-serine peptide linker can be used to link the protomers of the recombinant PIV3 F ectodomain trimer to the transmembrane domain A non-limiting example of a transmembrane domain for use with the disclosed embodiments includes an PIV3 F transmembrane domain, such as IIIILIMMIILFIINITIITI (residues 494-514 of SEQ ID NO: 9).

In some embodiments, the protomers of the recombinant PIV3 F ectodomain trimer include a full-length PIV3 F protein (minus the signal peptide) comprising an amino acid substitution (such as K108E) to remove the consensus furin cleavage site between $F_2$ and $F_1$ (if the consensus site is present in the native sequence), and 463V and 474Y (such as A463V and I474Y) cavity filling substitutions that stabilize the PIV3 F ectodomain trimer in a prefusion conformation.

In some embodiments, the protomers of the recombinant PIV3 F ectodomain trimer include a full-length PIV3 F protein (minus the signal peptide) comprising an amino acid substitution (such as K108E) to remove the consensus furin cleavage site between $F_2$ and $F_1$ (if the consensus site is present in the native sequence), and a non-native disulfide bond between 172C and 238C (such as I172C and N238C) substitutions, that stabilize the PIV3 F ectodomain trimer in a prefusion conformation. In some such embodiments, protomers further comprise 463V and/or 474Y (such as A463V and/or I474Y) cavity filling substitutions for stabilization in the prefusion conformation.

In some embodiments, the protomers of the recombinant PIV3 F ectodomain trimer include a full-length PIV3 F protein (minus the signal peptide) comprising an amino acid substitution (such as K108E) to remove the consensus furin cleavage site between $F_2$ and $F_1$ (if the consensus site is present in the native sequence), a non-native disulfide bond between 162C and 168C (such as Q162C and L168C) substitutions, and a non-native disulfide bond between 213C and 230C (such as I213C and G230C) substitutions that stabilize the PIV3 F ectodomain trimer in a prefusion conformation. In some such embodiments, protomers further comprise 463V and/or 474Y (such as A463V and/or I474Y) cavity filling substitutions for stabilization in the prefusion conformation.

The disclosed recombinant PIV3 F ectodomain trimers can be derived from any strain of PIV3. Exemplary sequences of native PIV3 F proteins that can be modified to generate a prefusion-stabilized PIV3 F protein include:

Bovine PIV3 F GENBANK: ABZ85923.1 (incorporated by reference herein)
(SEQ ID NO: 66)

MITIVITMILSLTPSSLCQIDITKLQSVGVLVNSPKGIKISQNFETRYLILSLIPKIEDSHSCGNQQIDQYKKLLDRLII
PLYDGLKLQKDVIVVNHESHNNTNLRTKRFFGEIIGTIAIGIATSAQITAAVALVEAKQARSDIDKLKEAIKDTNKAVQS
IQSSVGNLIVAVKSVQDYVNNEIVPSITRLGCEAAGLQLGIALTQHYSELTNIFGDNIGTLGEKGVKLQGIASLYRTNIT
EVFTTSTVDQYDIYDLLFTESIKMRVIDVDLSDYSITLQVRLPLLTKVSNTQIYKVDSISYNIQGKEWYIPLPHHIMTKG
AFLGGADIKECIESFSNYICPSDPGFILNHEMENCLSGNITQCPKTIVTSDIVPRYAFVDGGVIANCIPTTCTCNGIDNR
INQSPDQGIKIITYKECQIVGINGMLFKTNQEGTLAKYTFDNIKLNNSVALNPIDISLELNKAKSDLEESKRWIEKSNQK
LDSIGSWHQSSVTIIIIIVMIVVLLIINAIIIMIMIRYLRDRNRHLNNKDSEPYVLTNRQ

Bovine PIV3 F GENBANK: AHZ90086.1 (incorporated by reference herein)
(SEQ ID NO: 67)

MIITVITVILLLTPSSLCQIDITKLQNVGVLVNSPKGIKISQNFETRYLILSLIPKIDDSHSCGNQQIDQYKKLLDRLII
PLYDGLKLQRDVIVVNHESHNNTNLRTKRFFGEIIGTIAIGIATSAQITAAVALVEAKQARSDIDKLKEAIKDTNKAVQS
IQSSVGNLIVAVKSVQDYVNNEIVPSITRLGCEAAGLQLGIALTQHYSELTNIFGDNIGTLREKGVKLQGIASLYRTNIT
EVFTTSTVDQYDIYDLLFTESIKMRVIDVDLSDYSITLQVRLPLLTKVSNTQIYKVDSISYNIQGKEWYIPLPHHIMTKG
AFLGGADIKECIESFSNYICPSDPGFILNHELENCLSGNITQCPKTIVTSDIVPRYAFVDGGVIANCIPTTCTCNGIDNR
INQSPDQGIKIITYKECQIVGINGMLFKTNQEGTLAKYTFDDIKLNNSVALNPIDISLELNKAKSELEESKRWIEKSNHK
LDSIGSWYQSSATIIIIIVMIVVLLIINAIIIMITIKHLRARNRHPNNKDSEPYVLTNRQ

Caprine PIV3 F GENBANK: AIW42876.1 (incorporated by reference herein)
(SEQ ID NO: 68)

MIKKIICIFSMPILLSFCQVDIIKLQRVGILVSKPKSIKISQNFETRYLVLNLIPNIENAQSCGDQQIKQYKKLLDRLII
PLYDGLRLQQDIIVVDNNLKNNTNHRAKRFFGEIIGTIALGVATSAQITAAVALVEAKQARSDIERVKNAVRDTNKAVQS
IQGSVGNLIVAVKSVQDYVNNEIVPSIKRLGCEAAGLQLGIALTQHYSELTNIFGDNIGTLKEKGIKLQGIASLYHTNIT
EIFTTSTVDQYDIYDLLFTESIKMRVIDVDLNDYSITLQVRLPLLTKISDAQIYNVDSVSYNIGGTEWYIPLPRNIMTKG
AFLGGANLQDCIESFSDYICPSDPGFILNRDIENCLSGNITQCPKTLVISDIVPRYAFVDGGVIANCLSTTCTCNGIDNR
INQAPDQGIKIITYKDCQTIGINGMLFKTNQEGTLAAYTPVDITLNNSVNLDPIDLSIELNRARSDLAESKEWIKRSEAK
LDSVGSWYQSSTTEIIQIVMIIVLFIINIIVLIVLIKYSRSQNQSMNNHMNEPYILTNKVQ

Exemplary sequences of protomers of a PIV3 F ectodomain trimer stabilized in a prefusion conformation and including a C-terminal GCN4 domain are provided as follows:

Bovine PIV3 F GCN4 I172C-N238C/I474Y (based on ABZ85923.1)
(SEQ ID NO: 69)

QIDITKLQSVGVLVNSPKGIKISQNFETRYLILSLIPKIEDSHSCGNQQIDQYKKLLDRLIIPLYDGLKLQKDVIVVNHE
SHNNTNLRTKRFFGEIIGTIAIGIATSAQITAAVALVEAKQARSDIDKLKEAIKDTNKAVQSIQSSVGNLIVACKSVQDY
VNNEIVPSITRLGCEAAGLQLGIALTQHYSELTNIFGDNIGTLGEKGVKLQGIASLYRTCITEVFTTSTVDQYDIYDLLF
TESIKMRVIDVDLSDYSITLQVRLPLLTKVSNTQIYKVDSISYNIQGKEWYIPLPHHIMTKGAFLGGADIKECIESFSNY
ICPSDPGFILNHEMENCLSGNITQCPKTIVTSDIVPRYAFVDGGVIANCIPTTCTCNGIDNRINQSPDQGIKIITYKECQ
IVGINGMLFKTNQEGTLAKYTFDNIKLNNSVALNPIDISLELNKAKSDLEESKRWYEKSNQKLSAIEDKIEEILSKIYHI
ENEIARIKKLIGEAP

Bovine PIV3 F GCN4 I172C-N238C/I474Y (based on AHZ90086.1)
(SEQ ID NO: 70)

QIDITKLQNVGVLVNSPKGIKISQNFETRYLILSLIPKIDDSHSCGNQQIDQYKKLLDRLIIPLYDGLKLQRDVIVVNHE
SHNNTNLRTKRFFGEIIGTIAIGIATSAQITAAVALVEAKQARSDIDKLKEAIKDTNKAVQSIQSSVGNLIVACKSVQDY
VNNEIVPSITRLGCEAAGLQLGIALTQHYSELTNIFGDNIGTLREKGVKLQGIASLYRTCITEVFTTSTVDQYDIYDLLF
TESIKMRVIDVDLSDYSITLQVRLPLLTKVSNTQIYKVDSISYNIQGKEWYIPLPHHIMTKGAFLGGADIKECIESFSNY

-continued

ICPSDPGFILNHELENCLSGNITQCPKTIVTSDIVPRYAFVDGGVIANCIPTTCTCNGIDNRINQSPDQGIKIITYKECQ

IVGINGMLFKTNQEGTLAKYTFDDIKLNNSVALNPIDISLELNKAKSELEESKRWYEKSNHKLSAIEDKIEEILSKIYHI

ENEIARIKKLIGEAP

Caprine PIV3 F GCN4 I172C-N238C/I474Y (based on AIW42876.1)

(SEQ ID NO: 71)

QVDIIKLQRVGILVSKPKSIKISQNFETRYLVLNLIPNIENAQSCGDQQIKQYKKLLDRLIIPLYDGLRLQQDIIVVDNN

LKNNTNHRAKRFFGEIIGTIALGVATSAQITAAVALVEAKQARSDIERVKNAVRDTNKAVQSIQGSVGNLIVACKSVQDY

VNNEIVPSIKRLGCEAAGLQLGIALTQHYSELTNIFGDNIGTLKEKGIKLQGIASLYHTCITEIFTTSTVDQYDIYDLLF

TESIKMRVIDVDLNDYSITLQVRLPLLTKISDAQIYNVDSVSYNIGGTEWYIPLPRNIMTKGAFLGGANLQDCIESFSDY

ICPSDPGFILNRDIENCLSGNITQCPKTLVISDIVPRYAFVDGGVIANCLSTTCTCNGIDNRINQAPDQGIKIITYKDCQ

TIGINGMLFKTNQEGTLAAYTPVDITLNNSVNLDPIDLSIELNRARSDLAESKEWYKRSEAKLSAIEDKIEEILSKIYHI

ENEIARIKKLIGEAP

Bovine PIV3 F GCN4 I172C-N238C/A463V (based on ABZ85923.1)

(SEQ ID NO: 72)

QIDITKLQSVGVLVNSPKGIKISQNFETRYLILSLIPKIEDSHSCGNQQIDQYKKLLDRLIIPLYDGLKLQKDVIVVNHE

SHNNTNLRTKRFFGEIIGTIAIGIATSAQITAAVALVEAKQARSDIDKLKEAIKDTNKAVQSIQSSVGNLIVACKSVQDY

VNNEIVPSITRLGCEAAGLQLGIALTQHYSELTNIFGDNIGTLGEKGVKLQGIASLYRTCITEVFTTSTVDQYDIYDLLF

TESIKMRVIDVDLSDYSITLQVRLPLLTKVSNTQIYKVDSISYNIQGKEWYIPLPHHIMTKGAFLGGADIKECIESFSNY

ICPSDPGFILNHEMENCLSGNITQCPKTIVTSDIVPRYAFVDGGVIANCIPTTCTCNGIDNRINQSPDQGIKIITYKECQ

IVGINGMLFKTNQEGTLAKYTFDNIKLNNSVALNPIDISLELNKVKSDLEESKRWIEKSNQKLSAIEDKIEEILSKIYHI

ENEIARIKKLIGEAP

Bovine PIV3 F GCN4 I172C-N238C/A463V (based on AHZ90086.1)

(SEQ ID NO: 73)

QIDITKLQNVGVLVNSPKGIKISQNFETRYLILSLIPKIDDSHSCGNQQIDQYKKLLDRLIIPLYDGLKLQRDVIVVNHE

SHNNTNLRTKRFFGEIIGTIAIGIATSAQITAAVALVEAKQARSDIDKLKEAIKDTNKAVQSIQSSVGNLIVACKSVQDY

VNNEIVPSITRLGCEAAGLQLGIALTQHYSELTNIFGDNIGTLREKGVKLQGIASLYRTCITEVFTTSTVDQYDIYDLLF

TESIKMRVIDVDLSDYSITLQVRLPLLTKVSNTQIYKVDSISYNIQGKEWYIPLPHHIMTKGAFLGGADIKECIESFSNY

ICPSDPGFILNHELENCLSGNITQCPKTIVTSDIVPRYAFVDGGVIANCIPTTCTCNGIDNRINQSPDQGIKIITYKECQ

IVGINGMLFKTNQEGTLAKYTFDDIKLNNSVALNPIDISLELNKVKSELEESKRWIEKSNHKLSAIEDKIEEILSKIYHI

ENEIARIKKLIGEAP

Caprine PIV3 F GCN4 I172C-N238C/A463V (based on AIW42876.1)

(SEQ ID NO: 74)

QVDIIKLQRVGILVSKPKSIKISQNFETRYLVLNLIPNIENAQSCGDQQIKQYKKLLDRLIIPLYDGLRLQQDIIVVDNN

LKNNTNHRAKRFFGEIIGTIALGVATSAQITAAVALVEAKQARSDIERVKNAVRDTNKAVQSIQGSVGNLIVACKSVQDY

VNNEIVPSIKRLGCEAAGLQLGIALTQHYSELTNIFGDNIGTLKEKGIKLQGIASLYHTCITEIFTTSTVDQYDIYDLLF

TESIKMRVIDVDLNDYSITLQVRLPLLTKISDAQIYNVDSVSYNIGGTEWYIPLPRNIMTKGAFLGGANLQDCIESFSDY

ICPSDPGFILNRDIENCLSGNITQCPKTLVISDIVPRYAFVDGGVIANCLSTTCTCNGIDNRINQAPDQGIKIITYKDCQ

TIGINGMLFKTNQEGTLAAYTPVDITLNNSVNLDPIDLSIELNRVRSDLAESKEWIKRSEAKLSAIEDKIEEILSKIYHI

ENEIARIKKLIGEAP

In some embodiments, the protomers of the PIV3 F ectodomain trimer include an amino acid sequence set forth as residues 1-463 of any one of SEQ ID NOs: 69-74, or an amino acid sequence at least 90% identical thereto, wherein the C-terminus of the ectodomain trimer is linked to a trimerization domain (such as a GCN4 trimerization domain, for soluble ectodomain trimers) or a transmembrane domain (for membrane anchored embodiments). In some embodiments, the protomers of the PIV3 F ectodomain trimer include an amino acid sequence set forth as SEQ ID NO: 69-74, or an amino acid sequence at least 90% identical thereto.

Exemplary sequences of protomers of an PIV3 F ectodomain trimer stabilized in a prefusion conformation and linked to PIV3 TM and CT regions (for example, for use in an attenuated virus immunogen, or for DNA or RNA immunization) are provided as follows:

Bovine PIV3 F I172C-N238C/I474Y (based on ABZ85923.1)
(SEQ ID NO: 75)

QIDITKLQSVGVLVNSPKGIKISQNFETRYLILSLIPKIEDSHSCGNQQIDQYKKLLDRLIIPLYDGLKLQKDVIVVNHE
SHNNTNLRTKRFFGEIIGTIAIGIATSAQITAAVALVEAKQARSDIDKLKEAIKDTNKAVQSIQSSVGNLIVACKSVQDY
VNNEIVPSITRLGCEAAGLQLGIALTQHYSELTNIFGDNIGTLGEKGVKLQGIASLYRTCITEVFTTSTVDQYDIYDLLF
TESIKMRVIDVDLSDYSITLQVRLPLLTKVSNTQIYKVDSISYNIQGKEWYIPLPHHIMTKGAFLGGADIKECIESFSNY
ICPSDPGFILNHEMENCLSGNITQCPKTIVTSDIVPRYAFVDGGVIANCIPTTCTCNGIDNRINQSPDQGIKIITYKECQ
IVGINGMLFKTNQEGTLAKYTFDNIKLNNSVALNPIDISLELNKAKSDLEESKRWYEKSNQKLDSIGSWHQSSVTIIIII
VMIVVLLIINAIIIMIMIRYLRDRNRHLNNKDSEPYVLTNRQ

Bovine PIV3 F I172C-N238C/I474Y (based on AHZ90086.1)
(SEQ ID NO: 76)

QIDITKLQNVGVLVNSPKGIKISQNFETRYLILSLIPKIDDSHSCGNQQIDQYKKLLDRLIIPLYDGLKLQRDVIVVNHE
SHNNTNLRTKRFFGEIIGTIAIGIATSAQITAAVALVEAKQARSDIDKLKEAIKDTNKAVQSIQSSVGNLIVACKSVQDY
VNNEIVPSITRLGCEAAGLQLGIALTQHYSELTNIFGDNIGTLREKGVKLQGIASLYRTCITEVFTTSTVDQYDIYDLLF
TESIKMRVIDVDLSDYSITLQVRLPLLTKVSNTQIYKVDSISYNIQGKEWYIPLPHHIMTKGAFLGGADIKECIESFSNY
ICPSDPGFILNHELENCLSGNITQCPKTIVTSDIVPRYAFVDGGVIANCIPTTCTCNGIDNRINQSPDQGIKIITYKECQ
IVGINGMLFKTNQEGTLAKYTFDDIKLNNSVALNPIDISLELNKAKSELEESKRWYEKSNHKLDSIGSWYQSSATIIIII
VMIVVLLIINAIIIMITIKHLRARNRHPNNKDSEPYVLTNRQ

Caprine PIV3 F I172C-N238C/I474Y (based on AIW42876.1)
(SEQ ID NO: 77)

QVDIIKLQRVGILVSKPKSIKISQNFETRYLVLNLIPNIENAQSCGDQQIKQYKKLLDRLIIPLYDGLRLQQDIIVVDNN
LKNNTNHRAKRFFGEIIGTIALGVATSAQITAAVALVEAKQARSDIERVKNAVRDTNKAVQSIQGSVGNLIVACKSVQDY
VNNEIVPSIKRLGCEAAGLQLGIALTQHYSELTNIFGDNIGTLKEKGIKLQGIASLYHTCITEIFTTSTVDQYDIYDLLF
TESIKMRVIDVDLNDYSITLQVRLPLLTKISDAQIYNVDSVSYNIGGTEWYIPLPRNIMTKGAFLGGANLQDCIESFSDY
ICPSDPGFILNRDIENCLSGNITQCPKTLVISDIVPRYAFVDGGVIANCLSTTCTCNGIDNRINQAPDQGIKIITYKDCQ
TIGINGMLFKTNQEGTLAAYTPVDITLNNSVNLDPIDLSIELNRARSDLAESKEWYKRSEAKLDSVGSWYQSSTTEIIQI
VMIIVLFIINIIVLIVLIKYSRSQNQSMNNHMNEPYILTNKVQ

Bovine PIV3 F I172C-N238C/A463V (based on ABZ85923.1)
(SEQ ID NO: 78)

QIDITKLQSVGVLVNSPKGIKISQNFETRYLILSLIPKIEDSHSCGNQQIDQYKKLLDRLIIPLYDGLKLQKDVIVVNHE
SHNNTNLRTKRFFGEIIGTIAIGIATSAQITAAVALVEAKQARSDIDKLKEAIKDTNKAVQSIQSSVGNLIVACKSVQDY
VNNEIVPSITRLGCEAAGLQLGIALTQHYSELTNIFGDNIGTLGEKGVKLQGIASLYRTCITEVFTTSTVDQYDIYDLLF
TESIKMRVIDVDLSDYSITLQVRLPLLTKVSNTQIYKVDSISYNIQGKEWYIPLPHHIMTKGAFLGGADIKECIESFSNY
ICPSDPGFILNHEMENCLSGNITQCPKTIVTSDIVPRYAFVDGGVIANCIPTTCTCNGIDNRINQSPDQGIKIITYKECQ
IVGINGMLFKTNQEGTLAKYTFDNIKLNNSVALNPIDISLELNKVKSDLEESKRWIEKSNQKLDSIGSWHQSSVTIIIII
VMIVVLLIINAIIIMIMIRYLRDRNRHLNNKDSEPYVLTNRQ

Bovine PIV3 F I172C-N238C/A463V (based on AHZ90086.1)
(SEQ ID NO: 79)

QIDITKLQNVGVLVNSPKGIKISQNFETRYLILSLIPKIDDSHSCGNQQIDQYKKLLDRLIIPLYDGLKLQRDVIVVNHE
SHNNTNLRTKRFFGEIIGTIAIGIATSAQITAAVALVEAKQARSDIDKLKEAIKDTNKAVQSIQSSVGNLIVACKSVQDY
VNNEIVPSITRLGCEAAGLQLGIALTQHYSELTNIFGDNIGTLREKGVKLQGIASLYRTCITEVFTTSTVDQYDIYDLLF
TESIKMRVIDVDLSDYSITLQVRLPLLTKVSNTQIYKVDSISYNIQGKEWYIPLPHHIMTKGAFLGGADIKECIESFSNY
ICPSDPGFILNHELENCLSGNITQCPKTIVTSDIVPRYAFVDGGVIANCIPTTCTCNGIDNRINQSPDQGIKIITYKECQ
IVGINGMLFKTNQEGTLAKYTFDDIKLNNSVALNPIDISLELNKVKSELEESKRWIEKSNHKLDSIGSWYQSSATIIIII
VMIVVLLIINAIIIMITIKHLRARNRHPNNKDSEPYVLTNRQ

-continued

```
Caprine PIV3 F I172C-N238C/A463V (based on AIW42876.1)
                                                        (SEQ ID NO: 80)
QVDIIKLQRVGILVSKPKSIKISQNFETRYLVLNLIPNIENAQSCGDQQIKQYKKLLDRLIIPLYDGLRLQQDIIVVDNN

LKNNTNHRAKRFFGEIIGTIALGVATSAQITAAVALVEAKQARSDIERVKNAVRDTNKAVQSIQGSVGNLIVACKSVQDY

VNNEIVPSIKRLGCEAAGLQLGIALTQHYSELTNIFGDNIGTLKEKGIKLQGIASLYHTCITEIFTTSTVDQYDIYDLLF

TESIKMRVIDVDLNDYSITLQVRLPLLTKISDAQIYNVDSVSYNIGGTEWYIPLPRNIMTKGAFLGGANLQDCIESFSDY

ICPSDPGFILNRDIENCLSGNITQCPKTLVISDIVPRYAFVDGGVIANCLSTTCTCNGIDNRINQAPDQGIKIITYKDCQ

TIGINGMLFKTNQEGTLAAYTPVDITLNNSVNLDPIDLSIELNRVRSDLAESKEWIKRSEAKLDSVGSWYQSSTTEIIQI

VMIIVLFIINIIVLIVLIKYSRSQNQSMNNHMNEPYILTNKVQ
```

In some embodiments, the protomers of the PIV3 F ectodomain trimer include an amino acid sequence set forth as any one of SEQ ID NOs: 75-80, or an amino acid sequence at least 90% identical thereto.

E. hPIV4 F

In some embodiments, the immunogen comprises a recombinant hPIV4 F ectodomain trimer comprising protomers comprising one or more amino acid substitutions or deletions that stabilize the F ectodomain trimer in the prefusion conformation.

In some embodiments, the protomers of the recombinant hPIV4 F ectodomain trimer comprise Y457F and/or S471V substitutions for stabilization in the prefusion conformation. In some embodiments, the protomers of the recombinant hPIV4 F ectodomain trimer comprise Y457F and/or S471V substitutions, and a non-native disulfide bond between I166C and T232C substitutions for stabilization in the prefusion conformation.

In some embodiments, the recombinant hPIV4 F ectodomain trimer comprises protomers that are "single chain" proteins wherein the $F_2$ polypeptide and the $F_1$ ectodomain of each protomer are directly linked or linked via a peptide linker to form a contiguous polypeptide chain. In some embodiments, the recombinant $F_2$-$F_1$ ectodomain protomers in the disclosed recombinant hPIV4 F ectodomain trimers comprise a deletion of hPIV4 F positions 98-105, and a glycine-serine peptide linker between hPIV4 F positions 97-106; for example, the protomers of the hPIV4 F protein can each comprise a SEVQSRFF98-105GGGSGGGS (SEQ ID NO: 34 to SEQ ID NO: 32) substitution.

In several embodiments, the N-terminal position of the recombinant $F_2$ polypeptide in the protomer can be one of hPIV4 F positions 18-25 (such as position 21), and the C-terminal position of the $F_1$ ectodomain can be from the stem region of the ectodomain, such as one of hPIV4 F positions 470-486 (such as positions 475-480, for example, position 477).

In some embodiments, the protomers of the recombinant hPIV4 F ectodomain trimer include hPIV4 F positions 21-477, deletion of positions 98-105, insertion of a GGGSGGGS (SEQ ID NO: 32) peptide linker between position 97 and 106, Y457F and S471V cavity filling substitutions, and linkage to a C-terminal GCN4 trimerization domain.

In some embodiments, the protomers of the recombinant hPIV4 F ectodomain trimer include hPIV4 F positions 21-477, deletion of positions 98-105, insertion of a GGGSGGGS (SEQ ID NO: 32) peptide linker between position 97 and 106, Y457F and S471V cavity filling substitutions, a non-native disulfide bond between I166C and T232C substitutions, and linkage to a C-terminal GCN4 trimerization domain.

In some embodiments, the recombinant hPIV4 F ectodomain trimer can be a soluble protein complex, for example, for use as a recombinant subunit vaccine. In several such embodiments, the protomers of the recombinant hPIV4 F ectodomain trimer can each comprise a C-terminal linkage to a trimerization domain, such as a GCN4 trimerization domain. The trimerization domain promotes trimerization and stabilization of the membrane proximal aspect of the recombinant hPIV4 F ectodomain trimer. For example, a C-terminal residue of the protomers of the recombinant hPIV4 F ectodomain trimer (such as a residue of the stem region of the trimer) can be directly linked to the trimerization domain, or indirectly linked to the trimerization domain via a peptide linker. Exemplary linkers include glycine and glycine-serine linkers. Non-limiting examples of exogenous multimerization domains that promote stable trimers of soluble recombinant proteins include: the GCN4 leucine zipper, the trimerization motif from the lung surfactant protein (Hoppe et al. 1994 *FEBS Lett* 344:191-195), collagen (McAlinden et al. 2003 *J Biol Chem* 278:42200-42207) any of which can be linked to the C-terminus of the protomers of a recombinant hPIV4 F ectodomain to promote trimerization, as long as the recombinant hPIV4 F ectodomain trimer retains the prefusion conformation. In some examples, the protomers of the recombinant hPIV4 F ectodomain trimer can be linked to a GCN4 trimerization domain, for example, each protomer in the trimer can include a C-terminal linkage to the GCN4 trimerization domain, such as a linkage to any one of hPIV4 F positions 475-480, such as hPIV4 F position 477. In specific examples, the GCN4 fibritin trimerization domain can comprise the amino acid sequence IEDKIEEILSKIYHIENEIARIKKLIGEAP (residues 467-496 of SEQ ID NO: 7).

In other embodiments, the recombinant hPIV4 F ectodomain trimer can be a membrane anchored protein complex, for example, for use in an attenuated virus or virus like particle vaccine. Membrane anchoring can be accomplished, for example, by C-terminal linkage of the protomers of the recombinant hPIV4 F ectodomain trimer to a transmembrane domain and optionally a cytoplasmic tail, such as an hPIV4 F transmembrane domain and cytoplasmic tail. In some embodiments, one or more peptide linkers (such as a gly-ser linker, for example, a 10 amino acid glycine-serine peptide linker can be used to link the protomers of the recombinant hPIV4 F ectodomain trimer to the transmembrane domain A non-limiting example of a transmembrane domain for use with the disclosed embodiments is a hPIV4 F transmembrane domain, such as AIIILIILCILLILTVTICII (residues 487-507 of SEQ ID NO: 28).

Native hPIV4 F proteins from different hPIV4 strains, as well as nucleic acid sequences encoding such proteins and methods, are known. The disclosed recombinant hPIV4 F ectodomain trimers can be derived from any strain of hPIV4. Exemplary sequences of native hPIV4 F proteins include:

GENBANK: AHJ40477.2 (incorporated by reference herein)

(SEQ ID NO: 27)

MGVKGSSLIMIGLLISPITNLDITHLMNLGTVPTAIRSLVYYYTYTKPSYLTVDLIPNLKNLDQNCNYSSLNYYNKTALSL

IQPIADNINRLTKPIASSEVQSRFFGAVIGTIALGVATAAQVTAAIGLAKAQENAKLILTLKKAATETNEAVRDLANSNK

IVVKMISAIQNQINTIIQPAIDQINCQIKDLQVANILNLYLTEITTVFHNQLTNPALESISIQALKSLLGSTLPEVLSKL

DLNNISAASVMASGLIKGQIIAVDIPTMTLVLMVQIPSISPLRQAKIIDLTSITIHTNSQEVQAVVPARFLEIGSEILGF

DGSVCQITKDTIFCPYNDAYVLPIQQKRCLQGQTRDCVFTPVAGTFPRRFLTTYGTIVANCRDLVCSCLRPPQIIYQPDE

NPVTIIDKDLCTTLTLDSITIEIQKSINSTFRREVVLESTQVRSLTPLDLSTDLNQYNQLLKSAEDHIQRSTDYLNSINP

SIVNNNAIIILIILCILLILTVTICIIWLKYLTNEVKNVARNQRLNRDADLFHRIPSQIPVPRQ

GENBANK: AGU90035.1 (incorporated by reference herein)

(SEQ ID NO: 28)

MGVKGSSLIMIGLLISPITNLDITHLMNLGTVPTAIRSLVYYYTYTKPSYLTVDLIPNLKNLDQNCNYSSLNYYNKTALSL

IQPIADNINRLTKPITSSEVQSRFFGAVIGTIALGVATAAQVTAAIGLAKAQENAKLILTLKKAATETNEAVRDLANSNK

IVVKMISAIQNQINTIIQPAIDQINCQIKDLQVANILNLYLTEITTVFHNQLTNPALESISIQALKSLLGSTLPEVLSKL

DLNNISAASVMASGLIKGQIIAVDIPTMTLVLMVQIPSISPLRQAKIIDLTSITIHTNSQEVQAVVPARVLEIGSEILGF

DGSVCQITKDTVFCPYNDAYVLPIQQKRCLQGQTRDCVFTPVAGTFPRRFLTTYGTIVANCRDLVCSCLRPPQIIYQPDE

NPVTIIDKDLCTTLTLDSITIEIQKSINSTFRREVVLESTQVRSLTPLDLSTDLNQYNQLLKSAEDHIQRSTDYLNSINP

SIVNNNAIIILIILCILLILTVTICIIWLKYLTNEVKNVARNQRLNRDADLFHRIPSQIPVPRQ

Unless context indicates otherwise, reference to amino acid substitutions or deletions in hPIV4 F is made with reference to SEQ ID NO: 28. An exemplary sequence of a protomer of an hPIV4 F ectodomain trimer stabilized in a prefusion conformation is provided as the hPIV4_preF3 protein:

hPIV4_preF3

(SEQ ID NO: 29)

LDITHLMNLGTVPTAIRSLVYYYTYTKPSYLTVDLIPNLKNLDQNCNYSSL

NYYNKTALSLIQPIADNINRLTKPITSGGGSGGGSGAVIGTIALGVATAA

QVTAAIGLAKAQENAKLILTLKKAATETNEAVRDLANSNKIVVKMISAIQ

NQINTIIQPAIDQINCQIKDLQVANILNLYLTEITTVFHNQLTNPALESI

SIQALKSLLGSTLPEVLSKLDLNNISAASVMASGLIKGQIIAVDIPTMTL

VLMVQIPSISPLRQAKIIDLTSITIHTNSQEVQAVVPARVLEIGSEILGF

DGSVCQITKDTVFCPYNDAYVLPIQQKRCLQGQTRDCVFTPVAGTFPRRF

LTTYGTIVANCRDLVCSCLRPPQIIYQPDENPVTIIDKDLCTTLTLDSIT

IEIQKSINSTFRREVVLESTQVRSLTPLDLSTDLNQFNQLLKSAEDHIQR

VTDYLNSIEDKIEEILSKIYHIENEIARIKKLIGEAP hPIV4_preF3 includes a $F_1$-$F_2$ linker (SEVQSRFF98-105GGGSGGGS, SEQ ID NO: 34 to SEQ ID NO: 32), Y457F and S471V cavity filling substitutions, a C-term truncation at position 477, and C-terminal GCN4 trimerization domain.

An exemplary sequence of a protomer of an hPIV4 F ectodomain trimer stabilized in a prefusion conformation is provided as the hPIV4_preF4 protein:

hPIV4_preF4

(SEQ ID NO: 30)

LDITHLMNLGTVPTAIRSLVYYYTYTKPSYLTVDLIPNLKNLDQNCNYSSL

NYYNKTALSLIQPIADNINRLTKPITSGGGSGGGSGAVIGTIALGVATAA

-continued

QVTAAIGLAKAQENAKLILTLKKAATETNEAVRDLANSNKIVVKMCSAIQ

NQINTIIQPAIDQINCQIKDLQVANILNLYLTEITTVFHNQLTNPALESI

SIQALKSLLGSCLPEVLSKLDLNNISAASVMASGLIKGQIIAVDIPTMTL

VLMVQIPSISPLRQAKIIDLTSITIHTNSQEVQAVVPARVLEIGSEILGF

DGSVCQITKDTVFCPYNDAYVLPIQQKRCLQGQTRDCVFTPVAGTFPRRF

LTTYGTIVANCRDLVCSCLRPPQIIYQPDENPVTIIDKDLCTTLTLDSIT

IEIQKSINSTFRREVVLESTQVRSLTPLDLSTDLNQFNQLLKSAEDHIQR

VTDYLNSIEDKIEEILSKIYHIENEIARIKKLIGEAP hPIV4_preF4 includes a $F_1$-$F_2$ linker (SEVQSRFF98-105GGGSGGGS, SEQ ID NO: 34 to SEQ ID NO: 32), Y457F and S471V cavity filling substitutions, a non-native disulfide bond between I166C-T232C substitutions, a C-term truncation at position 477, and C-terminal GCN4 trimerization domain.

In some embodiments, the protomers of the hPIV4 F ectodomain trimer include an amino acid sequence set forth as residues 1-457 of any one of SEQ ID NOs: 29-30, or an amino acid sequence at least 90% identical thereto, wherein the C-terminus of the ectodomain trimer is linked to a trimerization domain (such as a GCN4 trimerization domain, for soluble ectodomain trimers) or a transmembrane domain (for membrane anchored embodiments). In some embodiments, the protomers of the hPIV4 F ectodomain trimer include an amino acid sequence set forth as SEQ ID NO: 29-30, or an amino acid sequence at least 90% identical thereto.

In some embodiments, the immunogen comprises a recombinant hPIV4 F ectodomain trimer comprising protomers comprising the one or more amino acid substitutions or deletions noted below for stabilizing the hPIV3 F ectodomain trimer in its prefusion conformation. For example, in some embodiments, the protomers of the recombinant hPIV4 F ectodomain trimer comprise a non-native disulfide bond between one of 172C-238C, 170C-242C, 213C-230C, 85C-222C, or 216C-221C substitutions for stabilization in the prefusion conformation. The residue numbering for these substitutions is made with reference to the PIV3 F sequence set forth as SEQ ID NO: 9, and the substitutions are introduced into hPIV1 F at residues corresponding to the hPIV3 F SEQ ID NO: 9 sequence. In some embodiments, the protomers of the recombinant hPIV3 F ectodomain trimer comprise two or more non-native disulfide bonds between sets of substitutions selected from 172C-238C, 170C-242C, 213C-230C, 85C-222C, or 216C-221C substitutions for stabilization in the prefusion conformation. Exemplary combinations for prefusion stabilization include: 162C-168C and 213C-230C; 162C-168 and 216C-221C; 162C-168C and 85C-222C; 213C-230C and 170C-242C; 213C-230C and 216C-221C; and 213C-230C and 85C-222C. In some embodiments, the hPIV4 F protomers further comprise cavinty filling substitutions corresponding to the hPIV3 F 463V and 474Y cavity filling substitutions for stabilization in the prefusion conformation. In several embodiments, the hPIV4 F ectodomain trimers can be soluble (e.g., can include a GCN4 trimerization domain as discussed above) or can be membrane anchored (e.g., the full-length hPIV4 F sequence is modified with the prefusion stabilizing amino acid substitutions).

F. Additional Description

The protomers in the recombinant PIV F ectodomain trimer can comprise modifications of the native PIV F sequence in addition to those noted above, such as amino acid substitutions, deletions or insertions, glycosylation and/or covalent linkage to unrelated proteins (e.g., a protein tag), as long as the recombinant PIV F ectodomain trimer remains stabilized in the prefusion conformation. These variations in sequence can be naturally occurring variations or they can be engineered through the use of genetic engineering technique known to those skilled in the art. Examples of such techniques are found in see, e.g., Sambrook et al. (Molecular Cloning: A Laboratory Manual, $4^{th}$ ed., Cold Spring Harbor, New York, 2012) and Ausubel et al. (In Current Protocols in Molecular Biology, John Wiley & Sons, New York, through supplement 104, 2013, both of which are incorporated herein by reference in their entirety.

In some embodiments, the protomers in the recombinant PIV F ectodomain trimer can comprise one or more amino acid substitutions compared to a corresponding native PIV F sequence. For example, in some embodiments, the $F_2$ polypeptide, $F_1$ ectodomain, or both, can include up to 20 (such as up to 1, 2, 3, 4, 5, 6, 7, 8, 9, 10, 11, 12, 13, 14, 15, 16, 17, 18, or 19) amino acid substitutions (such as conservative amino acid substitutions) compared to a native PIV F ectodomain sequence. The simplest modifications involve the substitution of one or more amino acids for amino acids having similar biochemical properties, such as conservative amino acid substitutions. Such substitutions are likely to have minimal impact on the activity of the resultant protein.

In some embodiments, protomers in the recombinant PIV F ectodomain trimer can be joined at either end to other unrelated sequences (for example non-PIV F protein sequences, non-viral envelope, or non-viral protein sequences)

In several embodiments, the recombinant PIV F ectodomain trimers disclosed herein are soluble in aqueous solution. In some embodiments, the recombinant PIV F ectodomain dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in aqueous solution (such as phosphate buffered saline (pH 7.4) or 350 mM NaCl (pH 7.0)) at room temperature (e.g., 20-22 degrees Celsius) and remain dissolved for at least 12 hours (such as at least 24 hours, at least 48 hours, at least one week, at least two weeks, at least one month, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$ (1 mM) and $MgCl_2$ (0.5 mM). The person of skill in the art is familiar with methods of determining if a protein remains in solution over time. For example, the concentration of the protein dissolved in an aqueous solution can be tested over time using standard methods.

In some embodiments, the recombinant PIV F ectodomain trimer can be provided as a homogenous population that does not include detectable PIV F ectodomain trimer in a post-fusion conformation. The conformation of the PIV F ectodomain trimer can be detected, for example, by negative stain electron microscopy and/or specific binding by appropriate pre- or post-fusion specific antibody. In some embodiments, at least about 95% of the recombinant PIV F ectodomain trimer (such as at least about 95%, 96%, 97%, 98%, 99% or 99.9% of the PIV F proteins) in the homogeneous population are stabilized in the prefusion conformation.

In some embodiments, the recombinant PIV F ectodomain trimer retains specific binding for a prefusion specific antibody following incubation at 50° C. for one hour in phosphate buffered saline. In some embodiments, the recombinant PIV F ectodomain trimer retains specific binding for a prefusion specific antibody following incubation at 4° C. for six months in phosphate buffered saline.

In certain embodiments, an immunogen provided herein may be further modified to contain additional nonproteinaceous moieties that are known in the art and readily available. The moieties suitable for derivatization of the immunogen include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the immunogen to be improved or altered, whether the immunogen derivative will be used in a therapy under defined conditions, etc.

The recombinant PIV F ectodomain can be derivatized or linked to another molecule (such as another peptide or protein). In general, the recombinant PIV F ectodomain is derivatized such that the binding to broadly neutralizing antibodies to a trimer of the recombinant PIV F protein is not affected adversely by the derivatization or labeling. For example, the recombinant PIV F ectodomain can be functionally linked (by chemical coupling, genetic fusion, noncovalent association or otherwise) to one or more other molecular entities, such as an antibody or protein or detection tag.

Some of the sequences of recombinant PIV F ectodomain provided herein include the sequence of protease cleavage sites (such as thrombin sites), protein tags (such as a His tag, a Strep Tag II, a Avi tag, etc.), and signal peptides; such sequences can be removed from an isolated immunogen including a recombinant PIV F ectodomain trimer for therapeutic use.

G. Protein Nanoparticles

In some embodiments a protein nanoparticle is provided that includes one or more of the disclosed recombinant PIV F ectodomain trimers (e.g., a hPIV3 F ectodomain trimer). Non-limiting example of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase, respectively. To construct such protein nanoparticles a protomer of the PIV F ectodomain trimer can be linked to a subunit of the protein nanoparticle (such as a ferritin protein, an encapsulin protein, a SOR protein, or a lumazine synthase protein) and expressed in cells under appropriate conditions. The fusion protein self-assembles into a nanoparticle any can be purified.

In some embodiments, a protomer of a disclosed recombinant PIV F ectodomain trimer (e.g., a PIV3 F ectodomain trimer) can be linked to a ferritin subunit to construct a ferritin nanoparticle. Ferritin nanoparticles and their use for immunization purposes (e.g., for immunization against influenza antigens) have been disclosed in the art (see, e.g., Kanekiyo et al., Nature, 499:102-106, 2013, incorporated by reference herein in its entirety). Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of the ferritin nanoparticle is made up of monomeric subunits, which are polypeptides having a molecule weight of approximately 17-20 kDa. An example of the amino acid sequence of one such monomeric ferritin subunit is represented by:

(SEQ ID NO: 35)
ESQVRQQFSKDIEKLLNEQVNKEMQSSNLYMSMSSWCYTHSLDGAGLFLF

DHAAEEYEHAKKLIIFLNENNVPVQLTSISAPEHKFEGLTQIFQKAYEHE

QHISESINNIVDHAIKSKDHATFNFLQWYVAEQHEEEVLFKDILDKIELI

GNENHGLYLADQYVKGIAKSRKS

Each monomeric subunit has the topology of a helix bundle which includes a four antiparallel helix motif, with a fifth shorter helix (the C-terminal helix) lying roughly perpendicular to the long axis of the 4 helix bundle. According to convention, the helices are labeled 'A, B, C, D & E' from the N-terminus respectively. The N-terminal sequence lies adjacent to the capsid three-fold axis and extends to the surface, while the E helices pack together at the four-fold axis with the C-terminus extending into the capsid core. The consequence of this packing creates two pores on the capsid surface. It is expected that one or both of these pores represent the point by which the hydrated iron diffuses into and out of the capsid. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are further described herein (see, e.g., Zhang, *Int. J. Mol. Sci.,* 12:5406-5421, 2011, which is incorporated herein by reference in its entirety).

In specific examples, the ferritin polypeptide is *E. coli* ferritin, *Helicobacter pylori* ferritin, human light chain ferritin, bullfrog ferritin or a hybrid thereof, such as *E. coli*-human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides for use to make a ferritin nanoparticle including a recombinant PIV F ectodomain trimer can be found in GENBANK®, for example at accession numbers ZP_03085328, ZP_06990637, EJB64322.1, AAA35832, NP_000137 AAA49532, AAA49525, AAA49524 and AAA49523, which are specifically incorporated by reference herein in their entirety as available Apr. 10, 2015. In some embodiments, a protomer of a recombinant PIV F ectodomain trimer (e.g., a hPIV3 F ectodomain trimer) can be linked to a ferritin subunit including an amino acid sequence at least 80% (such as at least 85%, at least 90%, at least 95%, or at least 97%) identical to amino acid sequence set forth as SEQ ID NO: 35.

In some embodiments, a protomer of a disclosed recombinant PIV F ectodomain trimer (e.g., a hPIV3 F ectodomain trimer) can be linked to a lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

(SEQ ID NO: 36)
MQIYEGKLTAEGLRFGIVASRFNHALVDRLVEGAIDAIVRHGGREEDITL

VRVPGSWEIPVAAGELARKEDIDAVIAIGVLIRGATPHEDYIASEVSKGL

ADLSLELRKPITFGVITADTLEQAIERAGTKHGNKGWEAALSAIEMANLF

KSLR.

In some embodiments, a protomer of a disclosed recombinant PIV F ectodomain trimer can be linked to a lumazine synthase subunit including an amino acid sequence at least 80% (such as at least 85%, at least 90%, at least 95%, or at least 97%) identical to amino acid sequence set forth as SEQ ID NO:36.

In some embodiments, a protomer of a disclosed recombinant PIV F ectodomain trimer (e.g., a hPIV3 F ectodomain trimer) can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as (SEQ ID NO: 37)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

-continued

```
AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.
```

In some embodiments, a protomer of a disclosed recombinant PIV F ectodomain trimer (e.g., a hPIV3 F ectodomain trimer) can be linked to an encapsulin subunit including an amino acid sequence at least 80% (such as at least 85%, at least 90%, at least 95%, or at least 97%) identical to amino acid sequence set forth as SEQ ID NO: 37.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60, or in some cases, 180 monomeric subunits. Methods of constructing encapsulin nanoparticles are further described (see, for example, Sutter et al., Nature Struct. and Mol. Biol., 15:939-947, 2008, which is incorporated by reference herein in its entirety). In specific examples, the encapsulin polypeptide is bacterial encapsulin, such as *Thermotoga maritime* or *Pyrococcus furiosus* or *Rhodococcus erythropolis* or *Myxococcus xanthus* encapsulin.

In some embodiments, a protomer of a disclosed recombinant PIV F ectodomain trimer (e.g., a hPIV3 F ectodomain trimer) can be linked to a Sulfur Oxygenase Reductase (SOR) subunit to construct a recombinant SOR nanoparticle. In some embodiments, the SOR subunit can include the amino acid sequence set forth as

```
                                      (SEQ ID NO: 38)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETE

TFQVVNPEALILLKF.
```

In some embodiments, a protomer of a disclosed recombinant PIV F ectodomain trimer (e.g., a hPIV3 F ectodomain trimer) can be linked to a SOR subunit including an amino acid sequence at least 80% (such as at least 85%, at least 90%, at least 95%, or at least 97%) identical to amino acid sequence set forth as SEQ ID NO: 38.

SOR proteins are microbial proteins (for example from the thermoacidophilic archaeon *Acidianus ambivalens* that form 24 subunit protein assemblies. Methods of constructing SOR nanoparticlesare described in Urich et al., Science, 311:996-1000, 2006, which is incorporated by reference herein in its entirety. An example of an amino acid sequence of a SOR protein for use to make SOR nanoparticles is set forth in Urich et al., Science, 311:996-1000, 2006, which is incorporated by reference herein in its entirety.

For production purposes, the recombinant PIV F ectodomain linked to the nanoparticle subunit can include an N-terminal signal peptide that is cleaved during cellular processing. For example, the recombinanthPIV F ectodomain protomer linked to the protein nanoparticle subunit can include a signal peptide at its N-terminus including, for example, a native PIV F signal peptide.

The protein nanoparticles can be expressed in appropriate cells (e.g., HEK 293 Freestyle cells) and fusion proteins are secreted from the cells self-assembled into nanoparticles. The nanoparticles can be purified using known techniques, for example by a few different chromatography procedures, e.g. Mono Q (anion exchange) followed by size exclusion (SUPEROSE® 6) chromatography.

Several embodiments include a monomeric subunit of a ferritin, encapsulin, SOR, or lumazine synthase protein, or any portion thereof which is capable of directing self-assembly of monomeric subunits into the globular form of the protein Amino acid sequences from monomeric subunits of any known ferritin, encapsulin, SOR, or lumazine synthase protein can be used to produce fusion proteins with the recombinant PIV F ectodomain, so long as the monomeric subunit is capable of self-assembling into a nanoparticle displaying the recombinant PIV F ectodomain trimer on its surface.

The fusion proteins need not comprise the full-length sequence of a monomeric subunit polypeptide of a ferritin, encapsulin, SOR, or lumazine synthase protein. Portions, or regions, of the monomeric subunit polypeptide can be utilized so long as the portion comprises amino acid sequences that direct self-assembly of monomeric subunits into the globular form of the protein.

III. Polynucleotides and Expression

Polynucleotides encoding a protomer of any of the disclosed PIV F ectodomain trimers (such as a hPIV1, hPIV2, hPIV3, cPIV3, bPIV3, or hPIV4 F ectodomain trimer) are also provided. These polynucleotides include DNA, cDNA and RNA sequences which encode the protomer. The genetic code can be used to construct a variety of functionally equivalent nucleic acids, such as nucleic acids which differ in sequence but which encode the same protein sequence, or encode a conjugate or fusion protein including the nucleic acid sequence.

In several embodiments, the nucleic acid molecule encodes a precursor of a protomer of the hPIV1, hPIV2, hPIV3, cPIV3, bPIV3, or hPIV4 F ectodomain trimer, that, when expressed in an appropriate cell, is processed into a protomer of the F ectodomain trimer that can self-assemble into the corresponding trimer. For example, the nucleic acid molecule can encode a protomer of the hPIV1, hPIV2, hPIV3, cPIV3, bPIV3, or hPIV4 F ectodomain trimer including a N-terminal signal sequence for entry into the cellular secretory system that is proteolytically cleaved in the during processing of the recombinant F ectodomain in the cell.

In several embodiments, the nucleic acid molecule encodes a $F_0$ polypeptide that, when expressed in an appropriate cell, is processed into a protomer of the hPIV1, hPIV2, hPIV3, cPIV3, bPIV3, or hPIV4 F ectodomain trimer including an $F_2$ polypeptide linked to a $F_1$ ectodomain, wherein the recombinant $F_2$-$F_1$ ectodomain protomer includes any of the stabilizing modifications described herein, and optionally can be linked to a trimerization domain, such as a GCN4 trimerization domain.

Exemplary nucleic acid sequences include:

hPIV1_880_preF2 (with signal peptide and Strep-His tag, SEQ ID NO: 81)
ATGCCCATGGGCAGCCTGCAGCCCCTGGCCACCCTGTACCTGCTGGGCATGCTGGTGGCCTCCGTGCTGGCCGGATCCCA

GATCCCTGTGGATAAGCTGAGCAACGTGGGCGTGATCATCAATGAGGGCAAGCTGCTGAAGATCGCCGGCTCTTACGAGA

GCCGGTATATCGTGCTGTCCCTGGTGCCATCTATCGACCTGCAGGATGGCTGCGGCACCACACAGATCATCCAGTACAAG

AACCTGCTGAATAGACTGCTGATCCCACTGAAGGACGCCCTGGATCTGCAGGAGAGCCTGATCACCATCACAAATGATAC

CACAGTGACCAACGACAATCCACAGACAAGGGGCTCCGGAGCCGTGATCGGAACCATCGCCCTGGGAGTGGCAACCGCAG

CACAGATCACAGCAGGAATCGCCCTGGCCGAGGCAAGGGAGGCCCGCAAGGATATCGCCCTGATCAAGGACTCTATCGTG

AAGACCCACAATAGCGTGGAGTTCATCCAGCGGGGCATCGGCGAGCAGATCATCGCCCTGAAGACACTGCAGGATTTTGT

GAACGACGAGATCCGGCCTGCCATCGGCGAGCTGAGATGTGAGACAACAGCCCTGAAGCTGGGCATCAAGCTGACCCAGC

ACTACTCCGAGCTGGCCACAGCCTTCAGCTCCAATCTGGGCACCATCGGCGAGAAGAGCCTGACACTGCAGGCCCTGTCT

AGCCTGTATTCCGCCAACATCACCGAGATCCTGTCCACAATCAAGAAGGACAAGTCTGATATCTACGACATCATCTATAC

CGAGCAGGTGAAGGGCACAGTGATCGACGTGGATCTGGAGAAGTATATGGTGACCCTGCTGGTGAAGATCCCAATCCTGT

CTGAGATCCCAGGCGTGCTGATCTACAGGGCCTCCTCTATCAGCTATAACATCGAGGGAGAGGAGTGGCACGTGGCAATC

CCCAACTACATCATCAATAAGGCCAGCTCCCTGGGAGGAGCAGATGTGACCAATTGCATCGAGTCTAAGCTGGCCTATAT

CTGTCCCAGAGATCCTACACAGCTGATCCCTGACAACCAGCAGAAGTGCATCCTGGGCGACGTGAGCAAGTGTCCCGTGA

CCAAAGTGATCAACAATCTGGTGCCTAAGTTCGCCTTTATCAACGGCGGCGTGGTGGCCAATTGCATCGCCTCCACCTGC

ACATGTGGCACCAACAGAATCCCCGTGAATCAGGATCGCTCTAAGGGCGTGACATTCCTGACCTACACAAACTGTGGCCT

GATCGGCATCAATGGCATCGAGCTGTATGCCAACAAGCGGGGCAGAGATACCACATGGGGCAATCAGATCATCAAGGTCG

GCCCTGCCGTGTCCATCAGGCCAGTGGACATCAGCCTGAACCTGGCCTCCATCACCAATTTTCTGGAGGAGATCAAGACA

GAGCTGATGAAGATCGAGGACAAGATCGAGGAGATCCTGTCTAAAATCTACCACATCGAGAACGAGATCGCCCGCATCAA

GAAGCTGATCGGCGAGGCCCCCGCTAGCGGAGGAGGACTGGAAGTGCTGTTCCAGGGCCCCGGGTCTGATTACAAGGACG

ATGACGATAAAGGCAGCGGCTCTGCCTGGTCACATCCCCAGTTTGAGAAGGGAGGCGGGAGCGGCGGAGGGAGCGGAGGC

TCCGCTTGGAGCCATCCCCAGTTTGAGAAAGGCAGCGGGCACCACCACCACCACCACCACCACTGA hPIV2-6 (with signal peptide and strep-His tag, SEQ ID NO: 82)
ATGCCCATGGGCAGCCTGCAGCCCCTGGCCACCCTGTACCTGCTGGGCATGCTGGTGGCCTCCGTGCTGGCCGGATCCGA

CGCCATCGCTGGAGATCAGCTGCTGAATATCGGCGTGATTCAGTCTAAGATCCGGAGTCTGATGTACTATACCGACGGCG

GGGCCAGCTTCATTGTGGTCAAACTGCTGCCCAACCTGCCCCCTTCCAACGGGACATGCAATATCACTTCTCTGGACGCC

TACAATGTGACCCTGTTTAAGCTGCTGACACCTCTGATCGAGAACCTGAGTAAAATTTCAACTGTGACCGATACAGGAGG

CGGGTCAGGAGGAGGGAGCGGAGTGGTCGTGGGCCTGGCCGCTCTGGGCGTGGCTACTGCAGCCCAGATCACCGCTGCAG

TGGCAATTGTCAAGGCAAACGCCAATGCCGCTGCAATCAACAATCTGGCCAGCTCCATTCAGAGTACTAACAAGGCAGTG

TCAGACGTGATCGATGCCAGCCGGACCATTGCTACAGCAGTGCAGGCTATCCAGGACAGAATTAATGGCGCAATCGTCAA

CGGGATTACATCAGCCAGCTGTAGGGCACACGATGCCCTGATCGGCAGCATTCTGAACCTGTACCTGACTGAGCTGACCA

CAATCTTCCATAACCAGATTACAAATCCCGCTCTGACTCCTCTGTCTATCCAGGCACTGCGCATTCTGCTGGGCAGTACC

CTGCCAATCGTGATTGAGTCAAAGCTGAACACCAATTTCAACACAGCCGAACTGCTGTCTAGTGGGCTGCTGACCGGACA

GATCATTTCCATCTCTCCCATGTATATGCAGATGCTGATCCAGATTAACGTGCCCACCTTCATCATGCAGCCCGGCGCCA

AGGTCATTGACCTGATCGCTATTAGCGCAAATCACAAACTGCAGGAAGTCGTGGTCCAGGTGCCTAACAGAATCCTGGAG

TACGCCAACGAACTGCAGAATTATCCTGCTAACGATTGCGTGGTCACACCAAATAGCGTGTTTTGTCGATACAACGAGGG

CTCCCCTATCCCAGAATCTCAGTATCAGTGCCTGCGGGGGAATCTGAACAGCTGTACTTTCACCCCAATCATTGGGAATT

TTCTGAAGAGATTCGCCTTTGCTAATGGAGTGCTGTACGCTAACTGCAAAAGCCTGCTGTGCAGGTGTGCCGACCCACCA

CACGTGGTCAGCCAGGACGATACTCAGGGCATCTCCATCATTGACATTAAGAGGTGTTCTGAGATGATGCTGGATACCTT

CAGTTTTCGCATCACATCAACTTTCAACGCTACTTATGTGACCGACTTTTCCATGATCAATGCCAACATTGTCCATCTGA

-continued

GCCCCCTGGATCTGTCCAATCAGATCAACTCTATTAATAAGAGCCTGAAATCCGCCGAGGACTGGATCGCTGATAGTAAT

TTCTTTGCCAACCAGGCTCGCACCGCAATGAAGCAGATTGAAGATAAGATCGAGGAAATTCTGTCTAAGATCTATCATAT

CGAGAACGAAATCGCACGAATTAAGAAACTGATCGGCGAAGCCCCTGCTAGCGGAGGAGGACTGGAAGTGCTGTTCCAGG

GCCCCGGGTCTGATTACAAGGACGATGACGATAAAGGCAGCGGCTCTGCCTGGTCACATCCCCAGTTTGAGAAGGGAGGC

GGGAGCGGCGGAGGGAGCGGAGGCTCCGCTTGGAGCCATCCCCAGTTTGAGAAAGGCAGCGGGCACCACCACCACCACCA

CCACCACTGA hPIV4_preF3 (with signal peptide and Strep-His tag, SEQ ID NO: 83)
ATGCCCATGGGCAGCCTGCAGCCCCTGGCCACCCTGTACCTGCTGGGCATGCTGGTGGCCTCCGTGCTGGCCGGATCCCT

GGATATCACCCACCTGATGAACCTGGGCACCGTGCCAACAGCCATCCGGTCTCTGGTGTACTATACCTACACAAAGCCTA

GCTATCTGACCGTGGATCTGATCCCAAACCTGAAGAATCTGGACCAGAACTGCAATTACAGCTCCCTGAACTACTATAAT

AAGACAGCCCTGTCCCTGATCCAGCCCATCGCCGACAACATCAATAGACTGACAAAGCCTATCACCTCCGGAGGAGGCTC

TGGAGGAGGCAGCGGAGCCGTGATCGGAACCATCGCCCTGGGAGTGGCAACAGCAGCACAGGTGACCGCCGCCATCGGCC

TGGCCAAGGCCCAGGAGAACGCCAAGCTGATCCTGACACTGAAGAAGGCCGCCACCGAGACAAATGAGGCCGTGAGGGAT

CTGGCCAACAGCAATAAGATCGTGGTGAAGATGATCTCCGCCATCCAGAACCAGATCAATACCATCATCCAGCCTGCCAT

CGATCAGATCAATTGTCAGATCAAGGACCTGCAGGTGGCCAACATCCTGAATCTGTATCTGACCGAGATCACCACAGTGT

TCCACAACCAGCTGACAAATCCAGCCCTGGAGTCTATCAGCATCCAGGCCCTGAAGTCCCTGCTGGGCTCTACCCTGCCA

GAGGTGCTGTCTAAGCTGGATCTGAACAATATCAGCGCCGCCTCCGTGATGGCCAGCGGACTGATCAAGGGCCAGATCAT

CGCCGTGGACATCCCTACCATGACACTGGTGCTGATGGTGCAGATCCCATCCATCTCTCCCCTGCGGCAGGCCAAGATCA

TCGATCTGACCTCTATCACAATCCACACCAACAGCCAGGAGGTGCAGGCAGTGGTGCCAGCCAGAGTGCTGGAGATCGGC

TCCGAGATCCTGGGCTTCGACGGCAGCGTGTGCCAGATCACAAAGGATACCGTGTTTTGTCCATACAATGACGCCTATGT

GCTGCCCATCCAGCAGAAGCGGTGCCTGCAGGGCCAGACCAGAGATTGCGTGTTCACCCCAGTGGCAGGCACCTTCCCTC

GGAGATTTCTGACCACATACGGCACAATCGTGGCCAACTGCAGGGATCTGGTGTGCTCCTGTCTGCGCCCCCCTCAGATC

ATCTATCAGCCTGACGAGAATCCAGTGACCATCATCGACAAGGACCTGTGCACCACACTGACACTGGACAGCATCACCAT

CGAGATCCAGAAGTCTATCAACAGCACATTCAGGCGCGAGGTGGTGCTGGAGAGCACACAGGTGAGGTCCCTGACCCCAC

TGGACCTGAGCACCGACCTGAACCAGTTTAATCAGCTGCTGAAGTCCGCCGAGGACCACATCCAGAGGGTGACCGATTAC

CTGAACTCCATCGAGGACAAGATCGAGGAGATCCTGTCTAAAATCTACCACATCGAGAATGAGATCGCCCGGATCAAGAA

GCTGATCGGCGAGGCCCCTGCTAGCGGAGGAGGACTGGAAGTGCTGTTCCAGGGCCCCGGGTCTGATTACAAGGACGATG

ACGATAAAGGCAGCGGCTCTGCCTGGTCACATCCCCAGTTTGAGAAGGGAGGCGGGAGCGGCGGAGGGAGCGGAGGCTCC

GCTTGGAGCCATCCCCAGTTTGAGAAAGGCAGCGGGCACCACCACCACCACCACCACCACTGA hPIV4_preF4 (with signal peptide and Strep-His tag, SEQ ID NO: 84)
ATGCCCATGGGCAGCCTGCAGCCCCTGGCCACCCTGTACCTGCTGGGCATGCTGGTGGCCTCCGTGCTGGCCGGATCCCT

GGATATCACCCACCTGATGAACCTGGGCACCGTGCCAACAGCCATCCGGTCTCTGGTGTACTATACCTACACAAAGCCTA

GCTATCTGACCGTGGATCTGATCCCAAACCTGAAGAATCTGGACCAGAACTGCAATTACAGCTCCCTGAACTACTATAAT

AAGACAGCCCTGTCCCTGATCCAGCCCATCGCCGACAACATCAATAGACTGACAAAGCCTATCACCTCCGGAGGAGGCTC

TGGAGGAGGCAGCGGAGCCGTGATCGGAACCATCGCCCTGGGAGTGGCAACAGCAGCACAGGTGACCGCCGCCATCGGCC

TGGCCAAGGCCCAGGAGAACGCCAAGCTGATCCTGACACTGAAGAAGGCCGCCACCGAGACAAATGAGGCCGTGAGGGAT

CTGGCCAACAGCAATAAGATCGTGGTGAAGATGTGCTCCGCCATCCAGAACCAGATCAATACCATCATCCAGCCTGCCAT

CGATCAGATCAATTGTCAGATCAAGGACCTGCAGGTGGCCAACATCCTGAATCTGTATCTGACCGAGATCACCACAGTGT

TCCACAACCAGCTGACAAATCCAGCCCTGGAGTCTATCAGCATCCAGGCCCTGAAGTCCCTGCTGGGCTCTTGTCTGCCA

GAGGTGCTGTCTAAGCTGGATCTGAACAATATCAGCGCCGCCTCCGTGATGGCCAGCGGACTGATCAAGGGCCAGATCAT

CGCCGTGGACATCCCTACCATGACACTGGTGCTGATGGTGCAGATCCCATCCATCTCTCCCCTGCGGCAGGCCAAGATCA

-continued

TCGATCTGACCTCTATCACAATCCACACCAACAGCCAGGAGGTGCAGGCAGTGGTGCCAGCCAGAGTGCTGGAGATCGGC

TCCGAGATCCTGGGCTTCGACGGCAGCGTGTGCCAGATCACAAAGGATACCGTGTTTTGTCCATACAATGACGCCTATGT

GCTGCCCATCCAGCAGAAGCGGTGCCTGCAGGGCCAGACCAGAGATTGCGTGTTCACCCCAGTGGCAGGCACCTTCCCTC

GGAGATTTCTGACCACATACGGCACAATCGTGGCCAACTGCAGGGATCTGGTGTGCTCCTGTCTGCGCCCCCCTCAGATC

ATCTATCAGCCTGACGAGAATCCAGTGACCATCATCGACAAGGACCTGTGCACCACACTGACACTGGACAGCATCACCAT

CGAGATCCAGAAGTCTATCAACAGCACATTCAGGCGCGAGGTGGTGCTGGAGAGCACACAGGTGAGGTCCCTGACCCCAC

TGGACCTGAGCACCGACCTGAACCAGTTTAATCAGCTGCTGAAGTCCGCCGAGGACCACATCCAGAGGGTGACCGATTAC

CTGAACTCCATCGAGGACAAGATCGAGGAGATCCTGTCTAAAATCTACCACATCGAGAATGAGATCGCCCGGATCAAGAA

GCTGATCGGCGAGGCCCCTGCTAGCGGAGGAGGACTGGAAGTGCTGTTCCAGGGCCCCGGGTCTGATTACAAGGACGATG

ACGATAAAGGCAGCGGCTCTGCCTGGTCACATCCCCAGTTTGAGAAGGGAGGCGGAGCGGCGGAGGGAGCGGAGGCTCC

GCTTGGAGCCATCCCCAGTTTGAGAAAGGCAGCGGGCACCACCACCACCACCACCACCACTGA

HPIV3 F GNC4 A463V, I474Y (SEQ ID NO: 85)

GGTACCGCCACCATGTACTCAATGCAGCTGGCCTCTTGCGTCACACTGACACTGGTCCTGCTGGTCAACTCACAGATCGA

CATCACTAAACTGCAGCACGTCGGGGTGCTGGTCAACTCCCCAAAGGGAATGAAAATTTCTCAGAATTTCGAGACAAGAT

ACCTGATCCTGAGCCTGATTCCCAAGATCGAAGATTCAAACAGCTGCGGGGACCAGCAGATTAAGCAGTACAAACGACTG

CTGGATCGGCTGATCATTCCTCTGTATGATGGACTGAAGCTGCAGAAAGACGTGATCGTCACAAATCAGGAGTCCAACGA

AAATACCGACCCAAGGACAGAGCGCTTCTTTGGAGGCGTGATCGGAACTATCGCACTGGGAGTCGCTACTTCTGCACAGA

TCACCGCAGCTGTGGCTCTGGTCGAGGCCAAGCAGGCTAAAAGTGATATTGAGAAGCTGAAAGAAGCCATCCGAGACACC

AACAAGGCTGTGCAGAGCGTCCAGAGCTCCGTGGGCAATCTGATTGTCGCCATCAAGTCAGTGCAGGATTACGTCAACAA

AGAGATTGTGCCCAGCATCGCACGCCTGGGGTGTGAAGCAGCAGGACTGCAGCTGGGAATCGCACTGACCCAGCACTACT

CCGAGCTGACAAACATTTTTGGGGACAATATCGGATCTCTGCAGGAAAAGGGCATCAAGCTGCAGGGCATCGCTAGTCTG

TATAGGACAAATATTACTGAGATCTTCACCACATCAACTGTGGACAAGTACGATATCTATGACCTGCTGTTTACCGAAAG

CATCAAGGTGAGAGTGATCGACGTGGATCTGAACGATTATTCCATTACTCTGCAGGTCAGACTGCCTCTGCTGACAAGGC

TGCTGAATACTCAGATCTACAAGGTGGACTCCATTTCTTATAACATCCAGAATCGGGAGTGGTACATTCCACTGCCCTCT

CACATCATGACCAAGGGCGCATTCCTGGGAGGCGCCGATGTGAAAGAGTGCATTGAAGCCTTCTCTAGTTATATCTGTCC

TAGCGACCCAGGATTTGTGCTGAACCATGAGATGGAAAGTTGCCTGTCAGGCAATATTAGTCAGTGTCCACGGACTACCG

TGACCTCAGATATCGTCCCCAGATACGCATTTGTGAACGGGGGAGTGGTCGCCAATTGCATCACAACTACCTGCACATGT

AACGGGATTGGAAACAGAATCAATCAGCCCCCTGACCAGGGCGTGAAGATCATTACACACAAAGAGTGTAACACTATCGG

CATTAATGGGATGCTGTTCAACACCAATAAGGAAGGCACACTGGCCTTTTATACTCCTGACGATATCACCCTGAACAATA

GCGTGGCTCTGGATCCAATCGACATTTCCATCGAGCTGAACAAGGTGAAATCTGACCTGGAAGAGAGTAAGGAATGGTAT

CGGAGATCAAATCAGAAACTGAGCGCTATTGAGGACAAGATCGAGGAGATCCTGAGCAAGATCTACCACATCGAGAACGA

GATCGCCAGAATCAAGAAGCTGATCGGCGAGGCCCCCGGAGGCCTGGTGCCTCGGGGCAGCCACCACCACCACCACCACA

GTGCTTGGAGCCACCCACAGTTTGAAAAATGATGAGCGGCCGCC

HPIV3 F GNC4 V170C-I242C, A463V, I474Y (SEQ ID NO: 86)

GGTACCGCCACCATGTACTCAATGCAGCTGGCCTCTTGCGTCACACTGACACTGGTCCTGCTGGTCAACTCACAGATCGA

CATCACTAAACTGCAGCACGTCGGGGTGCTGGTCAACTCCCCAAAGGGAATGAAAATTTCTCAGAATTTCGAGACAAGAT

ACCTGATCCTGAGCCTGATTCCCAAGATCGAAGATTCAAACAGCTGCGGGGACCAGCAGATTAAGCAGTACAAACGACTG

CTGGATCGGCTGATCATTCCTCTGTATGATGGACTGAAGCTGCAGAAAGACGTGATCGTCACAAATCAGGAGTCCAACGA

AAATACCGACCCAAGGACAGAGCGCTTCTTTGGAGGCGTGATCGGAACTATCGCACTGGGAGTCGCTACTTCTGCACAGA

TCACCGCAGCTGTGGCTCTGGTCGAGGCCAAGCAGGCTAAAAGTGATATTGAGAAGCTGAAAGAAGCCATCCGAGACACC

AACAAGGCTGTGCAGAGCGTCCAGAGCTCCGTGGGCAATCTGATTTGCGCCATCAAGTCAGTGCAGGATTACGTCAACAA

-continued

AGAGATTGTGCCCAGCATCGCACGCCTGGGGTGTGAAGCAGCAGGACTGCAGCTGGGAATCGCACTGACCCAGCACTACT

CCGAGCTGACAAACATTTTTGGGGACAATATCGGATCTCTGCAGGAAAAGGGCATCAAGCTGCAGGGCATCGCTAGTCTG

TATAGGACAAATATTACTGAGTGCTTCACCACATCAACTGTGGACAAGTACGATATCTATGACCTGCTGTTTACCGAAAG

CATCAAGGTGAGAGTGATCGACGTGGATCTGAACGATTATTCCATTACTCTGCAGGTCAGACTGCCTCTGCTGACAAGGC

TGCTGAATACTCAGATCTACAAGGTGGACTCCATTTCTTATAACATCCAGAATCGGGAGTGGTACATTCCACTGCCCCTCT

CACATCATGACCAAGGGCGCATTCCTGGGAGGCGCCGATGTGAAAGAGTGCATTGAAGCCTTCTCTAGTTATATCTGTCC

TAGCGACCCAGGATTTGTGCTGAACCATGAGATGGAAAGTTGCCTGTCAGGCAATATTAGTCAGTGTCCACGGACTACCG

TGACCTCAGATATCGTCCCCAGATACGCATTTGTGAACGGGGGAGTGGTCGCCAATTGCATCACAACTACCTGCACATGT

AACGGGATTGGAAACAGAATCAATCAGCCCCCTGACCAGGGCGTGAAGATCATTACACACAAAGAGTGTAACACTATCGG

CATTAATGGGATGCTGTTCAACACCAATAAGGAAGGCACACTGGCCTTTTATACTCCTGACGATATCACCCTGAACAATA

GCGTGGCTCTGGATCCAATCGACATTTCCATCGAGCTGAACAAGGTGAAATCTGACCTGGAAGAGAGTAAGGAATGGTAT

CGGAGATCAAATCAGAAACTGAGCGCTATTGAGGACAAGATCGAGGAGATCCTGAGCAAGATCTACCACATCGAGAACGA

GATCGCCAGAATCAAGAAGCTGATCGGCGAGGCCCCCGGAGGCCTGGTGCCTCGGGGCAGCCACCACCACCACCACCACA

GTGCTTGGAGCCACCCACAGTTTGAAAAATGATGAGCGGCCGCC

HPIV3 F GNC4 I213C-G230C, A463V, I474Y (SEQ ID NO: 87)

GGTACCGCCACCATGTACTCAATGCAGCTGGCCTCTTGCGTCACACTGACACTGGTCCTGCTGGTCAACTCACAGATCGA

CATCACTAAACTGCAGCACGTCGGGGTGCTGGTCAACTCCCCAAAGGGAATGAAAATTTCTCAGAATTTCGAGACAAGAT

ACCTGATCCTGAGCCTGATTCCCAAGATCGAAGATTCAAACAGCTGCGGGGACCAGCAGATTAAGCAGTACAAACGACTG

CTGGATCGGCTGATCATTCCTCTGTATGATGGACTGAAGCTGCAGAAAGACGTGATCGTCACAAATCAGGAGTCCAACGA

AAATACCGACCCAAGGACAGAGCGCTTCTTTGGAGGCGTGATCGGAACTATCGCACTGGGAGTCGCTACTTCTGCACAGA

TCACCGCAGCTGTGGCTCTGGTCGAGGCCAAGCAGGCTAAAAGTGATATTGAGAAGCTGAAAGAAGCCATCCGAGACACC

AACAAGGCTGTGCAGAGCGTCCAGAGCTCCGTGGGCAATCTGATTGTCGCCATCAAGTCAGTGCAGGATTACGTCAACAA

AGAGATTGTGCCCAGCATCGCACGCCTGGGGTGTGAAGCAGCAGGACTGCAGCTGGGAATCGCACTGACCCAGCACTACT

CCGAGCTGACAAACTGTTTTGGGGACAATATCGGATCTCTGCAGGAAAAGGGCATCAAGCTGCAGTGCATCGCTAGTCTG

TATAGGACAAATATTACTGAGATCTTCACCACATCAACTGTGGACAAGTACGATATCTATGACCTGCTGTTTACCGAAAG

CATCAAGGTGAGAGTGATCGACGTGGATCTGAACGATTATTCCATTACTCTGCAGGTCAGACTGCCTCTGCTGACAAGGC

TGCTGAATACTCAGATCTACAAGGTGGACTCCATTTCTTATAACATCCAGAATCGGGAGTGGTACATTCCACTGCCCCTCT

CACATCATGACCAAGGGCGCATTCCTGGGAGGCGCCGATGTGAAAGAGTGCATTGAAGCCTTCTCTAGTTATATCTGTCC

TAGCGACCCAGGATTTGTGCTGAACCATGAGATGGAAAGTTGCCTGTCAGGCAATATTAGTCAGTGTCCACGGACTACCG

TGACCTCAGATATCGTCCCCAGATACGCATTTGTGAACGGGGGAGTGGTCGCCAATTGCATCACAACTACCTGCACATGT

AACGGGATTGGAAACAGAATCAATCAGCCCCCTGACCAGGGCGTGAAGATCATTACACACAAAGAGTGTAACACTATCGG

CATTAATGGGATGCTGTTCAACACCAATAAGGAAGGCACACTGGCCTTTTATACTCCTGACGATATCACCCTGAACAATA

GCGTGGCTCTGGATCCAATCGACATTTCCATCGAGCTGAACAAGGTGAAATCTGACCTGGAAGAGAGTAAGGAATGGTAT

CGGAGATCAAATCAGAAACTGAGCGCTATTGAGGACAAGATCGAGGAGATCCTGAGCAAGATCTACCACATCGAGAACGA

GATCGCCAGAATCAAGAAGCTGATCGGCGAGGCCCCCGGAGGCCTGGTGCCTCGGGGCAGCCACCACCACCACCACCACA

GTGCTTGGAGCCACCCACAGTTTGAAAAATGATGAGCGGCCGCC

HPIV3 F GNC4 G85C-Q222C, A463V, I474Y (SEQ ID NO: 88)

TCTAGACCACCATGTACTCAATGCAGCTGGCCTCTTGCGTCACACTGACACTGGTCCTGCTGGTCAACTCACAGATCGAC

ATCACTAAACTGCAGCACGTCGGGGTGCTGGTCAACTCCCCAAAGGGAATGAAAATTTCTCAGAATTTCGAGACAAGATA

CCTGATCCTGAGCCTGATTCCCAAGATCGAAGATTCAAACAGCTGCGGGGACCAGCAGATTAAGCAGTACAAACGACTGC

-continued

TGGATCGGCTGATCATTCCTCTGTATGATTGCCTGAAGCTGCAGAAAGACGTGATCGTCACAAATCAGGAGTCCAACGAA

AATACCGACCCAAGGACAGAGCGCTTCTTTGGAGGCGTGATCGGAACTATCGCACTGGGAGTCGCTACTTCTGCACAGAT

CACCGCAGCTGTGGCTCTGGTCGAGGCCAAGCAGGCTAAAAGTGATATTGAGAAGCTGAAAGAAGCCATCCGAGACACCA

ACAAGGCTGTGCAGAGCGTCCAGAGCTCCGTGGGCAATCTGATTGTCGCCATCAAGTCAGTGCAGGATTACGTCAACAAA

GAGATTGTGCCCAGCATCGCACGCCTGGGGTGTGAAGCAGCAGGACTGCAGCTGGGAATCGCACTGACCCAGCACTACTC

CGAGCTGACAAACATTTTTGGGGACAATATCGGATCTCTGTGCGAAAAGGGCATCAAGCTGCAGGGCATCGCTAGTCTGT

ATAGGACAAATATTACTGAGATCTTCACCACATCAACTGTGGACAAGTACGATATCTATGACCTGCTGTTTACCGAAAGC

ATCAAGGTGAGAGTGATCGACGTGGATCTGAACGATTATTCCATTACTCTGCAGGTCAGACTGCCTCTGCTGACAAGGCT

GCTGAATACTCAGATCTACAAGGTGGACTCCATTTCTTATAACATCCAGAATCGGGAGTGGTACATTCCACTGCCCTCTC

ACATCATGACCAAGGGCGCATTCCTGGGAGGCGCCGATGTGAAAGAGTGCATTGAAGCCTTCTCTAGTTATATCTGTCCT

AGCGACCCAGGATTTGTGCTGAACCATGAGATGGAAAGTTGCCTGTCAGGCAATATTAGTCAGTGTCCACGGACTACCGT

GACCTCAGATATCGTCCCCAGATACGCATTTGTGAACGGGGGAGTGGTCGCCAATTGCATCACAACTACCTGCACATGTA

ACGGGATTGGAAACAGAATCAATCAGCCCCCTGACCAGGGCGTGAAGATCATTACACACAAAGAGTGTAACACTATCGGC

ATTAATGGGATGCTGTTCAACACCAATAAGGAAGGCACACTGGCCTTTTATACTCCTGACGATATCACCCTGAACAATAG

CGTGGCTCTGGATCCAATCGACATTTCCATCGAGCTGAACAAGGTGAAATCTGACCTGGAAGAGAGTAAGGAATGGTATC

GGAGATCAAATCAGAAACTGAGCGCTATTGAGGACAAGATCGAGGAGATCCTGAGCAAGATCTACCACATCGAGAACGAG

ATCGCCAGAATCAAGAAGCTGATCGGCGAGGCCCCCGGAGGCCTGGTGCCTCGGGGCAGCCACCACCACCACCACCACAG

TGCTTGGAGCCACCCACAGTTTGAAAAATGATGACCGCGG

HPIV3 F GNC4 D216C-L221C, A463V, I474Y (SEQ ID NO: 89)

TCTAGACCACCATGTACTCAATGCAGCTGGCCTCTTGCGTCACTGACACTGGTCCTGCTGGTCAACTCACAGATCGAC

ATCACTAAACTGCAGCACGTCGGGGTGCTGGTCAACTCCCCAAAGGGAATGAAAATTTCTCAGAATTTCGAGACAAGATA

CCTGATCCTGAGCCTGATTCCCAAGATCGAAGATTCAAACAGCTGCGGGGACCAGCAGATTAAGCAGTACAAACGACTGC

TGGATCGGCTGATCATTCCTCTGTATGATGGACTGAAGCTGCAGAAAGACGTGATCGTCACAAATCAGGAGTCCAACGAA

AATACCGACCCAAGGACAGAGCGCTTCTTTGGAGGCGTGATCGGAACTATCGCACTGGGAGTCGCTACTTCTGCACAGAT

CACCGCAGCTGTGGCTCTGGTCGAGGCCAAGCAGGCTAAAAGTGATATTGAGAAGCTGAAAGAAGCCATCCGAGACACCA

ACAAGGCTGTGCAGAGCGTCCAGAGCTCCGTGGGCAATCTGATTGTCGCCATCAAGTCAGTGCAGGATTACGTCAACAAA

GAGATTGTGCCCAGCATCGCACGCCTGGGGTGTGAAGCAGCAGGACTGCAGCTGGGAATCGCACTGACCCAGCACTACTC

CGAGCTGACAAACATTTTTGGGTGCAATATCGGATCTTGCCAGGAAAAGGGCATCAAGCTGCAGGGCATCGCTAGTCTGT

ATAGGACAAATATTACTGAGATCTTCACCACATCAACTGTGGACAAGTACGATATCTATGACCTGCTGTTTACCGAAAGC

ATCAAGGTGAGAGTGATCGACGTGGATCTGAACGATTATTCCATTACTCTGCAGGTCAGACTGCCTCTGCTGACAAGGCT

GCTGAATACTCAGATCTACAAGGTGGACTCCATTTCTTATAACATCCAGAATCGGGAGTGGTACATTCCACTGCCCTCTC

ACATCATGACCAAGGGCGCATTCCTGGGAGGCGCCGATGTGAAAGAGTGCATTGAAGCCTTCTCTAGTTATATCTGTCCT

AGCGACCCAGGATTTGTGCTGAACCATGAGATGGAAAGTTGCCTGTCAGGCAATATTAGTCAGTGTCCACGGACTACCGT

GACCTCAGATATCGTCCCCAGATACGCATTTGTGAACGGGGGAGTGGTCGCCAATTGCATCACAACTACCTGCACATGTA

ACGGGATTGGAAACAGAATCAATCAGCCCCCTGACCAGGGCGTGAAGATCATTACACACAAAGAGTGTAACACTATCGGC

ATTAATGGGATGCTGTTCAACACCAATAAGGAAGGCACACTGGCCTTTTATACTCCTGACGATATCACCCTGAACAATAG

CGTGGCTCTGGATCCAATCGACATTTCCATCGAGCTGAACAAGGTGAAATCTGACCTGGAAGAGAGTAAGGAATGGTATC

GGAGATCAAATCAGAAACTGAGCGCTATTGAGGACAAGATCGAGGAGATCCTGAGCAAGATCTACCACATCGAGAACGAG

ATCGCCAGAATCAAGAAGCTGATCGGCGAGGCCCCCGGAGGCCTGGTGCCTCGGGGCAGCCACCACCACCACCACCACAG

TGCTTGGAGCCACCCACAGTTTGAAAAATGATGACCGCGG

-continued

HPIV3 F GNC4 Q162C-L168C, A463V, I474Y (SEQ ID NO: 90)

TCTAGACCACCATGTACTCAATGCAGCTGGCCTCTTGCGTCACACTGACACTGGTCCTGCTGGTCAACTCACAGATCGAC

ATCACTAAACTGCAGCACGTCGGGGTGCTGGTCAACTCCCCAAAGGGAATGAAAATTTCTCAGAATTTCGAGACAAGATA

CCTGATCCTGAGCCTGATTCCCAAGATCGAAGATTCAAACAGCTGCGGGGACCAGCAGATTAAGCAGTACAAACGACTGC

TGGATCGGCTGATCATTCCTCTGTATGATGGACTGAAGCTGCAGAAAGACGTGATCGTCACAAATCAGGAGTCCAACGAA

AATACCGACCCAAGGACAGAGCGCTTCTTTGGAGGCGTGATCGGAACTATCGCACTGGGAGTCGCTACTTCTGCACAGAT

CACCGCAGCTGTGGCTCTGGTCGAGGCCAAGCAGGCTAAAAGTGATATTGAGAAGCTGAAAGAAGCCATCCGAGACACCA

ACAAGGCTGTGCAGAGCGTCTGCAGCTCCGTGGGCAATTGCATTGTCGCCATCAAGTCAGTGCAGGATTACGTCAACAAA

GAGATTGTGCCCAGCATCGCACGCCTGGGGTGTGAAGCAGCAGGACTGCAGCTGGGAATCGCACTGACCCAGCACTACTC

CGAGCTGACAAACATTTTTGGGGACAATATCGGATCTCTGCAGGAAAAGGGCATCAAGCTGCAGGGCATCGCTAGTCTGT

ATAGGACAAATATTACTGAGATCTTCACCACATCAACTGTGGACAAGTACGATATCTATGACCTGCTGTTTACCGAAAGC

ATCAAGGTGAGAGTGATCGACGTGGATCTGAACGATTATTCCATTACTCTGCAGGTCAGACTGCCTCTGCTGACAAGGCT

GCTGAATACTCAGATCTACAAGGTGGACTCCATTTCTTATAACATCCAGAATCGGGAGTGGTACATTCCACTGCCCTCTC

ACATCATGACCAAGGGCGCATTCCTGGGAGGCGCCGATGTGAAAGAGTGCATTGAAGCCTTCTCTAGTTATATCTGTCCT

AGCGACCCAGGATTTGTGCTGAACCATGAGATGGAAAGTTGCCTGTCAGGCAATATTAGTCAGTGTCCACGGACTACCGT

GACCTCAGATATCGTCCCCAGATACGCATTTGTGAACGGGGGAGTGGTCGCCAATTGCATCACAACTACCTGCACATGTA

ACGGGATTGGAAACAGAATCAATCAGCCCCCTGACCAGGGCGTGAAGATCATTACACACAAAGAGTGTAACACTATCGGC

ATTAATGGGATGCTGTTCAACACCAATAAGGAAGGCACACTGGCCTTTTATACTCCTGACGATATCACCCTGAACAATAG

CGTGGCTCTGGATCCAATCGACATTTCCATCGAGCTGAACAAGGTGAAATCTGACCTGGAAGAGAGTAAGGAATGGTATC

GGAGATCAAATCAGAAACTGAGCGCTATTGAGGACAAGATCGAGGAGATCCTGAGCAAGATCTACCACATCGAGAACGAG

ATCGCCAGAATCAAGAAGCTGATCGGCGAGGCCCCCGGAGGCCTGGTGCCTCGGGGCAGCCACCACCACCACCACCACAG

TGCTTGGAGCCACCCACAGTTTGAAAAATGATGACCGCGG

HPIV3 F GNC4 Q162C-L168C, I213C-G230C, A463V, I474Y (SEQ ID NO: 91)

GGTACCGCCACCATGTACTCAATGCAGCTGGCCTCTTGCGTCACACTGACACTGGTCCTGCTGGTCAACTCACAGATCGA

CATCACTAAACTGCAGCACGTCGGGGTGCTGGTCAACTCCCCAAAGGGAATGAAAATTTCTCAGAATTTCGAGACAAGAT

ACCTGATCCTGAGCCTGATTCCCAAGATCGAAGATTCAAACAGCTGCGGGGACCAGCAGATTAAGCAGTACAAACGACTG

CTGGATCGGCTGATCATTCCTCTGTATGATGGACTGAAGCTGCAGAAAGACGTGATCGTCACAAATCAGGAGTCCAACGA

AAATACCGACCCAAGGACAGAGCGCTTCTTTGGAGGCGTGATCGGAACTATCGCACTGGGAGTCGCTACTTCTGCACAGA

TCACCGCAGCTGTGGCTCTGGTCGAGGCCAAGCAGGCTAAAAGTGATATTGAGAAGCTGAAAGAAGCCATCCGAGACACC

AACAAGGCTGTGCAGAGCGTCTGCAGCTCCGTGGGCAATTGCATTGTCGCCATCAAGTCAGTGCAGGATTACGTCAACAA

AGAGATTGTGCCCAGCATCGCACGCCTGGGGTGTGAAGCAGCAGGACTGCAGCTGGGAATCGCACTGACCCAGCACTACT

CCGAGCTGACAAACTGTTTTGGGGACAATATCGGATCTCTGCAGGAAAAGGGCATCAAGCTGCAGTGCATCGCTAGTCTG

TATAGGACAAATATTACTGAGATCTTCACCACATCAACTGTGGACAAGTACGATATCTATGACCTGCTGTTTACCGAAAG

CATCAAGGTGAGAGTGATCGACGTGGATCTGAACGATTATTCCATTACTCTGCAGGTCAGACTGCCTCTGCTGACAAGGC

TGCTGAATACTCAGATCTACAAGGTGGACTCCATTTCTTATAACATCCAGAATCGGGAGTGGTACATTCCACTGCCCTCT

CACATCATGACCAAGGGCGCATTCCTGGGAGGCGCCGATGTGAAAGAGTGCATTGAAGCCTTCTCTAGTTATATCTGTCC

TAGCGACCCAGGATTTGTGCTGAACCATGAGATGGAAAGTTGCCTGTCAGGCAATATTAGTCAGTGTCCACGGACTACCG

TGACCTCAGATATCGTCCCCAGATACGCATTTGTGAACGGGGGAGTGGTCGCCAATTGCATCACAACTACCTGCACATGT

AACGGGATTGGAAACAGAATCAATCAGCCCCCTGACCAGGGCGTGAAGATCATTACACACAAAGAGTGTAACACTATCGG

CATTAATGGGATGCTGTTCAACACCAATAAGGAAGGCACACTGGCCTTTTATACTCCTGACGATATCACCCTGAACAATA

GCGTGGCTCTGGATCCAATCGACATTTCCATCGAGCTGAACAAGGTGAAATCTGACCTGGAAGAGAGTAAGGAATGGTAT

-continued

CGGAGATCAAATCAGAAACTGAGCGCTATTGAGGACAAGATCGAGGAGATCCTGAGCAAGATCTACCACATCGAGAACGA

GATCGCCAGAATCAAGAAGCTGATCGGCGAGGCCCCCGGAGGCCTGGTGCCTCGGGGCAGCCACCACCACCACCACCACA

GTGCTTGGAGCCACCCACAGTTTGAAAAATGATGAGCGGCCGCC

HPIV3 F GNC4 Q172C-L238C, A463V, I474Y (SEQ ID NO: 92)

GGTACCGCCACCATGTACTCAATGCAGCTGGCCTCTTGCGTCACACTGACACTGGTCCTGCTGGTCAACTCACAGATCGA

CATCACTAAACTGCAGCACGTCGGGGTGCTGGTCAACTCCCCAAAGGGAATGAAAATTTCTCAGAATTTCGAGACAAGAT

ACCTGATCCTGAGCCTGATTCCCAAGATCGAAGATTCAAACAGCTGCGGGGACCAGCAGATTAAGCAGTACAAACGACTG

CTGGATCGGCTGATCATTCCTCTGTATGATGGACTGAAGCTGCAGAAAGACGTGATCGTCACAAATCAGGAGTCCAACGA

AAATACCGACCCAAGGACAGAGCGCTTCTTTGGAGGCGTGATCGGAACTATCGCACTGGGAGTCGCTACTTCTGCACAGA

TCACCGCAGCTGTGGCTCTGGTCGAGGCCAAGCAGGCTAAAAGTGATATTGAGAAGCTGAAAGAAGCCATCCGAGACACC

AACAAGGCTGTGCAGAGCGTCCAGAGCTCCGTGGGCAATCTGATTGTCGCCTGCAAGTCAGTGCAGGATTACGTCAACAA

AGAGATTGTGCCCAGCATCGCACGCCTGGGGTGTGAAGCAGCAGGACTGCAGCTGGGAATCGCACTGACCCAGCACTACT

CCGAGCTGACAAACATTTTTGGGGACAATATCGGATCTCTGCAGGAAAAGGGCATCAAGCTGCAGGGCATCGCTAGTCTG

TATAGGACATGTATTACTGAGATCTTCACCACATCAACTGTGGACAAGTACGATATCTATGACCTGCTGTTTACCGAAAG

CATCAAGGTGAGAGTGATCGACGTGGATCTGAACGATTATTCCATTACTCTGCAGGTCAGACTGCCTCTGCTGACAAGGC

TGCTGAATACTCAGATCTACAAGGTGGACTCCATTTCTTATAACATCCAGAATCGGGAGTGGTACATTCCACTGCCCTCT

CACATCATGACCAAGGGCGCATTCCTGGGAGGCGCCGATGTGAAAGAGTGCATTGAAGCCTTCTCTAGTTATATCTGTCC

TAGCGACCCAGGATTTGTGCTGAACCATGAGATGGAAAGTTGCCTGTCAGGCAATATTAGTCAGTGTCCACGGACTACCG

TGACCTCAGATATCGTCCCCAGATACGCATTTGTGAACGGGGGAGTGGTCGCCAATTGCATCACAACTACCTGCACATGT

AACGGGATTGGAAACAGAATCAATCAGCCCCCTGACCAGGGCGTGAAGATCATTACACACAAAGAGTGTAACACTATCGG

CATTAATGGGATGCTGTTCAACACCAATAAGGAAGGCACACTGGCCTTTTATACTCCTGACGATATCACCCTGAACAATA

GCGTGGCTCTGGATCCAATCGACATTTCCATCGAGCTGAACAAGGTGAAATCTGACCTGGAAGAGAGTAAGGAATGGTAT

CGGAGATCAAATCAGAAACTGAGCGCTATTGAGGACAAGATCGAGGAGATCCTGAGCAAGATCTACCACATCGAGAACGA

GATCGCCAGAATCAAGAAGCTGATCGGCGAGGCCCCCGGAGGCCTGGTGCCTCGGGGCAGCCACCACCACCACCACCACA

GTGCTTGGAGCCACCCACAGTTTGAAAAATGATGAGCGGCCGCC

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013).

Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a protomer of the PIV F (such as hPIV1, hPIV2, hPIV3, or hPIV4 F) ectodomain trimer can include a recombinant DNA which is incorporated into a vector (such as an expression vector) into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a protomer of the PIV F (such as hPIV1, hPIV2, hPIV3, or hPIV4 F) ectodomain trimer can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the protomer of the PIV F (such as hPIV1, hPIV2, hPIV3, or hPIV4 F) ectodomain trimer can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), $4^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as $GnTI^{-/-}$ cells (ATCC® No. CRL-3022), or HEK-293F cells.

Transformation of a host cell with recombinant DNA can be carried out by conventional techniques. In some embodiments where the host is prokaryotic, such as, but not limited to, *E. coli*, competent cells which are capable of DNA uptake can be prepared from cells harvested after exponential growth phase and subsequently treated by the $CaCl_2$ method. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). Appropriate expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., *J. Virol.,* 79, 8828-8834, 2005, which is incorporated by reference herein).

Modifications can be made to a nucleic acid encoding a protomer of a disclosed recombinant hPIV1, hPIV2, hPIV3, or hPIV4 F ectodomain without diminishing its biological activity. Some modifications can be made to facilitate the cloning, expression, or incorporation of the targeting molecule into a fusion protein. Exemplary modifications include termination codons, a methionine added at the amino terminus to provide an initiation, site, additional amino acids placed on either terminus to create conveniently located restriction sites, or additional amino acids (such as poly His) to aid in purification steps.

In some embodiments, the nucleic acid encoding the protomer of a disclosed recombinant PIV F (such as hPIV1, hPIV2, hPIV3, or hPIV4 F) ectodomain protomer can be expressed in cells under conditions where the protomers self-assemble into trimers which are secreted from the cells into the cell media, for example as described for RSV F proteins (see, e.g., PCT Pub. WO2014160463, McLellan et al., *Science,* 340:1113-1117, 2013; McLellan et al., *Science,* 342:592-598, 2013, each of which is incorporated by reference herein in its entirety). In such embodiments, the protomer contains a leader sequence (signal peptide) that causes the protein to enter the secretory system, and the signal peptide is cleaved and the protomers form a trimer, before being secreted in the cell media. The medium can be centrifuged and recombinant hPIV1, hPIV2, hPIV3, or hPIV4 F ectodomain trimer purified from the supernatant.

IV. Viral Vectors

A nucleic acid molecule encoding a protomer of a disclosed recombinant PIV F (such as hPIV1, hPIV2, hPIV3, or hPIV4 F) ectodomain trimer can be included in a viral vector, for example for expression of the protomer to produce the corresponding recombinant PIV F ectodomain trimer in a host cell, or for immunization of a subject as disclosed herein. In some embodiments, the viral vectors are administered to a subject as part of a prime-boost vaccination. Typically such viral vectors include a nucleic acid molecule encoding a protomer of a disclosed recombinant PIV F (such as hPIV1, hPIV2, hPIV3, or hPIV4 F) ectodomain that is linked to a C-terminal transmembrane domain, for example the protomer can be linked to an transmembrane domain and cytosolic tail from a corresponding PIV F (such as hPIV1, hPIV2, hPIV3, or hPIV4 F) protein. In several embodiments, the viral vectors are included in a vaccine, such as a primer vaccine or a booster vaccine for use in a prime-boost vaccination.

In some examples, the viral vector encoding the protomer of the recombinant PIV F (such as hPIV1, hPIV2, hPIV3, or hPIV4 F) ectodomain protomer can be replication-competent. For example, the viral vector can have a mutation (e.g., insertion of nucleic acid encoding the protomer) in the viral genome that attenuates, but does not completely block viral replication in host cells.

In several embodiments, the viral vector encoding the protomer of the recombinant PIV F (such as hPIV1, hPIV2, hPIV3, or hPIV4 F) ectodomain is a viral vector that can be delivered via the respiratory tract. For example, a hPIV vector, such as bovine parainfluenza virus (BPIV) vector (e.g., a BPIV1, BPIV2, or BPIV3 vector) or human hPIV vector, a metapneumovirus (MPV) vector, a Sendia virus vector, or a measles virus vector, is used to express a disclosed antigen.

Additional viral vectors are also available for expression of the disclosed antigens, including polyoma, i.e., SV40 (Madzak et al., 1992, *J. Gen. Virol.,* 73:15331536), adenovirus (Berkner, 1992, *Cur. Top. Microbiol. Immunol.,* 158:39-6; Berliner et al., 1988, *Bio Techniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, *Curr. Top. Microbiol. Immunol.,* 158:91-123; On et al., 1990, *Gene,* 89:279-282), herpes viruses including HSV and EBV and CMV (Margolskee, 1992, *Curr. Top. Microbiol. Immunol.,* 158:67-90; Johnson et al., 1992, *J. Virol.,* 66:29522965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993,

*Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, *Curr. Top. Microbiol. Immunol.,* 158: 1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

V. Virus-Like Particles

In some embodiments, a virus-like particle (VLP) is provided that includes a disclosed recombinant PIV F (such as hPIV1, hPIV2, hPIV3, or hPIV4 F) ectodomain trimer. Typically such VLPs include a recombinant PIV F (such as hPIV1, hPIV2, hPIV3, or hPIV4 F) ectodomain trimer that is membrane anchored by a C-terminal transmembrane domain, for example the protomers of the recombinant PIV F ectodomain trimer each can be linked to an corresponding PIV F (such as hPIV1, hPIV2, hPIV3, or hPIV4 F) transmembrane domain and cytosolic tail. VLPs lack the viral components that are required for virus replication and thus represent a highly attenuated, replication-incompetent form of a virus. However, the VLP can display a polypeptide (e.g., a recombinant hPIV1, hPIV2, hPIV3, and/or hPIV4 F ectodomain trimer) that is analogous to that expressed on infectious virus particles and can eliciting an immune response to PIV (such as hPIV1, hPIV2, hPIV3, or hPIV4) when administered to a subject. Exemplary virus like particles and methods of their production, as well as viral proteins from several viruses that are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

VI. Immunogenic Compositions

Immunogenic compositions comprising a disclosed immunogen (e.g., recombinant hPIV1, hPIV2, hPIV3, or hPIV4 F ectodomain trimer, a nucleic acid molecule or vector encoding a protomer of the recombinant hPIV1, hPIV2, hPIV3, or hPIV4 F ectodomain trimer, or a protein nanoparticle or virus like particle comprising a disclosed recombinant hPIV1, hPIV2, hPIV3, or hPIV4 F ectodomain trimer) and a pharmaceutically acceptable carrier are also provided. Such compositions can be administered to subjects by a variety of administration modes, for example, intramuscular, subcutaneous, intravenous, intra-arterial, intra-articular, intraperitoneal, or parenteral routes. In several embodiments, a pharmaceutical composition including one or more of the disclosed immunogens are immunogenic compositions. Actual methods for preparing administrable compositions are described in more detail in such publications as *Remingtons Pharmaceutical Sciences,* 19th Ed., Mack Publishing Company, Easton, Pennsylvania, 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Adjuvants, such as aluminum hydroxide (ALHYDROGEL®, available from Brenntag Biosector, Copenhagen, Denmark and Amphogel®, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), TLR agonists (such as TLR-9 agonists), among many other suitable adjuvants well known in the art, can be included in the compositions. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some instances, the adjuvant formulation is a mineral salt, such as a calcium or aluminum (alum) salt, for example calcium phosphate, aluminum phosphate or aluminum hydroxide. In some embodiments, the adjuvant includes an oil and water emulsion, e.g., an oil-in-water emulsion (such as MF59 (Novartis) or AS03 (GlaxoSmithKline). One example of an oil-in-water emulsion comprises a metabolisable oil, such as squalene, a tocol such as a tocopherol, e.g., alpha-tocopherol, and a surfactant, such as sorbitan trioleate (Span 85) or polyoxyethylene sorbitan monooleate (Tween 80), in an aqueous carrier.

In some instances it may be desirable to combine a disclosed immunogen with other pharmaceutical products (e.g., vaccines) which induce protective responses to other agents. For example, a composition including a recombinant hPIV1, hPIV2, hPIV3, or hPIV4 F ectodomain trimer as described herein can be can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age). As such, a disclosed immunogen described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the composition can be provided as a sterile composition. The immunogenic composition typically contains an effective amount of a disclosed immunogen and can be prepared by conventional techniques. Typically, the amount of immunogen in each dose of the immunogenic composition is selected as an amount which induces an immune response without significant, adverse side effects. In some embodiments, the composition can be provided in unit dosage form for use to induce an immune response in a subject, for example, to inhibit hPIV1, hPIV2, hPIV3, or hPIV4 F infection in the subject. A unit dosage form contains a suitable single preselected dosage for administration to a subject, or suitable marked or measured multiples of two or more preselected unit dosages, and/or a metering mechanism for administering the unit dose or multiples thereof.

VII. Methods of Inducing an Immune Response

The disclosed immunogens (e.g., recombinant prefusion-stabilized hPIV1, hPIV2, hPIV3, or hPIV4 F ectodomain trimer, a nucleic acid molecule (such as an RNA molecule) or vector encoding a protomer of a disclosed prefusion-stabilized hPIV1, hPIV2, hPIV3, or hPIV4 F ectodomain trimer, or a protein nanoparticle or virus like particle comprising a disclosed prefusion-stabilized hPIV1, hPIV2, hPIV3, or hPIV4 F ectodomain trimer) can be administered to a subject to induce an immune response to hPIV F protein in the subject. In a particular example, the subject is a human. The immune response can be a protective immune response, for example a response that inhibits subsequent infection with hPIV1, hPIV2, hPIV3, or hPIV4. Elicitation of the immune response can also be used to treat or inhibit hPIV infection and illnesses associated therewith.

A subject can be selected for treatment that has, or is at risk for developing PIV infection (such as hPIV1, hPIV2, hPIV3, and/or hPIV4 infection), for example because of exposure or the possibility of exposure to hPIV1, hPIV2, hPIV3, and/or hPIV4. Following administration of a disclosed immunogen, the subject can be monitored for the PIV infection or symptoms associated therewith, or both.

Typical subjects intended for treatment with the therapeutics and methods of the present disclosure include humans. Because most humans are infected with hPIV1-3 by the age of 5, the entire birth cohort is included as a relevant population for immunization. Although hPIV4 infection is less common, the entire birth cohort a relevant population for immunization as most humans will be exposed to hPIV4 during their lifetime. This could be done, for example, by beginning an immunization regimen anytime from birth to 6 months of age, from 6 months of age to 5 years of age, in pregnant women (or women of child-bearing age) to protect their infants by passive transfer of antibody, family members of newborn infants or those still in utero, and subjects greater than 50 years of age. The scope of this disclosure is meant to include maternal immunization (for example, immunization of subject that is in the third trimester of pregnancy (such as at least 37 weeks pregnant), and/or wherein the fetus is at least early term, such as at least full term. In several embodiments, the subject is a human subject that is seronegative for hPIV specific antibodies. In some embodiments, the subject is no more than one year old, such as no more than 6 months old, no more than 3 months, or no more than 1 month old.

Subjects at greatest risk of hPIV infection with severe symptoms (e.g. requiring hospitalization) include children with prematurity, bronchopulmonary dysplasia, and congenital heart disease are most susceptible to severe disease. Atopy or a family history of atopy has also been associated with severe disease in infancy. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. Thus, these subjects can be selected for administration of the disclosed immunogens, or a nucleic acid or a viral vector encoding, expressing or including an immunogen.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize hPIV1, hPIV2, hPIV3, and/or hPIV4 infection. These and other routine methods allow the clinician to select patients in need of therapy using the methods and immunogenic compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The administration of a disclosed immunogen can be for prophylactic or therapeutic purpose. When provided prophylactically, the immunogen can be provided in advance of any symptom, for example in advance of infection. The prophylactic administration serves to prevent or ameliorate any subsequent infection. In some embodiments, the methods can involve selecting a subject at risk for contracting PIV infection (such as hPIV1, hPIV2, hPIV3, and/or hPIV4 infection), and administering a therapeutically effective amount of a disclosed immunogen to the subject. The immunogen can be provided prior to the anticipated exposure to hPIV so as to attenuate the anticipated severity, duration or extent of an infection and/or associated disease symptoms, after exposure or suspected exposure to the virus, or after the actual initiation of an infection. When provided therapeutically, the disclosed immunogens are provided at or after the onset of a symptom of PIV infection (such as hPIV1, hPIV2, hPIV3, and/or hPIV4 infection), or after diagnosis of PIV infection (such as hPIV1, hPIV2, hPIV3, and/or hPIV4 infection). Treatment of PIV (such as hPIV1, hPIV2, hPIV3, and/or hPIV4) by inhibiting PIV replication or infection (such as hPIV1, hPIV2, hPIV3, and/or hPIV4 replication or infection) can include delaying and/or reducing signs or symptoms of PIV infection (such as hPIV1, hPIV2, hPIV3, and/or hPIV4 infection) in a subject. In some examples, treatment using the methods disclosed herein prolongs the time of survival of the subject.

In some embodiments, administration of a disclosed immunogen to a subject can elicit the production of an immune response that is protective against serious lower respiratory tract disease, such as pneumonia and bronchiolitis, or croup, when the subject is subsequently infected or re-infected with a wild-type PIV (such as hPIV1, hPIV2, hPIV3, and/or hPIV4). While the naturally circulating virus may still be capable of causing infection, particularly in the upper respiratory tract, there can be a reduced possibility of rhinitis as a result of the vaccination and a possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

The immunogens described herein, and immunogenic compositions thereof, are provided to a subject in an amount effective to induce or enhance an immune response against PIV F protein in the subject, preferably a human. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to hPIV1, hPIV2, hPIV3, and/or hPIV4 F proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., inhibition of hPIV infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response.

In some embodiments, the prime-boost method can include DNA-primer and protein-boost vaccination protocol to a subject. The method can include two or more administrations of the nucleic acid molecule or the protein.

For protein therapeutics, typically, each human dose will comprise 1-1000 μg of protein, such as from about 1 μg to about 100 μg, for example, from about 1 μg to about 50 μg, such as about 1 μg, about 2 μg, about 5 μg, about 10 μg, about 15 μg, about 20 μg, about 25 μg, about 30 μg, about 40 μg, or about 50 μg. The amount utilized in an immunogenic composition is selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as a recombinant PIV F ectodomain or immunogenic fragment thereof, viral vector, or nucleic acid molecule in a immunogenic composition, can include an amount that is ineffective at eliciting an immune response by administration of a single dose, but that is effective upon administration of multiple dosages, for example in a prime-boost administration protocol.

Upon administration of a disclosed immunogen the immune system of the subject typically responds to the immunogenic composition by producing antibodies specific for viral protein. Such a response signifies that an immunologically effective dose was delivered to the subject.

For each particular subject, specific dosage regimens can be evaluated and adjusted over time according to the individual need and professional judgment of the person administering or supervising the administration of the immunogenic composition. The dosage and number of doses will depend on the setting, for example, in an adult or anyone primed by prior hPIV1, hPIV2, hPIV3, and/or hPIV4 infection or immunization, a single dose may be a sufficient booster. In naïve subjects, in some examples, at least two doses would be given, for example, at least three doses. In some embodiments, an annual boost is given, for example, along with an annual influenza vaccination.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, an hPIV1, hPIV2, hPIV3, and/or hPIV4 F protein.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Administration of an immunogenic composition that elicits an immune response to reduce or prevent an infection, can, but does not necessarily completely, eliminate such an infection, so long as the infection is measurably diminished. For example, administration of an effective amount of the agent can decrease the hPIV1, hPIV2, hPIV3, and/or hPIV4 infection (for example, as measured by infection of cells, or by number or percentage of subjects infected by hPIV1, hPIV2, hPIV3, and/or hPIV4) by a desired amount, for example by at least 10%, at least 20%, at least 50%, at least 60%, at least 70%, at least 80%, at least 90%, at least 95%, at least 98%, or even at least 100% (elimination or prevention of detectable hPIV1, hPIV2, hPIV3, and/or hPIV4 infection, as compared to a suitable control.

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity include, but are not limited to, plaque reduction neutralization (PRNT) assays, microneutralization assays, flow cytometry based assays, single-cycle infection assays. In some embodiments, the serum neutralization activity can be assayed using a panel of hPIV1, hPIV2, hPIV3, and/or hPIV4 pseudoviruses.

One approach to administration of nucleic acids is direct immunization with plasmid DNA, such as with a mammalian expression plasmid Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a disclosed immunogen can be administered to a subject to elicit an immune response to the F protein of PIV (such as hPIV1, hPIV2, hPIV3, and/or hPIV4). In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed prefusion-stabilized PIV ectodomain trimer (such as hPIV1, hPIV2, hPIV3, and/or hPIV4 ectodomain trimer) can be expressed by attenuated viral hosts (such as an attenuated hPIV vector or attenuated RSV vector) or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding a protomer of a disclosed PIV ectodomain trimer (such as hPIV1, hPIV2, hPIV3, and/or hPIV4 ectodomain trimer) is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

VIII. Additional Description of Certain Embodiments

Clause 1. An immunogen, comprising:

(A) a recombinant human parainfluenza virus (hPIV)1 F ectodomain trimer comprising three protomers each comprising one or more amino acid substitutions or deletions that stabilize the hPIV1 ectodomain trimer in a prefusion conformation;

(B) a recombinant hPIV2 F ectodomain trimer comprising three protomers each comprising one or more amino acid substitutions or deletions that stabilize the hPIV2 ectodomain trimer in a prefusion conformation;

(C) a recombinant hPIV3 F ectodomain trimer comprising three protomers each comprising one or more amino acid substitutions or deletions that stabilize the hPIV3 ectodomain trimer in a prefusion conformation; or (D) a recombinant hPIV4 F ectodomain trimer comprising three protomers each comprising one or more amino acid substitutions or deletions that stabilize the hPIV4 ectodomain trimer in a prefusion conformation.

Clause 2. The immunogen of clause 1, comprising:

(A) the hPIV1 F ectodomain trimer, wherein each protomer comprises A466I and S473I cavity filling substitutions that stabilize the hPIV1 F ectodomain trimer in a prefusion conformation;

(B) the hPIV3 F ectodomain trimer, wherein each protomer comprises one of:

a A463V cavity filling substitution; a E193P substitution; a I474Y cavity filling substitution; a S470V cavity filling substitution; a E145L cavity filling substitution; a S470L cavity filling substitution; a V1751 cavity filling substitution; a S477V cavity filling substitution; a V170I cavity filling substitution; A463V and I474Y cavity filling substitutions; Y178W, A463V, and I474Y cavity filling substitutions; V170L and I187F cavity filling substitutions; a non-native disulfide bond between I172C and N238C substitutions, and V170L and I187F cavity filling substitutions; a non-native disulfide bond between I172C and N238C substitutions, and a Y178W cavity filling substitution; a non-native disulfide bond between I172C and N238C substitutions, and a I474Y cavity filling substitution; a non-native disulfide bond between I172C and N238C substitutions, and A463V and I474Y cavity filling substitutions;

that stabilize the hPIV3 F ectodomain trimer in a prefusion conformation; or (C) the hPIV4 F ectodomain trimer, wherein each protomer comprises one of:

a non-native disulfide bond between I166C and T232C substitutions; or a non-native disulfide bond between I166C and T232C substitutions, and Y457F and S471I cavity filling substitutions;

that stabilize the hPIV4 F ectodomain trimer in a prefusion conformation;

Clause 3. The immunogen of any one of the prior clauses, wherein a protease cleavage site separating $F_2$ and $F_1$ proteins of the F ectodomain is mutated to inhibit protease cleavage of the cleavage site.

Clause 4. The immunogen of any one of the prior clauses, comprising (A) the hPIV1 F ectodomain trimer, wherein the protomers of the trimer comprise a deletion of hPIV1 residues 113-114 and wherein residues 112 and 115 are linked by a heterologous peptide linker.

(B) the hPIV2 F ectodomain trimer, wherein the protomers of the trimer comprise a deletion of hPIV2 residues 101-108 and wherein residues 100 and 109 are linked by a heterologous peptide linker.

(C) the hPIV3 F ectodomain trimer, wherein the protomers of the trimer comprise an amino acid substitution to remove a $F_1/F_2$ furin cleavage site between hPIV3 residues 109 and 110.

(D) the hPIV4 F ectodomain trimer, wherein the protomers of the trimer comprise a deletion of hPIV4 residues 98-105 and wherein residues 97 and 106 are linked by a heterologous peptide linker.

Clause 5. The immunogen of clause 4, comprising:

(A) the hPIV1 F ectodomain trimer, wherein the heterologous peptide linker comprises the amino acid sequence set forth as GS;

(B) the hPIV2 F ectodomain trimer, wherein the heterologous peptide linker comprises the amino acid sequence set forth as GGGSGGGS (SEQ ID NO: 32);

(C) the hPIV3 F ectodomain trimer, wherein the amino acid substitution to remove the $F_1/F_2$ furin cleavage site between hPIV3 residues 109 and 110 comprises a K108E substitution; or (D) the hPIV4 F ectodomain trimer, wherein the heterologous peptide linker comprises the amino acid sequence set forth as GGGSGGGS (SEQ ID NO: 32).

Clause 6. The immunogen of any one of the prior clauses, comprising:

(A) the hPIV1 F ectodomain trimer, wherein an N-terminal residue of a $F_2$ protein of the protomers is one of hPIV1 F residues 15-25;

(B) the hPIV2 F ectodomain trimer, wherein an N-terminal residue of a $F_2$ protein of the protomers is one of hPIV2 F residues 15-25;

(C) the hPIV3 F ectodomain trimer, wherein an N-terminal residue of a $F_2$ protein of the protomers is one of hPIV3 F residues 15-25; or (D) the hPIV4 F ectodomain trimer, wherein an N-terminal residue of a $F_2$ protein of the protomers is one of hPIV4 F residues 15-25.

Clause 7. The immunogen of any one of the prior clauses, comprising:

(A) the hPIV1 F ectodomain trimer, wherein a C-terminal residue of a $F_1$ ectodomain of the protomers is one of hPIV1 F residues 473-497;

(B) the hPIV2 F ectodomain trimer, wherein a C-terminal residue of a $F_1$ ectodomain of the protomers is one of hPIV2 F residues 473-493;

(C) the hPIV3 F ectodomain trimer, wherein a C-terminal residue of a $F_1$ ectodomain of the protomers is one of hPIV3 F residues 475-493; or (D) the hPIV4 F ectodomain trimer, wherein a C-terminal residue of a $F_1$ ectodomain of the protomers is one of hPIV4 F residues 470-486.

Clause 8. The immunogen of any one of the prior clauses, comprising:

(A) the hPIV1 F ectodomain trimer, wherein the protomers comprise or consist essentially of hPIV1 residues 22-112 and 115-479, wherein residues 112 and 115 are linked by a heterologous peptide linker;

(B) the hPIV2 F ectodomain trimer, wherein the protomers comprise or consist essentially of hPIV2 residues 22-100 and 109-484, wherein residues 100 and 109 are linked by a heterologous peptide linker;

(C) the hPIV3 F ectodomain trimer, wherein the protomers comprise or consist essentially of hPIV3 residues 19-484, and do not comprise a consensus furin cleavage site between the $F_2$ protein and $F_1$ ectodomain of the protomers; or (D) the hPIV4 F ectodomain trimer, wherein the protomers comprise or consist essentially of hPIV4 residues 21-97 and 106-477, wherein residues 97 and 106 are linked by a heterologous peptide linker.

Clause 9. The immunogen of any one of the prior clauses, comprising:

(A) the hPIV1 F ectodomain trimer, wherein the protomers comprise or consist essentially of the amino acid sequence set forth as residues 1-458 of SEQ ID NO: 4, or an amino acid sequence at least 90% identical thereto;

(B) the hPIV2 F ectodomain trimer, wherein the protomers comprise or consist essentially of the amino acid sequence set forth as residues 1-463 of SEQ ID NO: 7, or an amino acid sequence at least 90% identical thereto;

(C) the hPIV3 F ectodomain trimer, wherein the protomers comprise or consist essentially of the amino acid sequence set forth as residues 1-463 of any one of SEQ ID NOs: 10-26 or 39-50, or an amino acid sequence at least 90% identical thereto; or (D) the hPIV4 F ectodomain trimer, wherein the protomers comprise or consist essentially of the amino acid sequence set forth as residues 1-457 of any one of SEQ ID NOs: 29-30, or an amino acid sequence at least 90% identical thereto.

Clause 10. The immunogen of any one of the prior clauses, wherein the protomers of the recombinant hPIV1, hPIV2, hPIV3, or hPIV4 F ectodomain trimer further comprise one or more additional amino acid substitutions that stabilize the recombinant hPIV1, hPIV2, hPIV3, or hPIV4 F ectodomain trimer in the prefusion conformation.

Clause 11. The immunogen of any one or the prior clauses, wherein the recombinant hPIV1, hPIV2, hPIV3, or hPIV4 F ectodomain trimer specifically binds to a hPIV1, hPIV2, hPIV3, or hPIV4 F prefusion specific antibody, respectively.

Clause 12. The immunogen of any one of the prior clauses, wherein a C-terminal residue of the protomers in the ectodomain is linked to a trimerization domain by a peptide linker, or is directly linked to the trimerization domain Clause 13. The immunogen of clause 12, wherein the trimerization domain is a GCN4 trimerization domain Clause 14. The immunogen of clause 13, comprising:

(A) the hPIV1 F ectodomain trimer, wherein the protomers linked to the trimerization domain comprise or consist essentially of the amino acid sequence set forth as SEQ ID NO: 4, or an amino acid sequence at least 90% identical thereto;

(B) the hPIV2 F ectodomain trimer, wherein the protomers comprise or consist essentially of the amino acid sequence set forth as SEQ ID NO: 7, or an amino acid sequence at least 90% identical thereto;

(C) the hPIV3 F ectodomain trimer, wherein the protomers comprise or consist essentially of the amino acid sequence set forth as any one of SEQ ID NOS: 10-26 or 39-50, or an amino acid sequence at least 90% identical thereto; or (D) the hPIV4 F ectodomain trimer, wherein the protomers comprise or consist essentially of the amino acid sequence set forth as any one of SEQ ID NOS: 29-30, or an amino acid sequence at least 90% identical thereto.

Clause 15. The immunogen of any one of the prior clauses, wherein the recombinant hPIV1, hPIV2, hPIV3, or hPIV4 F ectodomain trimer is soluble.

Clause 16. The immunogen of any one of clauses 1-11, wherein a C-terminal residue of the protomers in the F ectodomain is linked to a transmembrane domain by a peptide linker, or is directly linked to the transmembrane domain Clause 17. The immunogen of any of clauses 1-11, wherein a C-terminal residue of the protomers in the F ectodomain is linked to a protein nanoparticle subunit by a peptide linker, or is directly linked to the protein nanoparticle subunit.

Clause 18. A protein nanoparticle, comprising the immunogen of clause 17.

Clause 19. A virus-like particle comprising the immunogen of any one of clauses 1-15 or 16.

Clause 20. An isolated nucleic acid molecule encoding the immunogen of any one of clauses 1-17.

Clause 21. An isolated nucleic acid molecule encoding a protomer of the recombinant hPIV1, hPIV2, hPIV3, or hPIV4 F ectodomain trimer of any one of clauses 1-17.

Clause 22. The nucleic acid molecule of clause 20 or clause 21, wherein the nucleic acid molecule encodes a precursor protein of the protomer of the recombinant hPIV1, hPIV2, hPIV3, or hPIV4 F ectodomain trimer.

Clause 23. The nucleic acid molecule of any of clauses 20-22, wherein the protomers of the recombinant hPIV1, hPIV2, hPIV3, or hPIV4 F ectodomain trimer are each linked to a C-terminal trimerization domain, particularly wherein the C-terminal trimerization domain is a GCN4 trimerization domain Clause 24. The nucleic acid molecule of any of clauses 20-22, wherein the protomers of the recombinant hPIV1, hPIV2, hPIV3, or hPIV4 F ectodomain trimer are each linked to a C-terminal transmembrane domain, particularly wherein the C-terminal transmembrane domain is a transmembrane domain of a respective hPIV1, hPIV2, hPIV3, or hPIV4 F protein.

Clause 25. The nucleic acid molecule of any one of clauses 20-24, operably linked to a promoter.

Clause 26. The nucleic acid molecule of any one of clauses 20-25, wherein the nucleic acid molecule is an RNA molecule.

Clause 27. A vector comprising the nucleic acid molecule of any of clauses 20-26.

Clause 28. The vector of clause 27, wherein the vector is a viral vector.

Clause 29. An immunogenic composition comprising the immunogen, the virus like particle, the protein nanoparticle, the nucleic acid molecule, or the vector of any of clauses 1-28.

Clause 30. The immunogenic composition of clause 29, comprising two or more of:

the recombinant hPIV1 F ectodomain trimer stabilized in the prefusion conformation;

the recombinant hPIV2 F ectodomain trimer stabilized in the prefusion conformation;

the recombinant hPIV3 F ectodomain trimer stabilized in the prefusion conformation; and the recombinant hPIV4 F ectodomain trimer stabilized in the prefusion conformation.

Clause 31. The immunogenic composition of clause 29, comprising each of:

the recombinant hPIV1 F ectodomain trimer stabilized in the prefusion conformation;

the recombinant hPIV2 F ectodomain trimer stabilized in the prefusion conformation;

the recombinant hPIV3 F ectodomain trimer stabilized in the prefusion conformation; and the recombinant hPIV4 F ectodomain trimer stabilized in the prefusion conformation.

Clause 32. A method of producing a recombinant hPIV1, hPIV2, hPIV3, or hPIV4 F ectodomain trimer stabilized in a prefusion conformation, comprising:

expressing the nucleic acid molecule or vector of any one of clauses 20-28 in a host cell to produce the recombinant hPIV1, hPIV2, hPIV3, or hPIV4 F ectodomain trimer are each linked; and purifying the recombinant hPIV1, hPIV2, hPIV3, or hPIV4 F ectodomain trimer.

Clause 33. The recombinant hPIV1, hPIV2, hPIV3, or hPIV4 F ectodomain trimer produced by the method of clause 32.

Clause 34. A method of inducing an immune response to hPIV1, hPIV2, hPIV3, or hPIV4 F protein in a human subject, comprising administering to the human subject an effective amount of the immunogen, the virus like particle, the protein nanoparticle, the nucleic acid molecule, the vector, or the immunogenic composition of any of clauses 1-31 to generate the immune response.

Clause 35. The method of clause 34, wherein the immune response treats or inhibits hPIV1, hPIV2, hPIV3, or hPIV4 infection.

Clause 36. The method of clause 34 or clause 35, wherein generating the immune response inhibits hPIV1, hPIV2, hPIV3, or hPIV4 replication in the subject.

Clause 37. The method of any one of clauses 34-36, comprising a prime-boost administration of the immunogen, the virus like particle, the protein nanoparticle, the nucleic acid molecule, the vector, or the immunogenic composition.

Clause 38. The method of any one of clauses 34-37, wherein the subject is at risk of or has an hPIV1, hPIV2, hPIV3, or hPIV4 infection.

Clause 39. The method of any one of clauses 34-38, wherein the subject is less than one year old.

Clause 40. The method of any one of clauses 34-38, wherein the subject is pregnant.

Clause 41. A method for inhibiting or preventing an hPIV1, hPIV2, hPIV3, or hPIV4 infection in an infant, comprising administering to a subject pregnant with the infant a therapeutically effective amount of the immunogen, the virus like particle, the protein nanoparticle, the nucleic acid molecule, the vector, or the immunogenic composition of any of clauses 1-31, to induce an immune response to hPIV1, hPIV2, hPIV3, or hPIV4 in the pregnant subject that provides passive immunity to the infant that inhibits or prevents hPIV1, hPIV2, hPIV3, or hPIV4 infection in the infant for at least the first six months following birth.

Clause 42. The method of clause 41, wherein the subject is in the third trimester of pregnancy.

Clause 43. The method of clause 41, wherein the infant is at least early term, particularly wherein the infant is at least full term.

Clause 44. The method of clause 43, wherein the subject is at least 37 weeks pregnant.

Clause 45. Use of the immunogen, the virus like particle, the protein nanoparticle, the nucleic acid molecule, the vector, or the immunogenic composition of any of clauses 1-31 to induce an immune response to hPIV1, hPIV2, hPIV3, or hPIV4 F protein in a subject.

EXAMPLES

The following examples are provided to illustrate particular features of certain embodiments, but the scope of the claims should not be limited to those features exemplified.

Example 1 hPIV3 F Proteins Stabilized in a Prefusion Conformation

The example illustrates embodiments of an hPIV3 F ectodomain trimer stabilized in a prefusion conformation by one or more amino acid substitutions. The prefusion-stabilized hPIV3 F proteins are useful, for example, for inducing a neutralizing immune response to hPIV3 in a subject.

Figure 2A:
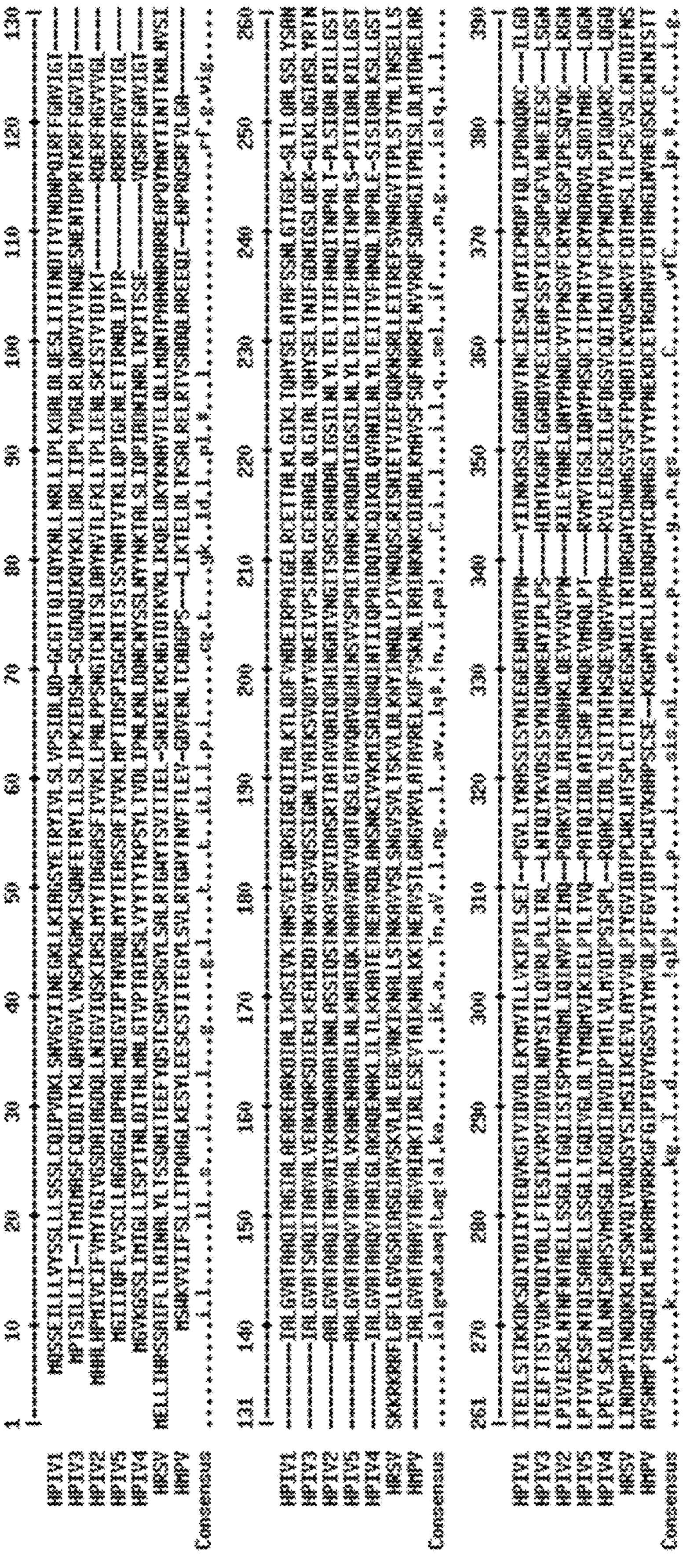
FIGS. 2A and 2B show a sequence alignment of the hPIV1 (SEQ ID NO: 2), hPIV2 (SEQ ID NO: 6), hPIV3 (SEQ ID NO: 9), hPIV4 (SEQ ID NO: 28), PIV5 (SEQ ID NO: 93), RSV (SEQ ID NO: 95), and MPV (SEQ ID NO: 94) F proteins. There is substantial sequence diversity between these proteins, particularly between the hPIV F proteins and the PIV5 (a parainfluenza virus that causes kennel cough in dogs), RSV, and MPV F proteins.
Figure 2B:
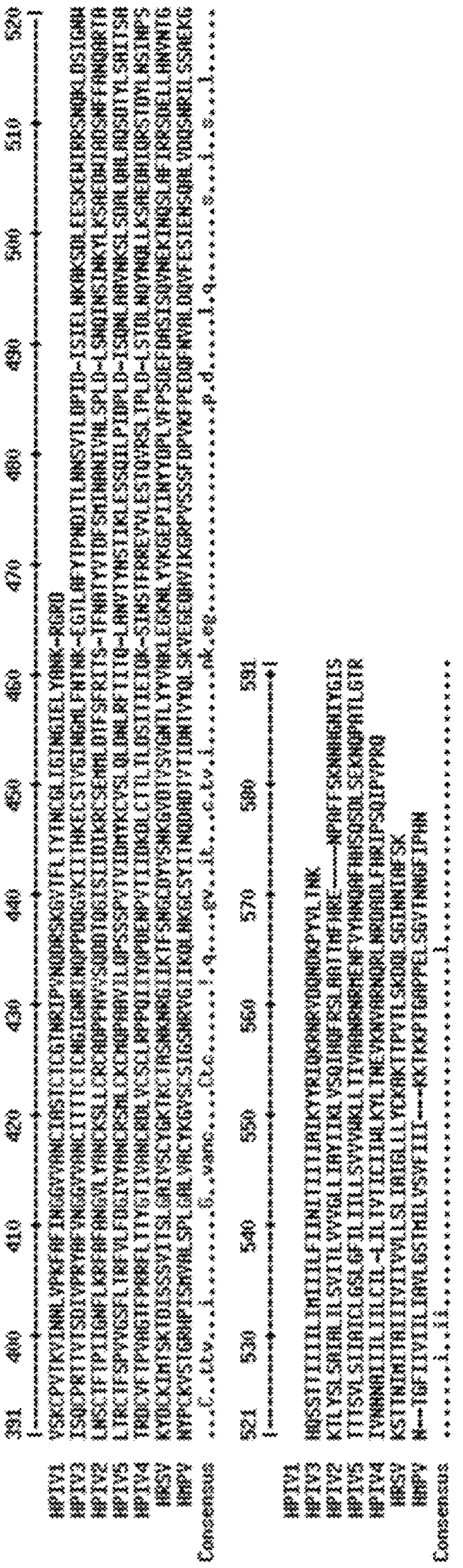

The hPIV3 F structure was modeled on prefusion PIVS F crystal structures (PDB IDs 4GIP and 4WSG) (see FIG. 1, showing structures of the RSV F trimer stabilized in its prefusion conformation, the PIVS F prefusion trimer, and the hPIV3 F postfusion structure). It is noted that the prefusion structure of RSV F trimers differs substantially from the pre fusion structure of PIVS F trimers (FIG. 1). Similarly, at the amino acid sequence level (see FIG. 2), the F proteins of RSV and PIVS (as well as those of hPIVs 1, 2, and 4) are substantially different from hPIV3.

Figure 3:
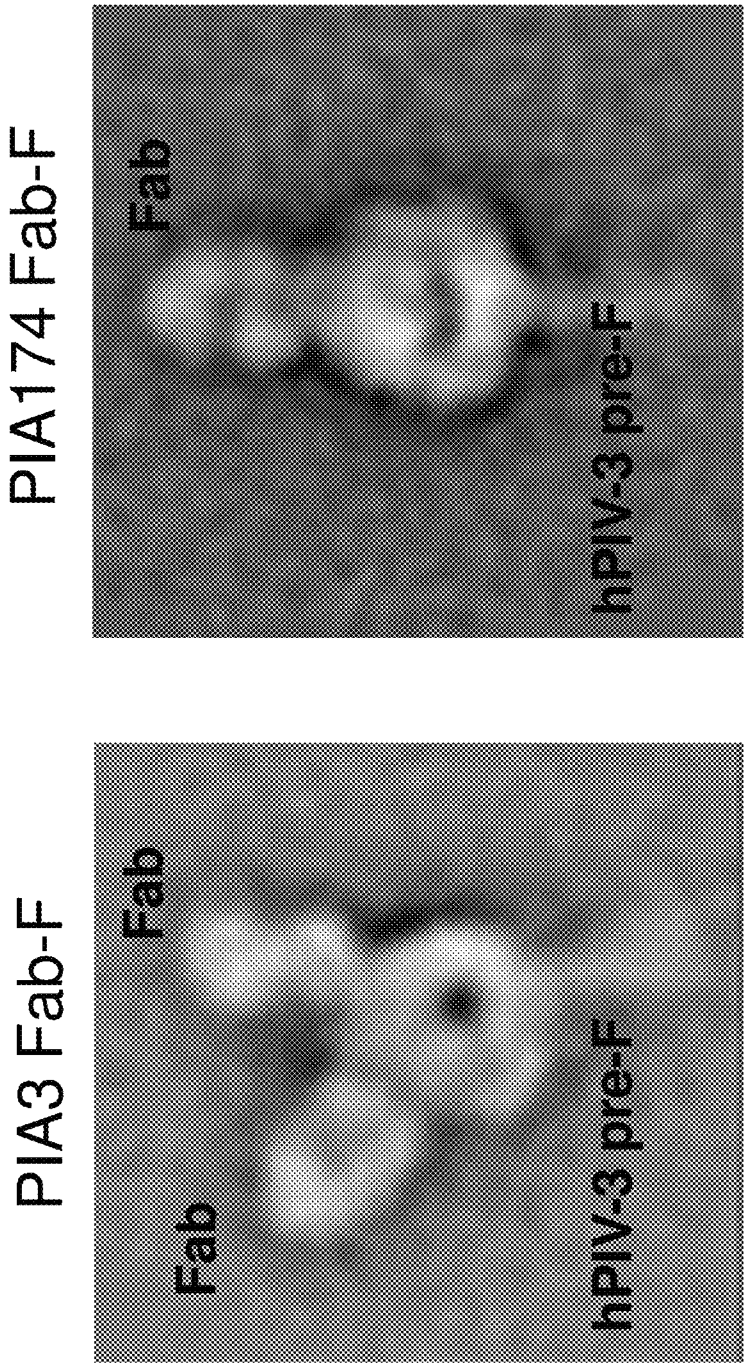
FIG. 3 shows a set of negative stain EM images showing PIA3 Fab and PIA174 Fab binding to hPIV3 F in its prefusion conformation. PIA3 binds to a membrane-distal site of the hPIV3 trimer that corresponds to the antigenic site Ø of RSV F, and the PIA174 antibody binds to a site at the apex of the hPIV3 F trimer.

When initially produced in cells, the hPIV3 F ectodomain linked to a C-terminal GCN4 trimerization domain forms trimers that are mostly in the prefusion conformation. However, when stored at 4° C., the metastable trimers undergo a progressive structural transformation to the hPIV3 F postfusion conformation (see FIG. 7). To generate reagents that can distinguish hPIV3 F proteins in the pre- and post-fusion conformations, mice were immunized with hPIV3 F protein linked to GCN4 and induced antibodies that selectively bind to the pre- or post-fusion structures of hPIV3 F were identified. Specifically, the PIA56 (post-fusion specific), PIA3 (pre-fusion specific) and PIA174 (pre-fusion specific) antibodies were identified. Negative stain EM shows that the PIA3 binds to a membrane-distal site of the hPIV3 trimer that corresponds to the antigenic site Ø of RSV F, and that the PIA174 antibody binds to a site at the apex of the hPIV3 F trimer (see FIG. 3).

Structure-based vaccine design was used to identify potential mutations for the stabilization of the hPIV3 F ectodomain in a prefusion conformation. Disulfide bond and cavity-filling stabilization mutations were introduced into a hPIV3 F ectodomain linked to a C-terminal GCN4 trimerization domain (the backbone sequence is according to GenBank Accession no. AGW51052.1, which is incorporated by reference herein), and the resulting mutants were screened in a 96-well microculture high-throughput mini-expression and ELISA assay using prefusion hPIV3 F antibodies PIA3 and PIA174 and postfusion hPIV3 F antibody PIA56 (FIG. 4). As illustrated in FIGS. 4 and 5, the following mutants have improved retention of the prefusion structure (by antigenic analysis) compared to hPIV3 F linked to GCN4 without stabilizing mutations:

hPIV3 F GCN4, E145L (SEQ ID NO: 10)
hPIV3 F GCN4, V170I (SEQ ID NO: 11)
hPIV3 F GCN4, V1751 (SEQ ID NO: 12)
hPIV3 F GCN4, Y178W (SEQ ID NO: 13)
hPIV3 F GCN4, E193P (SEQ ID NO: 14)
hPIV3 F GCN4, A463V (SEQ ID NO: 15)
hPIV3 F GCN4, S470L (SEQ ID NO: 16)
hPIV3 F GCN4, S470V (SEQ ID NO: 17)
hPIV3 F GCN4, I474Y (SEQ ID NO: 18)
hPIV3 F GCN4, S477V (SEQ ID NO: 19)
hPIV3 F GCN4, A463V, I474Y (SEQ ID NO: 20)
hPIV3 F GCN4, Y178W, A463V, I474Y (SEQ ID NO: 21)
hPIV3 F GCN4, I172C-N238C (SEQ ID NO: 22)
hPIV3 F GCN4, I172C-N238C, V170L, I187F (SEQ ID NO: 23)
hPIV3 F GCN4, 172C-238C, Y178W (SEQ ID NO: 24)
hPIV3 F GCN4, 172C-238C, I474Y (SEQ ID NO: 25)
hPIV3 F GCN4, 172C-238C, A463V, I474Y (SEQ ID NO: 26)

Figure 6A:
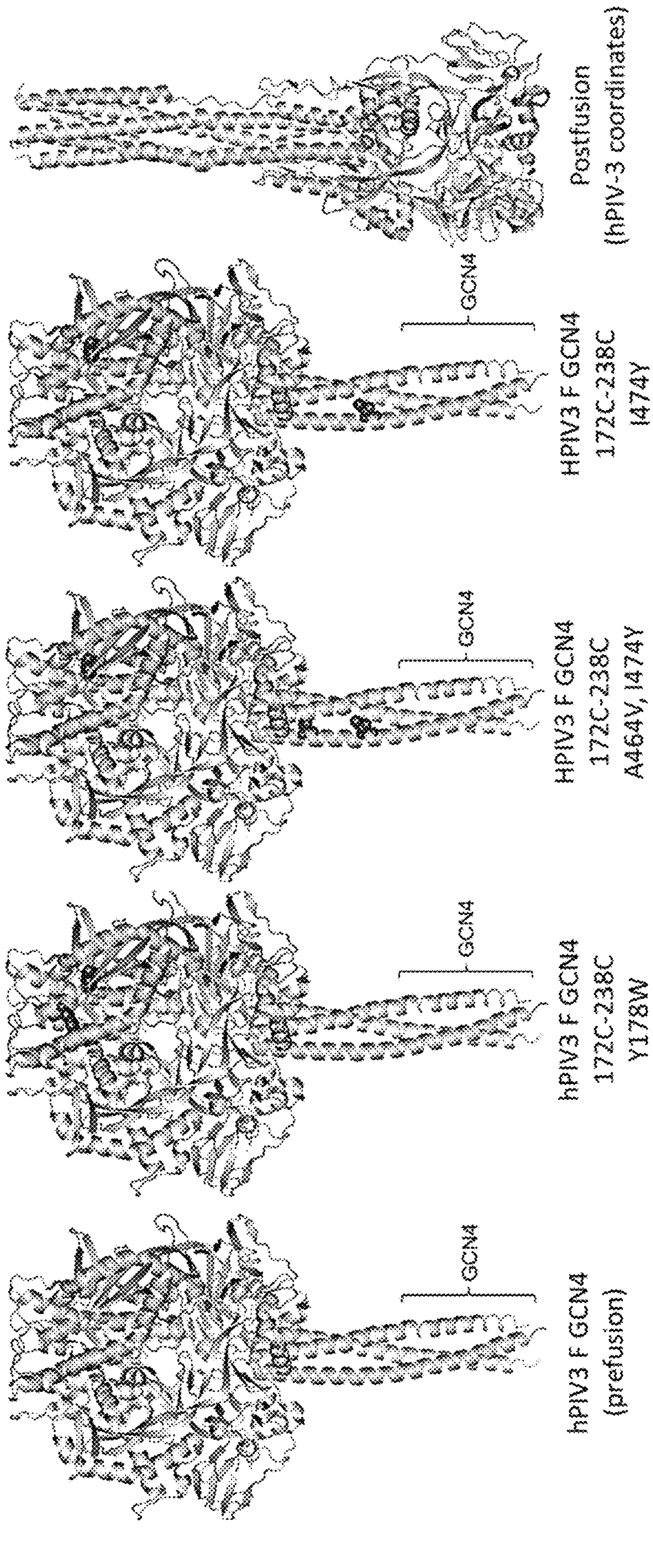
FIGS. 6A-6B shows a set of ribbon diagrams and negative stain EM images showing the pre- and post-fusion conformations of the hPIV3 F protein.
Figure 6B:
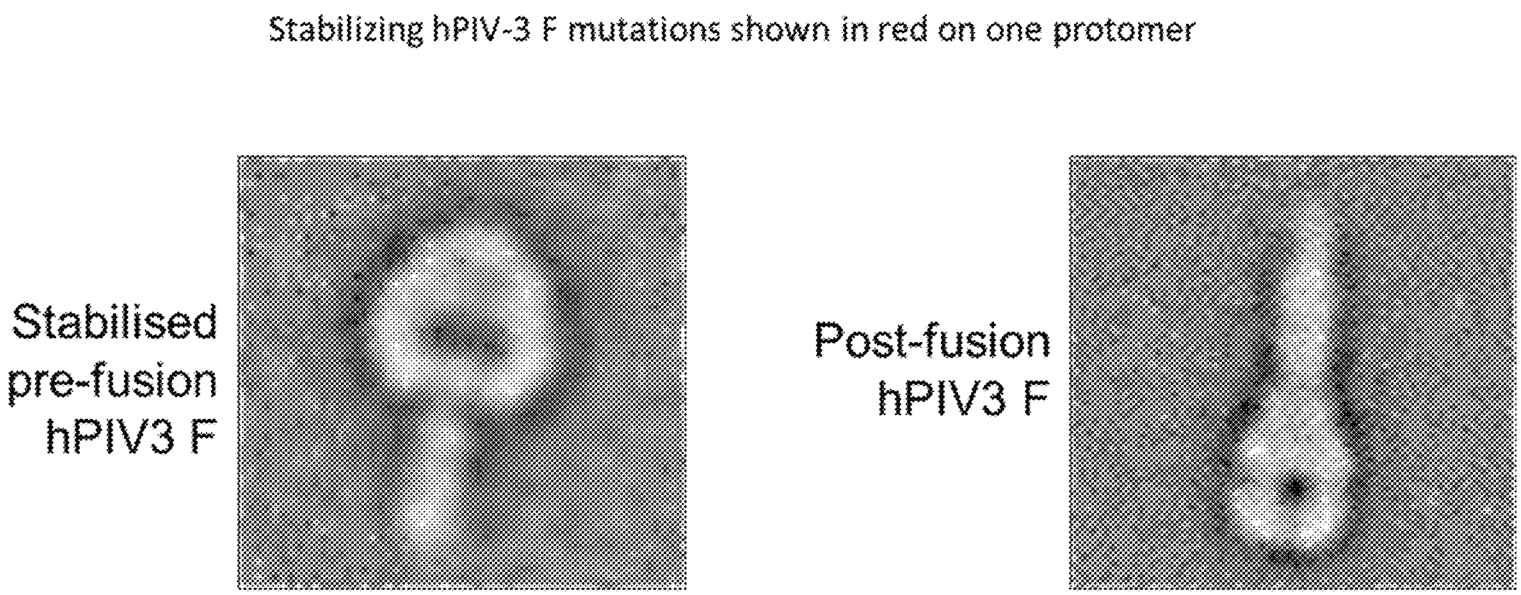
Figure 7:
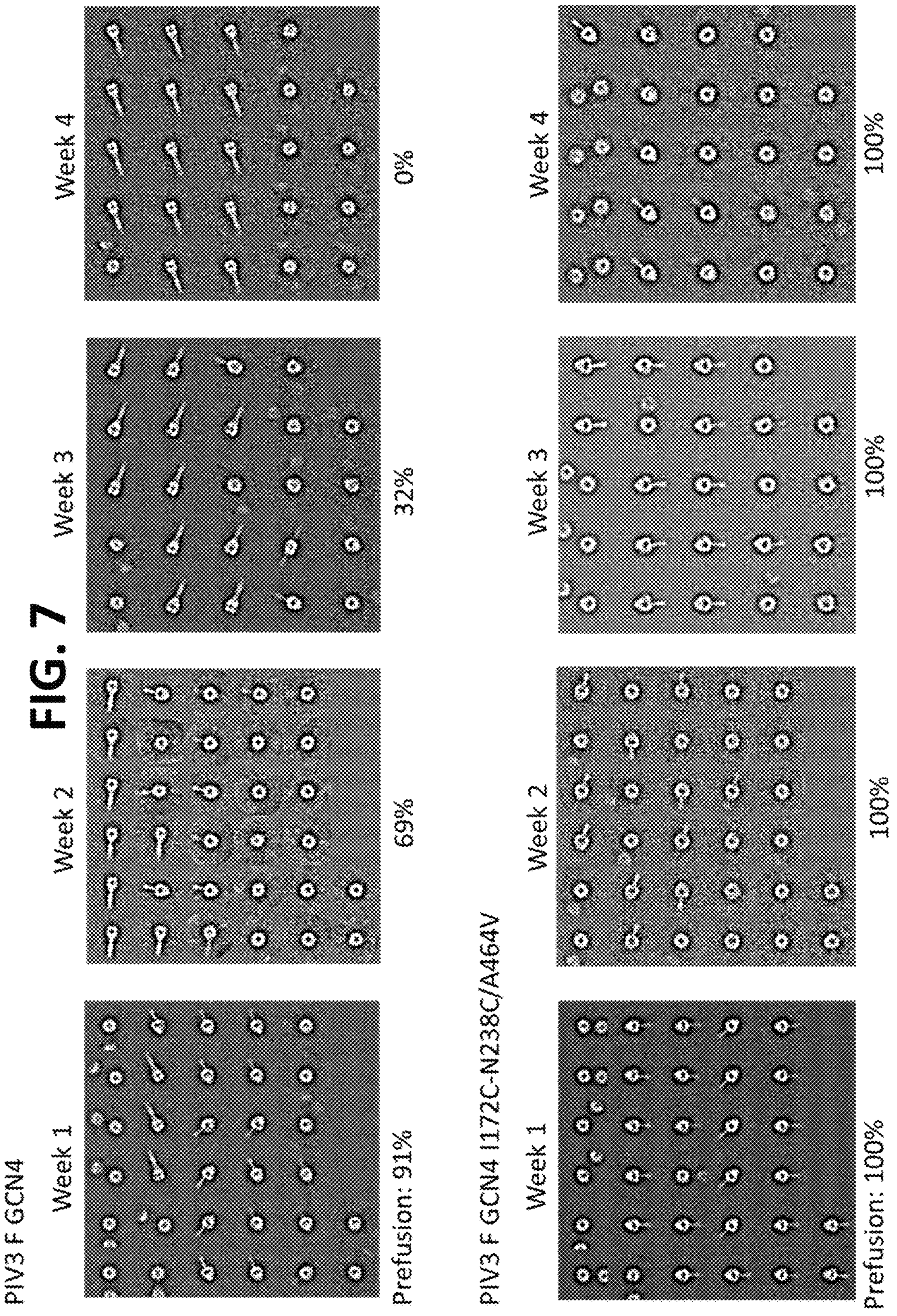
FIG. 7 shows a time-course analysis of hPIV3 F conformation for hPIV3 F variants incubated at 37° C. in PBS. hPIV3 F stabilized only with a C-terminal GCN4 trimerization domain (top row) had a steady reduction in the frequency of prefusion molecules observed. In contrast hPIV3 F with prefusion stabilizing mutations showed 100% retention of the prefusion conformation for 4 weeks.

Ribbon diagrams illustrating the structure of pre- and post-fusion forms of the hPIV F ectodomain are shown in FIG. 6. FIG. 6 also shows negative EM illustrating the preand post-fusion conformations of the hPIV3 F ectodomain. As illustrated in FIG. 6, negative EM staining can be used to distinguish hPIV3 F ectodomain trimers that are in the prefusion conformation from those that are in the postfusion conformation. Using this method, hPIV3 F ectodomain trimers including protomers linked to a C-terminal GCN4 trimerization domain were compared with corresponding trimers contain protomers linked to a C-terminal GCN4 trimerization domain and also including I172C, N238C, and A463V substitutions that stabilize the trimer in the prefusion conformation (FIG. 7). As shown in FIG. 7, hPIV3 F ectodomain trimers including the prefusion stabilizing I172C, N238C, and A463V substitutions (and a C-terminal GCN4 trimerization domain) retained the prefusion conformation over the course of 4 weeks at 37° C., whereas corresponding trimers that lack the I172C, N238C, and A463V substitutions did not. Similar results were obtained for hPIV3 F ectodomain trimers including the prefusion stabilizing A463V and I474Y substitutions (and a C-terminal GCN4 trimerization domain)

Figure 8A:
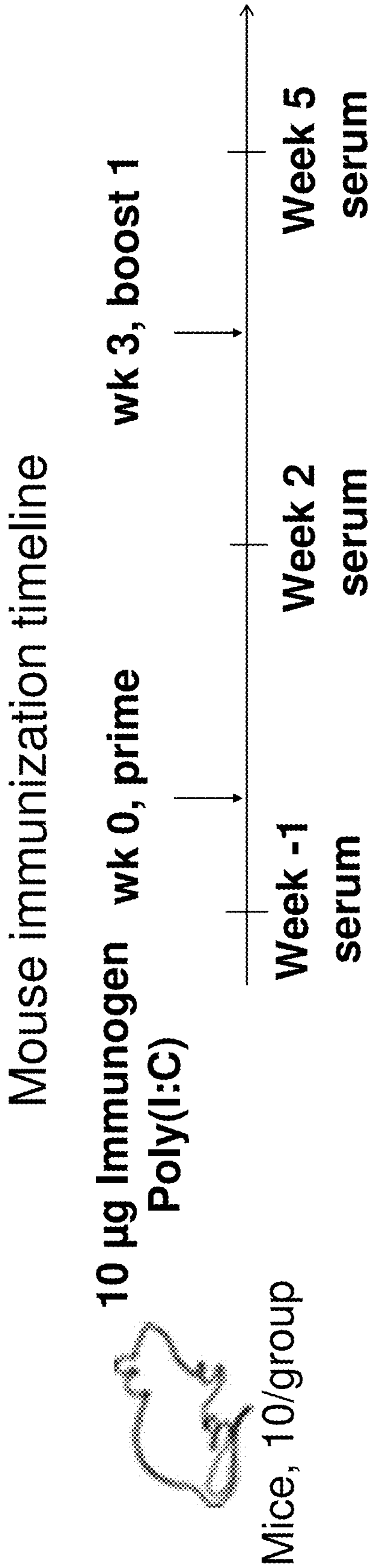
FIGS. 8A-8C show a set of graphs illustrating the immunogenicity of engineered hPIV3 F trimers. (A) Immunization schedule. (B) Neutralization titers at week 5 in CB6F1/J mice immunized with 2×10 μg of hPIV3 F GCN4; hPIV3 F GCN4 172C-238C Y178W; hPIV3 F GCN4 172C-238C A463V I474Y; hPIV3 F GCN4 172C-238C I474Y; or postfusion hPIV3 in poly I:C at weeks 0 and 3. (C) Neutralization titers at week 5 in CB6F1/J mice immunized with 2×10 μg of hPIV3 F GCN4; hPIV3 F GCN4 Y178W; hPIV3 F GCN4 A463V I474Y; hPIV3 F GCN4 172C-238C I464Y; or postfusion hPIV3 in poly I:C at weeks 0 and 3.
Figure 8B:
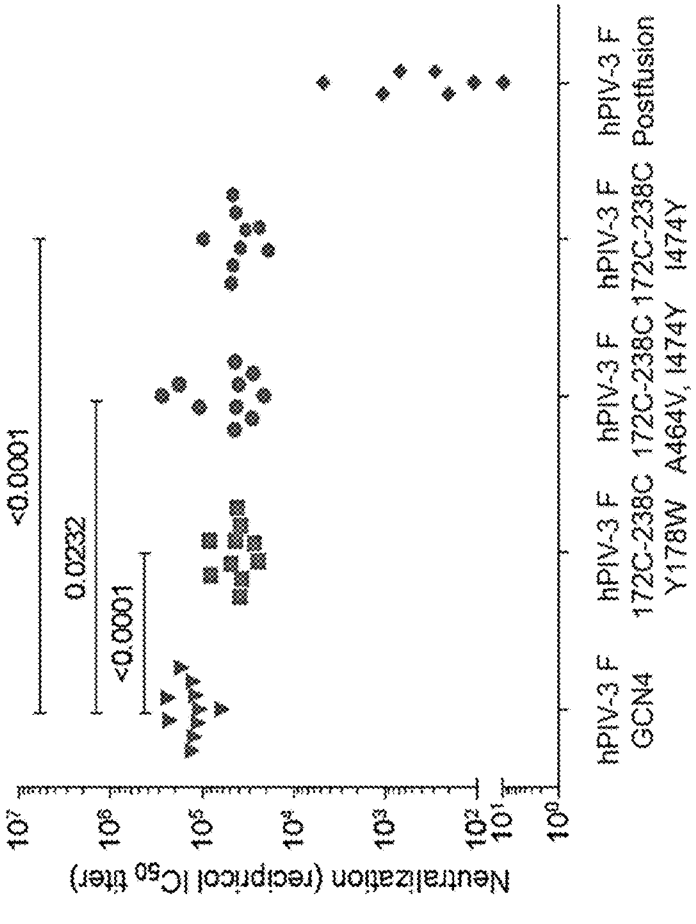
Figure 8C:
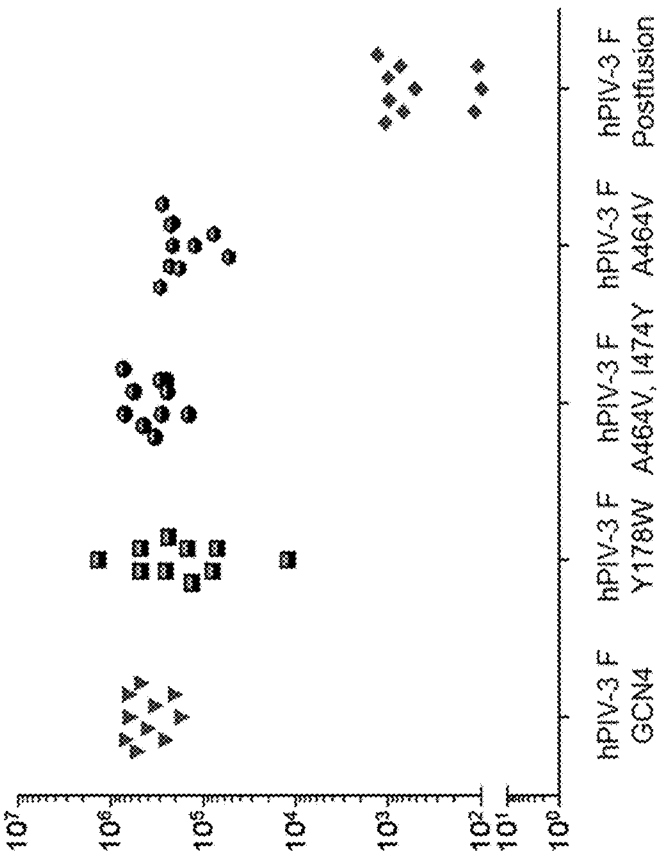

Immunization assays were conducted with several of the modified hPIV3 F ectodomain trimers to determine if these trimers could produce a neutralizing immune response in an animal model. CB6F1/J mice were immunized with 10 pg of hPIV3 F in poly I:C at weeks 0 and 3 and the neutralization titer of sera from the immunized mice was assayed as week 5 (see FIG. 8A). As shown in FIGS. 8B and 8C, the selected pre-fusion stabilized hPIV3 F ectodomain trimers all elicited increased titers of neutralizing antibodies compared to postfusion hPIV3 F.

Figure 9A:
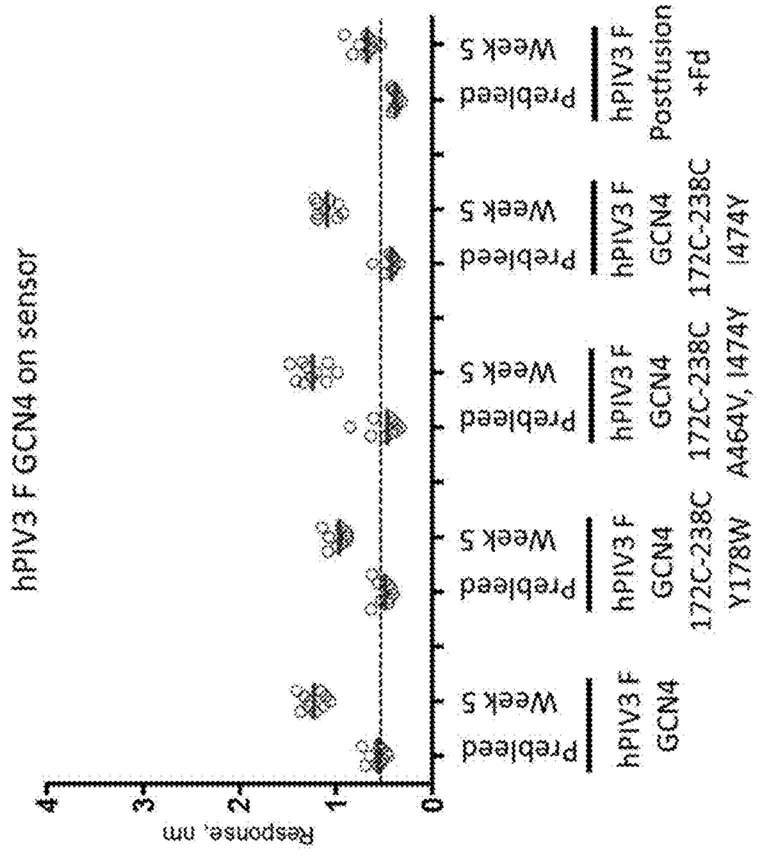
FIGS. 9A-9F show a set of graphs illustrating the immunogenicity of engineered hPIV3 F ectodomain trimers using an Octet binding assay. Octet binding titers for week 5 sera from CB6F1/J mice immunized with 2×10 μg of the indicated hPIV3 F in poly I:C at weeks 0 and 3 were probed with hPIV3 F GCN4 (FIG. 9A), hPIV3 F GCN4 172C-238C Y178W (FIG. 9B), hPIV3 F GCN4 172C-238C A463V I474Y (FIG. 9C), hPIV3 F GCN4 172C-238C I474Y (FIG. 9D), RSV F DS-Cav1 (FIG. 9E, negative control), hPIV3 F postfusion (FIG. 9F) linked to the sensor.
Figure 9B:
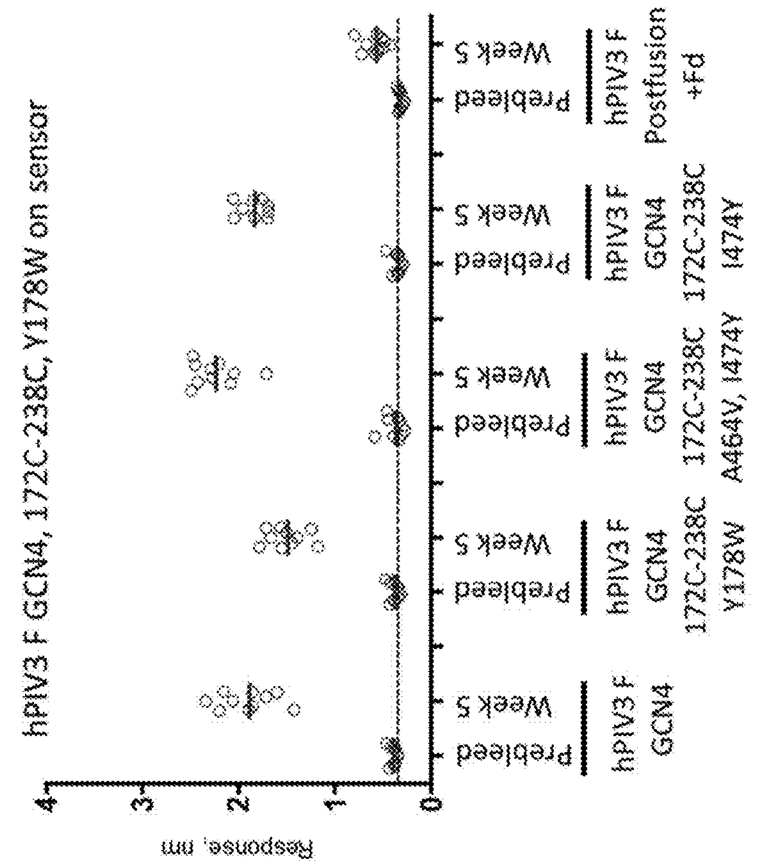
Figure 9C:
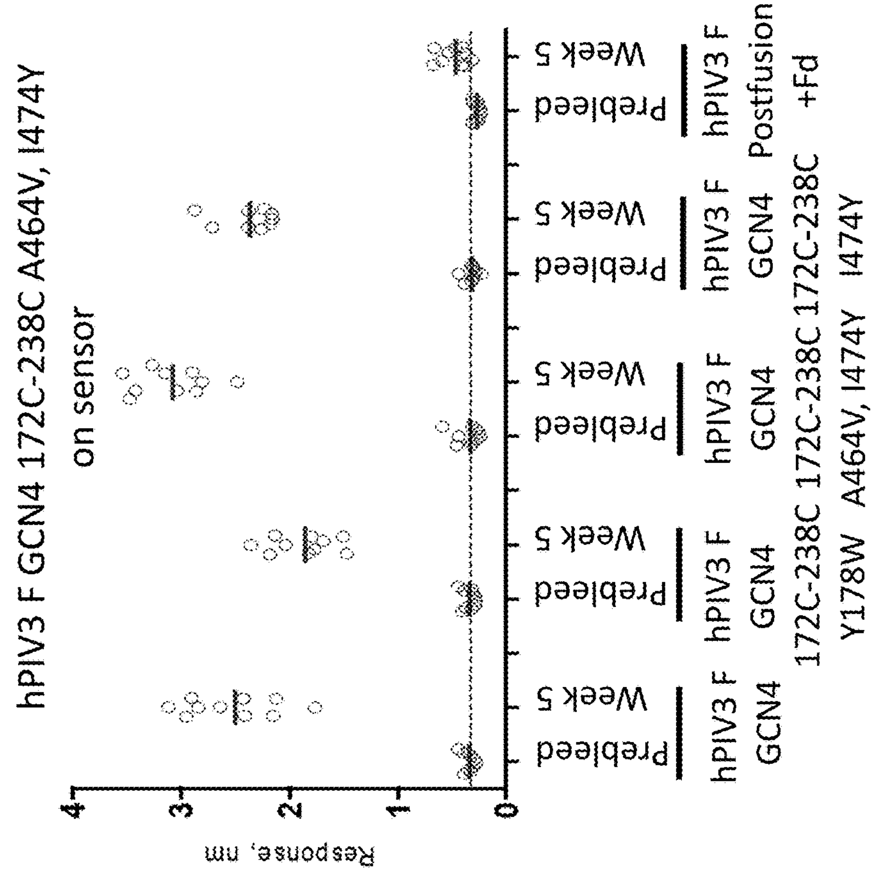
Figure 9D:
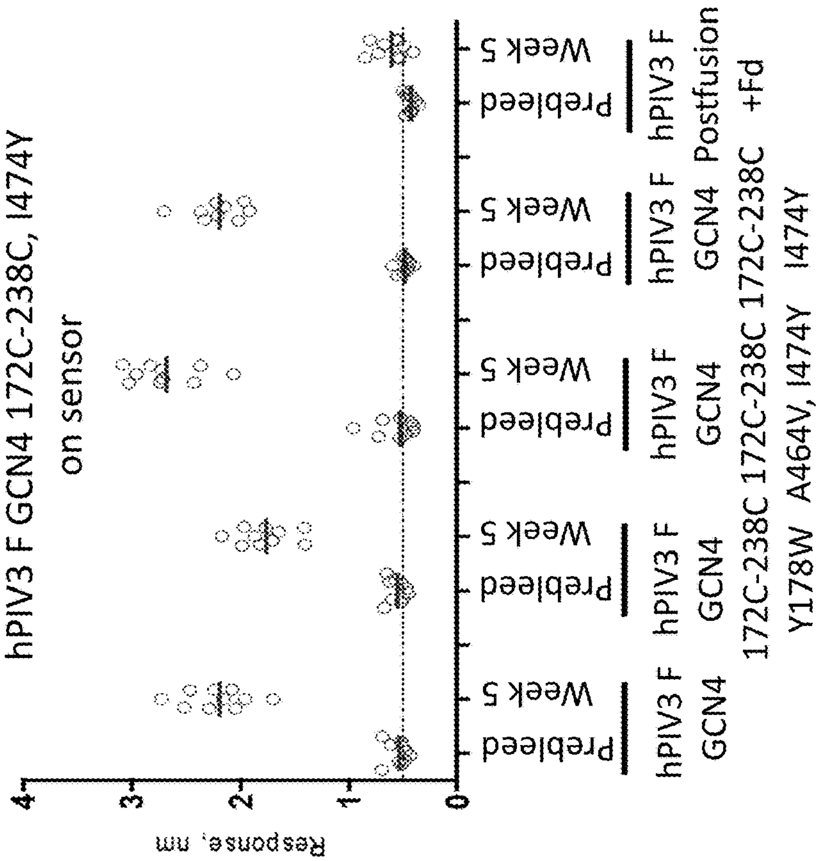
Figure 9F:
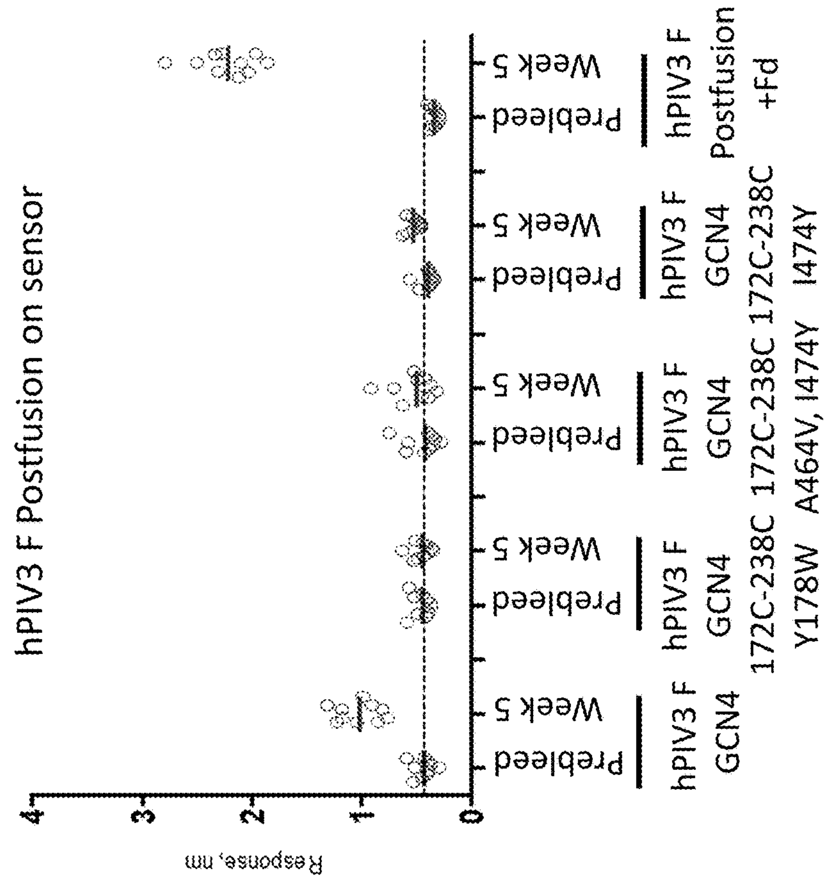
Figure 9E:
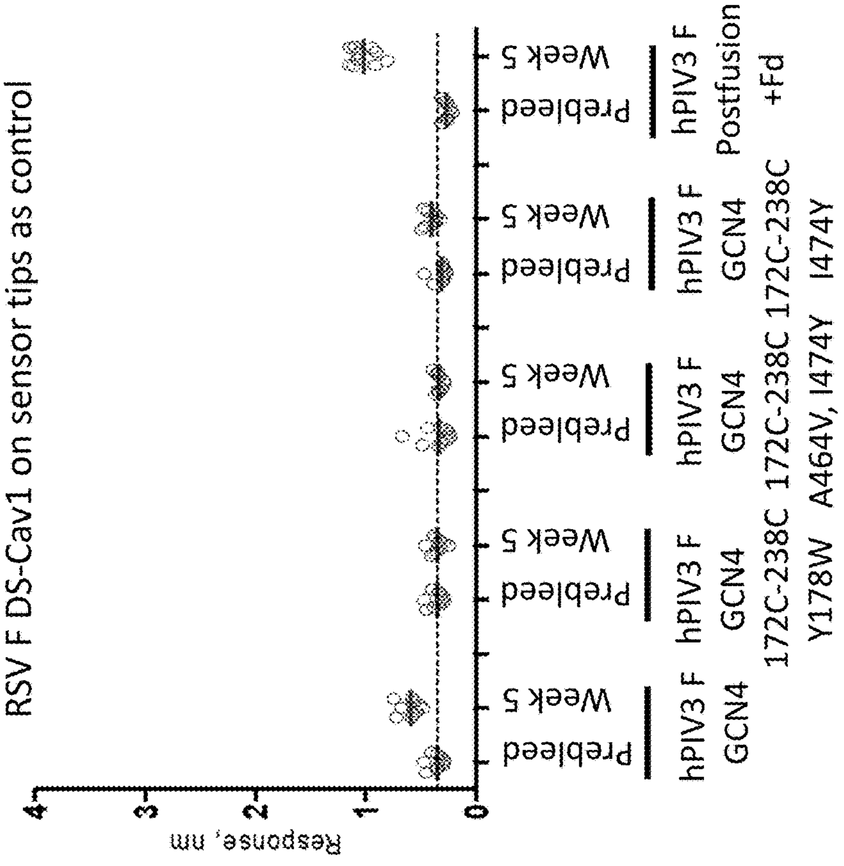

Sera from immunized mice was tested for binding to various prefusion-stabilized hPIV3 F ectodomain trimers using an Octet binding assay. hPIV3 F GCN4 (FIG. 9A), hPIV3 F GCN4 172C-238C Y178W (FIG. 9B), hPIV3 F GCN4 172C-238C A463V I474Y (FIG. 9C), hPIV3 F GCN4 172C-238C I474Y (FIG. 9D), RSV F DS-Cav1 (FIG. 9E, negative control), hPIV3 F postfusion (FIG. 9F) was linked to the sensor and sera from the indicated immunizations was assayed for binding.

Summary of Methods

Protein expression and purification. hPIV F mutations were made by site-directed mutagenesis using the Stratagene Quik-change procedure. hPIV F variants were expressed by transient transfection of Expi293F cells using 293Fectin (Invitrogen). Cell culture supernatants were harvested 5 days post transfection and centrifuged at 10,000 g to remove cell debris. The supernatants were sterile-filtered, and hPIV F proteins were purified by nickel and streptactin-affinity chromatography followed by size-exclusion chromatography. In some embodiments, the nickel and streptactin purification tags were removed for animal immunization and crystallization studies.

Screening of prefusion-stabilized hPIV F constructs. Prefusion hPIV F variants were derived from the native hPIV F sequences. A 96-well microplate-formatted transient gene expression approach was used to achieve high-throughput expression of various hPIV F proteins using a previously described high-throughput assay developed for HIV (Pancera et al., *PloS one,* 8, e55701, 2013). Briefly, 24 h prior to transfection HEK 293T cells were seeded in each well of a 96-well microplate at a density of $2.5\times10^5$ cells/ml in expression medium (high glucose DMEM supplemented with 10% ultra-low IgG fetal bovine serum and 1×-non-essential amino acids), and incubated at 37° C., 5% CO2 for 20 h. Plasmid DNA encoding a protomer of the variant hPIV3 F trimer and TrueFect-Max (United BioSystems, MD) were mixed and added to the growing cells, and the 96-well plate incubated at 37° C., 5% CO2. One day post transfection, enriched medium (high glucose DMEM plus 25% ultra-low IgG fetal bovine serum, 2× nonessential amino acids, 1× glutamine) was added to each well, and the 96-well plate was returned to the incubator for continuous culture. On day five, post transfection, supernatants with the expressed hPIV3 F variants were harvested and tested by ELISA for binding to pre- and post-fusion specific antibodies using Ni2+-NTA microplates. In some examples, after incubating the harvested supernatants at 4° C. for one week, ELISAs were repeated.

hPIV3 F antigenic characterization. A fortéBio Octet Red384 instrument was used to measure binding kinetics of hPIV3 F variants to antibodies that target the pre-fusion form. All assays were performed with agitation set to 1,000 rpm in phosphate-buffered saline (PBS) supplemented with 1% bovine serum albumin (BSA) to minimize nonspecific interactions. The final volume for all solutions was 50 μl/well. Assays were performed at 30° C. in tilted black 384-well plates (Geiger Bio-One). Ni-NTA sensor tips (ForteBio) were used to load his-tagged proteins for 300 s to capture. Biosensor tips were then equilibrated for 90 s in PBS+1% BSA prior to measuring association with antigen binding fragments (Fabs) in solution for 300 s; Fabs were then allowed to dissociate for 300 s-1200 s depending on the observed dissociation rate. Parallel correction to subtract systematic baseline drift was carried out by subtracting the measurements recorded for a loaded sensor incubated in PBS+1% BSA. Data analysis and curve fitting were carried out using Octet software, version 8.0. Experimental data were fitted with the binding equations describing a 1:1 interaction. Global and local analyses of the data sets assuming reversible binding (full dissociation) were carried out using nonlinear least-squares fitting allowing a single set of binding parameters to be obtained simultaneously for all of the concentrations used in each experiment.

Physical stability of hPIV3 F variants. To assess the physical stability of the pre-fusion conformation of designed hPIV3 F glycoproteins under various stress conditions, the proteins were treated with a variety of pharmaceutically relevant stresses such as extreme pH, high temperature, low and high osmolarity, and repeated freeze/thaw cycles while at a concentration of 50 μg/ml. The physical stability of treated hPIV3 F variants was evaluated by the preservation of hPIV3 antigenic site Ø after treatment as assessed by the hPIV3 F site Ø-specific antibody PIA3.

In pH treatments, the hPIV3 F ectodomain trimer solution was adjusted to pH 3.5 and pH 10 with appropriate buffers exchange and incubated at room temperature for 60 minutes and subsequently neutralized to pH 7.4. Temperature treatments were carried out by incubating the hPIV3 F ectodomain trimer solutions at 50° C. and 70° C. for 60 minutes in a PCR cycler with heated lid. In osmolality treatments, hPIV3 F ectodomain solutions originally containing 137 mM NaCl in PBS buffer were either diluted with 2.5 mM Tris buffer (pH 7.5) to an osmolality of 10 mM NaCl or adjusted with 4.5 M $MgCl_2$ to a final concentration of 3.0 M $MgCl_2$. Protein solutions were incubated for 60 minutes at room temperature and then returned to PBS buffer, and concentrated to 50 μg/ml. The freeze/thaw treatment was carried out by repeatedly freezing hPIV3 F ectodomain trimer solutions in liquid nitrogen and thawing at 37° C. ten times. All hPIV3 F ectodomain trimers were diluted to 40 μg/ml with PBS buffer, and their ability to bind PAI3 Fab was measured with an Octet instrument using the protocol described above. The degree of physical stability is reported as the ratio of steady state PAI3-binding level before and after stress treatment.

Negative stain electron microscopy. Samples were adsorbed to freshly glow-discharged carbon-film grids, rinsed twice with buffer and stained with freshly made 0.75% uranyl formate. Images were recorded on an FEI T20 microscope with a 2 k×2 k Eagle CCD camera at a pixel size of 1.5 Å. Image analysis and 2D averaging was performed with Bsoft (Heymann and Belnap, *J. Struct Biol.,* 157, 3, 2007) and EMAN (Ludtke, Baldwin, and Chiu, *J. Struct. Biol.,* 128, 82, 1999).

Mouse immunizations. All animal experiments were reviewed and approved by the Animal Care and Use Committee of the Vaccine Research Center, NIAID, NIH, under animal protocol 13-454, and all animals were housed and cared for in accordance with local, state, federal, and institute policies in an American Association for Accreditation of Laboratory Animal Care (AAALAC)-accredited facility at the NIH. Hybrid mice that were the first filial offspring of a cross between BALB/cJ females (C) and C57BL/6J males (B6) (The Jackson Laboratory) known as CB6F1/J at ages 6 weeks to 12 weeks were intramuscularly injected with hPIV3 F ectodomain trimer immunogens at week 0 and week 3. The frozen hPIV3 F ectodomain trimer variant immunogen proteins were thawed on ice and mixed with 5-fold w/w poly I:C (Invivogen) adjuvant (i.e. 10 μg hPIV3 F, 50 μg Poly I:C per animal per immunization), with injections taking place within 1 h of immunogen:adjuvant preparation. No adverse effect from immunization was observed. Blood was collected at least three days before immunization, and at week two, week five and week seven post initial immunization.

Viruses and cells. Viral stocks of hPIV3 were prepared and maintained using standard techniques.

hPIV3 neutralization assays. Sera were distributed as four-fold dilutions from 1:10 to 1:163840, mixed with an equal volume of recombinant mKate-Respiratory syncytial virus expressing prototypic F genes from subtype A (strain A2) and the Katushka fluorescent protein, and incubated at 37° C. for 1 h. Next, 50 μl of each serum dilution/virus mixture was added to HEp-2 cells, which had been seeded at a density of $2.4\times10^4$ in 30 μl MEM (minimal essential medium) in each well of 384-well black optical bottom plates, and incubated for 20-22 h before spectrophotometric analysis at 588 nm excitation and 635 nm emission (SpectraMax Paradigm, Molecular Devices, CA). The IC50 for each sample was calculated by curve fitting and non-linear regression using GraphPad Prism (GraphPad Software Inc., CA).

Sera antigenic analysis. Mouse sera from a subset of immunization groups were assessed for binding to prefusion hPIV3 F ectodomain trimer in the presence of antigenic site Ø antibody D25 and quaternary preferring antibody AM14 using a fortebio Octet HTX instrument. Week 5 sera were diluted 1:300 in 1% BSA/PBS. Anti penta His, (HIS1K) sensor tips obtained from fortéBio were equilibrated in PBS prior to running an assay. hPIV F trimeric protein at 20 ug/ml in 1% BSA/PBS was loaded onto HIS1K biosensors using the C-terminal His tag for 300 s. The sensor tips were subsequently equilibrated in 1% BSA/PBS for 60 s followed by capture of pre fusion specific antibodies D25 and AM14 at 50 ug/ml for 600 s. HIS1K tips loaded with DS-Cav1/D25 or AM14 were equilibrated for 180 s in 1% BSA/PBS followed by a serum association step for 300 s and a subsequent dissociation step for an additional 300 s. An identical assay was performed in the absence of antibodies D25 or AM14 to obtain serum response in the absence of competing antibodies. Data analysis was performed using Octet and GraphPad Prism 6 software.

Example 2 hPIV1 F Proteins Stabilized in a Prefusion Conformation

The example illustrates embodiments of an hPIV1 F ectodomain trimer stabilized in a prefusion conformation by one or more amino acid substitutions. The prefusion-stabilized hPIV1 F proteins are useful, for example, for inducing a neutralizing immune response to hPIV1 in a subject.

The hPIV1 F structure was modeled on prefusion PIVS F crystal structures (PDB IDs 4GIP and 4WSG) to identify potential mutations to stabilize hPIV1 F in its prefusion conformation. Initial experiments were conducted to identify hPIV1 F proteins from several strains of hPIV1 that expressed well in cellular expression systems. Higher-expressing F proteins were selected, and mutated to stabilize the F protein in its prefusion conformation. Stabilizing mutations included mutation of the hydrophobic residues in the FP region, addition of a C-terminal GCN4 trimerization domain, cavity filling mutations in the stem region, and non-native disulfide bonds. Several rounds of optimization of the pre-fusion stabilizing mutations were tested. Among the mutations tested include those listed in the following table:

| Name | Based on GenBank No. | Mutations |
|---|---|---|
| hPIV1_GCN4 | BAS30410.1 | C-term truncation at position 486, C-terminal GCN4 |
| hPIV1_GCN4_PIV5stem | BAS30410.1 | swap hPIV1 Stem for PIV5 stem, C-term truncation at position 486, C-terminal GCN4 |
| hPIV1-3 | | C-term truncation at position 472, C-terminal GCN4 |
| hPIV1-4 | | F1-F2 linker (RFF112-114GSG), C-term truncation at position 490, C-terminal GCN4 (including n-terminal MKQ residues) |
| hPIV1_420_preF1 | AFP49418.1 | C-term truncation at position 486, C-terminal GCN4 |
| hPIV1_420_preF2 | AFP49418.1 | L175C-N241C, C-term truncation at position 486, C-terminal GCN4 |
| hPIV1_420_preF3 | AFP49418.1 | N241Q, C-term truncation at position 486, C-terminal GCN4 |
| hPIV1_420_preF4 | AFP49418.1 | F1-F2 linker (RFF112-114GGS), C-term truncation at position 486, C-terminal GCN4 |
| hPIV1_420_preF5 | AFP49418.1 | F1-F2 linker (RFF112-114GGS), A466I, S473I, A480I, C-term truncation at position 486, C-terminal GCN4 |

-continued

| Name | Based on GenBank No. | Mutations |
|---|---|---|
| hPIV1_420_preF6 | AFP49418.1 | F1-F2 linker (RFF112-114GGS), C-term truncation at position 484, C-terminal GCN4 (including n-terminal MKQ residues) |
| hPIV1_880_preF1 | BAS30410.1 | F1-F2 linker (FF113-114GS), A466I, S473I, A480I, C-term truncation at position 486, C-terminal GCN4 |
| hPIV1_880_preF2 | BAS30410.1 | F1-F2 linker (FF113-114GS), A466I, S473I, C-term truncation at position 479, C-terminal GCN4 |
| hPIV1_880_preF3 | BAS30410.1 | F1-F2 linker (FF113-114GS), V117C-L430C, A466I, S473I, A480I, C-term truncation at position 486, C-terminal GCN4 |
| hPIV1_880_preF4 | BAS30410.1 | F1-F2 linker (FF113-114GS), I118C-L430C, A466I, S473I, A480I, C-term truncation at position 486, C-terminal GCN4 |

Figure 10:
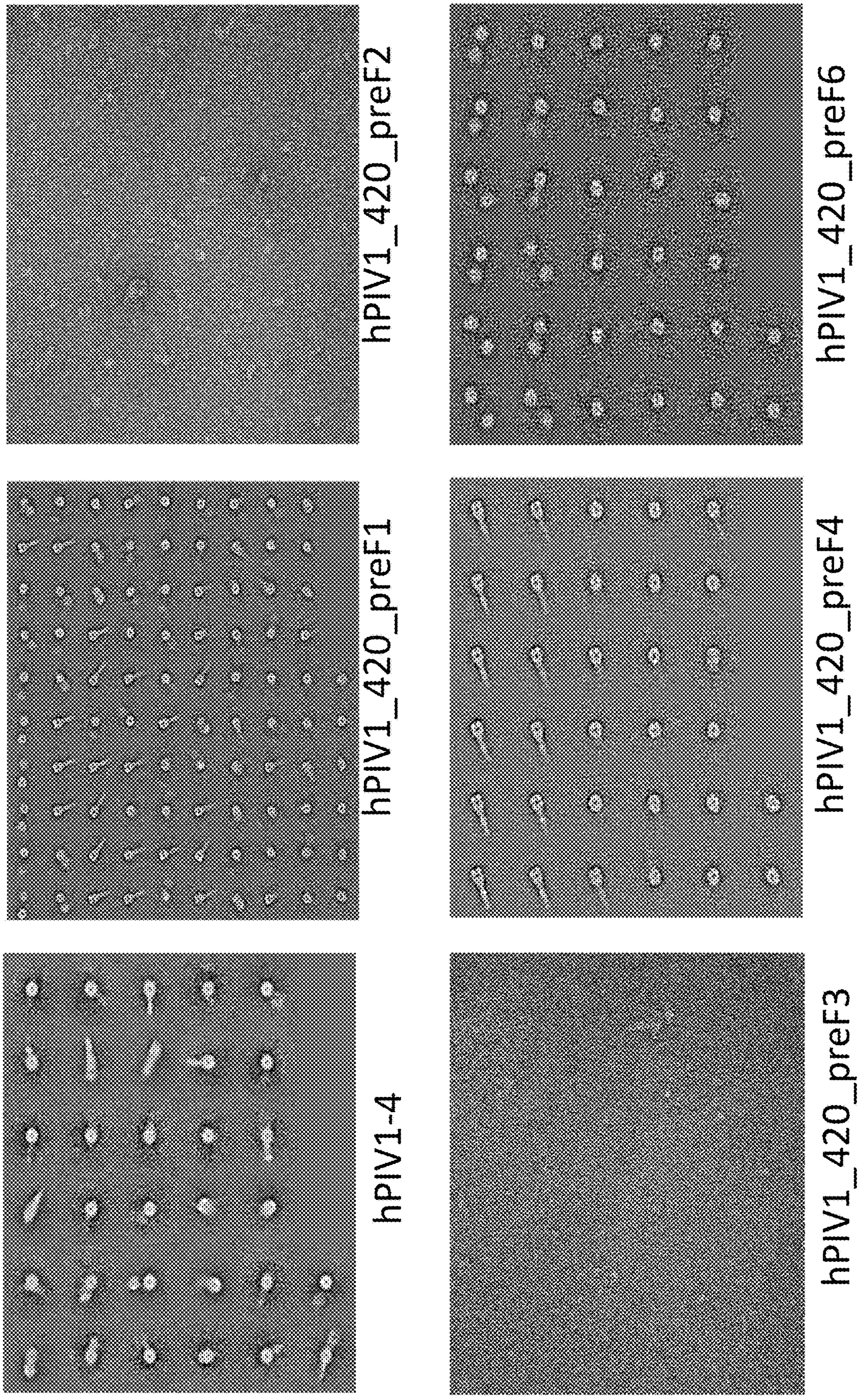
FIGS. 10 and 11 show negative stain EM images of several hPIV1 F ectodomain trimers containing mutations for stabilization in the prefusion conformation. Of these, the mutant with the best stabilization of the prefusion conformation was hPIV1_880_preF2.
Figure 11:
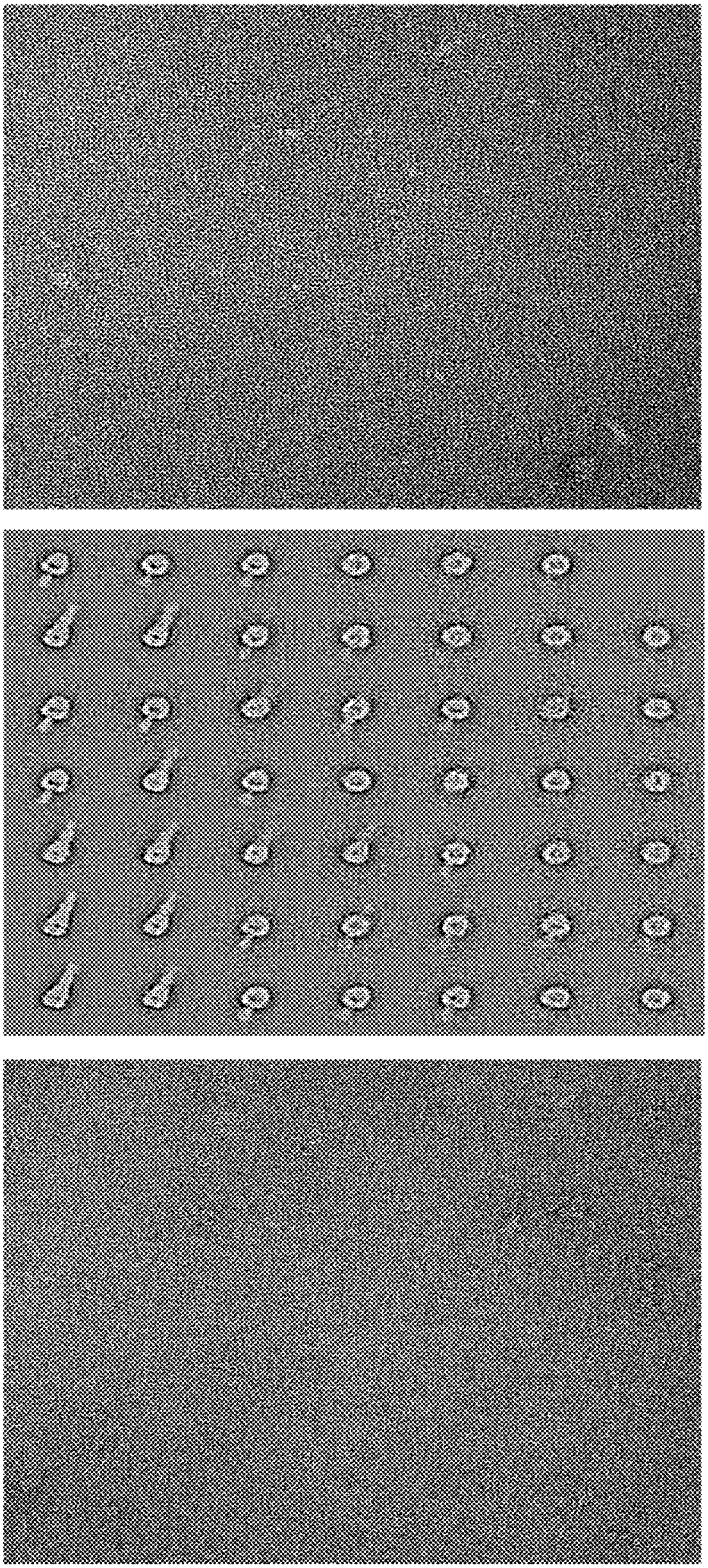

FIG. 10 shows negative stain EM data for several of the hPIV1 F mutants, illustrating examples with poor prefusion stabilization. Subsequent rounds of hPIV1 F prefusion stabilization identified mutants that retained the prefusion structure (see FIG. 11). Of these, the best retention of the prefusion structure was identified for the hPIV1_880_preF2 protein:

hPIV1_880_preF2 (SEQ ID NO: 4)

Figure 12:
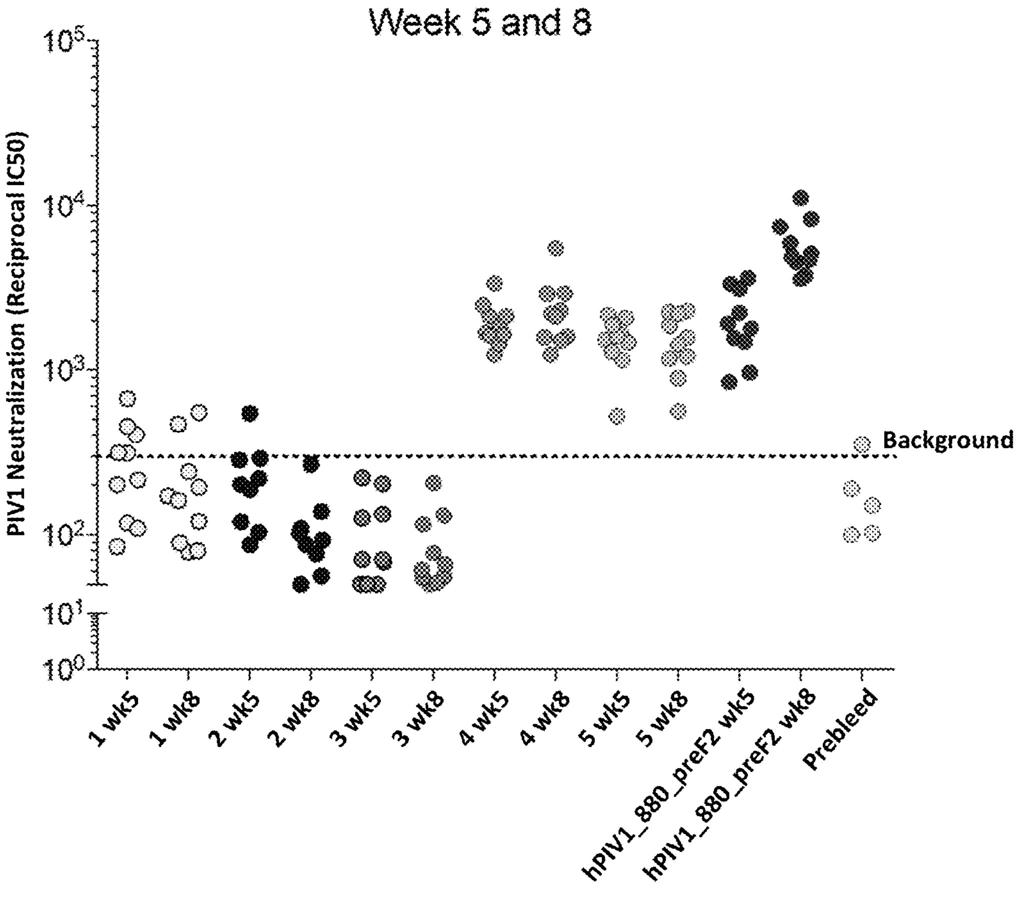
FIG. 12 shows a graph of results from immunogenicity assays in mice using prefusion-stabilized hPIV1 F ectodomain trimers. Mice were immunized according the schedule shown in FIG. 8A. Neutralization titers of serum collected at week 5 (wk5) and week 8 (wk8) post-immunization with 2×10 μg of various prefusion hPIV1 F ectodomain trimers, including the hPIV1_880_preF2 construct, are shown.

Several of the above prefusion constructs were purified and assayed for induction of a neutralizing immune response in mice as using the protocol described in Example 1. As shown in FIG. 12, sera from mice immunized with the hPIV1_880_preF2 immunogen successfully neutralized hPIV1 in an in vitro assay. Serum from the immunized mice was assayed for binding to hPIV1 F ectodomain trimers in the pre- and post fusion conformation using an Octet binding assay using the protocol described in Example 1 (FIG. 13).

Example 3 hPIV2 F Proteins Stabilized in a Prefusion Conformation

The example illustrates embodiments of an hPIV2 F ectodomain trimer stabilized in a prefusion conformation by one or more amino acid substitutions. The prefusion-stabilized hPIV2 F proteins are useful, for example, for inducing a neutralizing immune response to hPIV2 in a subject.

The hPIV2 F structure was modeled on prefusion hPIV2 F crystal structures (PDB IDs 4GIP and 4WSG) to identify potential mutations to stabilize hPIV2 F in its prefusion conformation. Initial experiments were conducted to identify hPIV2 F proteins from several strains of hPIV2 that expressed well in cellular expression systems. Higher-expressing F proteins were selected, and mutated to stabilize the F protein in its prefusion conformation. Stabilizing mutations included mutation of the hydrophobic residues in the FP region, addition of a C-terminal GCN4 trimerization domain, cavity filling mutations in the stem region, and non-native disulfide bonds. Several rounds of optimization of the pre-fusion stabilizing mutations were tested. In the published PIVS F prefusion structure, the GCN4 trimerization domain includes the sequence set forth as IEDKIEEILSKIYHIENEIARIKKLIGEAP (residues 467-496 of SEQ ID NO: 7). Surprisingly, hPIV2 F ectodomain trimers including this trimerization motif did not form as efficiently as the corresponding PIVS F ectodomain trimers. Based on an examination of the PIVS F and GCN4 structures, it was determined that incorporating three additional amino acid from GCN4 (MKQ) might be a better fit for the hPIV2 F ectodomain trimers, and incorporation of these amino acids was found to improve hPIV2 F ectodomain expression and trimerization. Among the mutations tested include those listed in the following table:

| Name | Based on GenBank No. | Mutations |
|---|---|---|
| hPIV2_GCN4 | | C-term truncation at position 480, C-terminal GCN4 |
| hPIV2_GCN4_PIV5stem | | swap hPIV2 Stem for PIV5 stem, C-term truncation at position 480, C-terminal GCN4 |
| hPIV2_GCN4_A127C_L220C | | A127C-L220C, C-term truncation at position 480, C-terminal GCN4 |
| hhPIV2_GCN4_A134C_I264C | | A134C-I264C, C-term truncation at position 480, C-terminal GCN4 |
| hPIV2_5 | AAA46842.1 | F1-F2 linker (KTRQKR101-106GSGSGS, SEQ ID NO: 33 to SEQ ID NO: 32), C-term truncation at position 473, C-terminal GCN4 |
| hPIV2_preF6 | AAA46842.1 | F1-F2 linker (KTRQKRFA101-108GGGSGGGS, SEQ ID NO: 33 to SEQ ID NO: 32), C-term truncation at position 484, C-terminal GCN4 (including n-terminal MKQ residues) |
| hPIV2_preF6_v2 | AAA46842.1 | F1-F2 linker (KTRQKRFA101-108GGGSGGGS, SEQ ID NO: 33 to SEQ ID NO: 32), V169C-T235C, C-term truncation at position 484, C-terminal GCN4 (including n-terminal MKQ residues) |

-continued

| Name | Based on GenBank No. | Mutations |
|---|---|---|
| hPIV2_preF6_v3 | AAA46842.1 | F1-F2 linker (KTRQKRFA101-108GGGSGGGS, SEQ ID NO: 33 to SEQ ID NO: 32), A467V, S474V, A478V, A481V, C-term truncation at position 484, C-terminal GCN4 (including n-terminal MKQ residues) |
| hPIV2_preF6_v4 | AAA46842.1 | F1-F2 linker (KTRQKRFA101-108GGGSGGGS, SEQ ID NO: 33 to SEQ ID NO: 32), A467V, S474V, F476Y, F477Y, A478V, A481V, C-term truncation at position 484, C-terminal GCN4 (including n-terminal MKQ residues) |

Figure 14A:
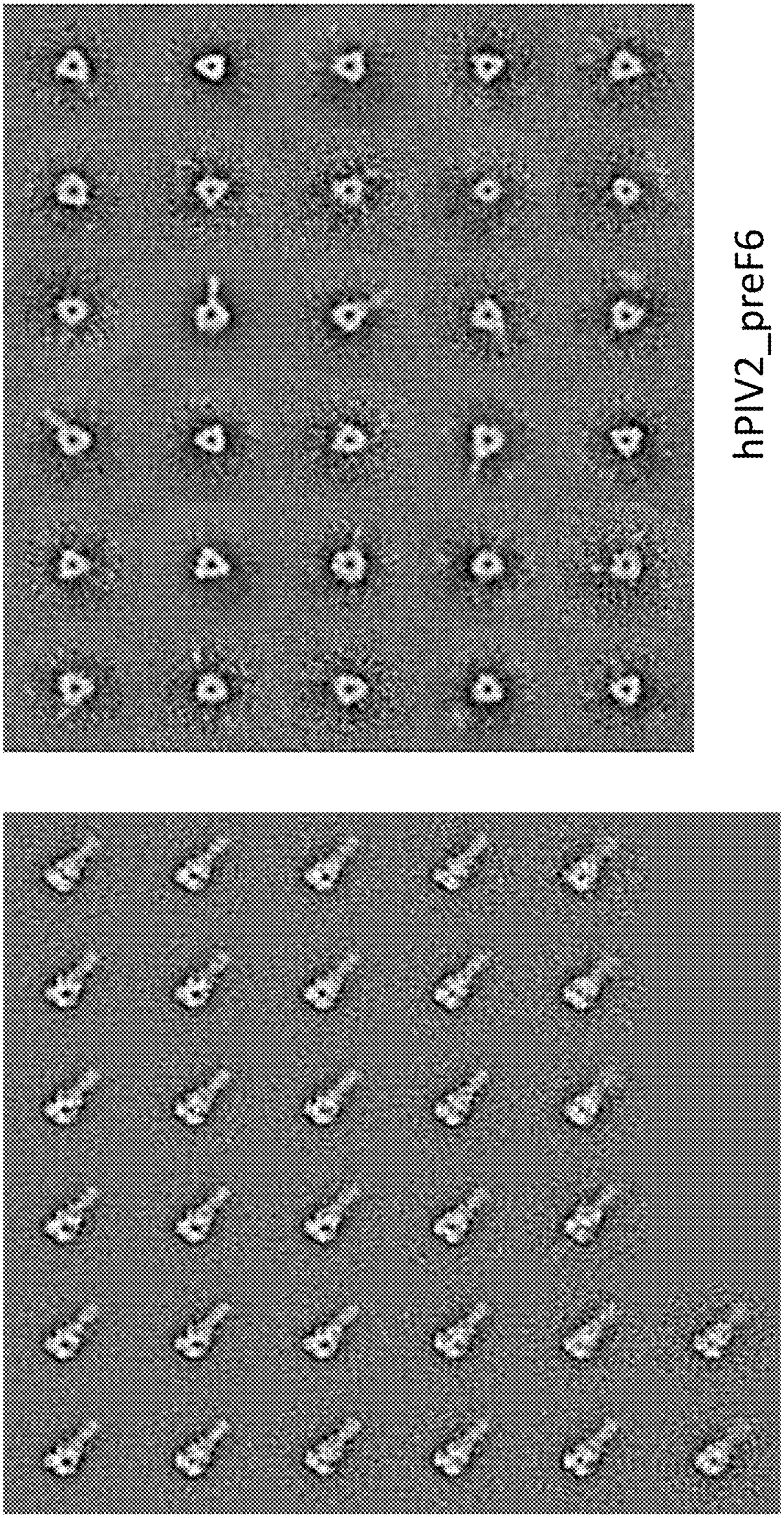
FIGS. 14A and 14B show negative stain EM images of several hPIV2 F ectodomain trimers containing mutations for stabilization in the prefusion conformation. Of these, the mutant with the best stabilization of the prefusion conformation was hPIV2_preF6 (shown in FIG. 14A).
Figure 14B:
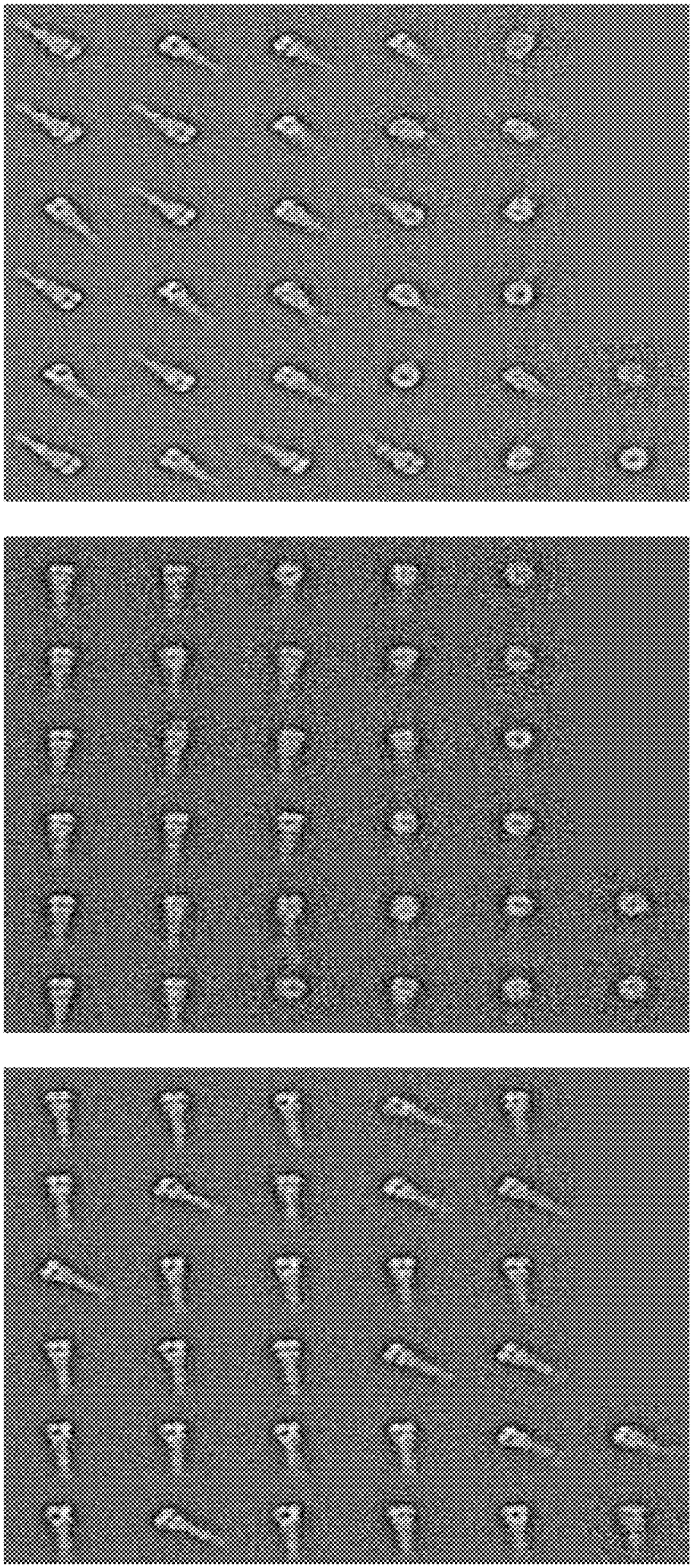

FIGS. 14A and 14B show negative stain EM data for several of the hPIV2 F mutants. Multiple rounds of hPIV2 F prefusion stabilization identified mutants that retained the prefusion structure; of these, the best retention of the prefusion structure was identified for the PIV2_preF6 protein: hPIV2_preF6 (SEQ ID NO: 7)

Figure 15:
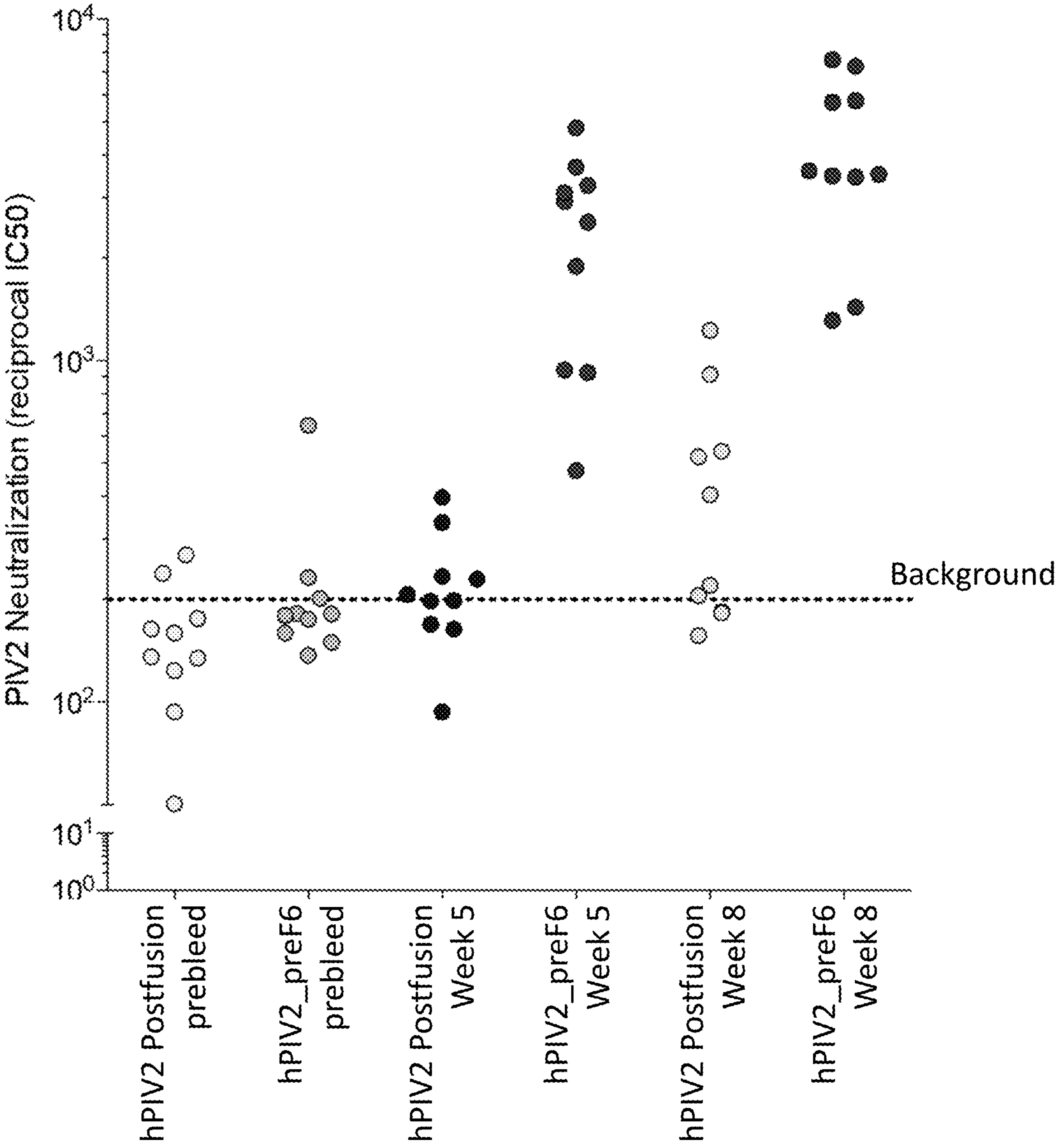
FIG. 15 show a graph of results from immunogenicity assays in mice using prefusion-stabilized hPIV2 F ectodomain trimers. Mice were immunized according the schedule shown in FIG. 8A. Neutralization titers of serum collected at week 5 and week 8 post-immunization with 2×10 μg of hPIV2 ectodomain trimer in a postfusion conformation and the hPIV2_preF6 ectodomain trimer in a prefusion conformation are shown.
Figure 16:
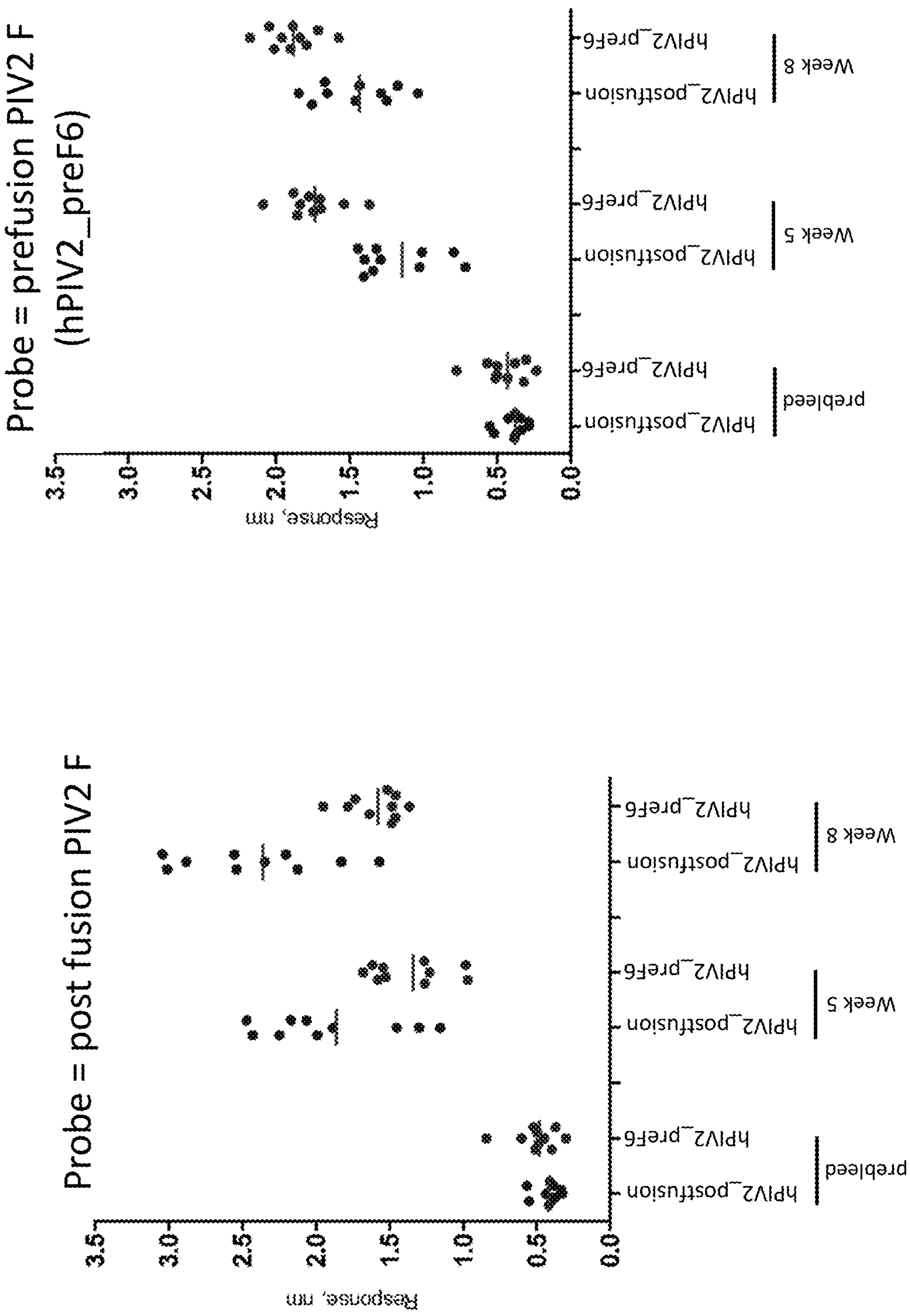
FIG. 16 shows a set of graphs of results from Octet binding assays using the serum from mice immunized with prefusion-stabilized hPIV2 F ectodomain trimers. Octet binding titers for week 0, 5, and 8 sera from CB6F1/J mice immunized with 2×10 μg of the indicated hPIV2 F trimers in poly I:C were probed with pre- or post-fusion hPIV2 F linked to the sensor.

The hPIV2_preF6 immunogen was purified and assayed for induction of a neutralizing immune response in mice as using the protocol described in Example 1. As shown in FIG. 15, sera from mice immunized with the hPIV2_preF6 immunogen successfully neutralized hPIV2 in an in vitro assay. Serum from the immunized mice was assayed for binding to hPIV2 F ectodomain trimers in the pre- and post fusion conformation using an Octet binding assay using the protocol described in Example 1 (FIG. 16).

Example 4 hPIV4 F Proteins Stabilized in a Prefusion Conformation

The example illustrates embodiments of an hPIV4 F ectodomain trimer stabilized in a prefusion conformation by one or more amino acid substitutions. The prefusion-stabilized hPIV4 F proteins are useful, for example, for inducing a neutralizing immune response to hPIV4 in a subject.

The hPIV4 F structure was modeled on prefusion hPIV2 F crystal structures (PDB IDs 4GIP and 4WSG) to identify potential mutations to stabilize hPIV4 F in its prefusion conformation. Initial experiments were conducted to identify hPIV4 F proteins from several strains of hPIV4 that expressed well in cellular expression systems. Higher-expressing F proteins were selected, and mutated to stabilize the F protein in its prefusion conformation. Stabilizing mutations included mutation of the hydrophobic residues in the FP region, addition of a C-terminal GCN4 trimerization domain, cavity filling mutations in the stem region, and non-native disulfide bonds. Several rounds of optimization of the pre-fusion stabilizing mutations were tested. Among the mutations tested include those listed in the following table:

| Name | Based on GenBank No. | Mutations |
|---|---|---|
| hPIV4_preF1 | AGU90035.1 | F1-F2 linker (SEVQSRFF98-105GGGSGGGS, SEQ ID NO: 34 to SEQ ID NO: 32), C-term truncation at position 4480, C-terminal GCN4 (including n-terminal MKQ residues) |
| hPIV4_preF2 | AGU90035.1 | F1-F2 linker (SEVQSRFF98-105GGGSGGGS, SEQ ID NO: 34 to SEQ ID NO: 32), I166C-T232C, C-term truncation at position 480, C-terminal GCN4 (including n-terminal MKQ residues) |
| hPIV4_preF3 | AGU90035.1 | F1-F2 linker (SEVQSRFF98-105GGGSGGGS, SEQ ID NO: 34 to SEQ ID NO: 32), Y457F, S471V, C-term truncation at position 477, C-terminal GCN4 |
| hPIV4_preF4 | AGU90035.1 | F1-F2 linker (SEVQSRFF98-105GGGSGGGS, SEQ ID NO: 34 to SEQ ID NO: 32), I166C-T232C, Y457F, S471V, C-term truncation at position 477, C-terminal GCN4 |
| hPIV4_preF5 | AGU90035.1 | F1-F2 linker (SEVQSRFF98-105GGGSGGGS, SEQ ID NO: 34 to SEQ ID NO: 32), Y457F, A464I, S471L, C-term truncation at position 480, C-terminal GCN4 (including n-terminal MKQ residues) |

Figure 17A:
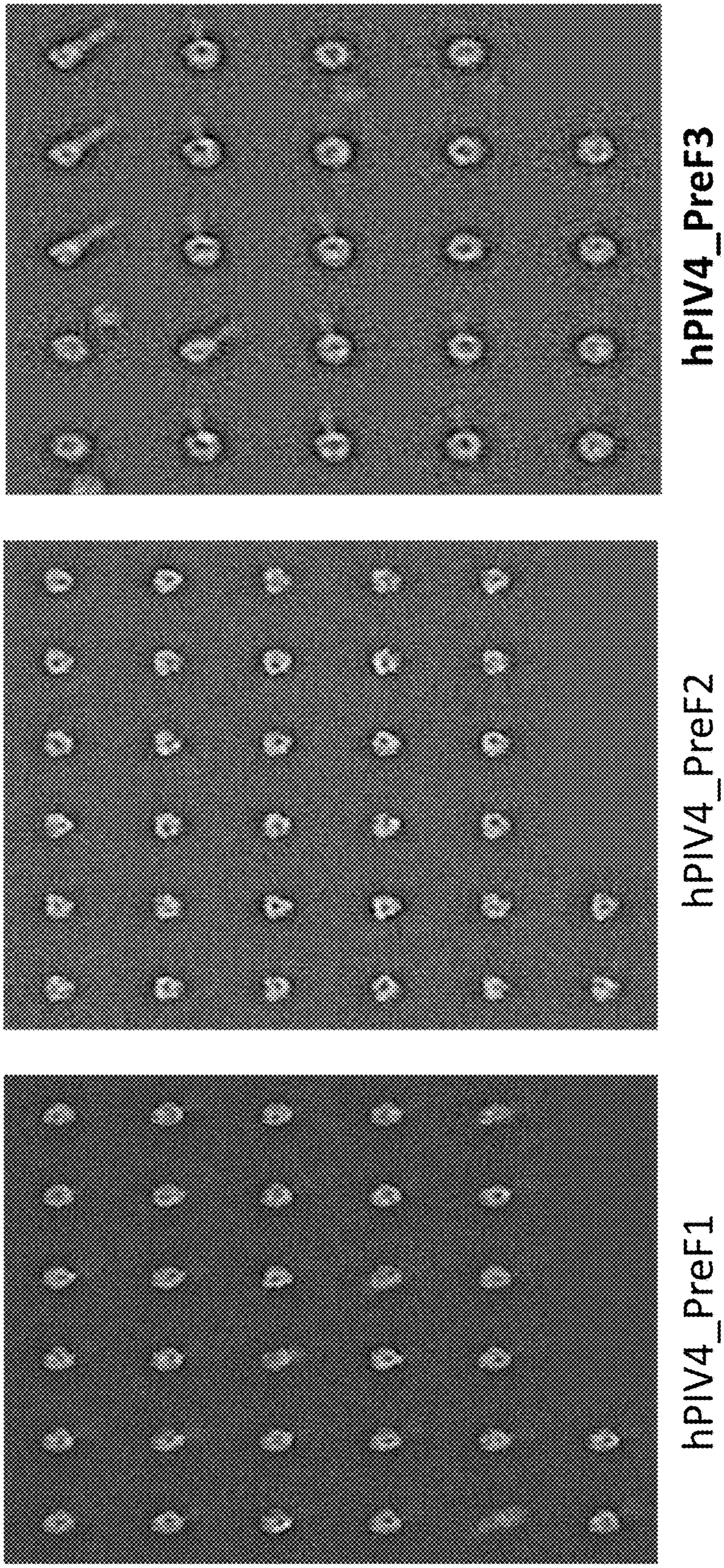
FIGS. 17A and 17B show negative stain EM images of several hPIV4 F ectodomain trimers containing mutations for stabilization in the prefusion conformation. Of these, the mutants with the greatest stabilization of the prefusion conformation were hPIV4_preF3 and hPIV4_preF4.
Figure 17B:
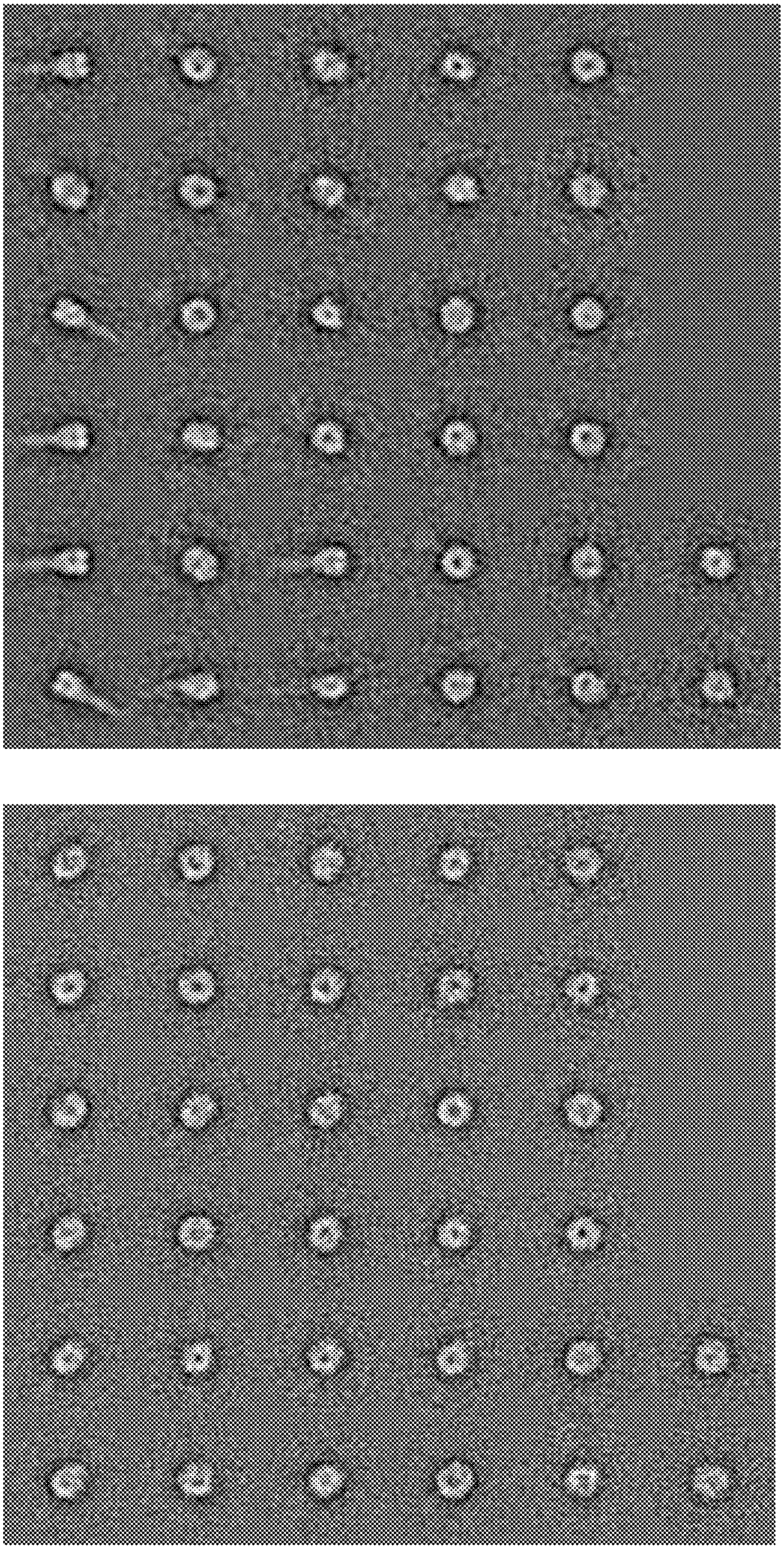

FIGS. 17A and 17B show negative stain EM data for several of the hPIV4 F mutants. Multiple rounds of hPIV4 F prefusion stabilization identified mutants that retained the prefusion structure; of these, the best retention of the prefusion structure was identified for the PIV4_preF3 and PIV4_preF4 proteins:

hPIV4_preF3

(SEQ ID NO: 29)

LDITHLMNLGTVPTAIRSLVYYTYTKPSYLTVDLIPNLKNLDQNCNYSSLNYYNKTALSLIQPIADNINRLTKPITSGGG

SGGGSGAVIGTIALGVATAAQVTAAIGLAKAQENAKLILTLKKAATETNEAVRDLANSNKIVVKMISAIQNQINTIIQPA

IDQINCQIKDLQVANILNLYLTEITTVFHNQLTNPALESISIQALKSLLGSTLPEVLSKLDLNNISAASVMASGLIKGQI

IAVDIPTMTLVLMVQIPSISPLRQAKIIDLTSITIHTNSQEVQAVVPARVLEIGSEILGFDGSVCQITKDTVFCPYNDAY

VLPIQQKRCLQGQTRDCVFTPVAGTFPRRFLTTYGTIVANCRDLVCSCLRPPQIIYQPDENPVTIIDKDLCTTLTLDSIT

IEIQKSINSTFRREVVLESTQVRSLTPLDLSTDLNQFNQLLKSAEDHIQRVTDYLNSIEDKIEEILSKIYHIENEIARIK

KLIGEAP hPIV4_preF4

(SEQ ID NO: 30)

LDITHLMNLGTVPTAIRSLVYYTYTKPSYLTVDLIPNLKNLDQNCNYSSLNYYNKTALSLIQPIADNINRLTKPITSGGG

SGGGSGAVIGTIALGVATAAQVTAAIGLAKAQENAKLILTLKKAATETNEAVRDLANSNKIVVKMCSAIQNQINTIIQPA

IDQINCQIKDLQVANILNLYLTEITTVFHNQLTNPALESISIQALKSLLGSCLPEVLSKLDLNNISAASVMASGLIKGQI

IAVDIPTMTLVLMVQIPSISPLRQAKIIDLTSITIHTNSQEVQAVVPARVLEIGSEILGFDGSVCQITKDTVFCPYNDAY

VLPIQQKRCLQGQTRDCVFTPVAGTFPRRFLTTYGTIVANCRDLVCSCLRPPQIIYQPDENPVTIIDKDLCTTLTLDSIT

IEIQKSINSTFRREVVLESTQVRSLTPLDLSTDLNQFNQLLKSAEDHIQRVTDYLNSIEDKIEEILSKIYHIENEIARIK

KLIGEAP

Figure 18:
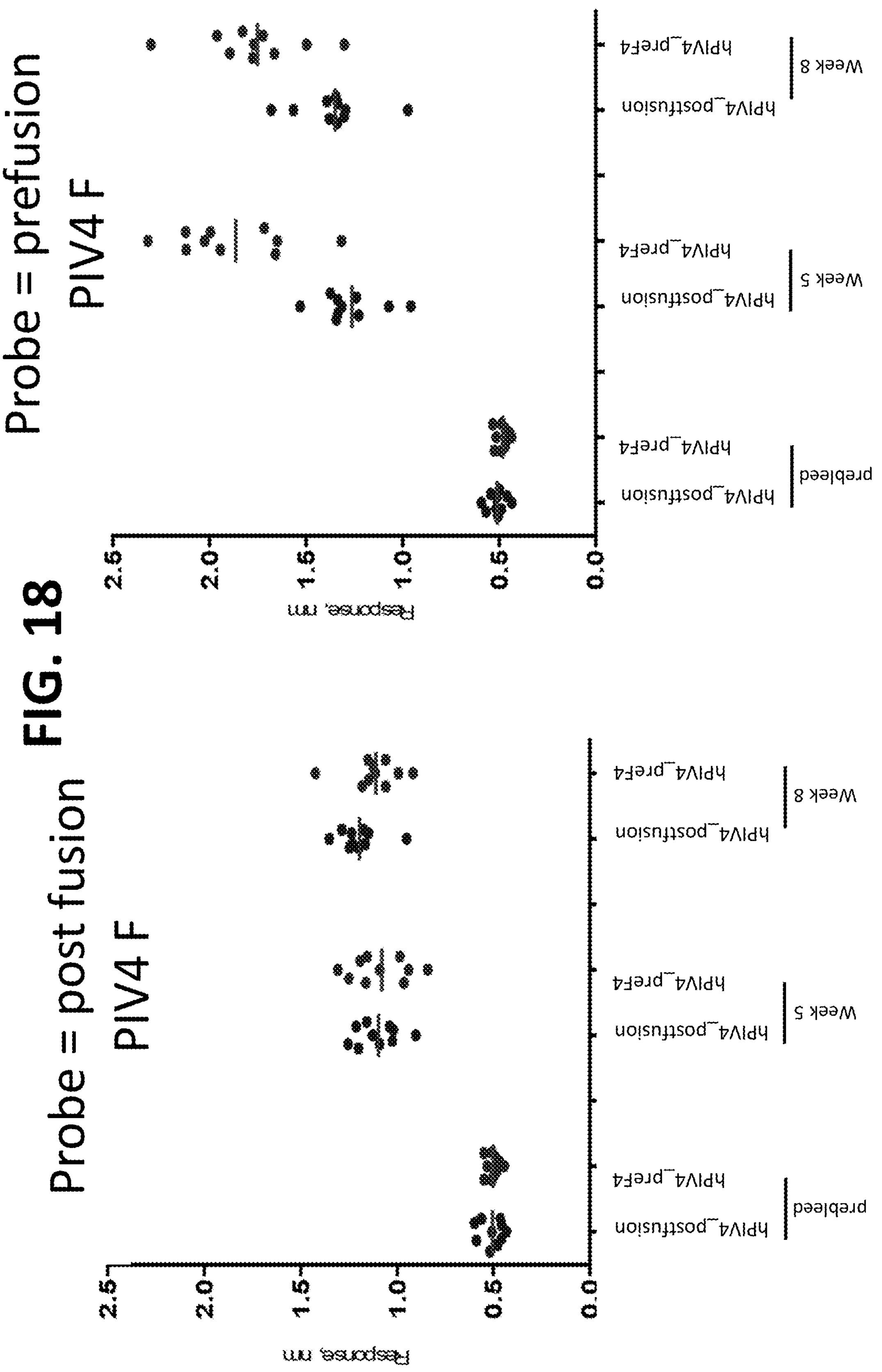
FIG. 18 show a set of graphs of results from Octet binding assays using the serum from mice immunized with prefusion-stabilized hPIV4 F ectodomain trimers. Octet binding titers for week 0, 5, and 8 sera from CB6F1/J mice immunized with 2×10 μg of the indicated hPIV4 F trimers in poly I:C were probed with pre- or post-fusion hPIV4 F linked to the sensor.

The hPIV4_preF4 immunogen was purified and assayed for induction of a neutralizing immune response in mice. Serum from the immunized mice was assayed for binding to hPIV4 F ectodomain trimers in the pre- and post-fusion conformation using an Octet binding assay using the protocol described in Example 1 (FIG. 18).

Example 5

Immunization Assays

This example describes use of compositions comprising a combination of prefusion stabilized hPIV1, hPIV2, hPIV3, and hPIV4 F ectodomain trimers for induction of a neutralizing immune response to hPIV1-4 in animal models.

Figure 19C:
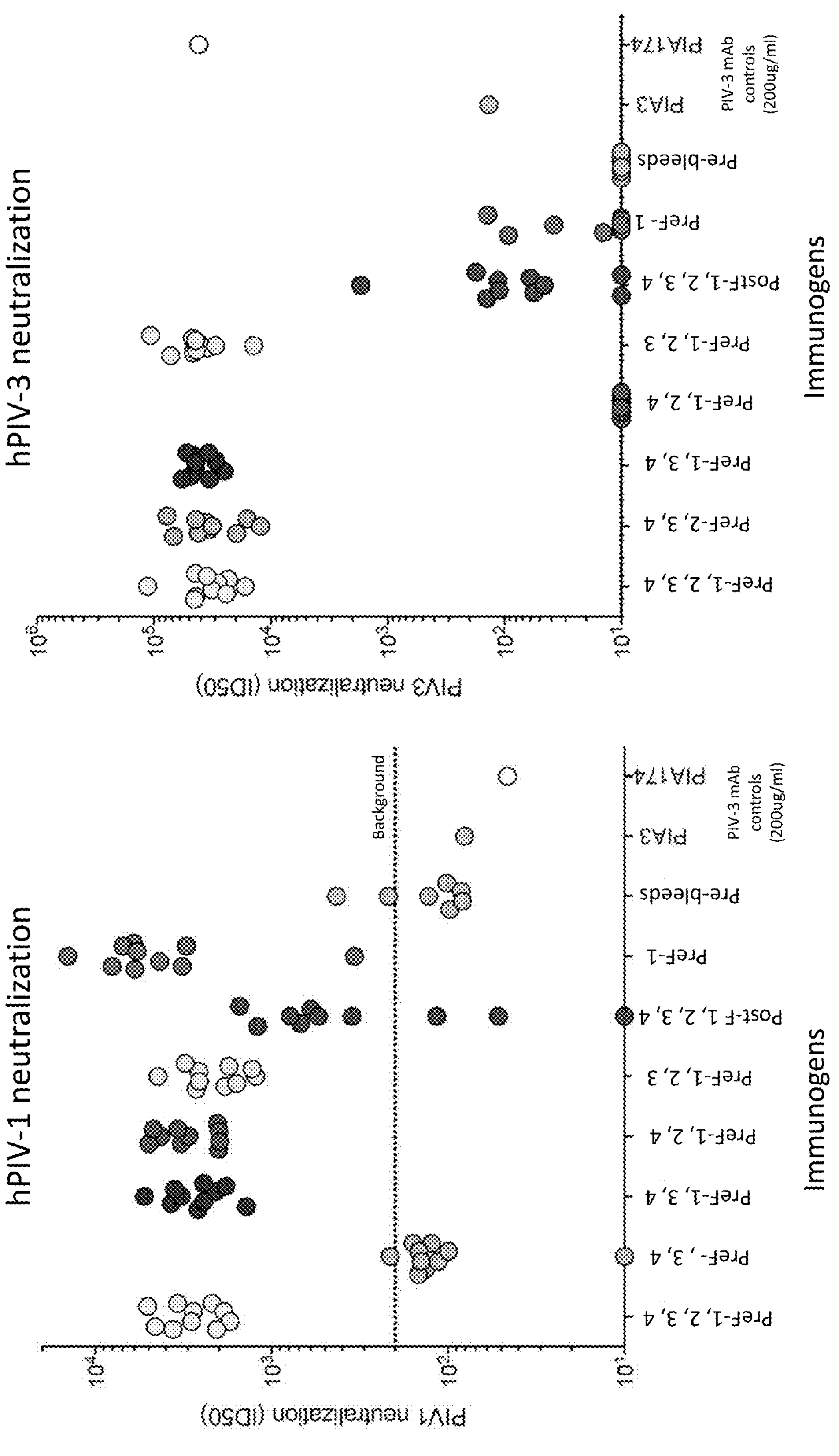
Figure 19D:
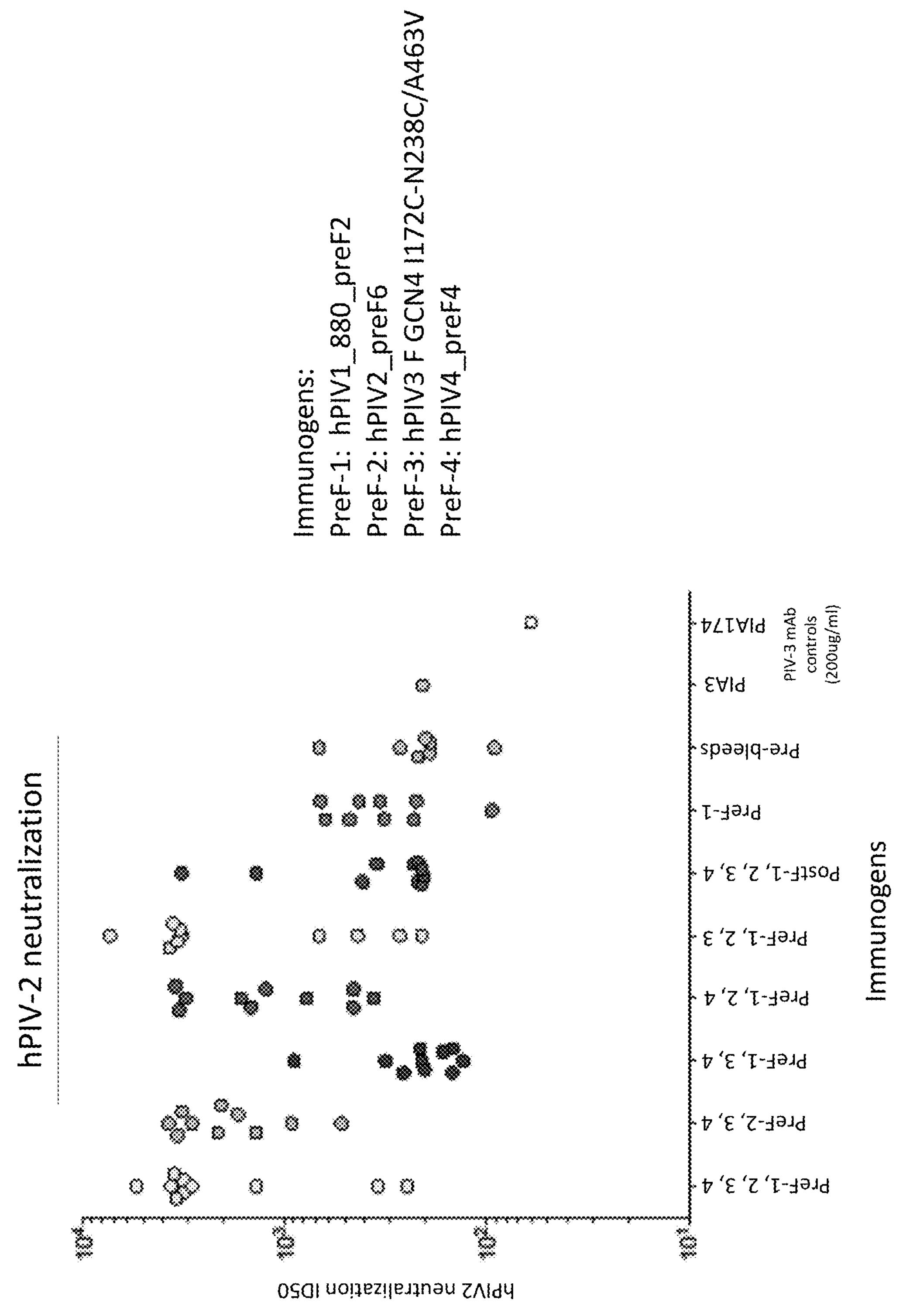

CB6F1/J mice were immunized with 2×10 pg of various combinations of hPIV1-4 F in poly I:C at weeks 0 and 3 (see FIG. 19). The F ectodomain trimers used for immunization included the hPIV1_880_preF2, hPIV2_preF6, hPIV3 F GCN4 I172C-N238C/A463V, and hPIV4_preF4 ectodomain timers. Octet binding readout of sera collected at week 5 from immunized mice was assayed using pre- and post-fusion hPIV3 F probes (FIG. 19A) and pre- and post-fusion hPIV4 F probes (FIG. 19B). The collected sera was also assayed for hPIV1, 2, and 3 neutralization activity (FIGS. 19C and 19D). As shown in FIG. 19, the polyvalent vaccination successfully elicited a neutralizing immune response to each of the hPIV F ectodomain trimers in the immunogenic composition.

Figure 20B:
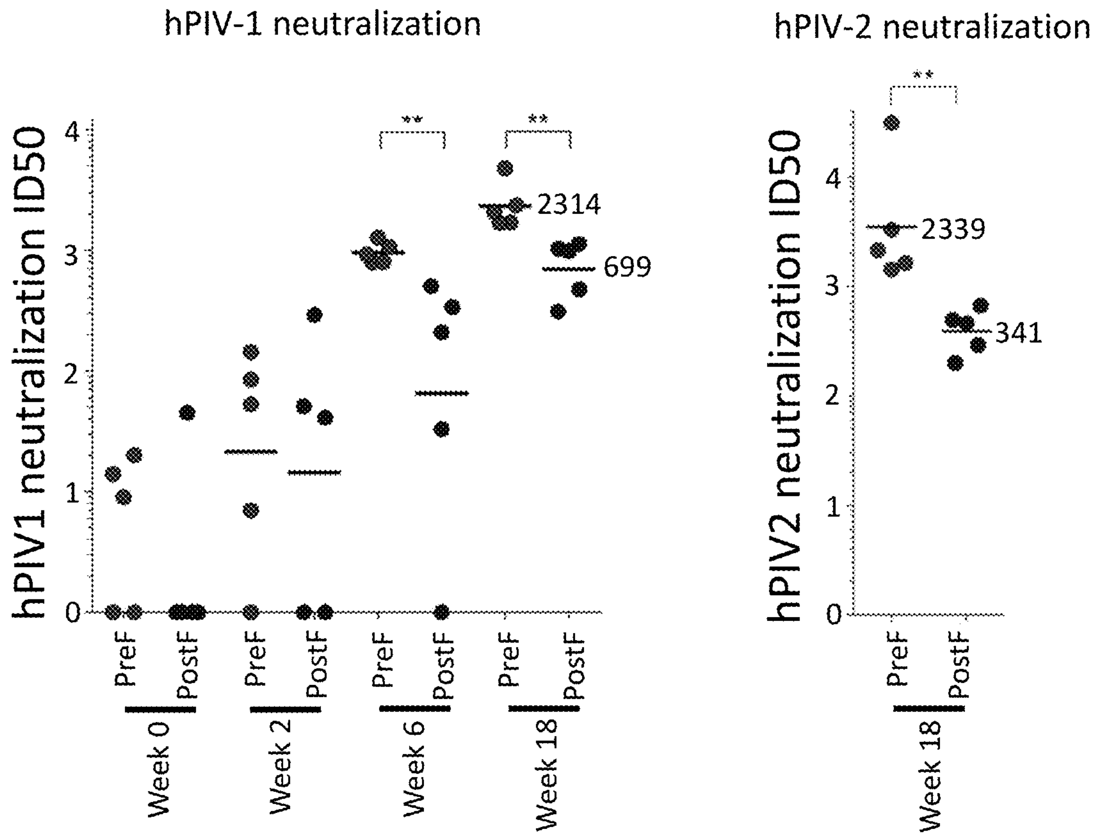
Figure 20C:
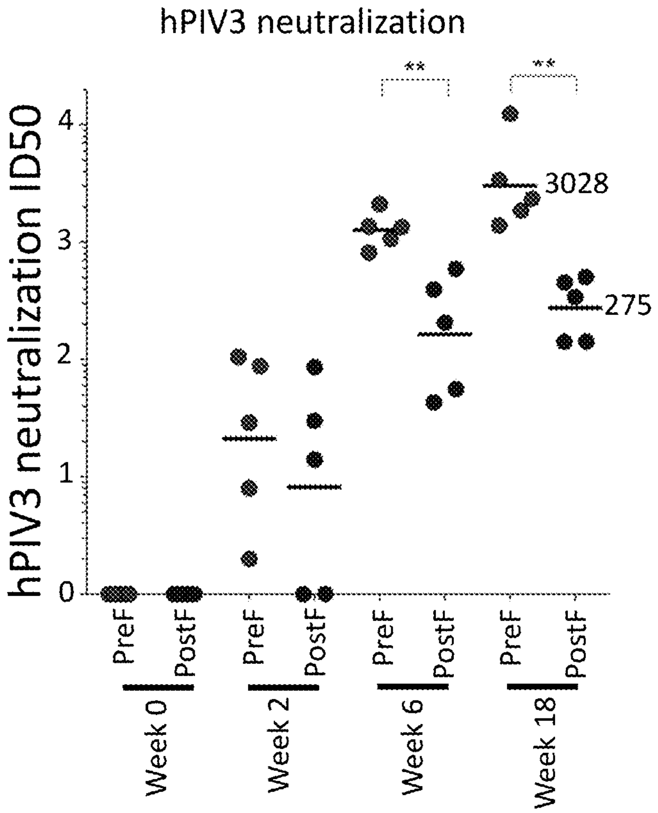
Figure 20D:
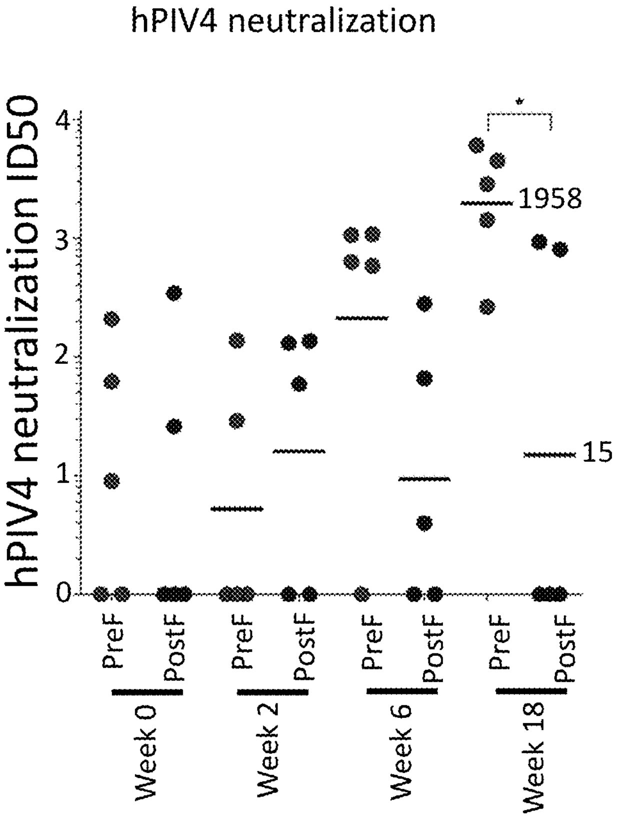
Figure 20E:
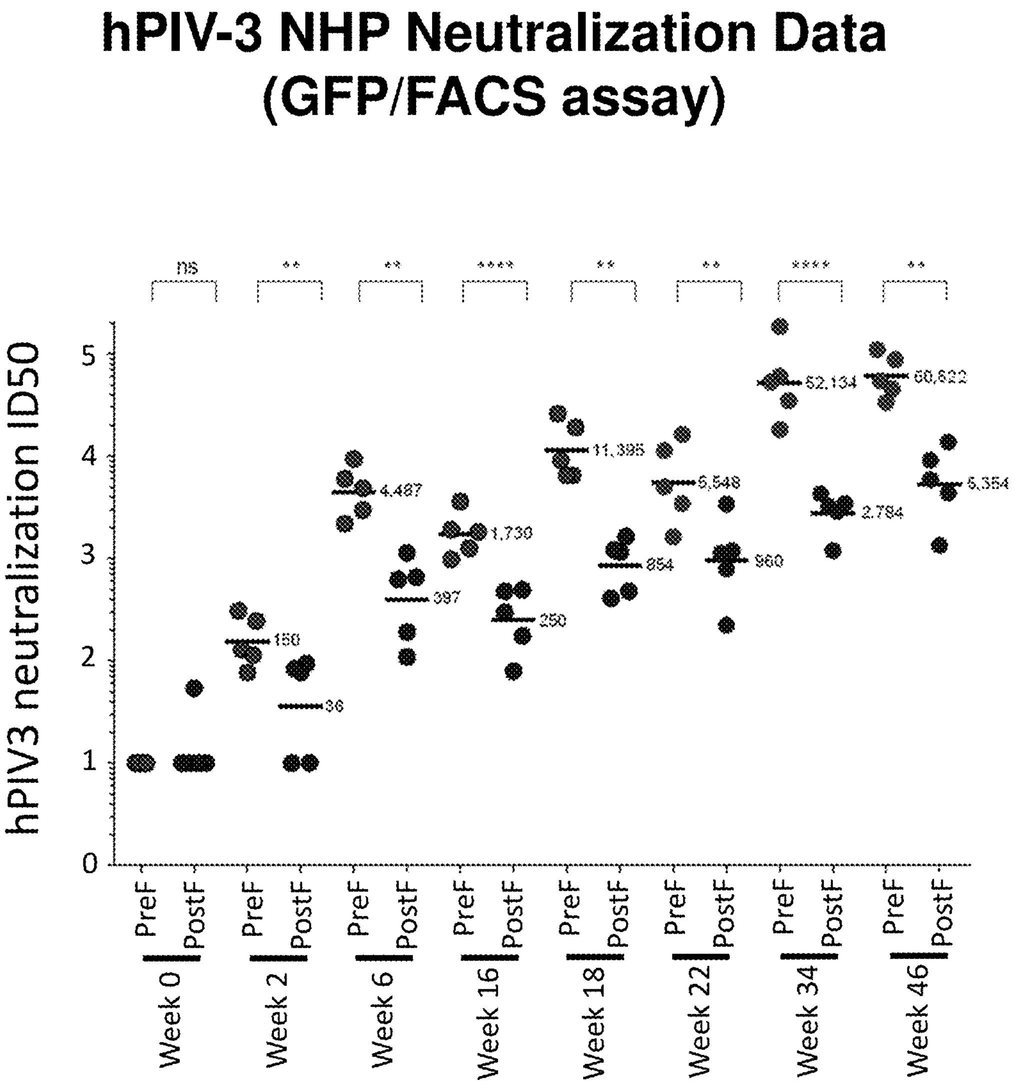

In an additional study, non-human primates were immunized with the combinations of prefusion-stabilized hPIV1-4 F proteins in poly I:C-LC. The assay protocol is illustrated in FIG. 20A. The F ectodomain trimers used for immunization included the hPIV1_880_preF2, hPIV2_preF6, hPIV3 F GCN4 A464V/I474Y, and hPIV4_preF4 ectodomain timers Immune sera was collected at various time points and assessed for neutralization of hPIV1, hPIV2, hPIV3, and hPIV4 (FIGS. 20B-20E). As shown in the figures, the response elicited by immunization with the combination of prefusion-stabilized hPIV F proteins provided broad and potent neutralization of hPIV1-4. Furthermore, additional 2 boosts with 100 ug hPIV3 prefusion F immunogen augmented the neutralization titers to hPIV3 ($IC_{50}$ of over 60,000) beyond what had been achieved with hPIV1-4 quadrivalent immunization.

Example 6

Prefusion Stabilized hPIV3 F Ectodomain Trimers

This example illustrates design and characterization of additional prefusion-stabilized hPIV3 F ectodomain trimers for inducing an immune response to hPIV3.

The binding characteristic of several different prefusion-stabilized hPIV3 constructs for the PIA3 and PIA174 antibodies are shown in FIG. 21. As discussed above, PIA3 specifically binds to an epitope of hPIV3 that appears similar in structure to the antigenic site Ø of RSV F. The PIA174 antibody specifically binds to hPIV3 F trimer at its membrane-distal apex. The on- and off-rates of the binding of these antibodies to several different prefusion stabilized hPIV3 constructs were assessed. As shown in FIG. 21, the Koff rate of PIA174 binding to hPIV3 F is increased in prefusion stabilized constructs containing the 172C-238C disulfide.

Figure 22A:
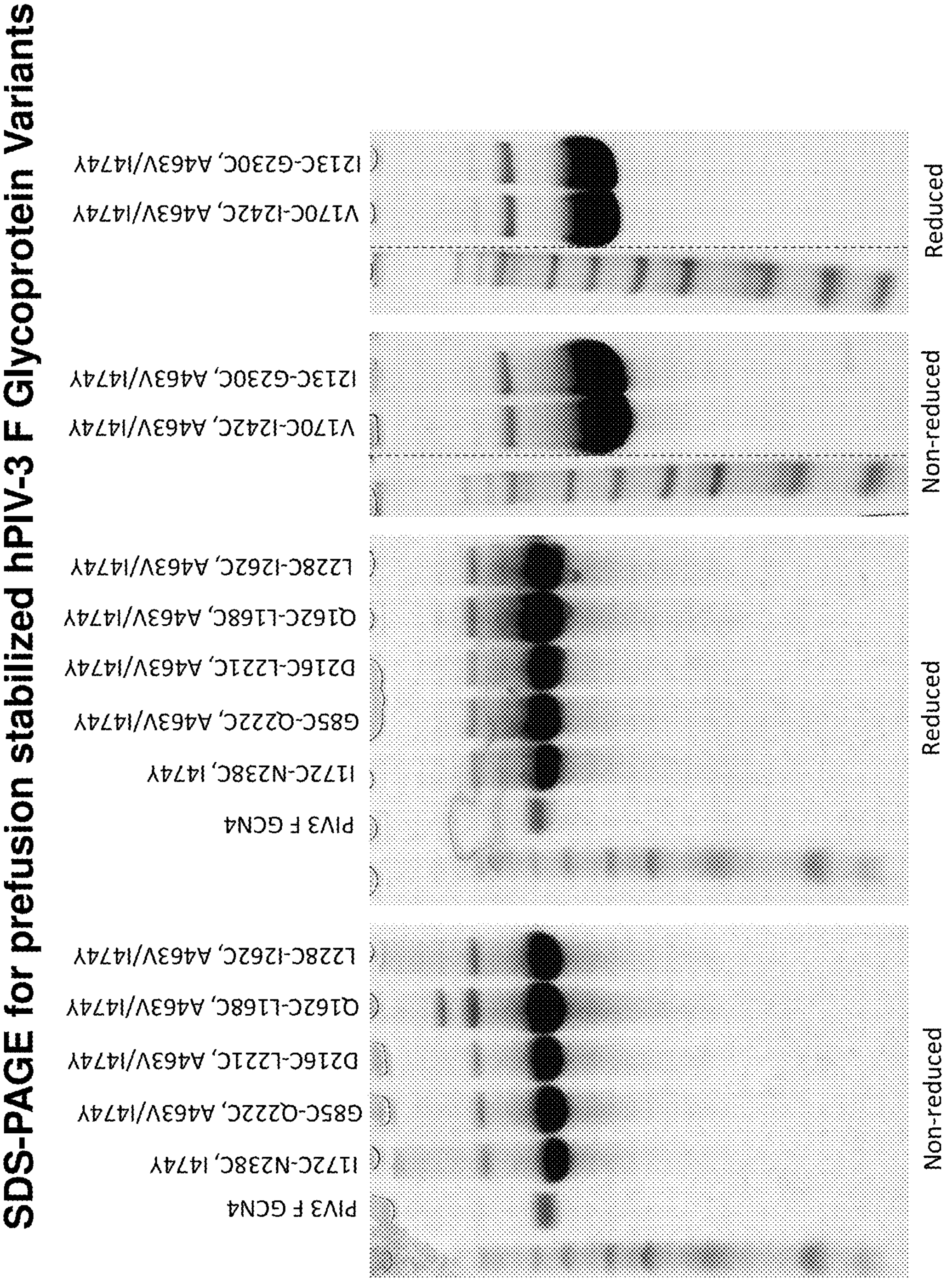
FIGS. 22A-22T illustrate production, design, negative stain EM, antigenicity, and physical stability of prefusion stabilized hPIV3 F ectodomain trimers, including trimers that lack the 172C-238C disulfide bond.
Figure 22B:
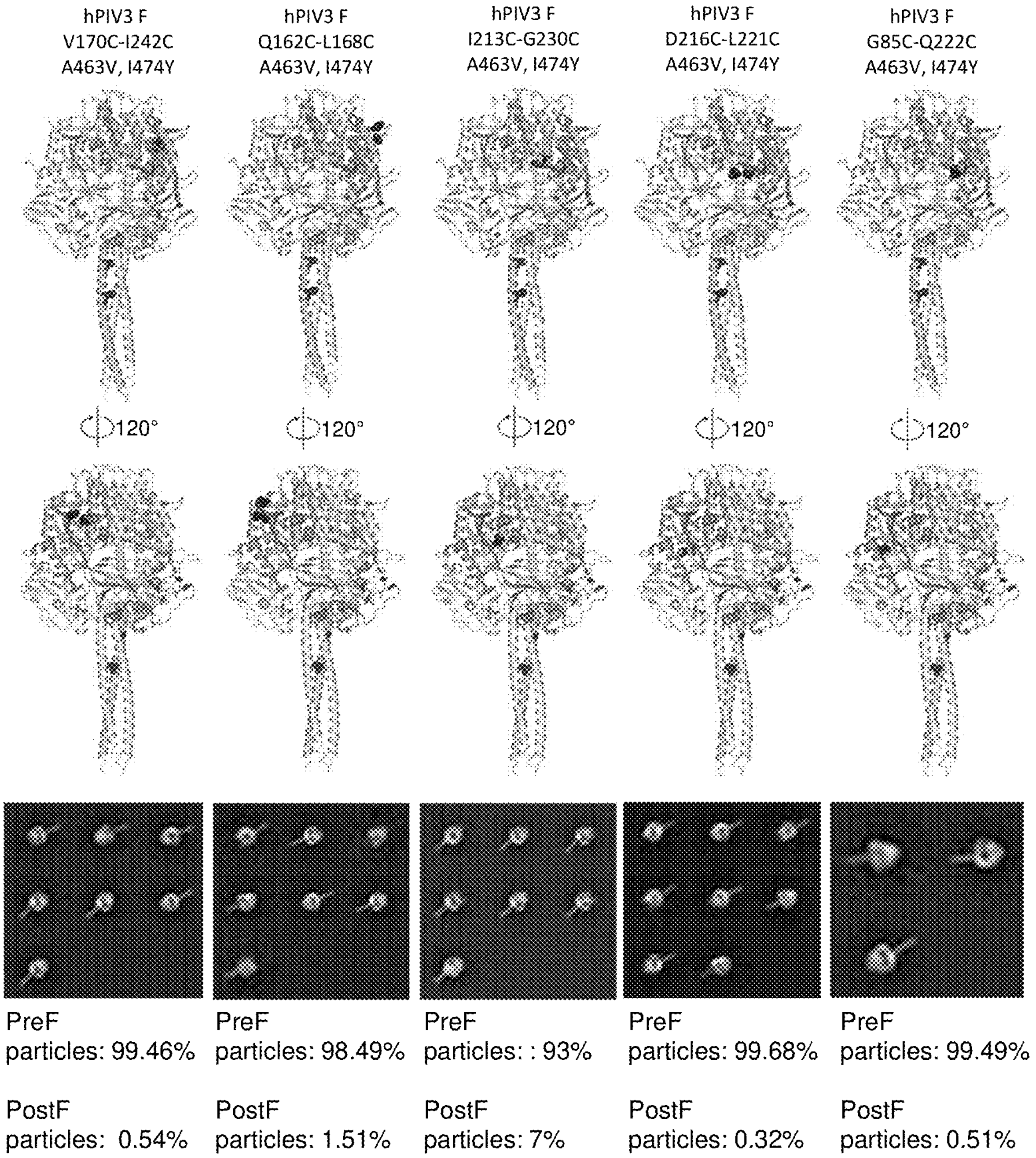
Figure 22G:
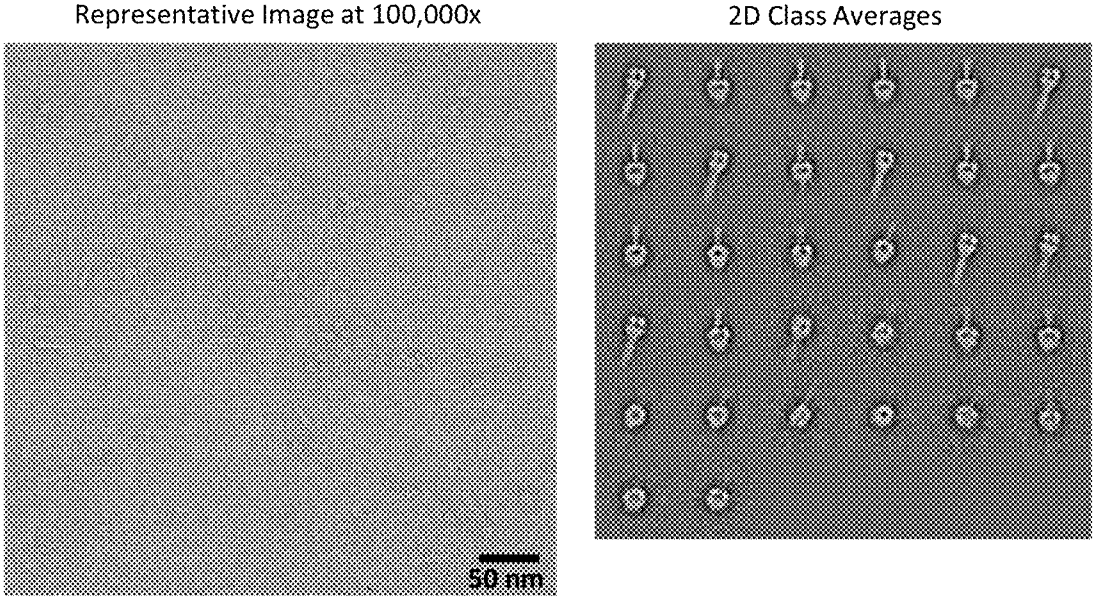
Figure 22H:
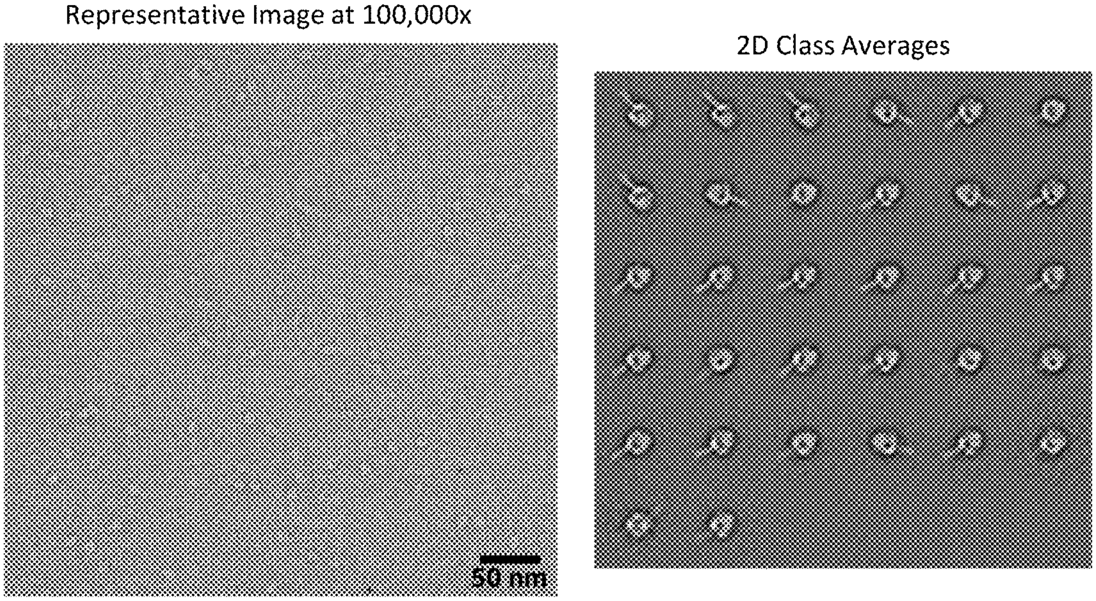
Figure 22O:
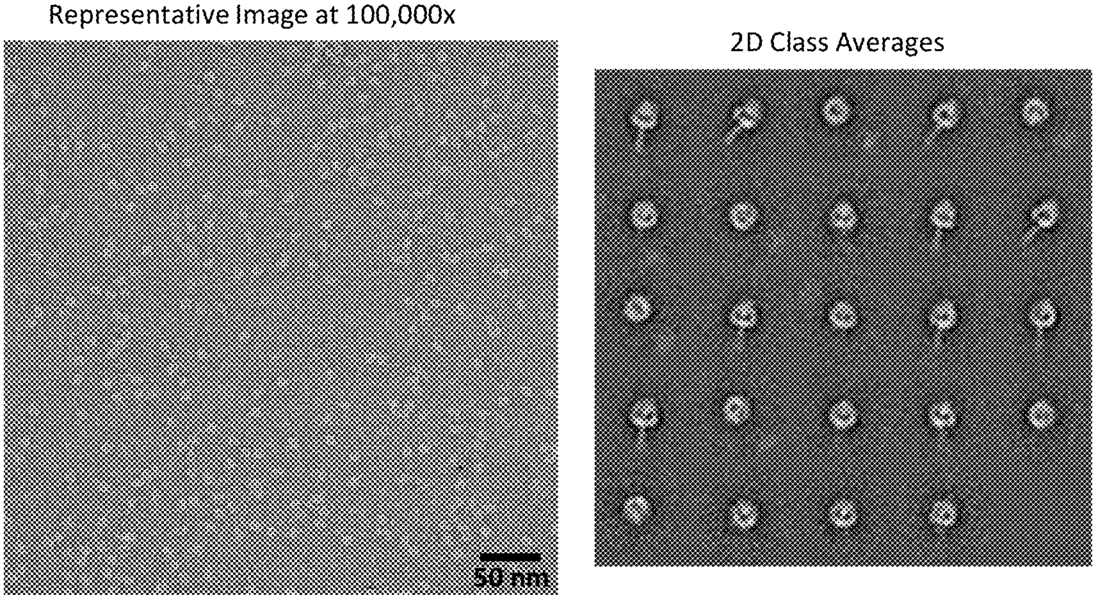
Figure 22P:
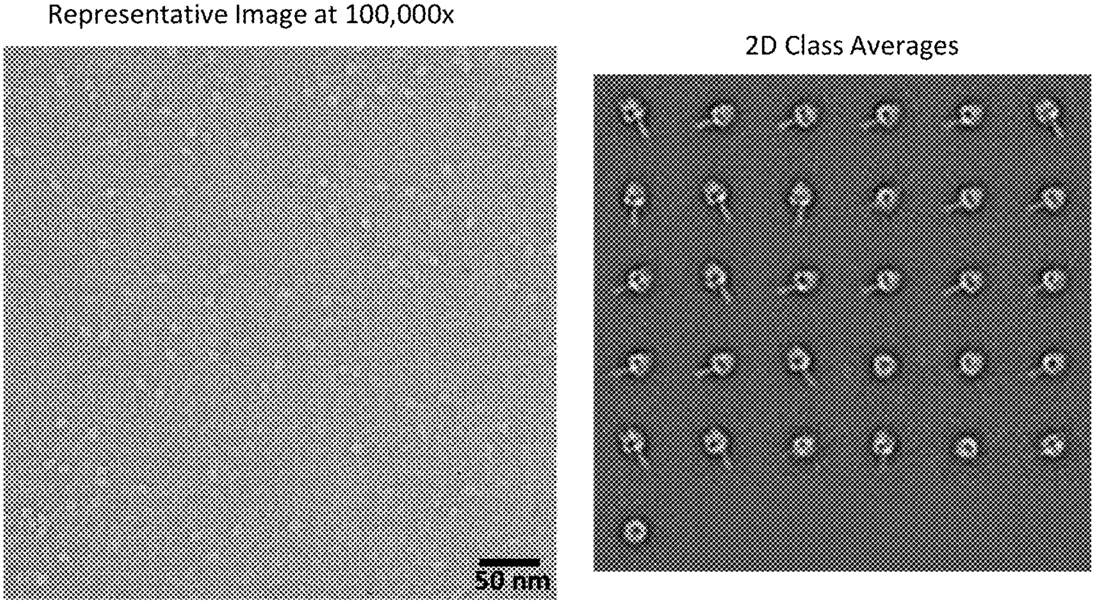
Figure 23A:
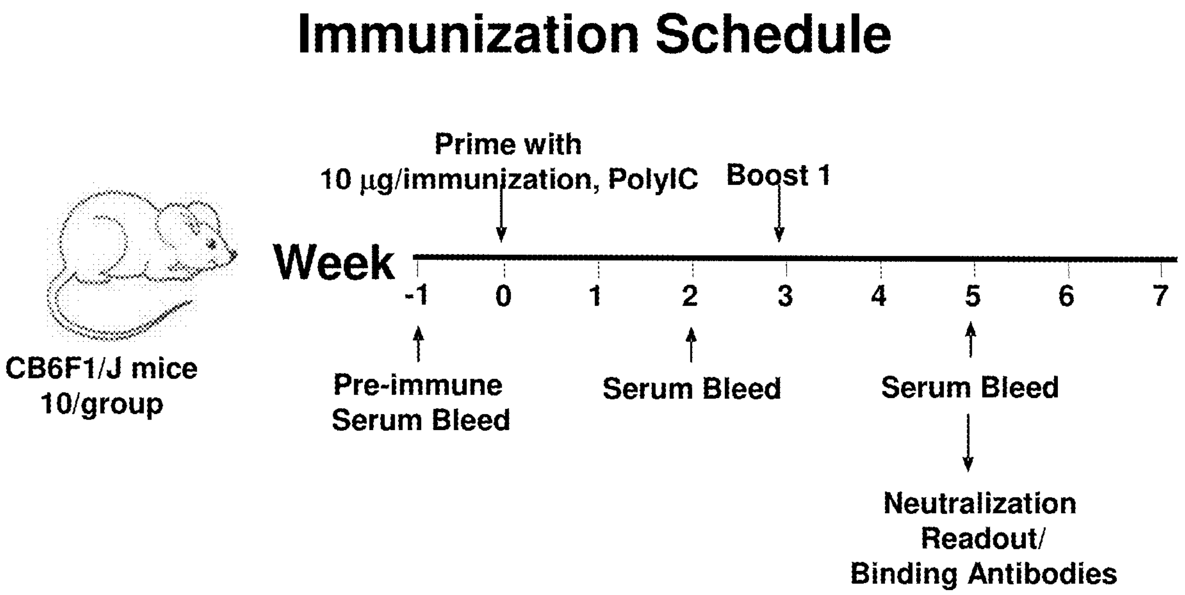
FIGS. 23A-23D show results from immunization assays using engineered hPIV3 F trimers. The immunization scheme is shown in FIG. 23A.
Figure 23B:
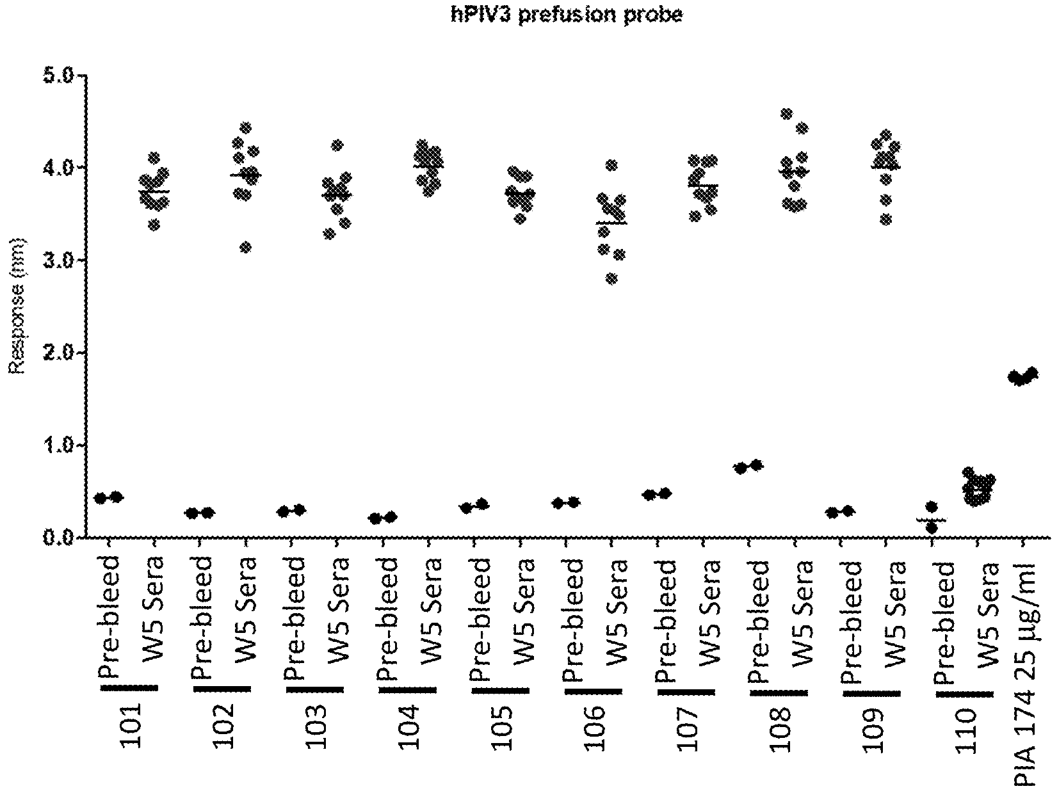
Figure 23C:
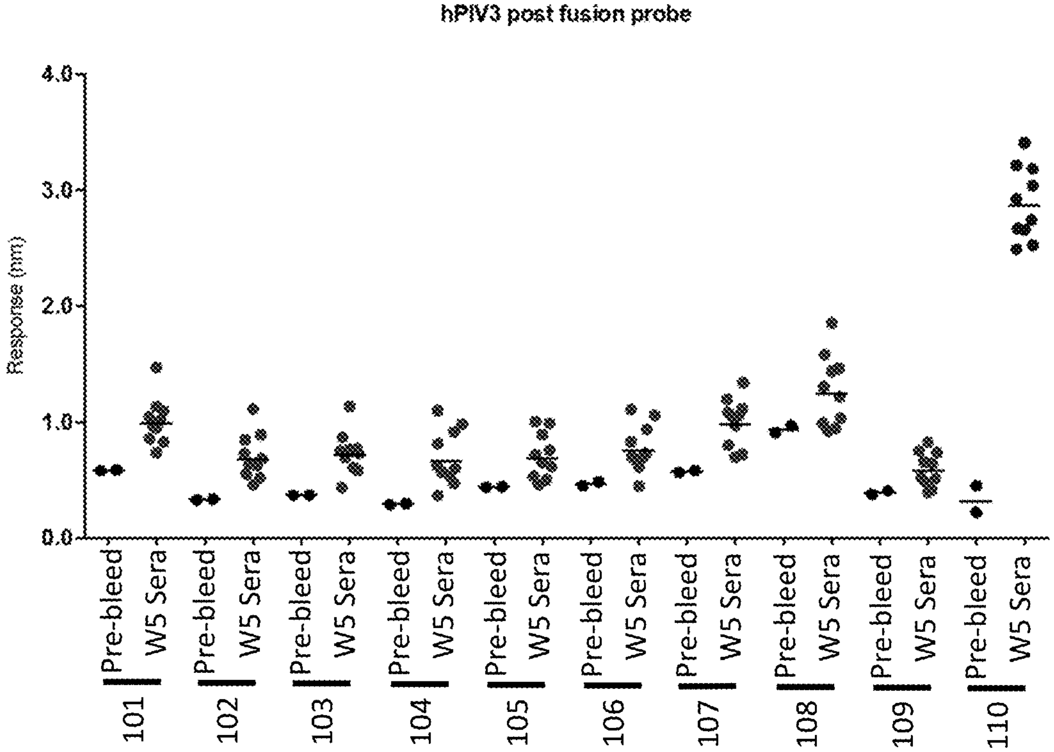
Figure 23D:
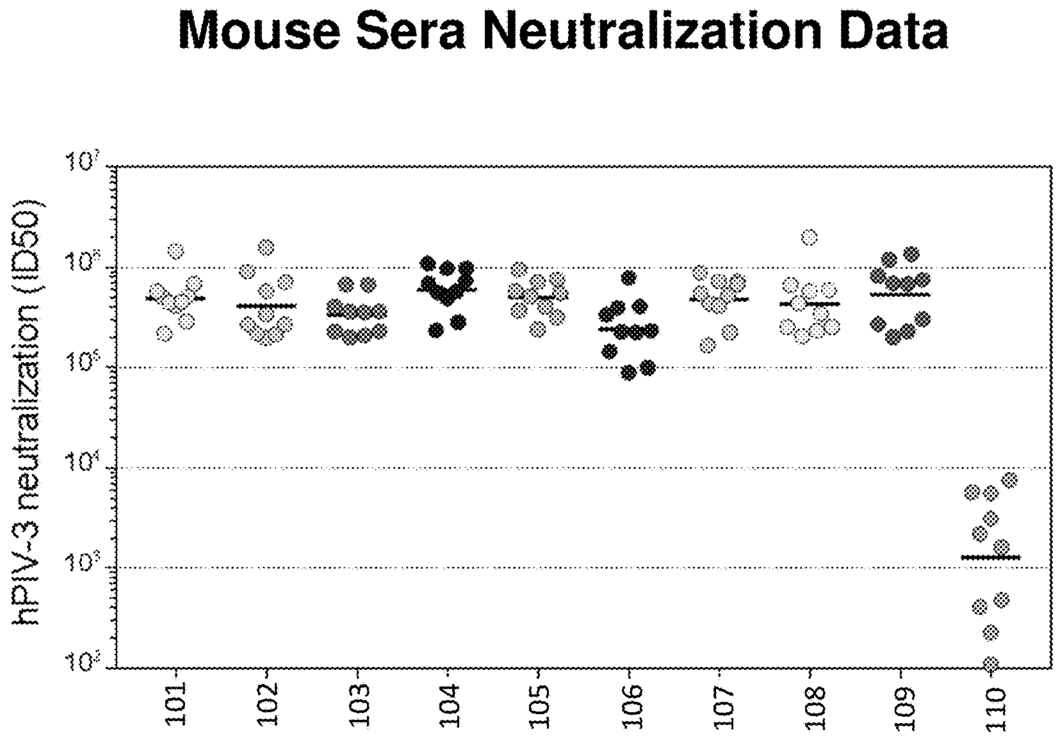

Accordingly, amino acid substitutions for stabilizing the hPIV3 F protein in its prefusion conformation other than 172C-238C were identified and assessed. hPIV3 F ectodomains including these mutations were expressed, purified, and assessed by negative stain EM and binding to PIA3 and PIA174 (FIG. 22). hPIV3 F ectodomain trimers with GNC4 trimerization domain and one of the following sets of substitutions: V170C-I242C, A463V, I474Y (SEQ ID NO: 39), I213C-G230C, A463V, I474Y (SEQ ID NO: 40), G85C-Q222C, A463V, I474Y (SEQ ID NO: 41), D216C-L221C, A463V, I474Y (SEQ ID NO: 42), Q162C-L168C, A463V, I474Y (SEQ ID NO: 43) were each stabilized in a prefusion conformation (FIG. 22B), and provided substantially reduced Koff rate for PIA174 binding relative to the corresponding prefusion hPIV3 F construct with 172C-238C (FIG. 22C). Based on these results, additional constructs were generated that contained two sets of stabilizing disulfide bonds (FIG. 22D). The sequences of the protomers of the hPIV3 F ectodomain trimers are as follows:

hPIV3 F GNC4 V170C-1242C, A463V, I474Y (SEQ ID NO: 39)
hPIV3 F GNC4 I213C-G230C, A463V, I474Y (SEQ ID NO: 40)
hPIV3 F GNC4 G85C-Q222C, A463V, I474Y (SEQ ID NO: 41)
hPIV3 F GNC4 D216C-L221C, A463V, I474Y (SEQ ID NO: 42)
hPIV3 F GNC4 Q162C-L168C, A463V, I474Y (SEQ ID NO: 43)
hPIV3 F GNC4 V170C-1242C, Q162C-L168C, A463V, I474Y (SEQ ID NO: 44)
hPIV3 F GNC4 Q162C-L168C, I213C-G230C, A463V, I474Y (SEQ ID NO: 45)
hPIV3 F GNC4 Q162C-L168C, D216C-L221C, A463V, I474Y (SEQ ID NO: 46)
hPIV3 F GNC4 Q162C-L168C, G85C-Q222C, A463V, I474Y (SEQ ID NO: 47)
hPIV3 F GNC4 I213C-G230C, V170C-1242C, A463V, I474Y (SEQ ID NO: 48)
hPIV3 F GNC4 I213C-G230C, D216C-L221C, A463V, I474Y (SEQ ID NO: 49)
hPIV3 F GNC4 I213C-G230C, G85C-Q222C, A463V, I474Y (SEQ ID NO: 50)

hPIV3 F ectodomains with GNC4 trimerization domain and including these mutations were expressed, purified, and assessed for binding to PIA3 and PIA174 (FIG. 22E), and for retention of physical stability based on various conditions (FIG. 22F). Following purification, the hPIV3 F ectodomain trimers were assessed by negative stain EM to determine pre- and post-fusion conformation retention (FIGS. 22G-22T).

Prefusion-stabilized hPIV3 F ectodomain trimers formed from the above protomer sequences were assessed for elicitation of a neutralizing immune response in mice (FIG. 23). FIG. 23 shows the immunization protocol. CB6F1/J mice were immunized with 2×10 pg of the various hPIV3 F ectodomain trimers in poly I:C at weeks 0 and 3. Octet binding readout of sera collected at week 5 from immunized mice was assayed using pre- and post-fusion hPIV3 F probes (FIGS. 23B and 23C). The collected sera was also assessed for hPIV3 neutralization activity (FIG. 23D). Each of the immunogens induced an immune response that neutralized hPIV3.

Example 7

Prefusion Stabilized Bovine and Caprine PIV3 F Ectodomain Trimers

Based on the successful stabilization of hPIV3 F ectodomain trimers as discussed above, the corresponding stabilizing amino acid substitutions were introduced into bovine and caprine PIV3 F sequences to determine if the amino acid substitutions would stabilize non-human PIV3 F proteins.

Bovine PIV3 F sequences based on GenBank Nos. ABZ85923.1 and AHZ90086.1, and caprine PIV3 F sequence based on GenBank No. AIW42876.1, were modified to include the I172C-N238C disulfide bond and one of the A463V or I474Y cavity filling amino acid substitutions. Additionally, the sequences were truncated at the C-terminal end of the ectodomain and linked to a GCN4 trimerization domain. The corresponding amino acid sequences of these constructs are provided as:

bPIV3 F GCN4 I172C-N238C/I474Y (based on ABZ85923.1)(SEQ ID NO: 69)
bPIV3 F GCN4 I172C-N238C/I474Y (based on AHZ90086.1) (SEQ ID NO: 70)
cPIV3 F GCN4 I172C-N238C/I474Y (based on AIW42876.1) (SEQ ID NO: 71)
bPIV3 F GCN4 I172C-N238C/A463V (based on ABZ85923.1) (SEQ ID NO: 72)
bPIV3 F GCN4 I172C-N238C/A463V (based on AHZ90086.1) (SEQ ID NO: 73)
cPIV3 F GCN4 I172C-N238C/A463V (based on AIW42876.1) (SEQ ID NO: 74)

Figure 24:
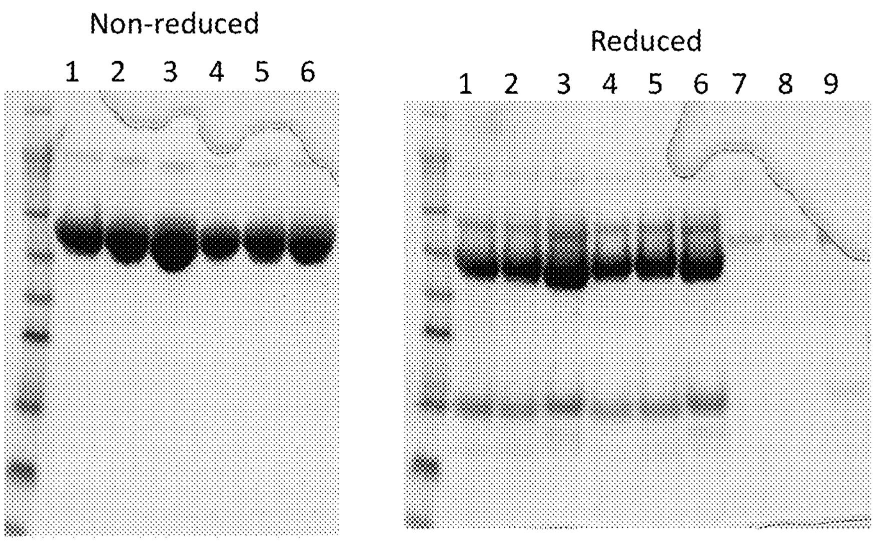
FIG. 24 shows a coomassie stained gel of prefusion stabilized bPIV3 F and cPIV3 F proteins run under non-reducing and reducing conditions. Control bPIV3 F and cPIV3 F proteins that are linked to a GCN4 trimerization domain, but lack any prefusion stabilizing mutations were also tested and expressed poorly.
Figure 25:
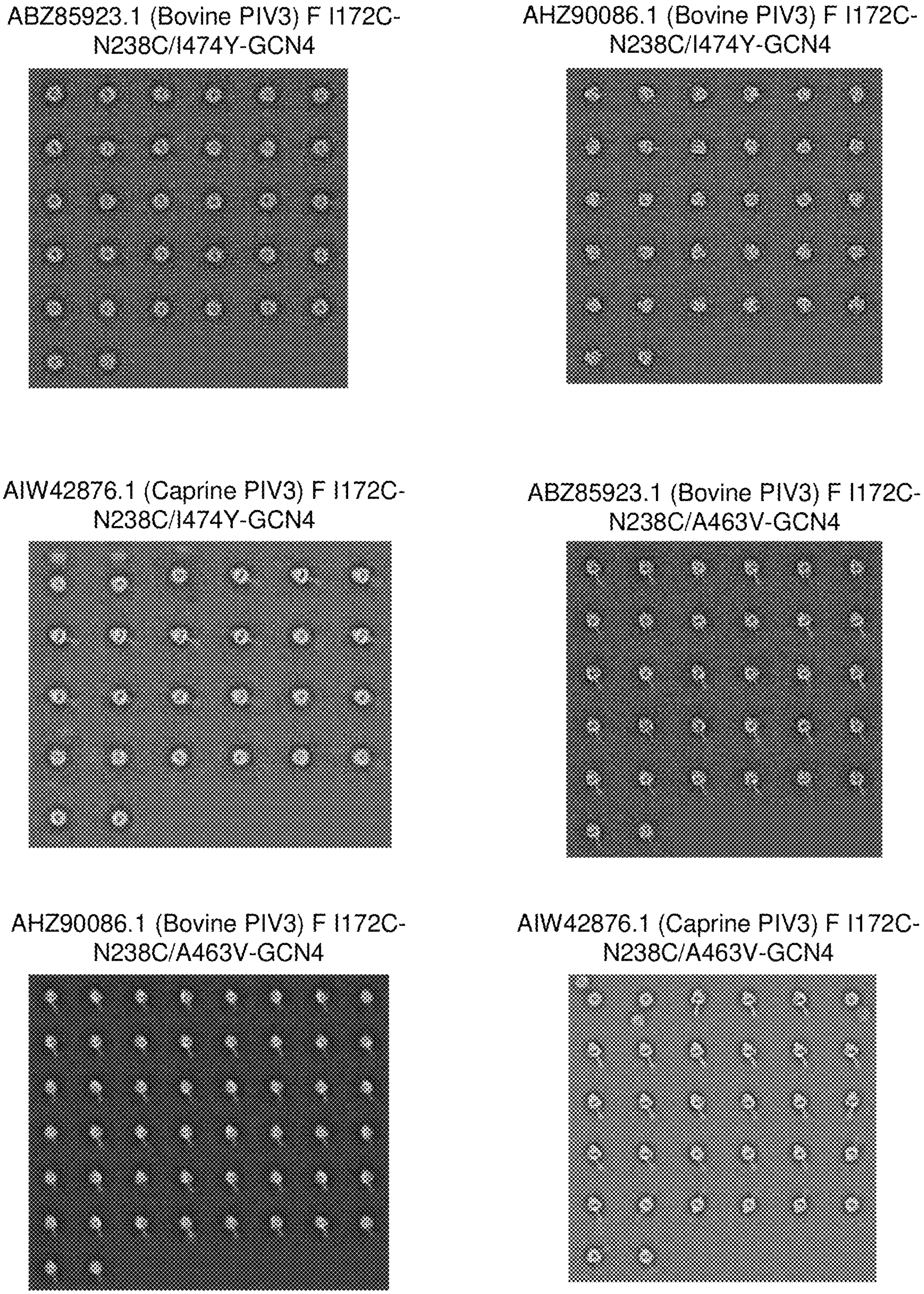
FIG. 25 shows negative stain EM images of bPIV3 F and cPIV3 F ectodomain trimers containing the indicated amino acid substitutions. Approximately 100% of the assessed bPIV3 F and cPIV3 F ectodomain trimers were identified to be in the prefusion conformation.

The bPIV3 and cPIV3 F ectodomain trimers including the above mutations were expressed and purified (FIG. 24) using the procedures discussed above for hPIV F proteins, and assessed by negative stain EM (FIG. 25). The bPIV3 and cPIV3 F ectodomain trimers with the prefusion stabilizing mutations were all readily expressed and purified (FIG. 24), and retained the prefusion conformation by EM (FIG. 25, approximately 100% of the PIV3 F molecules were in the prefusion conformation). In contrast, corresponding bPIV3 F and cPIV3 F ectodomains linked to GCN4 by lacking the prefusion stabilizing modifications did not express well in cells.

It will be apparent that the precise details of the methods or compositions described may be varied or modified without departing from the spirit of the described embodiments. We claim all such modifications and variations that fall within the scope and spirit of the claims below.

The invention claimed is:

1. An immunogen, comprising:

a recombinant human parainfluenza virus 1 (hPIV1) F ectodomain trimer comprising protomers comprising one or more amino acid substitutions that stabilize the hPIV1 ectodomain trimer in a prefusion conformation, wherein the one or more amino acid substitutions comprise A466I and S473I cavity filling substitutions, wherein the amino acid numbering is according to a reference hPIV1 F sequence set forth as SEQ ID NO: 2.

2. The immunogen of claim 1, wherein the protomers further comprise a mutation to inhibit cleavage of a $F_2/F_1$ protease cleavage site.

3. The immunogen of claim 2, wherein the mutation comprises a deletion of hPIV1 residues 113 and 114 with residues 112 and 115 linked by a heterologous peptide linker.

4. The immunogen of claim 3, wherein the heterologous peptide linker consists of the amino acid sequence set forth as GS.

5. The immunogen of claim 1, wherein one or more amino acid substitutions further comprise a non-native disulfide bond between 175C-241C, 173C-245C, 206C-233C, 88C-225C, 219C-224C, or 165C-171C substitutions.

6. The immunogen of claim 1, wherein a C-terminal residue of the protomers is one of hPIV1 F residues 473-497.

7. The immunogen of claim 1, wherein the protomers comprise or consist essentially of hPIV1 residues 22-112 and 115-479 with residues 112 and 115 linked by a heterologous peptide linker and comprise the one or more amino acid substitutions to stabilize the trimer in the prefusion conformation.

8. The immunogen of claim 1, wherein the protomers comprise or consist essentially of an amino acid sequence at least 90% identical to residues 1-458 of SEQ ID NO: 4, wherein the protomers comprise the one or more amino acid substitutions.

9. The immunogen of claim 8, wherein the protomers comprise or consist essentially of the amino acid sequence set forth as residues 1-458 of SEQ ID NO: 4.

10. The immunogen of claim 1, wherein a C-terminal residue of the protomers in the ectodomain is linked to a trimerization domain by a peptide linker, or is directly linked to the trimerization domain.

11. The immunogen of claim 10, wherein the trimerization domain is a GCN4 trimerization domain.

12. The immunogen of claim 10, wherein the protomers linked to the trimerization domain comprise or consist essentially of an amino acid sequence at least 90% identical to residues 1-458 of SEQ ID NO: 4, wherein the protomers comprise the one or more amino acid substitutions.

13. The immunogen of claim 12, wherein the protomers linked to the trimerization domain comprise or consist essentially of the amino acid sequence set forth as SEQ ID NO: 4.

14. The immunogen of claim 1, wherein the protomers further comprise one or more additional amino acid substitutions.

15. The immunogen of claim 1, wherein the recombinant hPIV1 F ectodomain trimer is soluble.

16. The immunogen of claim 1, wherein the C-terminal residue of the protomers in the F ectodomain is linked to a transmembrane domain by a peptide linker, or is directly linked to the transmembrane domain.

17. The immunogen of claim 1, wherein the C-terminal residue of the protomers in the F ectodomain is linked to a protein nanoparticle subunit by a peptide linker, or is directly linked to the protein nanoparticle subunit.

18. A protein nanoparticle, comprising the immunogen of claim 1.

19. A virus-like particle comprising the immunogen of claim 1.

20. An isolated nucleic acid molecule encoding a protomer of the recombinant hPIV1 F ectodomain trimer of claim 1.

21. An immunogenic composition comprising the immunogen of claim 1, a virus like particle comprising the immunogen, a protein nanoparticle comprising the immunogen, or a nucleic acid molecule encoding the immunogen.

22. A method of inducing an immune response to hPIV1 F protein in a subject, comprising administering to the subject an effective amount of the immunogen of claim 1, a virus like particle comprising the immunogen, a protein nanoparticle comprising the immunogen, or a nucleic acid molecule encoding the immunogen to generate the immune response.

23. The method of claim 22, wherein the immune response inhibits an hPIV1 infection.

* * * * *

```
                    SEQUENCE LISTING


<160> NUMBER OF SEQ ID NOS: 95

<210> SEQ ID NO 1
<211> LENGTH: 555
<212> TYPE: PRT
<213> ORGANISM: human parainfluenza virus 1

<400> SEQUENCE: 1

Met Gln Lys Ser Glu Ile Leu Phe Leu Ile Tyr Ser Ser Leu Leu Leu
1               5                   10                  15
```

```
Ser Ser Ser Leu Cys Gln Ile Pro Val Asp Lys Leu Ser Asn Val Gly
            20                  25                  30

Val Ile Ile Asn Glu Gly Lys Leu Leu Lys Ile Ala Gly Ser Tyr Glu
        35                  40                  45

Ser Arg Tyr Ile Val Leu Ser Leu Val Pro Ser Ile Asp Leu Glu Asp
    50                  55                  60

Gly Cys Gly Thr Thr Gln Ile Ile Gln Tyr Lys Asn Leu Leu Asn Arg
65                  70                  75                  80

Leu Leu Ile Pro Leu Lys Asp Ala Leu Asp Leu Gln Glu Ser Leu Ile
                85                  90                  95

Thr Ile Thr Asn Asp Thr Thr Val Thr Asn Asp Asn Pro Gln Ser Arg
            100                 105                 110

Phe Phe Gly Ala Val Ile Gly Thr Ile Ala Leu Gly Val Ala Thr Ala
        115                 120                 125

Ala Gln Ile Thr Ala Gly Ile Ala Leu Ala Glu Ala Arg Glu Ala Arg
    130                 135                 140

Lys Asp Ile Ala Leu Ile Lys Asp Ser Ile Ile Lys Thr His Asn Ser
145                 150                 155                 160

Val Glu Leu Ile Gln Arg Gly Ile Gly Glu Gln Ile Ile Ala Leu Lys
                165                 170                 175

Thr Leu Gln Asp Phe Val Asn Asn Glu Ile Arg Pro Ala Ile Gly Glu
            180                 185                 190

Leu Arg Cys Glu Thr Thr Ala Leu Lys Leu Gly Ile Lys Leu Thr Gln
        195                 200                 205

His Tyr Ser Glu Leu Ala Thr Ala Phe Ser Ser Asn Leu Gly Thr Ile
    210                 215                 220

Gly Glu Lys Ser Leu Thr Leu Gln Ala Leu Ser Ser Leu Tyr Ser Ala
225                 230                 235                 240

Asn Ile Thr Glu Ile Leu Ser Thr Ile Lys Lys Asp Lys Ser Asp Ile
                245                 250                 255

Tyr Asp Ile Ile Tyr Thr Glu Gln Val Lys Gly Thr Val Ile Asp Val
            260                 265                 270

Asp Leu Glu Lys Tyr Met Val Thr Leu Leu Val Lys Ile Pro Ile Leu
        275                 280                 285

Ser Glu Ile Pro Gly Val Leu Ile Tyr Arg Ala Ser Ser Ile Ser Tyr
    290                 295                 300

Asn Ile Glu Gly Glu Glu Trp His Val Ala Ile Pro Asn Tyr Ile Ile
305                 310                 315                 320

Asn Lys Ala Ser Ser Leu Gly Gly Ala Asp Val Thr Asn Cys Ile Glu
                325                 330                 335

Ser Arg Leu Ala Tyr Ile Cys Pro Arg Asp Pro Thr Gln Leu Ile Pro
            340                 345                 350

Asp Asn Gln Gln Lys Cys Ile Leu Gly Asp Val Ser Lys Cys Pro Val
        355                 360                 365

Thr Lys Val Ile Asn Asn Leu Val Pro Lys Phe Ala Phe Ile Asn Gly
    370                 375                 380

Gly Val Val Ala Asn Cys Ile Ala Ser Thr Cys Thr Cys Gly Thr Asn
385                 390                 395                 400

Arg Ile Pro Val Asn Gln Asp Arg Ser Arg Gly Val Thr Phe Leu Thr
                405                 410                 415

Tyr Thr Asn Cys Gly Leu Ile Gly Ile Asn Gly Ile Glu Leu Tyr Ala
            420                 425                 430
```

```
Asn Lys Arg Gly Arg Asp Thr Thr Trp Gly Asn Gln Ile Ile Lys Val
        435                 440                 445

Gly Pro Ala Val Ser Ile Arg Pro Val Asp Ile Ser Leu Asn Leu Ala
    450                 455                 460

Ser Ala Thr Asn Phe Leu Glu Glu Ser Lys Ile Glu Leu Met Lys Ala
465                 470                 475                 480

Lys Ala Ile Ile Ser Ala Val Gly Gly Trp His Asn Thr Glu Ser Thr
                485                 490                 495

Gln Ile Ile Ile Ile Ile Ile Val Cys Ile Leu Ile Ile Ile Ile Cys
            500                 505                 510

Gly Ile Leu Tyr Tyr Leu Tyr Arg Val Arg Arg Leu Leu Val Met Ile
        515                 520                 525

Asn Ser Thr His Asn Ser Pro Val Asn Thr Tyr Thr Leu Glu Ser Arg
    530                 535                 540

Met Arg Asn Pro Tyr Ile Gly Asn Asn Ser Asn
545                 550                 555


<210> SEQ ID NO 2
<211> LENGTH: 580
<212> TYPE: PRT
<213> ORGANISM: human parainfluenza virus 1

<400> SEQUENCE: 2

Met Gln Ser Ser Glu Val Leu Leu Leu Val Tyr Ser Ser Leu Leu Leu
1               5                   10                  15

Ser Ser Ser Leu Cys Gln Ile Pro Val Asp Lys Leu Ser Asn Val Gly
            20                  25                  30

Val Ile Ile Asn Glu Gly Lys Leu Leu Lys Ile Ala Gly Ser Tyr Glu
        35                  40                  45

Ser Arg Tyr Ile Val Leu Ser Leu Val Pro Ser Ile Asp Leu Gln Asp
    50                  55                  60

Gly Cys Gly Thr Thr Gln Ile Ile Gln Tyr Lys Asn Leu Leu Asn Arg
65                  70                  75                  80

Leu Leu Ile Pro Leu Lys Asp Ala Leu Asp Leu Gln Glu Ser Leu Ile
                85                  90                  95

Thr Ile Thr Asn Asp Thr Thr Val Thr Asn Asp Asn Pro Gln Thr Arg
            100                 105                 110

Phe Phe Gly Ala Val Ile Gly Thr Ile Ala Leu Gly Val Ala Thr Ala
        115                 120                 125

Ala Gln Ile Thr Ala Gly Ile Ala Leu Ala Glu Ala Arg Glu Ala Arg
    130                 135                 140

Lys Asp Ile Ala Leu Ile Lys Asp Ser Ile Val Lys Thr His Asn Ser
145                 150                 155                 160

Val Glu Phe Ile Gln Arg Gly Ile Gly Glu Gln Ile Ile Ala Leu Lys
                165                 170                 175

Thr Leu Gln Asp Phe Val Asn Asp Glu Ile Arg Pro Ala Ile Gly Glu
            180                 185                 190

Leu Arg Cys Glu Thr Thr Ala Leu Lys Leu Gly Ile Lys Leu Thr Gln
        195                 200                 205

His Tyr Ser Glu Leu Ala Thr Ala Phe Ser Ser Asn Leu Gly Thr Ile
    210                 215                 220

Gly Glu Lys Ser Leu Thr Leu Gln Ala Leu Ser Ser Leu Tyr Ser Ala
225                 230                 235                 240

Asn Ile Thr Glu Ile Leu Ser Thr Ile Lys Lys Asp Lys Ser Asp Ile
                245                 250                 255
```

```
Tyr Asp Ile Ile Tyr Thr Glu Gln Val Lys Gly Thr Val Ile Asp Val
            260                 265                 270

Asp Leu Glu Lys Tyr Met Val Thr Leu Leu Val Lys Ile Pro Ile Leu
        275                 280                 285

Ser Glu Ile Pro Gly Val Leu Ile Tyr Arg Ala Ser Ser Ile Ser Tyr
    290                 295                 300

Asn Ile Glu Gly Glu Glu Trp His Val Ala Ile Pro Asn Tyr Ile Ile
305                 310                 315                 320

Asn Lys Ala Ser Ser Leu Gly Gly Ala Asp Val Thr Asn Cys Ile Glu
                325                 330                 335

Ser Lys Leu Ala Tyr Ile Cys Pro Arg Asp Pro Thr Gln Leu Ile Pro
            340                 345                 350

Asp Asn Gln Gln Lys Cys Ile Leu Gly Asp Val Ser Lys Cys Pro Val
        355                 360                 365

Thr Lys Val Ile Asn Asn Leu Val Pro Lys Phe Ala Phe Ile Asn Gly
    370                 375                 380

Gly Val Val Ala Asn Cys Ile Ala Ser Thr Cys Thr Cys Gly Thr Asn
385                 390                 395                 400

Arg Ile Pro Val Asn Gln Asp Arg Ser Lys Gly Val Thr Phe Leu Thr
                405                 410                 415

Tyr Thr Asn Cys Gly Leu Ile Gly Ile Asn Gly Ile Glu Leu Tyr Ala
            420                 425                 430

Asn Lys Arg Gly Arg Asp Thr Thr Trp Gly Asn Gln Ile Ile Lys Val
        435                 440                 445

Gly Pro Ala Val Ser Ile Arg Pro Val Asp Ile Ser Leu Asn Leu Ala
    450                 455                 460

Ser Ala Thr Asn Phe Leu Glu Glu Ser Lys Thr Glu Leu Met Lys Ala
465                 470                 475                 480

Arg Ala Ile Ile Ser Ala Val Gly Gly Trp His Asn Lys Glu Ser Thr
                485                 490                 495

Gln Ile Ile Ile Ile Ile Ile Val Cys Val Leu Ile Ile Ile Ile Cys
            500                 505                 510

Ser Ile Leu Tyr Tyr Leu Tyr Arg Val Arg Arg Leu Leu Ile Met Ile
        515                 520                 525

Asn Ser Thr Asn Asn Ser Pro Ile Asn Ala Tyr Thr Leu Glu Ser Arg
    530                 535                 540

Met Lys Asn Pro Tyr Met Gly Asn His Ser Asn Lys Ile Arg Ser Ser
545                 550                 555                 560

Ile Leu His Thr Tyr Asn Asn Gln Ile Tyr Pro Gln Leu Leu Ser Asp
                565                 570                 575

Val Val Arg Lys
            580
```

<210> SEQ ID NO 3
<211> LENGTH: 555
<212> TYPE: PRT
<213> ORGANISM: human parainfluenza virus 1

<400> SEQUENCE: 3

```
Met Gln Ser Ser Glu Ile Leu Ile Leu Val Tyr Ser Ser Leu Leu Leu
1               5                   10                  15

Ser Ser Ser Leu Cys Gln Ile Pro Val Asp Lys Leu Ser Asn Val Gly
            20                  25                  30

Val Ile Ile Asn Glu Gly Lys Leu Leu Lys Ile Ala Gly Ser Tyr Glu
```

```
        35                  40                  45

Ser Arg Tyr Ile Val Leu Ser Leu Val Pro Ser Ile Asp Leu Gln Asp
    50                  55                  60

Gly Cys Gly Thr Thr Gln Ile Ile Gln Tyr Lys Asn Leu Leu Asn Arg
65                  70                  75                  80

Leu Leu Ile Pro Leu Lys Asp Ala Leu Asp Leu Gln Glu Ser Leu Ile
                85                  90                  95

Thr Ile Thr Asn Asp Thr Thr Val Thr Asn Asp Asn Pro Gln Thr Arg
            100                 105                 110

Phe Phe Gly Ala Val Ile Gly Thr Ile Ala Leu Gly Val Ala Thr Ala
        115                 120                 125

Ala Gln Ile Thr Ala Gly Ile Ala Leu Ala Glu Ala Arg Glu Ala Arg
    130                 135                 140

Lys Asp Ile Ala Leu Ile Lys Asp Ser Ile Val Lys Thr His Asn Ser
145                 150                 155                 160

Val Glu Phe Ile Gln Arg Gly Ile Gly Glu Gln Ile Ile Ala Leu Lys
                165                 170                 175

Thr Leu Gln Asp Phe Val Asn Asp Glu Ile Pro Pro Ala Ile Gly Glu
            180                 185                 190

Leu Arg Cys Glu Thr Thr Ala Met Lys Leu Gly Ile Lys Leu Thr Gln
        195                 200                 205

His Tyr Ser Glu Leu Ala Thr Ala Phe Ser Ser Asn Leu Gly Thr Ile
    210                 215                 220

Gly Glu Lys Ser Leu Thr Leu Gln Ala Leu Ser Ser Leu Tyr Ser Ala
225                 230                 235                 240

Asn Ile Thr Glu Ile Leu Ser Thr Ile Lys Lys Asp Lys Ser Asp Ile
                245                 250                 255

Tyr Asp Ile Ile Tyr Thr Glu Gln Val Lys Gly Thr Val Ile Asp Val
            260                 265                 270

Asp Leu Glu Lys Tyr Met Val Thr Leu Leu Val Lys Ile Pro Ile Leu
        275                 280                 285

Ser Glu Ile Pro Gly Val Leu Ile Tyr Arg Ala Ser Ser Ile Ser Tyr
    290                 295                 300

Asn Ile Glu Gly Glu Glu Trp His Val Ala Ile Pro Asn Tyr Ile Ile
305                 310                 315                 320

Ser Lys Ala Ser Ser Leu Gly Gly Ala Asp Val Thr Asn Cys Ile Glu
                325                 330                 335

Ser Lys Leu Ala Tyr Ile Cys Pro Arg Asp Pro Thr Gln Leu Ile Pro
            340                 345                 350

Asp Asn Gln Gln Lys Cys Ile Leu Gly Asp Val Ser Lys Cys Pro Val
        355                 360                 365

Thr Lys Val Ile Asn Asn Leu Val Pro Lys Phe Ala Phe Ile Asn Gly
    370                 375                 380

Gly Val Val Ala Asn Cys Ile Ala Ser Thr Cys Thr Cys Gly Thr Asn
385                 390                 395                 400

Arg Ile Pro Val Asn Gln Asp Arg Ser Lys Gly Val Thr Phe Leu Thr
                405                 410                 415

Tyr Thr Asn Cys Gly Leu Ile Gly Ile Asn Gly Ile Glu Leu Tyr Gly
            420                 425                 430

Asn Lys Arg Gly Arg Asp Thr Thr Trp Gly Asn Gln Ile Ile Lys Glu
        435                 440                 445

Gly Pro Ala Val Ser Ile Arg Pro Val Asp Ile Ser Leu Asn Leu Ala
    450                 455                 460
```

```
Ser Ala Thr Asn Phe Leu Glu Glu Ser Lys Thr Glu Leu Met Lys Ala
465                 470                 475                 480

Arg Ala Ile Ile Ser Ala Val Gly Gly Trp His Asn Thr Glu Ser Thr
                485                 490                 495

Gln Ile Ile Ile Ile Ile Ile Val Cys Ile Leu Ile Ile Ile Ile Cys
            500                 505                 510

Gly Ile Leu Tyr Tyr Leu Tyr Arg Val Arg Arg Leu Leu Val Met Ile
        515                 520                 525

Asn Ser Thr Asn Asn Ser Pro Ile Asn Ala Tyr Thr Leu Glu Ser Arg
    530                 535                 540

Met Arg Asn Pro Tyr Met Gly Asn His Ser Asn
545                 550                 555


<210> SEQ ID NO 4
<211> LENGTH: 488
<212> TYPE: PRT
<213> ORGANISM: Artificial Sequence
<220> FEATURE:
<223> OTHER INFORMATION: Recombinant parainfluenza virus F sequence

<400> SEQUENCE: 4

Gln Ile Pro Val Asp Lys Leu Ser Asn Val Gly Val Ile Ile Asn Glu
1               5                   10                  15

Gly Lys Leu Leu Lys Ile Ala Gly Ser Tyr Glu Ser Arg Tyr Ile Val
            20                  25                  30

Leu Ser Leu Val Pro Ser Ile Asp Leu Gln Asp Gly Cys Gly Thr Thr
        35                  40                  45

Gln Ile Ile Gln Tyr Lys Asn Leu Leu Asn Arg Leu Leu Ile Pro Leu
    50                  55                  60

Lys Asp Ala Leu Asp Leu Gln Glu Ser Leu Ile Thr Ile Thr Asn Asp
65                  70                  75                  80

Thr Thr Val Thr Asn Asp Asn Pro Gln Thr Arg Gly Ser Gly Ala Val
                85                  90                  95

Ile Gly Thr Ile Ala Leu Gly Val Ala Thr Ala Ala Gln Ile Thr Ala
            100                 105                 110

Gly Ile Ala Leu Ala Glu Ala Arg Glu Ala Arg Lys Asp Ile Ala Leu
        115                 120                 125

Ile Lys Asp Ser Ile Val Lys Thr His Asn Ser Val Glu Phe Ile Gln
    130                 135                 140

Arg Gly Ile Gly Glu Gln Ile Ile Ala Leu Lys Thr Leu Gln Asp Phe
145                 150                 155                 160

Val Asn Asp Glu Ile Arg Pro Ala Ile Gly Glu Leu Arg Cys Glu Thr
                165                 170                 175

Thr Ala Leu Lys Leu Gly Ile Lys Leu Thr Gln His Tyr Ser Glu Leu
            180                 185                 190

Ala Thr Ala Phe Ser Ser Asn Leu Gly Thr Ile Gly Glu Lys Ser Leu
        195                 200                 205

Thr Leu Gln Ala Leu Ser Ser Leu Tyr Ser Ala Asn Ile Thr Glu Ile
    210                 215                 220

Leu Ser Thr Ile Lys Lys Asp Lys Ser Asp Ile Tyr Asp Ile Ile Tyr
225                 230                 235                 240

Thr Glu Gln Val Lys Gly Thr Val Ile Asp Val Asp Leu Glu Lys Tyr
                245                 250                 255

Met Val Thr Leu Leu Val Lys Ile Pro Ile Leu Ser Glu Ile Pro Gly
            260                 265                 270
```

```
Val Leu Ile Tyr Arg Ala Ser Ser Ile Ser Tyr Asn Ile Glu Gly Glu
        275                 280                 285

Glu Trp His Val Ala Ile Pro Asn Tyr Ile Ile Asn Lys Ala Ser Ser
    290                 295                 300

Leu Gly Gly Ala Asp Val Thr Asn Cys Ile Glu Ser Lys Leu Ala Tyr
305                 310                 315                 320

Ile Cys Pro Arg Asp Pro Thr Gln Leu Ile Pro Asp Asn Gln Gln Lys
                325                 330                 335

Cys Ile Leu Gly Asp Val Ser Lys Cys Pro Val Thr Lys Val Ile Asn
            340                 345                 350

Asn Leu Val Pro Lys Phe Ala Phe Ile Asn Gly Gly Val Val Ala Asn
        355                 360                 365

Cys Ile Ala Ser Thr Cys Thr Cys Gly Thr Asn Arg Ile Pro Val Asn
    370                 375                 380

Gln Asp Arg Ser Lys Gly Val Thr Phe Leu Thr Tyr Thr Asn Cys Gly
385                 390                 395                 400

Leu Ile Gly Ile Asn Gly Ile Glu Leu Tyr Ala Asn Lys Arg Gly Arg
                405                 410                 415

Asp Thr Thr Trp Gly Asn Gln Ile Ile Lys Val Gly Pro Ala Val Ser
            420                 425                 430

Ile Arg Pro Val Asp Ile Ser Leu Asn Leu Ala Ser Ile Thr Asn Phe
        435                 440                 445

Leu Glu Glu Ile Lys Thr Glu Leu Met Lys Ile Glu Asp Lys Ile Glu
    450                 455                 460

Glu Ile Leu Ser Lys Ile Tyr His Ile Glu Asn Glu Ile Ala Arg Ile
465                 470                 475                 480

Lys Lys Leu Ile Gly Glu Ala Pro
                485


<210> SEQ ID NO 5
<211> LENGTH: 551
<212> TYPE: PRT
<213> ORGANISM: human parainfluenza virus 2

<400> SEQUENCE: 5

Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Ile
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Thr
                85                  90                  95

Val Thr Asp Thr Lys Thr Arg Gln Lys Arg Phe Ala Gly Val Val Val
            100                 105                 110

Gly Leu Ala Ala Leu Gly Val Ala Thr Ala Ala Gln Ile Thr Ala Ala
        115                 120                 125

Val Ala Ile Val Lys Ala Asn Ala Asn Ala Ala Ala Ile Asn Asn Leu
    130                 135                 140

Ala Ser Ser Ile Gln Ser Thr Asn Lys Ala Val Ser Asp Val Ile Asp
```

```
145                 150                 155                 160

Ala Ser Arg Thr Ile Ala Thr Ala Val Gln Ala Ile Gln Asp His Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Asn Leu Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ile Ala Ile Ser Ala Asn His Lys Leu Gln Glu
    290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Cys
                325                 330                 335

Cys Arg Tyr Asn Glu Gly Ser Pro Ile Pro Glu Ser Gln Tyr Gln Cys
            340                 345                 350

Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
    370                 375                 380

Lys Ser Leu Leu Cys Arg Cys Ala Asp Pro Pro His Val Val Ser Gln
385                 390                 395                 400

Asp Asp Thr Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Ile Val His Leu
        435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
            500                 505                 510

Ile Lys Leu Val Ser Gln Ile His Gln Phe Arg Ser Leu Ala Ala Thr
        515                 520                 525

Thr Met Phe His Arg Glu Asn Pro Ala Phe Phe Ser Lys Asn Asn His
    530                 535                 540

Gly Asn Ile Tyr Gly Ile Ser
545                 550
```

<210> SEQ ID NO 6

<211> LENGTH: 551
<212> TYPE: PRT
<213> ORGANISM: human parainfluenza virus 2

<400> SEQUENCE: 6

```
Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Ile
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Thr
                85                  90                  95

Val Thr Asp Thr Lys Thr Arg Gln Lys Arg Phe Ala Gly Val Val Val
            100                 105                 110

Gly Leu Ala Ala Leu Gly Val Ala Thr Ala Ala Gln Ile Thr Ala Ala
        115                 120                 125

Val Ala Ile Val Lys Ala Asn Ala Asn Ala Ala Ala Ile Asn Asn Leu
    130                 135                 140

Ala Ser Ser Ile Gln Ser Thr Asn Lys Ala Val Ser Asp Val Ile Asp
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Asn Phe Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ile Ala Ile Ser Ala Asn His Lys Leu Gln Glu
    290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
            340                 345                 350

Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
    370                 375                 380

Lys Ser Leu Leu Cys Arg Cys Ala Asp Pro Pro His Val Val Ser Gln
```

```
385                 390                 395                 400

Asp Asp Thr Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Ile Val His Leu
        435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
            500                 505                 510

Ile Lys Leu Val Ser Gln Ile His Gln Phe Arg Ser Leu Ala Ala Thr
        515                 520                 525

Thr Met Phe His Arg Glu Asn Pro Ala Phe Phe Ser Lys Asn Asn His
    530                 535                 540

Gly Asn Ile Tyr Gly Ile Ser
545                 550


<210> SEQ ID NO 7
<211> LENGTH: 496
<212> TYPE: PRT
<213> ORGANISM: Artificial Sequence
<220> FEATURE:
<223> OTHER INFORMATION: Recombinant parainfluenza virus F sequence

<400> SEQUENCE: 7

Asp Ala Ile Ala Gly Asp Gln Leu Leu Asn Ile Gly Val Ile Gln Ser
1               5                   10                  15

Lys Ile Arg Ser Leu Met Tyr Tyr Thr Asp Gly Gly Ala Ser Phe Ile
            20                  25                  30

Val Val Lys Leu Leu Pro Asn Leu Pro Pro Ser Asn Gly Thr Cys Asn
        35                  40                  45

Ile Thr Ser Leu Asp Ala Tyr Asn Val Thr Leu Phe Lys Leu Leu Thr
    50                  55                  60

Pro Leu Ile Glu Asn Leu Ser Lys Ile Ser Thr Val Thr Asp Thr Gly
65                  70                  75                  80

Gly Gly Ser Gly Gly Gly Ser Gly Val Val Val Gly Leu Ala Ala Leu
                85                  90                  95

Gly Val Ala Thr Ala Ala Gln Ile Thr Ala Ala Val Ala Ile Val Lys
            100                 105                 110

Ala Asn Ala Asn Ala Ala Ala Ile Asn Asn Leu Ala Ser Ser Ile Gln
        115                 120                 125

Ser Thr Asn Lys Ala Val Ser Asp Val Ile Asp Ala Ser Arg Thr Ile
    130                 135                 140

Ala Thr Ala Val Gln Ala Ile Gln Asp Arg Ile Asn Gly Ala Ile Val
145                 150                 155                 160

Asn Gly Ile Thr Ser Ala Ser Cys Arg Ala His Asp Ala Leu Ile Gly
                165                 170                 175

Ser Ile Leu Asn Leu Tyr Leu Thr Glu Leu Thr Thr Ile Phe His Asn
            180                 185                 190

Gln Ile Thr Asn Pro Ala Leu Thr Pro Leu Ser Ile Gln Ala Leu Arg
```

```
        195                 200                 205

Ile Leu Leu Gly Ser Thr Leu Pro Ile Val Ile Glu Ser Lys Leu Asn
    210                 215                 220

Thr Asn Phe Asn Thr Ala Glu Leu Leu Ser Ser Gly Leu Leu Thr Gly
225                 230                 235                 240

Gln Ile Ile Ser Ile Ser Pro Met Tyr Met Gln Met Leu Ile Gln Ile
                245                 250                 255

Asn Val Pro Thr Phe Ile Met Gln Pro Gly Ala Lys Val Ile Asp Leu
            260                 265                 270

Ile Ala Ile Ser Ala Asn His Lys Leu Gln Glu Val Val Val Gln Val
        275                 280                 285

Pro Asn Arg Ile Leu Glu Tyr Ala Asn Glu Leu Gln Asn Tyr Pro Ala
    290                 295                 300

Asn Asp Cys Val Val Thr Pro Asn Ser Val Phe Cys Arg Tyr Asn Glu
305                 310                 315                 320

Gly Ser Pro Ile Pro Glu Ser Gln Tyr Gln Cys Leu Arg Gly Asn Leu
                325                 330                 335

Asn Ser Cys Thr Phe Thr Pro Ile Ile Gly Asn Phe Leu Lys Arg Phe
            340                 345                 350

Ala Phe Ala Asn Gly Val Leu Tyr Ala Asn Cys Lys Ser Leu Leu Cys
        355                 360                 365

Arg Cys Ala Asp Pro Pro His Val Val Ser Gln Asp Asp Thr Gln Gly
    370                 375                 380

Ile Ser Ile Ile Asp Ile Lys Arg Cys Ser Glu Met Met Leu Asp Thr
385                 390                 395                 400

Phe Ser Phe Arg Ile Thr Ser Thr Phe Asn Ala Thr Tyr Val Thr Asp
                405                 410                 415

Phe Ser Met Ile Asn Ala Asn Ile Val His Leu Ser Pro Leu Asp Leu
            420                 425                 430

Ser Asn Gln Ile Asn Ser Ile Asn Lys Ser Leu Lys Ser Ala Glu Asp
        435                 440                 445

Trp Ile Ala Asp Ser Asn Phe Phe Ala Asn Gln Ala Arg Thr Ala Met
    450                 455                 460

Lys Gln Ile Glu Asp Lys Ile Glu Glu Ile Leu Ser Lys Ile Tyr His
465                 470                 475                 480

Ile Glu Asn Glu Ile Ala Arg Ile Lys Lys Leu Ile Gly Glu Ala Pro
                485                 490                 495


<210> SEQ ID NO 8
<211> LENGTH: 539
<212> TYPE: PRT
<213> ORGANISM: Artificial Sequence
<220> FEATURE:
<223> OTHER INFORMATION: Recombinant parainfluenza virus F sequence

<400> SEQUENCE: 8

Met Pro Thr Ser Ile Leu Leu Ile Ile Thr Thr Met Ile Met Ala Ser
1               5                   10                  15

Phe Cys Gln Ile Asp Ile Thr Lys Leu Gln His Val Gly Val Leu Val
            20                  25                  30

Asn Ser Pro Lys Gly Met Lys Ile Ser Gln Asn Phe Glu Thr Arg Tyr
        35                  40                  45

Leu Ile Leu Ser Leu Ile Pro Lys Ile Glu Asp Ser Asn Ser Cys Gly
    50                  55                  60

Asp Gln Gln Ile Lys Gln Tyr Lys Arg Leu Leu Asp Arg Leu Ile Ile
```

-continued

```
65                  70                  75                  80

Pro Leu Tyr Asp Gly Leu Arg Leu Gln Lys Asp Val Ile Val Ser Asn
                85                  90                  95

Gln Glu Ser Asn Glu Asn Thr Asp Pro Arg Thr Lys Arg Phe Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Arg Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Thr Leu Gln Val Arg Leu Pro Leu Leu Thr Arg Leu
        275                 280                 285

Leu Asn Thr Gln Ile Tyr Arg Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Val Val
        355                 360                 365

Lys Ser Asp Ile Val Pro Arg Tyr Ala Phe Val Asn Gly Gly Val Val
    370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495
```

```
Val Leu Ile Met Ile Ile Ile Leu Phe Ile Ile Asn Val Thr Ile Ile
            500                 505                 510

Ile Ile Ala Val Lys Tyr Tyr Arg Ile Gln Lys Arg Asn Arg Val Asp
        515                 520                 525

Gln Asn Asp Lys Pro Tyr Val Leu Thr Asn Lys
    530                 535


<210> SEQ ID NO 9
<211> LENGTH: 539
<212> TYPE: PRT
<213> ORGANISM: human parainfluenza virus 3

<400> SEQUENCE: 9

Met Leu Ile Ser Ile Leu Ser Ile Ile Thr Thr Met Ile Met Ala Ser
1               5                   10                  15

His Cys Gln Ile Asp Ile Thr Lys Leu Gln His Val Gly Val Leu Val
            20                  25                  30

Asn Ser Pro Lys Gly Met Lys Ile Ser Gln Asn Phe Glu Thr Arg Tyr
        35                  40                  45

Leu Ile Leu Ser Leu Ile Pro Lys Ile Glu Asp Ser Asn Ser Cys Gly
    50                  55                  60

Asp Gln Gln Ile Lys Gln Tyr Lys Arg Leu Leu Asp Arg Leu Ile Ile
65                  70                  75                  80

Pro Leu Tyr Asp Gly Leu Lys Leu Gln Lys Asp Val Ile Val Thr Asn
                85                  90                  95

Gln Glu Ser Asn Glu Asn Thr Asp Pro Arg Thr Glu Arg Phe Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Lys Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Val Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Thr Leu Gln Val Arg Leu Pro Leu Leu Thr Arg Leu
        275                 280                 285

Leu Asn Thr Gln Ile Tyr Lys Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
```

```
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Thr Val
        355                 360                 365

Thr Ser Asp Ile Val Pro Arg Tyr Ala Phe Val Asn Gly Gly Val Val
    370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asp Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Ser Trp His Gln Ser Ser Thr Thr Ile Ile Ile
                485                 490                 495

Ile Leu Ile Met Met Ile Ile Leu Phe Ile Ile Asn Ile Thr Ile Ile
            500                 505                 510

Thr Ile Ala Ile Lys Tyr Tyr Arg Ile Gln Lys Arg Asn Arg Val Asp
        515                 520                 525

Gln Asn Asp Lys Pro Tyr Val Leu Thr Asn Lys
    530                 535


<210> SEQ ID NO 10
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 10

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Leu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
```

```
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Ile Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495
```

<210> SEQ ID NO 11
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 11

```
Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
```

-continued

```
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Ile Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445
```

Leu Glu Glu Ser Lys Glu Trp Ile Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495

<210> SEQ ID NO 12
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 12

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Ile Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

```
Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Ile Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 13
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 13

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Trp
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190
```

```
Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Ile Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 14
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 14

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60
```

```
Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Pro Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Ile Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480
```

```
Glu Asn Glu Ile Ala Arg Ile Lys Lys Leu Ile Gly Glu Ala Pro
                485                 490                 495


<210> SEQ ID NO 15
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 15

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350
```

```
Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Ile Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 16
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 16

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220
```

Phe Thr Thr Ser Thr Val Asp Lys Tyr Asp Ile Tyr Asp Leu Leu Phe
225 230 235 240

Thr Glu Ser Ile Lys Val Arg Val Ile Asp Val Asp Leu Asn Asp Tyr
245 250 255

Ser Ile Thr Leu Gln Val Arg Leu Pro Leu Leu Thr Arg Leu Leu Asn
260 265 270

Thr Gln Ile Tyr Lys Val Asp Ser Ile Ser Tyr Asn Ile Gln Asn Arg
275 280 285

Glu Trp Tyr Ile Pro Leu Pro Ser His Ile Met Thr Lys Gly Ala Phe
290 295 300

Leu Gly Gly Ala Asp Val Lys Glu Cys Ile Glu Ala Phe Ser Ser Tyr
305 310 315 320

Ile Cys Pro Ser Asp Pro Gly Phe Val Leu Asn His Glu Met Glu Ser
325 330 335

Cys Leu Ser Gly Asn Ile Ser Gln Cys Pro Arg Thr Thr Val Thr Ser
340 345 350

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Ala Lys Ser Asp
435 440 445

Leu Glu Glu Leu Lys Glu Trp Ile Arg Arg Ser Asn Gln Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 17
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 17

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

-continued

```
Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Val Lys Glu Trp Ile Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495
```

<210> SEQ ID NO 18
<211> LENGTH: 495
<212> TYPE: PRT

<213> ORGANISM: Artificial Sequence
<220> FEATURE:
<223> OTHER INFORMATION: Recombinant parainfluenza virus F sequence

<400> SEQUENCE: 18

```
Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
```

```
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 19
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 19

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
```

-continued

```
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Ile Arg Arg Val Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 20
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 20

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
```

```
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 21
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 21

Gln Ile Asp Ile Thr Lys Leu Gln His Val Gly Val Leu Val Asn Ser
```

-continued

```
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Trp
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430
```

Leu Asp Pro Ile Asp Ile Ser Ile Glu Leu Asn Lys Val Lys Ser Asp
435 440 445

Leu Glu Glu Ser Lys Glu Trp Tyr Arg Arg Ser Asn Gln Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 22
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 22

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Gln
130 135 140

Ser Ser Val Gly Asn Leu Ile Val Ala Cys Lys Ser Val Gln Asp Tyr
145 150 155 160

Val Asn Lys Glu Ile Val Pro Ser Ile Ala Arg Leu Gly Cys Glu Ala
165 170 175

Ala Gly Leu Gln Leu Gly Ile Ala Leu Thr Gln His Tyr Ser Glu Leu
180 185 190

Thr Asn Ile Phe Gly Asp Asn Ile Gly Ser Leu Gln Glu Lys Gly Ile
195 200 205

Lys Leu Gln Gly Ile Ala Ser Leu Tyr Arg Thr Cys Ile Thr Glu Ile
210 215 220

Phe Thr Thr Ser Thr Val Asp Lys Tyr Asp Ile Tyr Asp Leu Leu Phe
225 230 235 240

Thr Glu Ser Ile Lys Val Arg Val Ile Asp Val Asp Leu Asn Asp Tyr
245 250 255

Ser Ile Thr Leu Gln Val Arg Leu Pro Leu Leu Thr Arg Leu Leu Asn
260 265 270

Thr Gln Ile Tyr Lys Val Asp Ser Ile Ser Tyr Asn Ile Gln Asn Arg
275 280 285

Glu Trp Tyr Ile Pro Leu Pro Ser His Ile Met Thr Lys Gly Ala Phe
290 295 300

```
Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Ile Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 23
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 23

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Leu Ala Cys Lys Ser Val Gln Asp Tyr
145                 150                 155                 160

Val Asn Lys Glu Ile Val Pro Ser Phe Ala Arg Leu Gly Cys Glu Ala
                165                 170                 175
```

Ala Gly Leu Gln Leu Gly Ile Ala Leu Thr Gln His Tyr Ser Glu Leu
180 185 190

Thr Asn Ile Phe Gly Asp Asn Ile Gly Ser Leu Gln Glu Lys Gly Ile
195 200 205

Lys Leu Gln Gly Ile Ala Ser Leu Tyr Arg Thr Cys Ile Thr Glu Ile
210 215 220

Phe Thr Thr Ser Thr Val Asp Lys Tyr Asp Ile Tyr Asp Leu Leu Phe
225 230 235 240

Thr Glu Ser Ile Lys Val Arg Val Ile Asp Val Asp Leu Asn Asp Tyr
245 250 255

Ser Ile Thr Leu Gln Val Arg Leu Pro Leu Leu Thr Arg Leu Leu Asn
260 265 270

Thr Gln Ile Tyr Lys Val Asp Ser Ile Ser Tyr Asn Ile Gln Asn Arg
275 280 285

Glu Trp Tyr Ile Pro Leu Pro Ser His Ile Met Thr Lys Gly Ala Phe
290 295 300

Leu Gly Gly Ala Asp Val Lys Glu Cys Ile Glu Ala Phe Ser Ser Tyr
305 310 315 320

Ile Cys Pro Ser Asp Pro Gly Phe Val Leu Asn His Glu Met Glu Ser
325 330 335

Cys Leu Ser Gly Asn Ile Ser Gln Cys Pro Arg Thr Thr Val Thr Ser
340 345 350

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Ala Lys Ser Asp
435 440 445

Leu Glu Glu Ser Lys Glu Trp Ile Arg Arg Ser Asn Gln Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 24
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 24

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

-continued

```
Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Trp
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Ile Arg Arg Ser Asn Gln Lys Leu Ser
    450                 455                 460
```

```
Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 25
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 25

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Cys Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Cys Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335
```

-continued

Cys Leu Ser Gly Asn Ile Ser Gln Cys Pro Arg Thr Thr Val Thr Ser
340 345 350

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Ala Lys Ser Asp
435 440 445

Leu Glu Glu Ser Lys Glu Trp Tyr Arg Arg Ser Asn Gln Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 26
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 26

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Gln
130 135 140

Ser Ser Val Gly Asn Leu Ile Val Ala Cys Lys Ser Val Gln Asp Tyr
145 150 155 160

Val Asn Lys Glu Ile Val Pro Ser Ile Ala Arg Leu Gly Cys Glu Ala
165 170 175

Ala Gly Leu Gln Leu Gly Ile Ala Leu Thr Gln His Tyr Ser Glu Leu
180 185 190

Thr Asn Ile Phe Gly Asp Asn Ile Gly Ser Leu Gln Glu Lys Gly Ile
195 200 205

-continued

```
Lys Leu Gln Gly Ile Ala Ser Leu Tyr Arg Thr Cys Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 27
<211> LENGTH: 544
<212> TYPE: PRT
<213> ORGANISM: human parainfluenza virus 4

<400> SEQUENCE: 27

Met Gly Val Lys Gly Ser Ser Leu Ile Met Ile Gly Leu Leu Ile Ser
1               5                   10                  15

Pro Ile Thr Asn Leu Asp Ile Thr His Leu Met Asn Leu Gly Thr Val
            20                  25                  30

Pro Thr Ala Ile Arg Ser Leu Val Tyr Tyr Thr Tyr Thr Lys Pro Ser
        35                  40                  45

Tyr Leu Thr Val Asp Leu Ile Pro Asn Leu Lys Asn Leu Asp Gln Asn
    50                  55                  60

Cys Asn Tyr Ser Ser Leu Asn Tyr Tyr Asn Lys Thr Ala Leu Ser Leu
65                  70                  75                  80

Ile Gln Pro Ile Ala Asp Asn Ile Asn Arg Leu Thr Lys Pro Ile Ala
                85                  90                  95
```

```
Ser Ser Glu Val Gln Ser Arg Phe Phe Gly Ala Val Ile Gly Thr Ile
            100                 105                 110

Ala Leu Gly Val Ala Thr Ala Ala Gln Val Thr Ala Ala Ile Gly Leu
        115                 120                 125

Ala Lys Ala Gln Glu Asn Ala Lys Leu Ile Leu Thr Leu Lys Lys Ala
    130                 135                 140

Ala Thr Glu Thr Asn Glu Ala Val Arg Asp Leu Ala Asn Ser Asn Lys
145                 150                 155                 160

Ile Val Val Lys Met Ile Ser Ala Ile Gln Asn Gln Ile Asn Thr Ile
                165                 170                 175

Ile Gln Pro Ala Ile Asp Gln Ile Asn Cys Gln Ile Lys Asp Leu Gln
            180                 185                 190

Val Ala Asn Ile Leu Asn Leu Tyr Leu Thr Glu Ile Thr Thr Val Phe
        195                 200                 205

His Asn Gln Leu Thr Asn Pro Ala Leu Glu Ser Ile Ser Ile Gln Ala
    210                 215                 220

Leu Lys Ser Leu Leu Gly Ser Thr Leu Pro Glu Val Leu Ser Lys Leu
225                 230                 235                 240

Asp Leu Asn Asn Ile Ser Ala Ala Ser Val Met Ala Ser Gly Leu Ile
                245                 250                 255

Lys Gly Gln Ile Ile Ala Val Asp Ile Pro Thr Met Thr Leu Val Leu
            260                 265                 270

Met Val Gln Ile Pro Ser Ile Ser Pro Leu Arg Gln Ala Lys Ile Ile
        275                 280                 285

Asp Leu Thr Ser Ile Thr Ile His Thr Asn Ser Gln Glu Val Gln Ala
    290                 295                 300

Val Val Pro Ala Arg Phe Leu Glu Ile Gly Ser Glu Ile Leu Gly Phe
305                 310                 315                 320

Asp Gly Ser Val Cys Gln Ile Thr Lys Asp Thr Ile Phe Cys Pro Tyr
                325                 330                 335

Asn Asp Ala Tyr Val Leu Pro Ile Gln Gln Lys Arg Cys Leu Gln Gly
            340                 345                 350

Gln Thr Arg Asp Cys Val Phe Thr Pro Val Ala Gly Thr Phe Pro Arg
        355                 360                 365

Arg Phe Leu Thr Thr Tyr Gly Thr Ile Val Ala Asn Cys Arg Asp Leu
    370                 375                 380

Val Cys Ser Cys Leu Arg Pro Pro Gln Ile Ile Tyr Gln Pro Asp Glu
385                 390                 395                 400

Asn Pro Val Thr Ile Ile Asp Lys Asp Leu Cys Thr Thr Leu Thr Leu
                405                 410                 415

Asp Ser Ile Thr Ile Glu Ile Gln Lys Ser Ile Asn Ser Thr Phe Arg
            420                 425                 430

Arg Glu Val Val Leu Glu Ser Thr Gln Val Arg Ser Leu Thr Pro Leu
        435                 440                 445

Asp Leu Ser Thr Asp Leu Asn Gln Tyr Asn Gln Leu Leu Lys Ser Ala
    450                 455                 460

Glu Asp His Ile Gln Arg Ser Thr Asp Tyr Leu Asn Ser Ile Asn Pro
465                 470                 475                 480

Ser Ile Val Asn Asn Asn Ala Ile Ile Ile Leu Ile Ile Leu Cys Ile
                485                 490                 495

Leu Leu Ile Leu Thr Val Thr Ile Cys Ile Ile Trp Leu Lys Tyr Leu
            500                 505                 510
```

```
Thr Asn Glu Val Lys Asn Val Ala Arg Asn Gln Arg Leu Asn Arg Asp
        515                 520                 525

Ala Asp Leu Phe His Arg Ile Pro Ser Gln Ile Pro Val Pro Arg Gln
    530                 535                 540


<210> SEQ ID NO 28
<211> LENGTH: 544
<212> TYPE: PRT
<213> ORGANISM: human parainfluenza virus 4

<400> SEQUENCE: 28

Met Gly Val Lys Gly Ser Ser Leu Ile Met Ile Gly Leu Leu Ile Ser
1               5                   10                  15

Pro Ile Thr Asn Leu Asp Ile Thr His Leu Met Asn Leu Gly Thr Val
            20                  25                  30

Pro Thr Ala Ile Arg Ser Leu Val Tyr Tyr Thr Tyr Thr Lys Pro Ser
        35                  40                  45

Tyr Leu Thr Val Asp Leu Ile Pro Asn Leu Lys Asn Leu Asp Gln Asn
    50                  55                  60

Cys Asn Tyr Ser Ser Leu Asn Tyr Tyr Asn Lys Thr Ala Leu Ser Leu
65                  70                  75                  80

Ile Gln Pro Ile Ala Asp Asn Ile Asn Arg Leu Thr Lys Pro Ile Thr
                85                  90                  95

Ser Ser Glu Val Gln Ser Arg Phe Phe Gly Ala Val Ile Gly Thr Ile
            100                 105                 110

Ala Leu Gly Val Ala Thr Ala Ala Gln Val Thr Ala Ala Ile Gly Leu
        115                 120                 125

Ala Lys Ala Gln Glu Asn Ala Lys Leu Ile Leu Thr Leu Lys Lys Ala
    130                 135                 140

Ala Thr Glu Thr Asn Glu Ala Val Arg Asp Leu Ala Asn Ser Asn Lys
145                 150                 155                 160

Ile Val Val Lys Met Ile Ser Ala Ile Gln Asn Gln Ile Asn Thr Ile
                165                 170                 175

Ile Gln Pro Ala Ile Asp Gln Ile Asn Cys Gln Ile Lys Asp Leu Gln
            180                 185                 190

Val Ala Asn Ile Leu Asn Leu Tyr Leu Thr Glu Ile Thr Thr Val Phe
        195                 200                 205

His Asn Gln Leu Thr Asn Pro Ala Leu Glu Ser Ile Ser Ile Gln Ala
    210                 215                 220

Leu Lys Ser Leu Leu Gly Ser Thr Leu Pro Glu Val Leu Ser Lys Leu
225                 230                 235                 240

Asp Leu Asn Asn Ile Ser Ala Ala Ser Val Met Ala Ser Gly Leu Ile
                245                 250                 255

Lys Gly Gln Ile Ile Ala Val Asp Ile Pro Thr Met Thr Leu Val Leu
            260                 265                 270

Met Val Gln Ile Pro Ser Ile Ser Pro Leu Arg Gln Ala Lys Ile Ile
        275                 280                 285

Asp Leu Thr Ser Ile Thr Ile His Thr Asn Ser Gln Glu Val Gln Ala
    290                 295                 300

Val Val Pro Ala Arg Val Leu Glu Ile Gly Ser Glu Ile Leu Gly Phe
305                 310                 315                 320

Asp Gly Ser Val Cys Gln Ile Thr Lys Asp Thr Val Phe Cys Pro Tyr
                325                 330                 335

Asn Asp Ala Tyr Val Leu Pro Ile Gln Gln Lys Arg Cys Leu Gln Gly
            340                 345                 350
```

```
Gln Thr Arg Asp Cys Val Phe Thr Pro Val Ala Gly Thr Phe Pro Arg
        355                 360                 365

Arg Phe Leu Thr Thr Tyr Gly Thr Ile Val Ala Asn Cys Arg Asp Leu
    370                 375                 380

Val Cys Ser Cys Leu Arg Pro Pro Gln Ile Ile Tyr Gln Pro Asp Glu
385                 390                 395                 400

Asn Pro Val Thr Ile Ile Asp Lys Asp Leu Cys Thr Thr Leu Thr Leu
                405                 410                 415

Asp Ser Ile Thr Ile Glu Ile Gln Lys Ser Ile Asn Ser Thr Phe Arg
            420                 425                 430

Arg Glu Val Val Leu Glu Ser Thr Gln Val Arg Ser Leu Thr Pro Leu
        435                 440                 445

Asp Leu Ser Thr Asp Leu Asn Gln Tyr Asn Gln Leu Leu Lys Ser Ala
    450                 455                 460

Glu Asp His Ile Gln Arg Ser Thr Asp Tyr Leu Asn Ser Ile Asn Pro
465                 470                 475                 480

Ser Ile Val Asn Asn Asn Ala Ile Ile Ile Leu Ile Ile Leu Cys Ile
                485                 490                 495

Leu Leu Ile Leu Thr Val Thr Ile Cys Ile Ile Trp Leu Lys Tyr Leu
            500                 505                 510

Thr Asn Glu Val Lys Asn Val Ala Arg Asn Gln Arg Leu Asn Arg Asp
        515                 520                 525

Ala Asp Leu Phe His Arg Ile Pro Ser Gln Ile Pro Val Pro Arg Gln
    530                 535                 540


<210> SEQ ID NO 29
<211> LENGTH: 487
<212> TYPE: PRT
<213> ORGANISM: Artificial Sequence
<220> FEATURE:
<223> OTHER INFORMATION: Recombinant parainfluenza virus F sequence

<400> SEQUENCE: 29

Leu Asp Ile Thr His Leu Met Asn Leu Gly Thr Val Pro Thr Ala Ile
1               5                   10                  15

Arg Ser Leu Val Tyr Tyr Thr Tyr Thr Lys Pro Ser Tyr Leu Thr Val
            20                  25                  30

Asp Leu Ile Pro Asn Leu Lys Asn Leu Asp Gln Asn Cys Asn Tyr Ser
        35                  40                  45

Ser Leu Asn Tyr Tyr Asn Lys Thr Ala Leu Ser Leu Ile Gln Pro Ile
    50                  55                  60

Ala Asp Asn Ile Asn Arg Leu Thr Lys Pro Ile Thr Ser Gly Gly Gly
65                  70                  75                  80

Ser Gly Gly Gly Ser Gly Ala Val Ile Gly Thr Ile Ala Leu Gly Val
                85                  90                  95

Ala Thr Ala Ala Gln Val Thr Ala Ala Ile Gly Leu Ala Lys Ala Gln
            100                 105                 110

Glu Asn Ala Lys Leu Ile Leu Thr Leu Lys Lys Ala Ala Thr Glu Thr
        115                 120                 125

Asn Glu Ala Val Arg Asp Leu Ala Asn Ser Asn Lys Ile Val Val Lys
    130                 135                 140

Met Ile Ser Ala Ile Gln Asn Gln Ile Asn Thr Ile Ile Gln Pro Ala
145                 150                 155                 160

Ile Asp Gln Ile Asn Cys Gln Ile Lys Asp Leu Gln Val Ala Asn Ile
                165                 170                 175
```

Leu Asn Leu Tyr Leu Thr Glu Ile Thr Thr Val Phe His Asn Gln Leu
180 185 190

Thr Asn Pro Ala Leu Glu Ser Ile Ser Ile Gln Ala Leu Lys Ser Leu
195 200 205

Leu Gly Ser Thr Leu Pro Glu Val Leu Ser Lys Leu Asp Leu Asn Asn
210 215 220

Ile Ser Ala Ala Ser Val Met Ala Ser Gly Leu Ile Lys Gly Gln Ile
225 230 235 240

Ile Ala Val Asp Ile Pro Thr Met Thr Leu Val Leu Met Val Gln Ile
245 250 255

Pro Ser Ile Ser Pro Leu Arg Gln Ala Lys Ile Ile Asp Leu Thr Ser
260 265 270

Ile Thr Ile His Thr Asn Ser Gln Glu Val Gln Ala Val Val Pro Ala
275 280 285

Arg Val Leu Glu Ile Gly Ser Glu Ile Leu Gly Phe Asp Gly Ser Val
290 295 300

Cys Gln Ile Thr Lys Asp Thr Val Phe Cys Pro Tyr Asn Asp Ala Tyr
305 310 315 320

Val Leu Pro Ile Gln Gln Lys Arg Cys Leu Gln Gly Gln Thr Arg Asp
325 330 335

Cys Val Phe Thr Pro Val Ala Gly Thr Phe Pro Arg Arg Phe Leu Thr
340 345 350

Thr Tyr Gly Thr Ile Val Ala Asn Cys Arg Asp Leu Val Cys Ser Cys
355 360 365

Leu Arg Pro Pro Gln Ile Ile Tyr Gln Pro Asp Glu Asn Pro Val Thr
370 375 380

Ile Ile Asp Lys Asp Leu Cys Thr Thr Leu Thr Leu Asp Ser Ile Thr
385 390 395 400

Ile Glu Ile Gln Lys Ser Ile Asn Ser Thr Phe Arg Arg Glu Val Val
405 410 415

Leu Glu Ser Thr Gln Val Arg Ser Leu Thr Pro Leu Asp Leu Ser Thr
420 425 430

Asp Leu Asn Gln Phe Asn Gln Leu Leu Lys Ser Ala Glu Asp His Ile
435 440 445

Gln Arg Val Thr Asp Tyr Leu Asn Ser Ile Glu Asp Lys Ile Glu Glu
450 455 460

Ile Leu Ser Lys Ile Tyr His Ile Glu Asn Glu Ile Ala Arg Ile Lys
465 470 475 480

Lys Leu Ile Gly Glu Ala Pro
485

<210> SEQ ID NO 30
<211> LENGTH: 487
<212> TYPE: PRT
<213> ORGANISM: Artificial Sequence
<220> FEATURE:
<223> OTHER INFORMATION: Recombinant parainfluenza virus F sequence

<400> SEQUENCE: 30

Leu Asp Ile Thr His Leu Met Asn Leu Gly Thr Val Pro Thr Ala Ile
1 5 10 15

Arg Ser Leu Val Tyr Tyr Thr Tyr Thr Lys Pro Ser Tyr Leu Thr Val
20 25 30

Asp Leu Ile Pro Asn Leu Lys Asn Leu Asp Gln Asn Cys Asn Tyr Ser
35 40 45

Ser Leu Asn Tyr Tyr Asn Lys Thr Ala Leu Ser Leu Ile Gln Pro Ile
50 55 60

Ala Asp Asn Ile Asn Arg Leu Thr Lys Pro Ile Thr Ser Gly Gly Gly
65 70 75 80

Ser Gly Gly Gly Ser Gly Ala Val Ile Gly Thr Ile Ala Leu Gly Val
85 90 95

Ala Thr Ala Ala Gln Val Thr Ala Ala Ile Gly Leu Ala Lys Ala Gln
100 105 110

Glu Asn Ala Lys Leu Ile Leu Thr Leu Lys Lys Ala Ala Thr Glu Thr
115 120 125

Asn Glu Ala Val Arg Asp Leu Ala Asn Ser Asn Lys Ile Val Val Lys
130 135 140

Met Cys Ser Ala Ile Gln Asn Gln Ile Asn Thr Ile Ile Gln Pro Ala
145 150 155 160

Ile Asp Gln Ile Asn Cys Gln Ile Lys Asp Leu Gln Val Ala Asn Ile
165 170 175

Leu Asn Leu Tyr Leu Thr Glu Ile Thr Thr Val Phe His Asn Gln Leu
180 185 190

Thr Asn Pro Ala Leu Glu Ser Ile Ser Ile Gln Ala Leu Lys Ser Leu
195 200 205

Leu Gly Ser Cys Leu Pro Glu Val Leu Ser Lys Leu Asp Leu Asn Asn
210 215 220

Ile Ser Ala Ala Ser Val Met Ala Ser Gly Leu Ile Lys Gly Gln Ile
225 230 235 240

Ile Ala Val Asp Ile Pro Thr Met Thr Leu Val Leu Met Val Gln Ile
245 250 255

Pro Ser Ile Ser Pro Leu Arg Gln Ala Lys Ile Ile Asp Leu Thr Ser
260 265 270

Ile Thr Ile His Thr Asn Ser Gln Glu Val Gln Ala Val Val Pro Ala
275 280 285

Arg Val Leu Glu Ile Gly Ser Glu Ile Leu Gly Phe Asp Gly Ser Val
290 295 300

Cys Gln Ile Thr Lys Asp Thr Val Phe Cys Pro Tyr Asn Asp Ala Tyr
305 310 315 320

Val Leu Pro Ile Gln Gln Lys Arg Cys Leu Gln Gly Gln Thr Arg Asp
325 330 335

Cys Val Phe Thr Pro Val Ala Gly Thr Phe Pro Arg Arg Phe Leu Thr
340 345 350

Thr Tyr Gly Thr Ile Val Ala Asn Cys Arg Asp Leu Val Cys Ser Cys
355 360 365

Leu Arg Pro Pro Gln Ile Ile Tyr Gln Pro Asp Glu Asn Pro Val Thr
370 375 380

Ile Ile Asp Lys Asp Leu Cys Thr Thr Leu Thr Leu Asp Ser Ile Thr
385 390 395 400

Ile Glu Ile Gln Lys Ser Ile Asn Ser Thr Phe Arg Arg Glu Val Val
405 410 415

Leu Glu Ser Thr Gln Val Arg Ser Leu Thr Pro Leu Asp Leu Ser Thr
420 425 430

Asp Leu Asn Gln Phe Asn Gln Leu Leu Lys Ser Ala Glu Asp His Ile
435 440 445

Gln Arg Val Thr Asp Tyr Leu Asn Ser Ile Glu Asp Lys Ile Glu Glu
450 455 460

```
Ile Leu Ser Lys Ile Tyr His Ile Glu Asn Glu Ile Ala Arg Ile Lys
465                 470                 475                 480

Lys Leu Ile Gly Glu Ala Pro
                485
```

<210> SEQ ID NO 31
<211> LENGTH: 33
<212> TYPE: PRT
<213> ORGANISM: Artificial Sequence
<220> FEATURE:
<223> OTHER INFORMATION: GCN4 trimerization domain

<400> SEQUENCE: 31

```
Met Lys Gln Val Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Ala
            20                  25                  30

Pro
```

<210> SEQ ID NO 32
<211> LENGTH: 8
<212> TYPE: PRT
<213> ORGANISM: Artificial Sequence
<220> FEATURE:
<223> OTHER INFORMATION: Peptide linker

<400> SEQUENCE: 32

```
Gly Gly Gly Ser Gly Gly Gly Ser
1               5
```

<210> SEQ ID NO 33
<211> LENGTH: 8
<212> TYPE: PRT
<213> ORGANISM: Artificial Sequence
<220> FEATURE:
<223> OTHER INFORMATION: parainfluenza virus F peptide

<400> SEQUENCE: 33

```
Lys Thr Arg Gln Lys Arg Phe Ala
1               5
```

<210> SEQ ID NO 34
<211> LENGTH: 8
<212> TYPE: PRT
<213> ORGANISM: Artificial Sequence
<220> FEATURE:
<223> OTHER INFORMATION: parainfluenza virus F peptide

<400> SEQUENCE: 34

```
Ser Glu Val Gln Ser Arg Phe Phe
1               5
```

<210> SEQ ID NO 35
<211> LENGTH: 173
<212> TYPE: PRT
<213> ORGANISM: Artificial Sequence
<220> FEATURE:
<223> OTHER INFORMATION: Self-assembling protein nanoparticle sequence

<400> SEQUENCE: 35

```
Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30
```

Met Ser Ser Trp Cys Tyr Thr His Ser Leu Asp Gly Ala Gly Leu Phe
35 40 45

Leu Phe Asp His Ala Ala Glu Glu Tyr Glu His Ala Lys Lys Leu Ile
50 55 60

Ile Phe Leu Asn Glu Asn Asn Val Pro Val Gln Leu Thr Ser Ile Ser
65 70 75 80

Ala Pro Glu His Lys Phe Glu Gly Leu Thr Gln Ile Phe Gln Lys Ala
85 90 95

Tyr Glu His Glu Gln His Ile Ser Glu Ser Ile Asn Asn Ile Val Asp
100 105 110

His Ala Ile Lys Ser Lys Asp His Ala Thr Phe Asn Phe Leu Gln Trp
115 120 125

Tyr Val Ala Glu Gln His Glu Glu Glu Val Leu Phe Lys Asp Ile Leu
130 135 140

Asp Lys Ile Glu Leu Ile Gly Asn Glu Asn His Gly Leu Tyr Leu Ala
145 150 155 160

Asp Gln Tyr Val Lys Gly Ile Ala Lys Ser Arg Lys Ser
165 170

<210> SEQ ID NO 36
<211> LENGTH: 154
<212> TYPE: PRT
<213> ORGANISM: Artificial Sequence
<220> FEATURE:
<223> OTHER INFORMATION: Self-assembling protein nanoparticle sequence

<400> SEQUENCE: 36

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Pro Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Ile Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Lys His Gly Asn Lys Gly Trp Glu Ala Ala Leu Ser Ala Ile
130 135 140

Glu Met Ala Asn Leu Phe Lys Ser Leu Arg
145 150

<210> SEQ ID NO 37
<211> LENGTH: 265
<212> TYPE: PRT
<213> ORGANISM: Artificial Sequence
<220> FEATURE:
<223> OTHER INFORMATION: Self-assembling protein nanoparticle sequence

<400> SEQUENCE: 37

Met Glu Phe Leu Lys Arg Ser Phe Ala Pro Leu Thr Glu Lys Gln Trp
1 5 10 15

Gln Glu Ile Asp Asn Arg Ala Arg Glu Ile Phe Lys Thr Gln Leu Tyr
20 25 30

Gly Arg Lys Phe Val Asp Val Glu Gly Pro Tyr Gly Trp Glu Tyr Ala
35 40 45

Ala His Pro Leu Gly Glu Val Glu Val Leu Ser Asp Glu Asn Glu Val
50 55 60

Val Lys Trp Gly Leu Arg Lys Ser Leu Pro Leu Ile Glu Leu Arg Ala
65 70 75 80

Thr Phe Thr Leu Asp Leu Trp Glu Leu Asp Asn Leu Glu Arg Gly Lys
85 90 95

Pro Asn Val Asp Leu Ser Ser Leu Glu Glu Thr Val Arg Lys Val Ala
100 105 110

Glu Phe Glu Asp Glu Val Ile Phe Arg Gly Cys Glu Lys Ser Gly Val
115 120 125

Lys Gly Leu Leu Ser Phe Glu Glu Arg Lys Ile Glu Cys Gly Ser Thr
130 135 140

Pro Lys Asp Leu Leu Glu Ala Ile Val Arg Ala Leu Ser Ile Phe Ser
145 150 155 160

Lys Asp Gly Ile Glu Gly Pro Tyr Thr Leu Val Ile Asn Thr Asp Arg
165 170 175

Trp Ile Asn Phe Leu Lys Glu Glu Ala Gly His Tyr Pro Leu Glu Lys
180 185 190

Arg Val Glu Glu Cys Leu Arg Gly Gly Lys Ile Ile Thr Thr Pro Arg
195 200 205

Ile Glu Asp Ala Leu Val Val Ser Glu Arg Gly Gly Asp Phe Lys Leu
210 215 220

Ile Leu Gly Gln Asp Leu Ser Ile Gly Tyr Glu Asp Arg Glu Lys Asp
225 230 235 240

Ala Val Arg Leu Phe Ile Thr Glu Thr Phe Thr Phe Gln Val Val Asn
245 250 255

Pro Glu Ala Leu Ile Leu Leu Lys Phe
260 265

<210> SEQ ID NO 38
<211> LENGTH: 265
<212> TYPE: PRT
<213> ORGANISM: Artificial Sequence
<220> FEATURE:
<223> OTHER INFORMATION: Self-assembling protein nanoparticle sequence

<400> SEQUENCE: 38

Met Glu Phe Leu Lys Arg Ser Phe Ala Pro Leu Thr Glu Lys Gln Trp
1 5 10 15

Gln Glu Ile Asp Asn Arg Ala Arg Glu Ile Phe Lys Thr Gln Leu Tyr
20 25 30

Gly Arg Lys Phe Val Asp Val Glu Gly Pro Tyr Gly Trp Glu Tyr Ala
35 40 45

Ala His Pro Leu Gly Glu Val Glu Val Leu Ser Asp Glu Asn Glu Val
50 55 60

Val Lys Trp Gly Leu Arg Lys Ser Leu Pro Leu Ile Glu Leu Arg Ala
65 70 75 80

Thr Phe Thr Leu Asp Leu Trp Glu Leu Asp Asn Leu Glu Arg Gly Lys
85 90 95

Pro Asn Val Asp Leu Ser Ser Leu Glu Glu Thr Val Arg Lys Val Ala
100 105 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 39
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 39

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Cys Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Cys
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495

<210> SEQ ID NO 40
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 40

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

```
Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Cys Phe Gly Asp Asn Ile Gly Ser Leu Gln Glu Lys Gly Ile
        195                 200                 205

Lys Leu Gln Cys Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495
```

<210> SEQ ID NO 41
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 41

```
Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Cys Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Cys Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365
```

```
Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 42
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 42

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Cys Asn Ile Gly Ser Cys Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240
```

Thr Glu Ser Ile Lys Val Arg Val Ile Asp Val Asp Leu Asn Asp Tyr
245 250 255

Ser Ile Thr Leu Gln Val Arg Leu Pro Leu Leu Thr Arg Leu Leu Asn
260 265 270

Thr Gln Ile Tyr Lys Val Asp Ser Ile Ser Tyr Asn Ile Gln Asn Arg
275 280 285

Glu Trp Tyr Ile Pro Leu Pro Ser His Ile Met Thr Lys Gly Ala Phe
290 295 300

Leu Gly Gly Ala Asp Val Lys Glu Cys Ile Glu Ala Phe Ser Ser Tyr
305 310 315 320

Ile Cys Pro Ser Asp Pro Gly Phe Val Leu Asn His Glu Met Glu Ser
325 330 335

Cys Leu Ser Gly Asn Ile Ser Gln Cys Pro Arg Thr Thr Val Thr Ser
340 345 350

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Val Lys Ser Asp
435 440 445

Leu Glu Glu Ser Lys Glu Trp Tyr Arg Arg Ser Asn Gln Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 43
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 43

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

-continued

```
Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Cys
    130                 135                 140

Ser Ser Val Gly Asn Cys Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495
```

<210> SEQ ID NO 44
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 44

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Cys
    130                 135                 140

Ser Ser Val Gly Asn Cys Ile Cys Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Cys
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr

```
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 45
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 45

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Cys
    130                 135                 140

Ser Ser Val Gly Asn Cys Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Cys Phe Gly Asp Asn Ile Gly Ser Leu Gln Glu Lys Gly Ile
        195                 200                 205

Lys Leu Gln Cys Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
```

```
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 46
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 46

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Cys
    130                 135                 140

Ser Ser Val Gly Asn Cys Ile Val Ala Ile Lys Ser Val Gln Asp Tyr
```

```
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Cys Asn Ile Gly Ser Cys Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 47
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 47

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
```

```
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Cys Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Cys
    130                 135                 140

Ser Ser Val Gly Asn Cys Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Cys Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445
```

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495

<210> SEQ ID NO 48
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 48

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Cys Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Cys Phe Gly Asp Asn Ile Gly Ser Leu Gln Glu Lys Gly Ile
        195                 200                 205

Lys Leu Gln Cys Ile Ala Ser Leu Tyr Arg Thr Asn Ile Thr Glu Cys
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
325 330 335

Cys Leu Ser Gly Asn Ile Ser Gln Cys Pro Arg Thr Thr Val Thr Ser
340 345 350

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Val Lys Ser Asp
435 440 445

Leu Glu Glu Ser Lys Glu Trp Tyr Arg Arg Ser Asn Gln Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 49
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 49

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Gln
130 135 140

Ser Ser Val Gly Asn Leu Ile Val Ala Ile Lys Ser Val Gln Asp Tyr
145 150 155 160

Val Asn Lys Glu Ile Val Pro Ser Ile Ala Arg Leu Gly Cys Glu Ala
165 170 175

Ala Gly Leu Gln Leu Gly Ile Ala Leu Thr Gln His Tyr Ser Glu Leu
180 185 190

Thr Asn Cys Phe Gly Cys Asn Ile Gly Ser Cys Gln Glu Lys Gly Ile
195 200 205

Lys Leu Gln Cys Ile Ala Ser Leu Tyr Arg Thr Asn Ile Thr Glu Ile
210 215 220

Phe Thr Thr Ser Thr Val Asp Lys Tyr Asp Ile Tyr Asp Leu Leu Phe
225 230 235 240

Thr Glu Ser Ile Lys Val Arg Val Ile Asp Val Asp Leu Asn Asp Tyr
245 250 255

Ser Ile Thr Leu Gln Val Arg Leu Pro Leu Leu Thr Arg Leu Leu Asn
260 265 270

Thr Gln Ile Tyr Lys Val Asp Ser Ile Ser Tyr Asn Ile Gln Asn Arg
275 280 285

Glu Trp Tyr Ile Pro Leu Pro Ser His Ile Met Thr Lys Gly Ala Phe
290 295 300

Leu Gly Gly Ala Asp Val Lys Glu Cys Ile Glu Ala Phe Ser Ser Tyr
305 310 315 320

Ile Cys Pro Ser Asp Pro Gly Phe Val Leu Asn His Glu Met Glu Ser
325 330 335

Cys Leu Ser Gly Asn Ile Ser Gln Cys Pro Arg Thr Thr Val Thr Ser
340 345 350

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Val Lys Ser Asp
435 440 445

Leu Glu Glu Ser Lys Glu Trp Tyr Arg Arg Ser Asn Gln Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 50
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 50

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

```
Tyr Asp Cys Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Cys Phe Gly Asp Asn Ile Gly Ser Leu Cys Glu Lys Gly Ile
        195                 200                 205

Lys Leu Gln Cys Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Ser
    450                 455                 460

Ala Ile Glu Asp Lys Ile Glu Glu Ile Leu Ser Lys Ile Tyr His Ile
465                 470                 475                 480
```

-continued

```
Glu Asn Glu Ile Ala Arg Ile Lys Lys Leu Ile Gly Glu Ala Pro
                485                 490                 495
```

<210> SEQ ID NO 51
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 51

```
Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350
```

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Val Lys Ser Asp
435 440 445

Leu Glu Glu Ser Lys Glu Trp Tyr Arg Arg Ser Asn Gln Lys Leu Asp
450 455 460

Ser Ile Gly Ser Trp His Gln Ser Ser Thr Thr Ile Ile Ile Ile Leu
465 470 475 480

Ile Met Met Ile Ile Leu Phe Ile Ile Asn Ile Thr Ile Ile Thr Ile
485 490 495

Ala Ile Lys Tyr Tyr Arg Ile Gln Lys Arg Asn Arg Val Asp Gln Asn
500 505 510

Asp Lys Pro Tyr Val Leu Thr Asn Lys
515 520

<210> SEQ ID NO 52
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 52

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Gln
130 135 140

Ser Ser Val Gly Asn Leu Ile Val Ala Cys Lys Ser Val Gln Asp Tyr
145 150 155 160

Val Asn Lys Glu Ile Val Pro Ser Ile Ala Arg Leu Gly Cys Glu Ala
165 170 175

Ala Gly Leu Gln Leu Gly Ile Ala Leu Thr Gln His Tyr Ser Glu Leu
180 185 190

-continued

```
Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Cys Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Ala Lys Ser Asp
        435                 440                 445

Leu Glu Glu Ser Lys Glu Trp Ile Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520


<210> SEQ ID NO 53
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 53

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30
```

-continued

```
Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Cys Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Cys Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
```

```
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520


<210> SEQ ID NO 54
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 54

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Cys Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Cys
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
```

290 295 300

Leu Gly Gly Ala Asp Val Lys Glu Cys Ile Glu Ala Phe Ser Ser Tyr
305 310 315 320

Ile Cys Pro Ser Asp Pro Gly Phe Val Leu Asn His Glu Met Glu Ser
325 330 335

Cys Leu Ser Gly Asn Ile Ser Gln Cys Pro Arg Thr Thr Val Thr Ser
340 345 350

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Val Lys Ser Asp
435 440 445

Leu Glu Glu Ser Lys Glu Trp Tyr Arg Arg Ser Asn Gln Lys Leu Asp
450 455 460

Ser Ile Gly Ser Trp His Gln Ser Ser Thr Thr Ile Ile Ile Ile Leu
465 470 475 480

Ile Met Met Ile Ile Leu Phe Ile Ile Asn Ile Thr Ile Ile Thr Ile
485 490 495

Ala Ile Lys Tyr Tyr Arg Ile Gln Lys Arg Asn Arg Val Asp Gln Asn
500 505 510

Asp Lys Pro Tyr Val Leu Thr Asn Lys
515 520

<210> SEQ ID NO 55
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 55

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Gln

```
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Cys Phe Gly Asp Asn Ile Gly Ser Leu Gln Glu Lys Gly Ile
        195                 200                 205

Lys Leu Gln Cys Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520
```

<210> SEQ ID NO 56
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 56

```
Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Cys Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Cys Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400
```

```
Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520


<210> SEQ ID NO 57
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 57

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Gln
    130                 135                 140

Ser Ser Val Gly Asn Leu Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Cys Asn Ile Gly Ser Cys Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240
```

```
Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520
```

<210> SEQ ID NO 58
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 58

```
Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80
```

```
Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Cys
    130                 135                 140

Ser Ser Val Gly Asn Cys Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Ser Leu Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495
```

Ala Ile Lys Tyr Tyr Arg Ile Gln Lys Arg Asn Arg Val Asp Gln Asn
500 505 510

Asp Lys Pro Tyr Val Leu Thr Asn Lys
515 520

<210> SEQ ID NO 59
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 59

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Cys
130 135 140

Ser Ser Val Gly Asn Cys Ile Cys Ala Ile Lys Ser Val Gln Asp Tyr
145 150 155 160

Val Asn Lys Glu Ile Val Pro Ser Ile Ala Arg Leu Gly Cys Glu Ala
165 170 175

Ala Gly Leu Gln Leu Gly Ile Ala Leu Thr Gln His Tyr Ser Glu Leu
180 185 190

Thr Asn Ile Phe Gly Asp Asn Ile Gly Ser Leu Gln Glu Lys Gly Ile
195 200 205

Lys Leu Gln Gly Ile Ala Ser Leu Tyr Arg Thr Asn Ile Thr Glu Cys
210 215 220

Phe Thr Thr Ser Thr Val Asp Lys Tyr Asp Ile Tyr Asp Leu Leu Phe
225 230 235 240

Thr Glu Ser Ile Lys Val Arg Val Ile Asp Val Asp Leu Asn Asp Tyr
245 250 255

Ser Ile Thr Leu Gln Val Arg Leu Pro Leu Leu Thr Arg Leu Leu Asn
260 265 270

Thr Gln Ile Tyr Lys Val Asp Ser Ile Ser Tyr Asn Ile Gln Asn Arg
275 280 285

Glu Trp Tyr Ile Pro Leu Pro Ser His Ile Met Thr Lys Gly Ala Phe
290 295 300

Leu Gly Gly Ala Asp Val Lys Glu Cys Ile Glu Ala Phe Ser Ser Tyr
305 310 315 320

Ile Cys Pro Ser Asp Pro Gly Phe Val Leu Asn His Glu Met Glu Ser
325 330 335

```
Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520


<210> SEQ ID NO 60
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 60

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Cys
    130                 135                 140

Ser Ser Val Gly Asn Cys Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175
```

```
Ala Gly Leu Gln Leu Gly Ile Ala Leu Thr Gln His Tyr Ser Glu Leu
            180                 185                 190

Thr Asn Cys Phe Gly Asp Asn Ile Gly Ser Leu Gln Glu Lys Gly Ile
        195                 200                 205

Lys Leu Gln Cys Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520
```

<210> SEQ ID NO 61
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 61

```
Gln Ile Asp Ile Thr Lys Leu Gln His Val Gly Val Leu Val Asn Ser
1               5                   10                  15
```

```
Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
        115                 120                 125

Leu Lys Glu Ala Ile Arg Asp Thr Asn Lys Ala Val Gln Ser Val Cys
    130                 135                 140

Ser Ser Val Gly Asn Cys Ile Val Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Cys Asn Ile Gly Ser Cys Gln Glu Lys Gly Ile
        195                 200                 205

Lys Leu Gln Gly Ile Ala Ser Leu Tyr Arg Thr Asn Ile Thr Glu Ile
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
```

-continued 435 440 445

Leu Glu Glu Ser Lys Glu Trp Tyr Arg Arg Ser Asn Gln Lys Leu Asp
450 455 460

Ser Ile Gly Ser Trp His Gln Ser Ser Thr Thr Ile Ile Ile Ile Leu
465 470 475 480

Ile Met Met Ile Ile Leu Phe Ile Ile Asn Ile Thr Ile Ile Thr Ile
485 490 495

Ala Ile Lys Tyr Tyr Arg Ile Gln Lys Arg Asn Arg Val Asp Gln Asn
500 505 510

Asp Lys Pro Tyr Val Leu Thr Asn Lys
515 520

<210> SEQ ID NO 62
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 62

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Cys Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Cys
130 135 140

Ser Ser Val Gly Asn Cys Ile Val Ala Ile Lys Ser Val Gln Asp Tyr
145 150 155 160

Val Asn Lys Glu Ile Val Pro Ser Ile Ala Arg Leu Gly Cys Glu Ala
165 170 175

Ala Gly Leu Gln Leu Gly Ile Ala Leu Thr Gln His Tyr Ser Glu Leu
180 185 190

Thr Asn Ile Phe Gly Asp Asn Ile Gly Ser Leu Cys Glu Lys Gly Ile
195 200 205

Lys Leu Gln Gly Ile Ala Ser Leu Tyr Arg Thr Asn Ile Thr Glu Ile
210 215 220

Phe Thr Thr Ser Thr Val Asp Lys Tyr Asp Ile Tyr Asp Leu Leu Phe
225 230 235 240

Thr Glu Ser Ile Lys Val Arg Val Ile Asp Val Asp Leu Asn Asp Tyr
245 250 255

Ser Ile Thr Leu Gln Val Arg Leu Pro Leu Leu Thr Arg Leu Leu Asn
260 265 270

Thr Gln Ile Tyr Lys Val Asp Ser Ile Ser Tyr Asn Ile Gln Asn Arg

```
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520


<210> SEQ ID NO 63
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 63

Gln Ile Asp Ile Thr Lys Leu Gln His Val Gly Val Leu Val Asn Ser
1               5                   10                  15

Pro Lys Gly Met Lys Ile Ser Gln Asn Phe Glu Thr Arg Tyr Leu Ile
            20                  25                  30

Leu Ser Leu Ile Pro Lys Ile Glu Asp Ser Asn Ser Cys Gly Asp Gln
        35                  40                  45

Gln Ile Lys Gln Tyr Lys Arg Leu Leu Asp Arg Leu Ile Ile Pro Leu
    50                  55                  60

Tyr Asp Gly Leu Lys Leu Gln Lys Asp Val Ile Val Thr Asn Gln Glu
65                  70                  75                  80

Ser Asn Glu Asn Thr Asp Pro Arg Thr Glu Arg Phe Phe Gly Gly Val
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Lys Ser Asp Ile Glu Lys
```

```
        115                 120                 125

Leu Lys Glu Ala Ile Arg Asp Thr Asn Lys Ala Val Gln Ser Val Gln
    130                 135                 140

Ser Ser Val Gly Asn Leu Ile Cys Ala Ile Lys Ser Val Gln Asp Tyr
145                 150                 155                 160

Val Asn Lys Glu Ile Val Pro Ser Ile Ala Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Cys Phe Gly Asp Asn Ile Gly Ser Leu Gln Glu Lys Gly Ile
        195                 200                 205

Lys Leu Gln Cys Ile Ala Ser Leu Tyr Arg Thr Asn Ile Thr Glu Cys
    210                 215                 220

Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520

<210> SEQ ID NO 64
```

<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 64

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Gly Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Gln
130 135 140

Ser Ser Val Gly Asn Leu Ile Val Ala Ile Lys Ser Val Gln Asp Tyr
145 150 155 160

Val Asn Lys Glu Ile Val Pro Ser Ile Ala Arg Leu Gly Cys Glu Ala
165 170 175

Ala Gly Leu Gln Leu Gly Ile Ala Leu Thr Gln His Tyr Ser Glu Leu
180 185 190

Thr Asn Cys Phe Gly Cys Asn Ile Gly Ser Cys Gln Glu Lys Gly Ile
195 200 205

Lys Leu Gln Cys Ile Ala Ser Leu Tyr Arg Thr Asn Ile Thr Glu Ile
210 215 220

Phe Thr Thr Ser Thr Val Asp Lys Tyr Asp Ile Tyr Asp Leu Leu Phe
225 230 235 240

Thr Glu Ser Ile Lys Val Arg Val Ile Asp Val Asp Leu Asn Asp Tyr
245 250 255

Ser Ile Thr Leu Gln Val Arg Leu Pro Leu Leu Thr Arg Leu Leu Asn
260 265 270

Thr Gln Ile Tyr Lys Val Asp Ser Ile Ser Tyr Asn Ile Gln Asn Arg
275 280 285

Glu Trp Tyr Ile Pro Leu Pro Ser His Ile Met Thr Lys Gly Ala Phe
290 295 300

Leu Gly Gly Ala Asp Val Lys Glu Cys Ile Glu Ala Phe Ser Ser Tyr
305 310 315 320

Ile Cys Pro Ser Asp Pro Gly Phe Val Leu Asn His Glu Met Glu Ser
325 330 335

Cys Leu Ser Gly Asn Ile Ser Gln Cys Pro Arg Thr Thr Val Thr Ser
340 345 350

Asp Ile Val Pro Arg Tyr Ala Phe Val Asn Gly Gly Val Val Ala Asn
355 360 365

Cys Ile Thr Thr Thr Cys Thr Cys Asn Gly Ile Gly Asn Arg Ile Asn
370 375 380

Gln Pro Pro Asp Gln Gly Val Lys Ile Ile Thr His Lys Glu Cys Asn
385 390 395 400

Thr Ile Gly Ile Asn Gly Met Leu Phe Asn Thr Asn Lys Glu Gly Thr
405 410 415

Leu Ala Phe Tyr Thr Pro Asp Asp Ile Thr Leu Asn Asn Ser Val Ala
420 425 430

Leu Asp Pro Ile Asp Ile Ser Ile Glu Leu Asn Lys Val Lys Ser Asp
435 440 445

Leu Glu Glu Ser Lys Glu Trp Tyr Arg Arg Ser Asn Gln Lys Leu Asp
450 455 460

Ser Ile Gly Ser Trp His Gln Ser Ser Thr Thr Ile Ile Ile Ile Leu
465 470 475 480

Ile Met Met Ile Ile Leu Phe Ile Ile Asn Ile Thr Ile Ile Thr Ile
485 490 495

Ala Ile Lys Tyr Tyr Arg Ile Gln Lys Arg Asn Arg Val Asp Gln Asn
500 505 510

Asp Lys Pro Tyr Val Leu Thr Asn Lys
515 520

<210> SEQ ID NO 65
<211> LENGTH: 521
<212> TYPE: PRT
<213> ORGANISM: Artificial Sequence
<220> FEATURE:
<223> OTHER INFORMATION: Recombinant parainfluenza virus F sequence

<400> SEQUENCE: 65

Gln Ile Asp Ile Thr Lys Leu Gln His Val Gly Val Leu Val Asn Ser
1 5 10 15

Pro Lys Gly Met Lys Ile Ser Gln Asn Phe Glu Thr Arg Tyr Leu Ile
20 25 30

Leu Ser Leu Ile Pro Lys Ile Glu Asp Ser Asn Ser Cys Gly Asp Gln
35 40 45

Gln Ile Lys Gln Tyr Lys Arg Leu Leu Asp Arg Leu Ile Ile Pro Leu
50 55 60

Tyr Asp Cys Leu Lys Leu Gln Lys Asp Val Ile Val Thr Asn Gln Glu
65 70 75 80

Ser Asn Glu Asn Thr Asp Pro Arg Thr Glu Arg Phe Phe Gly Gly Val
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Lys Ser Asp Ile Glu Lys
115 120 125

Leu Lys Glu Ala Ile Arg Asp Thr Asn Lys Ala Val Gln Ser Val Gln
130 135 140

Ser Ser Val Gly Asn Leu Ile Val Ala Ile Lys Ser Val Gln Asp Tyr
145 150 155 160

Val Asn Lys Glu Ile Val Pro Ser Ile Ala Arg Leu Gly Cys Glu Ala
165 170 175

Ala Gly Leu Gln Leu Gly Ile Ala Leu Thr Gln His Tyr Ser Glu Leu
180 185 190

Thr Asn Cys Phe Gly Asp Asn Ile Gly Ser Leu Cys Glu Lys Gly Ile
195 200 205

Lys Leu Gln Cys Ile Ala Ser Leu Tyr Arg Thr Asn Ile Thr Glu Ile
210 215 220

```
Phe Thr Thr Ser Thr Val Asp Lys Tyr Asp Ile Tyr Asp Leu Leu Phe
225                 230                 235                 240

Thr Glu Ser Ile Lys Val Arg Val Ile Asp Val Asp Leu Asn Asp Tyr
                245                 250                 255

Ser Ile Thr Leu Gln Val Arg Leu Pro Leu Leu Thr Arg Leu Leu Asn
            260                 265                 270

Thr Gln Ile Tyr Lys Val Asp Ser Ile Ser Tyr Asn Ile Gln Asn Arg
        275                 280                 285

Glu Trp Tyr Ile Pro Leu Pro Ser His Ile Met Thr Lys Gly Ala Phe
    290                 295                 300

Leu Gly Gly Ala Asp Val Lys Glu Cys Ile Glu Ala Phe Ser Ser Tyr
305                 310                 315                 320

Ile Cys Pro Ser Asp Pro Gly Phe Val Leu Asn His Glu Met Glu Ser
                325                 330                 335

Cys Leu Ser Gly Asn Ile Ser Gln Cys Pro Arg Thr Thr Val Thr Ser
            340                 345                 350

Asp Ile Val Pro Arg Tyr Ala Phe Val Asn Gly Gly Val Val Ala Asn
        355                 360                 365

Cys Ile Thr Thr Thr Cys Thr Cys Asn Gly Ile Gly Asn Arg Ile Asn
    370                 375                 380

Gln Pro Pro Asp Gln Gly Val Lys Ile Ile Thr His Lys Glu Cys Asn
385                 390                 395                 400

Thr Ile Gly Ile Asn Gly Met Leu Phe Asn Thr Asn Lys Glu Gly Thr
                405                 410                 415

Leu Ala Phe Tyr Thr Pro Asp Asp Ile Thr Leu Asn Asn Ser Val Ala
            420                 425                 430

Leu Asp Pro Ile Asp Ile Ser Ile Glu Leu Asn Lys Val Lys Ser Asp
        435                 440                 445

Leu Glu Glu Ser Lys Glu Trp Tyr Arg Arg Ser Asn Gln Lys Leu Asp
    450                 455                 460

Ser Ile Gly Ser Trp His Gln Ser Ser Thr Thr Ile Ile Ile Ile Leu
465                 470                 475                 480

Ile Met Met Ile Ile Leu Phe Ile Ile Asn Ile Thr Ile Ile Thr Ile
                485                 490                 495

Ala Ile Lys Tyr Tyr Arg Ile Gln Lys Arg Asn Arg Val Asp Gln Asn
            500                 505                 510

Asp Lys Pro Tyr Val Leu Thr Asn Lys
        515                 520


<210> SEQ ID NO 66
<211> LENGTH: 540
<212> TYPE: PRT
<213> ORGANISM: bovine parainfluenza virus 3

<400> SEQUENCE: 66

Met Ile Ile Ile Val Ile Thr Met Ile Leu Ser Leu Thr Pro Ser Ser
1               5                   10                  15

Leu Cys Gln Ile Asp Ile Thr Lys Leu Gln Ser Val Gly Val Leu Val
            20                  25                  30

Asn Ser Pro Lys Gly Ile Lys Ile Ser Gln Asn Phe Glu Thr Arg Tyr
        35                  40                  45

Leu Ile Leu Ser Leu Ile Pro Lys Ile Glu Asp Ser His Ser Cys Gly
    50                  55                  60

Asn Gln Gln Ile Asp Gln Tyr Lys Lys Leu Leu Asp Arg Leu Ile Ile
```

```
65                  70                  75                  80

Pro Leu Tyr Asp Gly Leu Lys Leu Gln Lys Asp Val Ile Val Val Asn
                85                  90                  95

His Glu Ser His Asn Asn Thr Asn Leu Arg Thr Lys Arg Phe Phe Gly
            100                 105                 110

Glu Ile Ile Gly Thr Ile Ala Ile Gly Ile Ala Thr Ser Ala Gln Ile
        115                 120                 125

Thr Ala Ala Val Ala Leu Val Glu Ala Lys Gln Ala Arg Ser Asp Ile
    130                 135                 140

Asp Lys Leu Lys Glu Ala Ile Lys Asp Thr Asn Lys Ala Val Gln Ser
145                 150                 155                 160

Ile Gln Ser Ser Val Gly Asn Leu Ile Val Ala Val Lys Ser Val Gln
                165                 170                 175

Asp Tyr Val Asn Asn Glu Ile Val Pro Ser Ile Thr Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Thr Leu Gly Glu Lys
    210                 215                 220

Gly Val Lys Leu Gln Gly Ile Ala Ser Leu Tyr Arg Thr Asn Ile Thr
225                 230                 235                 240

Glu Val Phe Thr Thr Ser Thr Val Asp Gln Tyr Asp Ile Tyr Asp Leu
                245                 250                 255

Leu Phe Thr Glu Ser Ile Lys Met Arg Val Ile Asp Val Asp Leu Ser
            260                 265                 270

Asp Tyr Ser Ile Thr Leu Gln Val Arg Leu Pro Leu Leu Thr Lys Val
        275                 280                 285

Ser Asn Thr Gln Ile Tyr Lys Val Asp Ser Ile Ser Tyr Asn Ile Gln
    290                 295                 300

Gly Lys Glu Trp Tyr Ile Pro Leu Pro His His Ile Met Thr Lys Gly
305                 310                 315                 320

Ala Phe Leu Gly Gly Ala Asp Ile Lys Glu Cys Ile Glu Ser Phe Ser
                325                 330                 335

Asn Tyr Ile Cys Pro Ser Asp Pro Gly Phe Ile Leu Asn His Glu Met
            340                 345                 350

Glu Asn Cys Leu Ser Gly Asn Ile Thr Gln Cys Pro Lys Thr Ile Val
        355                 360                 365

Thr Ser Asp Ile Val Pro Arg Tyr Ala Phe Val Asp Gly Gly Val Ile
    370                 375                 380

Ala Asn Cys Ile Pro Thr Thr Cys Thr Cys Asn Gly Ile Asp Asn Arg
385                 390                 395                 400

Ile Asn Gln Ser Pro Asp Gln Gly Ile Lys Ile Ile Thr Tyr Lys Glu
                405                 410                 415

Cys Gln Ile Val Gly Ile Asn Gly Met Leu Phe Lys Thr Asn Gln Glu
            420                 425                 430

Gly Thr Leu Ala Lys Tyr Thr Phe Asp Asn Ile Lys Leu Asn Asn Ser
        435                 440                 445

Val Ala Leu Asn Pro Ile Asp Ile Ser Leu Glu Leu Asn Lys Ala Lys
    450                 455                 460

Ser Asp Leu Glu Glu Ser Lys Arg Trp Ile Glu Lys Ser Asn Gln Lys
465                 470                 475                 480

Leu Asp Ser Ile Gly Ser Trp His Gln Ser Ser Val Thr Ile Ile Ile
                485                 490                 495
```

Ile Ile Val Met Ile Val Val Leu Leu Ile Ile Asn Ala Ile Ile Ile
500 505 510

Met Ile Met Ile Arg Tyr Leu Arg Asp Arg Asn Arg His Leu Asn Asn
515 520 525

Lys Asp Ser Glu Pro Tyr Val Leu Thr Asn Arg Gln
530 535 540

<210> SEQ ID NO 67
<211> LENGTH: 540
<212> TYPE: PRT
<213> ORGANISM: bovine parainfluenza virus 3

<400> SEQUENCE: 67

Met Ile Ile Thr Val Ile Thr Val Ile Leu Leu Leu Thr Pro Ser Ser
1 5 10 15

Leu Cys Gln Ile Asp Ile Thr Lys Leu Gln Asn Val Gly Val Leu Val
20 25 30

Asn Ser Pro Lys Gly Ile Lys Ile Ser Gln Asn Phe Glu Thr Arg Tyr
35 40 45

Leu Ile Leu Ser Leu Ile Pro Lys Ile Asp Asp Ser His Ser Cys Gly
50 55 60

Asn Gln Gln Ile Asp Gln Tyr Lys Lys Leu Leu Asp Arg Leu Ile Ile
65 70 75 80

Pro Leu Tyr Asp Gly Leu Lys Leu Gln Arg Asp Val Ile Val Val Asn
85 90 95

His Glu Ser His Asn Asn Thr Asn Leu Arg Thr Lys Arg Phe Phe Gly
100 105 110

Glu Ile Ile Gly Thr Ile Ala Ile Gly Ile Ala Thr Ser Ala Gln Ile
115 120 125

Thr Ala Ala Val Ala Leu Val Glu Ala Lys Gln Ala Arg Ser Asp Ile
130 135 140

Asp Lys Leu Lys Glu Ala Ile Lys Asp Thr Asn Lys Ala Val Gln Ser
145 150 155 160

Ile Gln Ser Ser Val Gly Asn Leu Ile Val Ala Val Lys Ser Val Gln
165 170 175

Asp Tyr Val Asn Asn Glu Ile Val Pro Ser Ile Thr Arg Leu Gly Cys
180 185 190

Glu Ala Ala Gly Leu Gln Leu Gly Ile Ala Leu Thr Gln His Tyr Ser
195 200 205

Glu Leu Thr Asn Ile Phe Gly Asp Asn Ile Gly Thr Leu Arg Glu Lys
210 215 220

Gly Val Lys Leu Gln Gly Ile Ala Ser Leu Tyr Arg Thr Asn Ile Thr
225 230 235 240

Glu Val Phe Thr Thr Ser Thr Val Asp Gln Tyr Asp Ile Tyr Asp Leu
245 250 255

Leu Phe Thr Glu Ser Ile Lys Met Arg Val Ile Asp Val Asp Leu Ser
260 265 270

Asp Tyr Ser Ile Thr Leu Gln Val Arg Leu Pro Leu Leu Thr Lys Val
275 280 285

Ser Asn Thr Gln Ile Tyr Lys Val Asp Ser Ile Ser Tyr Asn Ile Gln
290 295 300

Gly Lys Glu Trp Tyr Ile Pro Leu Pro His His Ile Met Thr Lys Gly
305 310 315 320

Ala Phe Leu Gly Gly Ala Asp Ile Lys Glu Cys Ile Glu Ser Phe Ser 325 330 335

Asn Tyr Ile Cys Pro Ser Asp Pro Gly Phe Ile Leu Asn His Glu Leu
340 345 350

Glu Asn Cys Leu Ser Gly Asn Ile Thr Gln Cys Pro Lys Thr Ile Val
355 360 365

Thr Ser Asp Ile Val Pro Arg Tyr Ala Phe Val Asp Gly Gly Val Ile
370 375 380

Ala Asn Cys Ile Pro Thr Thr Cys Thr Cys Asn Gly Ile Asp Asn Arg
385 390 395 400

Ile Asn Gln Ser Pro Asp Gln Gly Ile Lys Ile Ile Thr Tyr Lys Glu
405 410 415

Cys Gln Ile Val Gly Ile Asn Gly Met Leu Phe Lys Thr Asn Gln Glu
420 425 430

Gly Thr Leu Ala Lys Tyr Thr Phe Asp Asp Ile Lys Leu Asn Asn Ser
435 440 445

Val Ala Leu Asn Pro Ile Asp Ile Ser Leu Glu Leu Asn Lys Ala Lys
450 455 460

Ser Glu Leu Glu Glu Ser Lys Arg Trp Ile Glu Lys Ser Asn His Lys
465 470 475 480

Leu Asp Ser Ile Gly Ser Trp Tyr Gln Ser Ser Ala Thr Ile Ile Ile
485 490 495

Ile Ile Val Met Ile Val Val Leu Leu Ile Ile Asn Ala Ile Ile Ile
500 505 510

Met Ile Thr Ile Lys His Leu Arg Ala Arg Asn Arg His Pro Asn Asn
515 520 525

Lys Asp Ser Glu Pro Tyr Val Leu Thr Asn Arg Gln
530 535 540

<210> SEQ ID NO 68
<211> LENGTH: 541
<212> TYPE: PRT
<213> ORGANISM: caprine parainfluenza virus 3

<400> SEQUENCE: 68

Met Ile Lys Lys Ile Ile Cys Ile Phe Ser Met Pro Ile Leu Leu Ser
1 5 10 15

Phe Cys Gln Val Asp Ile Ile Lys Leu Gln Arg Val Gly Ile Leu Val
20 25 30

Ser Lys Pro Lys Ser Ile Lys Ile Ser Gln Asn Phe Glu Thr Arg Tyr
35 40 45

Leu Val Leu Asn Leu Ile Pro Asn Ile Glu Asn Ala Gln Ser Cys Gly
50 55 60

Asp Gln Gln Ile Lys Gln Tyr Lys Lys Leu Leu Asp Arg Leu Ile Ile
65 70 75 80

Pro Leu Tyr Asp Gly Leu Arg Leu Gln Gln Asp Ile Ile Val Val Asp
85 90 95

Asn Asn Leu Lys Asn Asn Thr Asn His Arg Ala Lys Arg Phe Phe Gly
100 105 110

Glu Ile Ile Gly Thr Ile Ala Leu Gly Val Ala Thr Ser Ala Gln Ile
115 120 125

Thr Ala Ala Val Ala Leu Val Glu Ala Lys Gln Ala Arg Ser Asp Ile
130 135 140

Glu Arg Val Lys Asn Ala Val Arg Asp Thr Asn Lys Ala Val Gln Ser
145 150 155 160

```
Ile Gln Gly Ser Val Gly Asn Leu Ile Val Ala Val Lys Ser Val Gln
                165                 170                 175

Asp Tyr Val Asn Asn Glu Ile Val Pro Ser Ile Lys Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Thr Leu Lys Glu Lys
    210                 215                 220

Gly Ile Lys Leu Gln Gly Ile Ala Ser Leu Tyr His Thr Asn Ile Thr
225                 230                 235                 240

Glu Ile Phe Thr Thr Ser Thr Val Asp Gln Tyr Asp Ile Tyr Asp Leu
                245                 250                 255

Leu Phe Thr Glu Ser Ile Lys Met Arg Val Ile Asp Val Asp Leu Asn
            260                 265                 270

Asp Tyr Ser Ile Thr Leu Gln Val Arg Leu Pro Leu Leu Thr Lys Ile
        275                 280                 285

Ser Asp Ala Gln Ile Tyr Asn Val Asp Ser Val Ser Tyr Asn Ile Gly
    290                 295                 300

Gly Thr Glu Trp Tyr Ile Pro Leu Pro Arg Asn Ile Met Thr Lys Gly
305                 310                 315                 320

Ala Phe Leu Gly Gly Ala Asn Leu Gln Asp Cys Ile Glu Ser Phe Ser
                325                 330                 335

Asp Tyr Ile Cys Pro Ser Asp Pro Gly Phe Ile Leu Asn Arg Asp Ile
            340                 345                 350

Glu Asn Cys Leu Ser Gly Asn Ile Thr Gln Cys Pro Lys Thr Leu Val
        355                 360                 365

Ile Ser Asp Ile Val Pro Arg Tyr Ala Phe Val Asp Gly Gly Val Ile
    370                 375                 380

Ala Asn Cys Leu Ser Thr Thr Cys Thr Cys Asn Gly Ile Asp Asn Arg
385                 390                 395                 400

Ile Asn Gln Ala Pro Asp Gln Gly Ile Lys Ile Ile Thr Tyr Lys Asp
                405                 410                 415

Cys Gln Thr Ile Gly Ile Asn Gly Met Leu Phe Lys Thr Asn Gln Glu
            420                 425                 430

Gly Thr Leu Ala Ala Tyr Thr Pro Val Asp Ile Thr Leu Asn Asn Ser
        435                 440                 445

Val Asn Leu Asp Pro Ile Asp Leu Ser Ile Glu Leu Asn Arg Ala Arg
    450                 455                 460

Ser Asp Leu Ala Glu Ser Lys Glu Trp Ile Lys Arg Ser Glu Ala Lys
465                 470                 475                 480

Leu Asp Ser Val Gly Ser Trp Tyr Gln Ser Ser Thr Thr Glu Ile Ile
                485                 490                 495

Gln Ile Val Met Ile Ile Val Leu Phe Ile Ile Asn Ile Ile Val Leu
            500                 505                 510

Ile Val Leu Ile Lys Tyr Ser Arg Ser Gln Asn Gln Ser Met Asn Asn
        515                 520                 525

His Met Asn Glu Pro Tyr Ile Leu Thr Asn Lys Val Gln
    530                 535                 540
```

<210> SEQ ID NO 69
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 69

Gln Ile Asp Ile Thr Lys Leu Gln Ser Val Gly Val Leu Val Asn Ser
1               5                   10                  15

Pro Lys Gly Ile Lys Ile Ser Gln Asn Phe Glu Thr Arg Tyr Leu Ile
            20                  25                  30

Leu Ser Leu Ile Pro Lys Ile Glu Asp Ser His Ser Cys Gly Asn Gln
        35                  40                  45

Gln Ile Asp Gln Tyr Lys Lys Leu Leu Asp Arg Leu Ile Ile Pro Leu
    50                  55                  60

Tyr Asp Gly Leu Lys Leu Gln Lys Asp Val Ile Val Val Asn His Glu
65                  70                  75                  80

Ser His Asn Asn Thr Asn Leu Arg Thr Lys Arg Phe Phe Gly Glu Ile
                85                  90                  95

Ile Gly Thr Ile Ala Ile Gly Ile Ala Thr Ser Ala Gln Ile Thr Ala
            100                 105                 110

Ala Val Ala Leu Val Glu Ala Lys Gln Ala Arg Ser Asp Ile Asp Lys
        115                 120                 125

Leu Lys Glu Ala Ile Lys Asp Thr Asn Lys Ala Val Gln Ser Ile Gln
    130                 135                 140

Ser Ser Val Gly Asn Leu Ile Val Ala Cys Lys Ser Val Gln Asp Tyr
145                 150                 155                 160

Val Asn Asn Glu Ile Val Pro Ser Ile Thr Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Gly Glu Lys Gly Val
        195                 200                 205

Lys Leu Gln Gly Ile Ala Ser Leu Tyr Arg Thr Cys Ile Thr Glu Val
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Ser Asp Tyr
                245                 250                 255

Ser Ile Thr Leu Gln Val Arg Leu Pro Leu Leu Thr Lys Val Ser Asn
            260                 265                 270

Thr Gln Ile Tyr Lys Val Asp Ser Ile Ser Tyr Asn Ile Gln Gly Lys
        275                 280                 285

Glu Trp Tyr Ile Pro Leu Pro His His Ile Met Thr Lys Gly Ala Phe
    290                 295                 300

Leu Gly Gly Ala Asp Ile Lys Glu Cys Ile Glu Ser Phe Ser Asn Tyr
305                 310                 315                 320

Ile Cys Pro Ser Asp Pro Gly Phe Ile Leu Asn His Glu Met Glu Asn
                325                 330                 335

Cys Leu Ser Gly Asn Ile Thr Gln Cys Pro Lys Thr Ile Val Thr Ser
            340                 345                 350

Asp Ile Val Pro Arg Tyr Ala Phe Val Asp Gly Gly Val Ile Ala Asn
        355                 360                 365

Cys Ile Pro Thr Thr Cys Thr Cys Asn Gly Ile Asp Asn Arg Ile Asn
    370                 375                 380

Gln Ser Pro Asp Gln Gly Ile Lys Ile Ile Thr Tyr Lys Glu Cys Gln
385                 390                 395                 400

Ile Val Gly Ile Asn Gly Met Leu Phe Lys Thr Asn Gln Glu Gly Thr

```
                405                 410                 415

Leu Ala Lys Tyr Thr Phe Asp Asn Ile Lys Leu Asn Asn Ser Val Ala
            420                 425                 430

Leu Asn Pro Ile Asp Ile Ser Leu Glu Leu Asn Lys Ala Lys Ser Asp
        435                 440                 445

Leu Glu Glu Ser Lys Arg Trp Tyr Glu Lys Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 70
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 70

Gln Ile Asp Ile Thr Lys Leu Gln Asn Val Gly Val Leu Val Asn Ser
1               5                   10                  15

Pro Lys Gly Ile Lys Ile Ser Gln Asn Phe Glu Thr Arg Tyr Leu Ile
            20                  25                  30

Leu Ser Leu Ile Pro Lys Ile Asp Asp Ser His Ser Cys Gly Asn Gln
        35                  40                  45

Gln Ile Asp Gln Tyr Lys Lys Leu Leu Asp Arg Leu Ile Ile Pro Leu
    50                  55                  60

Tyr Asp Gly Leu Lys Leu Gln Arg Asp Val Ile Val Val Asn His Glu
65                  70                  75                  80

Ser His Asn Asn Thr Asn Leu Arg Thr Lys Arg Phe Phe Gly Glu Ile
                85                  90                  95

Ile Gly Thr Ile Ala Ile Gly Ile Ala Thr Ser Ala Gln Ile Thr Ala
            100                 105                 110

Ala Val Ala Leu Val Glu Ala Lys Gln Ala Arg Ser Asp Ile Asp Lys
        115                 120                 125

Leu Lys Glu Ala Ile Lys Asp Thr Asn Lys Ala Val Gln Ser Ile Gln
    130                 135                 140

Ser Ser Val Gly Asn Leu Ile Val Ala Cys Lys Ser Val Gln Asp Tyr
145                 150                 155                 160

Val Asn Asn Glu Ile Val Pro Ser Ile Thr Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Arg Glu Lys Gly Val
        195                 200                 205

Lys Leu Gln Gly Ile Ala Ser Leu Tyr Arg Thr Cys Ile Thr Glu Val
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Ser Asp Tyr
                245                 250                 255

Ser Ile Thr Leu Gln Val Arg Leu Pro Leu Leu Thr Lys Val Ser Asn
            260                 265                 270

Thr Gln Ile Tyr Lys Val Asp Ser Ile Ser Tyr Asn Ile Gln Gly Lys
```

-continued

```
        275                 280                 285

Glu Trp Tyr Ile Pro Leu Pro His His Ile Met Thr Lys Gly Ala Phe
    290                 295                 300

Leu Gly Gly Ala Asp Ile Lys Glu Cys Ile Glu Ser Phe Ser Asn Tyr
305                 310                 315                 320

Ile Cys Pro Ser Asp Pro Gly Phe Ile Leu Asn His Glu Leu Glu Asn
                325                 330                 335

Cys Leu Ser Gly Asn Ile Thr Gln Cys Pro Lys Thr Ile Val Thr Ser
            340                 345                 350

Asp Ile Val Pro Arg Tyr Ala Phe Val Asp Gly Gly Val Ile Ala Asn
        355                 360                 365

Cys Ile Pro Thr Thr Cys Thr Cys Asn Gly Ile Asp Asn Arg Ile Asn
    370                 375                 380

Gln Ser Pro Asp Gln Gly Ile Lys Ile Ile Thr Tyr Lys Glu Cys Gln
385                 390                 395                 400

Ile Val Gly Ile Asn Gly Met Leu Phe Lys Thr Asn Gln Glu Gly Thr
                405                 410                 415

Leu Ala Lys Tyr Thr Phe Asp Asp Ile Lys Leu Asn Asn Ser Val Ala
            420                 425                 430

Leu Asn Pro Ile Asp Ile Ser Leu Glu Leu Asn Lys Ala Lys Ser Glu
        435                 440                 445

Leu Glu Glu Ser Lys Arg Trp Tyr Glu Lys Ser Asn His Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 71
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 71

Gln Val Asp Ile Ile Lys Leu Gln Arg Val Gly Ile Leu Val Ser Lys
1               5                   10                  15

Pro Lys Ser Ile Lys Ile Ser Gln Asn Phe Glu Thr Arg Tyr Leu Val
            20                  25                  30

Leu Asn Leu Ile Pro Asn Ile Glu Asn Ala Gln Ser Cys Gly Asp Gln
        35                  40                  45

Gln Ile Lys Gln Tyr Lys Lys Leu Leu Asp Arg Leu Ile Ile Pro Leu
    50                  55                  60

Tyr Asp Gly Leu Arg Leu Gln Gln Asp Ile Ile Val Val Asp Asn Asn
65                  70                  75                  80

Leu Lys Asn Asn Thr Asn His Arg Ala Lys Arg Phe Phe Gly Glu Ile
                85                  90                  95

Ile Gly Thr Ile Ala Leu Gly Val Ala Thr Ser Ala Gln Ile Thr Ala
            100                 105                 110

Ala Val Ala Leu Val Glu Ala Lys Gln Ala Arg Ser Asp Ile Glu Arg
        115                 120                 125

Val Lys Asn Ala Val Arg Asp Thr Asn Lys Ala Val Gln Ser Ile Gln
    130                 135                 140

Gly Ser Val Gly Asn Leu Ile Val Ala Cys Lys Ser Val Gln Asp Tyr
```

145 150 155 160

Val Asn Asn Glu Ile Val Pro Ser Ile Lys Arg Leu Gly Cys Glu Ala
165 170 175

Ala Gly Leu Gln Leu Gly Ile Ala Leu Thr Gln His Tyr Ser Glu Leu
180 185 190

Thr Asn Ile Phe Gly Asp Asn Ile Gly Thr Leu Lys Glu Lys Gly Ile
195 200 205

Lys Leu Gln Gly Ile Ala Ser Leu Tyr His Thr Cys Ile Thr Glu Ile
210 215 220

Phe Thr Thr Ser Thr Val Asp Gln Tyr Asp Ile Tyr Asp Leu Leu Phe
225 230 235 240

Thr Glu Ser Ile Lys Met Arg Val Ile Asp Val Asp Leu Asn Asp Tyr
245 250 255

Ser Ile Thr Leu Gln Val Arg Leu Pro Leu Leu Thr Lys Ile Ser Asp
260 265 270

Ala Gln Ile Tyr Asn Val Asp Ser Val Ser Tyr Asn Ile Gly Gly Thr
275 280 285

Glu Trp Tyr Ile Pro Leu Pro Arg Asn Ile Met Thr Lys Gly Ala Phe
290 295 300

Leu Gly Gly Ala Asn Leu Gln Asp Cys Ile Glu Ser Phe Ser Asp Tyr
305 310 315 320

Ile Cys Pro Ser Asp Pro Gly Phe Ile Leu Asn Arg Asp Ile Glu Asn
325 330 335

Cys Leu Ser Gly Asn Ile Thr Gln Cys Pro Lys Thr Leu Val Ile Ser
340 345 350

Asp Ile Val Pro Arg Tyr Ala Phe Val Asp Gly Gly Val Ile Ala Asn
355 360 365

Cys Leu Ser Thr Thr Cys Thr Cys Asn Gly Ile Asp Asn Arg Ile Asn
370 375 380

Gln Ala Pro Asp Gln Gly Ile Lys Ile Ile Thr Tyr Lys Asp Cys Gln
385 390 395 400

Thr Ile Gly Ile Asn Gly Met Leu Phe Lys Thr Asn Gln Glu Gly Thr
405 410 415

Leu Ala Ala Tyr Thr Pro Val Asp Ile Thr Leu Asn Asn Ser Val Asn
420 425 430

Leu Asp Pro Ile Asp Leu Ser Ile Glu Leu Asn Arg Ala Arg Ser Asp
435 440 445

Leu Ala Glu Ser Lys Glu Trp Tyr Lys Arg Ser Glu Ala Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 72
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 72

Gln Ile Asp Ile Thr Lys Leu Gln Ser Val Gly Val Leu Val Asn Ser
1 5 10 15

Pro Lys Gly Ile Lys Ile Ser Gln Asn Phe Glu Thr Arg Tyr Leu Ile

```
            20                  25                  30

Leu Ser Leu Ile Pro Lys Ile Glu Asp Ser His Ser Cys Gly Asn Gln
        35                  40                  45

Gln Ile Asp Gln Tyr Lys Lys Leu Leu Asp Arg Leu Ile Ile Pro Leu
    50                  55                  60

Tyr Asp Gly Leu Lys Leu Gln Lys Asp Val Ile Val Val Asn His Glu
65                  70                  75                  80

Ser His Asn Asn Thr Asn Leu Arg Thr Lys Arg Phe Phe Gly Glu Ile
                85                  90                  95

Ile Gly Thr Ile Ala Ile Gly Ile Ala Thr Ser Ala Gln Ile Thr Ala
            100                 105                 110

Ala Val Ala Leu Val Glu Ala Lys Gln Ala Arg Ser Asp Ile Asp Lys
        115                 120                 125

Leu Lys Glu Ala Ile Lys Asp Thr Asn Lys Ala Val Gln Ser Ile Gln
    130                 135                 140

Ser Ser Val Gly Asn Leu Ile Val Ala Cys Lys Ser Val Gln Asp Tyr
145                 150                 155                 160

Val Asn Asn Glu Ile Val Pro Ser Ile Thr Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Gly Glu Lys Gly Val
        195                 200                 205

Lys Leu Gln Gly Ile Ala Ser Leu Tyr Arg Thr Cys Ile Thr Glu Val
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Ser Asp Tyr
                245                 250                 255

Ser Ile Thr Leu Gln Val Arg Leu Pro Leu Leu Thr Lys Val Ser Asn
            260                 265                 270

Thr Gln Ile Tyr Lys Val Asp Ser Ile Ser Tyr Asn Ile Gln Gly Lys
        275                 280                 285

Glu Trp Tyr Ile Pro Leu Pro His His Ile Met Thr Lys Gly Ala Phe
    290                 295                 300

Leu Gly Gly Ala Asp Ile Lys Glu Cys Ile Glu Ser Phe Ser Asn Tyr
305                 310                 315                 320

Ile Cys Pro Ser Asp Pro Gly Phe Ile Leu Asn His Glu Met Glu Asn
                325                 330                 335

Cys Leu Ser Gly Asn Ile Thr Gln Cys Pro Lys Thr Ile Val Thr Ser
            340                 345                 350

Asp Ile Val Pro Arg Tyr Ala Phe Val Asp Gly Gly Val Ile Ala Asn
        355                 360                 365

Cys Ile Pro Thr Thr Cys Thr Cys Asn Gly Ile Asp Asn Arg Ile Asn
    370                 375                 380

Gln Ser Pro Asp Gln Gly Ile Lys Ile Ile Thr Tyr Lys Glu Cys Gln
385                 390                 395                 400

Ile Val Gly Ile Asn Gly Met Leu Phe Lys Thr Asn Gln Glu Gly Thr
                405                 410                 415

Leu Ala Lys Tyr Thr Phe Asp Asn Ile Lys Leu Asn Asn Ser Val Ala
            420                 425                 430

Leu Asn Pro Ile Asp Ile Ser Leu Glu Leu Asn Lys Val Lys Ser Asp
        435                 440                 445
```

```
Leu Glu Glu Ser Lys Arg Trp Ile Glu Lys Ser Asn Gln Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 73
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 73

Gln Ile Asp Ile Thr Lys Leu Gln Asn Val Gly Val Leu Val Asn Ser
1               5                   10                  15

Pro Lys Gly Ile Lys Ile Ser Gln Asn Phe Glu Thr Arg Tyr Leu Ile
            20                  25                  30

Leu Ser Leu Ile Pro Lys Ile Asp Asp Ser His Ser Cys Gly Asn Gln
        35                  40                  45

Gln Ile Asp Gln Tyr Lys Lys Leu Leu Asp Arg Leu Ile Ile Pro Leu
    50                  55                  60

Tyr Asp Gly Leu Lys Leu Gln Arg Asp Val Ile Val Val Asn His Glu
65                  70                  75                  80

Ser His Asn Asn Thr Asn Leu Arg Thr Lys Arg Phe Phe Gly Glu Ile
                85                  90                  95

Ile Gly Thr Ile Ala Ile Gly Ile Ala Thr Ser Ala Gln Ile Thr Ala
            100                 105                 110

Ala Val Ala Leu Val Glu Ala Lys Gln Ala Arg Ser Asp Ile Asp Lys
        115                 120                 125

Leu Lys Glu Ala Ile Lys Asp Thr Asn Lys Ala Val Gln Ser Ile Gln
    130                 135                 140

Ser Ser Val Gly Asn Leu Ile Val Ala Cys Lys Ser Val Gln Asp Tyr
145                 150                 155                 160

Val Asn Asn Glu Ile Val Pro Ser Ile Thr Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Arg Glu Lys Gly Val
        195                 200                 205

Lys Leu Gln Gly Ile Ala Ser Leu Tyr Arg Thr Cys Ile Thr Glu Val
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Ser Asp Tyr
                245                 250                 255

Ser Ile Thr Leu Gln Val Arg Leu Pro Leu Leu Thr Lys Val Ser Asn
            260                 265                 270

Thr Gln Ile Tyr Lys Val Asp Ser Ile Ser Tyr Asn Ile Gln Gly Lys
        275                 280                 285

Glu Trp Tyr Ile Pro Leu Pro His His Ile Met Thr Lys Gly Ala Phe
    290                 295                 300

Leu Gly Gly Ala Asp Ile Lys Glu Cys Ile Glu Ser Phe Ser Asn Tyr
305                 310                 315                 320
```

Ile Cys Pro Ser Asp Pro Gly Phe Ile Leu Asn His Glu Leu Glu Asn
325 330 335

Cys Leu Ser Gly Asn Ile Thr Gln Cys Pro Lys Thr Ile Val Thr Ser
340 345 350

Asp Ile Val Pro Arg Tyr Ala Phe Val Asp Gly Gly Val Ile Ala Asn
355 360 365

Cys Ile Pro Thr Thr Cys Thr Cys Asn Gly Ile Asp Asn Arg Ile Asn
370 375 380

Gln Ser Pro Asp Gln Gly Ile Lys Ile Ile Thr Tyr Lys Glu Cys Gln
385 390 395 400

Ile Val Gly Ile Asn Gly Met Leu Phe Lys Thr Asn Gln Glu Gly Thr
405 410 415

Leu Ala Lys Tyr Thr Phe Asp Asp Ile Lys Leu Asn Asn Ser Val Ala
420 425 430

Leu Asn Pro Ile Asp Ile Ser Leu Glu Leu Asn Lys Val Lys Ser Glu
435 440 445

Leu Glu Glu Ser Lys Arg Trp Ile Glu Lys Ser Asn His Lys Leu Ser
450 455 460

Ala Ile Glu Asp Lys Ile Glu Glu Ile Leu Ser Lys Ile Tyr His Ile
465 470 475 480

Glu Asn Glu Ile Ala Arg Ile Lys Lys Leu Ile Gly Glu Ala Pro
485 490 495

<210> SEQ ID NO 74
<211> LENGTH: 495
<212> TYPE: PRT
<213> ORGANISM: Artificial Sequence
<220> FEATURE:
<223> OTHER INFORMATION: Recombinant parainfluenza virus F sequence

<400> SEQUENCE: 74

Gln Val Asp Ile Ile Lys Leu Gln Arg Val Gly Ile Leu Val Ser Lys
1 5 10 15

Pro Lys Ser Ile Lys Ile Ser Gln Asn Phe Glu Thr Arg Tyr Leu Val
20 25 30

Leu Asn Leu Ile Pro Asn Ile Glu Asn Ala Gln Ser Cys Gly Asp Gln
35 40 45

Gln Ile Lys Gln Tyr Lys Lys Leu Leu Asp Arg Leu Ile Ile Pro Leu
50 55 60

Tyr Asp Gly Leu Arg Leu Gln Gln Asp Ile Ile Val Val Asp Asn Asn
65 70 75 80

Leu Lys Asn Asn Thr Asn His Arg Ala Lys Arg Phe Phe Gly Glu Ile
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Arg Ser Asp Ile Glu Arg
115 120 125

Val Lys Asn Ala Val Arg Asp Thr Asn Lys Ala Val Gln Ser Ile Gln
130 135 140

Gly Ser Val Gly Asn Leu Ile Val Ala Cys Lys Ser Val Gln Asp Tyr
145 150 155 160

Val Asn Asn Glu Ile Val Pro Ser Ile Lys Arg Leu Gly Cys Glu Ala
165 170 175

Ala Gly Leu Gln Leu Gly Ile Ala Leu Thr Gln His Tyr Ser Glu Leu
180 185 190

```
Thr Asn Ile Phe Gly Asp Asn Ile Gly Thr Leu Lys Glu Lys Gly Ile
        195                 200                 205

Lys Leu Gln Gly Ile Ala Ser Leu Tyr His Thr Cys Ile Thr Glu Ile
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Asn Asp Tyr
                245                 250                 255

Ser Ile Thr Leu Gln Val Arg Leu Pro Leu Leu Thr Lys Ile Ser Asp
            260                 265                 270

Ala Gln Ile Tyr Asn Val Asp Ser Val Ser Tyr Asn Ile Gly Gly Thr
        275                 280                 285

Glu Trp Tyr Ile Pro Leu Pro Arg Asn Ile Met Thr Lys Gly Ala Phe
    290                 295                 300

Leu Gly Gly Ala Asn Leu Gln Asp Cys Ile Glu Ser Phe Ser Asp Tyr
305                 310                 315                 320

Ile Cys Pro Ser Asp Pro Gly Phe Ile Leu Asn Arg Asp Ile Glu Asn
                325                 330                 335

Cys Leu Ser Gly Asn Ile Thr Gln Cys Pro Lys Thr Leu Val Ile Ser
            340                 345                 350

Asp Ile Val Pro Arg Tyr Ala Phe Val Asp Gly Gly Val Ile Ala Asn
        355                 360                 365

Cys Leu Ser Thr Thr Cys Thr Cys Asn Gly Ile Asp Asn Arg Ile Asn
    370                 375                 380

Gln Ala Pro Asp Gln Gly Ile Lys Ile Ile Thr Tyr Lys Asp Cys Gln
385                 390                 395                 400

Thr Ile Gly Ile Asn Gly Met Leu Phe Lys Thr Asn Gln Glu Gly Thr
                405                 410                 415

Leu Ala Ala Tyr Thr Pro Val Asp Ile Thr Leu Asn Asn Ser Val Asn
            420                 425                 430

Leu Asp Pro Ile Asp Leu Ser Ile Glu Leu Asn Arg Val Arg Ser Asp
        435                 440                 445

Leu Ala Glu Ser Lys Glu Trp Ile Lys Arg Ser Glu Ala Lys Leu Ser
    450                 455                 460

Ala Ile Glu Asp Lys Ile Glu Glu Ile Leu Ser Lys Ile Tyr His Ile
465                 470                 475                 480

Glu Asn Glu Ile Ala Arg Ile Lys Lys Leu Ile Gly Glu Ala Pro
                485                 490                 495


<210> SEQ ID NO 75
<211> LENGTH: 522
<212> TYPE: PRT
<213> ORGANISM: Artificial Sequence
<220> FEATURE:
<223> OTHER INFORMATION: Recombinant parainfluenza virus F sequence

<400> SEQUENCE: 75

Gln Ile Asp Ile Thr Lys Leu Gln Ser Val Gly Val Leu Val Asn Ser
1               5                   10                  15

Pro Lys Gly Ile Lys Ile Ser Gln Asn Phe Glu Thr Arg Tyr Leu Ile
            20                  25                  30

Leu Ser Leu Ile Pro Lys Ile Glu Asp Ser His Ser Cys Gly Asn Gln
        35                  40                  45

Gln Ile Asp Gln Tyr Lys Lys Leu Leu Asp Arg Leu Ile Ile Pro Leu
    50                  55                  60
```

```
Tyr Asp Gly Leu Lys Leu Gln Lys Asp Val Ile Val Val Asn His Glu
65                  70                  75                  80

Ser His Asn Asn Thr Asn Leu Arg Thr Lys Arg Phe Phe Gly Glu Ile
                85                  90                  95

Ile Gly Thr Ile Ala Ile Gly Ile Ala Thr Ser Ala Gln Ile Thr Ala
            100                 105                 110

Ala Val Ala Leu Val Glu Ala Lys Gln Ala Arg Ser Asp Ile Asp Lys
        115                 120                 125

Leu Lys Glu Ala Ile Lys Asp Thr Asn Lys Ala Val Gln Ser Ile Gln
    130                 135                 140

Ser Ser Val Gly Asn Leu Ile Val Ala Cys Lys Ser Val Gln Asp Tyr
145                 150                 155                 160

Val Asn Asn Glu Ile Val Pro Ser Ile Thr Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Gly Glu Lys Gly Val
        195                 200                 205

Lys Leu Gln Gly Ile Ala Ser Leu Tyr Arg Thr Cys Ile Thr Glu Val
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Ser Asp Tyr
                245                 250                 255

Ser Ile Thr Leu Gln Val Arg Leu Pro Leu Leu Thr Lys Val Ser Asn
            260                 265                 270

Thr Gln Ile Tyr Lys Val Asp Ser Ile Ser Tyr Asn Ile Gln Gly Lys
        275                 280                 285

Glu Trp Tyr Ile Pro Leu Pro His His Ile Met Thr Lys Gly Ala Phe
    290                 295                 300

Leu Gly Gly Ala Asp Ile Lys Glu Cys Ile Glu Ser Phe Ser Asn Tyr
305                 310                 315                 320

Ile Cys Pro Ser Asp Pro Gly Phe Ile Leu Asn His Glu Met Glu Asn
                325                 330                 335

Cys Leu Ser Gly Asn Ile Thr Gln Cys Pro Lys Thr Ile Val Thr Ser
            340                 345                 350

Asp Ile Val Pro Arg Tyr Ala Phe Val Asp Gly Gly Val Ile Ala Asn
        355                 360                 365

Cys Ile Pro Thr Thr Cys Thr Cys Asn Gly Ile Asp Asn Arg Ile Asn
    370                 375                 380

Gln Ser Pro Asp Gln Gly Ile Lys Ile Ile Thr Tyr Lys Glu Cys Gln
385                 390                 395                 400

Ile Val Gly Ile Asn Gly Met Leu Phe Lys Thr Asn Gln Glu Gly Thr
                405                 410                 415

Leu Ala Lys Tyr Thr Phe Asp Asn Ile Lys Leu Asn Asn Ser Val Ala
            420                 425                 430

Leu Asn Pro Ile Asp Ile Ser Leu Glu Leu Asn Lys Ala Lys Ser Asp
        435                 440                 445

Leu Glu Glu Ser Lys Arg Trp Tyr Glu Lys Ser Asn Gln Lys Leu Asp
    450                 455                 460

Ser Ile Gly Ser Trp His Gln Ser Ser Val Thr Ile Ile Ile Ile Ile
465                 470                 475                 480
```

```
Val Met Ile Val Val Leu Leu Ile Ile Asn Ala Ile Ile Ile Met Ile
                485                 490                 495

Met Ile Arg Tyr Leu Arg Asp Arg Asn Arg His Leu Asn Asn Lys Asp
            500                 505                 510

Ser Glu Pro Tyr Val Leu Thr Asn Arg Gln
        515                 520


<210> SEQ ID NO 76
<211> LENGTH: 522
<212> TYPE: PRT
<213> ORGANISM: Artificial Sequence
<220> FEATURE:
<223> OTHER INFORMATION: Recombinant parainfluenza virus F sequence

<400> SEQUENCE: 76

Gln Ile Asp Ile Thr Lys Leu Gln Asn Val Gly Val Leu Val Asn Ser
1               5                   10                  15

Pro Lys Gly Ile Lys Ile Ser Gln Asn Phe Glu Thr Arg Tyr Leu Ile
            20                  25                  30

Leu Ser Leu Ile Pro Lys Ile Asp Asp Ser His Ser Cys Gly Asn Gln
        35                  40                  45

Gln Ile Asp Gln Tyr Lys Lys Leu Leu Asp Arg Leu Ile Ile Pro Leu
    50                  55                  60

Tyr Asp Gly Leu Lys Leu Gln Arg Asp Val Ile Val Val Asn His Glu
65                  70                  75                  80

Ser His Asn Asn Thr Asn Leu Arg Thr Lys Arg Phe Phe Gly Glu Ile
                85                  90                  95

Ile Gly Thr Ile Ala Ile Gly Ile Ala Thr Ser Ala Gln Ile Thr Ala
            100                 105                 110

Ala Val Ala Leu Val Glu Ala Lys Gln Ala Arg Ser Asp Ile Asp Lys
        115                 120                 125

Leu Lys Glu Ala Ile Lys Asp Thr Asn Lys Ala Val Gln Ser Ile Gln
    130                 135                 140

Ser Ser Val Gly Asn Leu Ile Val Ala Cys Lys Ser Val Gln Asp Tyr
145                 150                 155                 160

Val Asn Asn Glu Ile Val Pro Ser Ile Thr Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Arg Glu Lys Gly Val
        195                 200                 205

Lys Leu Gln Gly Ile Ala Ser Leu Tyr Arg Thr Cys Ile Thr Glu Val
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Ser Asp Tyr
                245                 250                 255

Ser Ile Thr Leu Gln Val Arg Leu Pro Leu Leu Thr Lys Val Ser Asn
            260                 265                 270

Thr Gln Ile Tyr Lys Val Asp Ser Ile Ser Tyr Asn Ile Gln Gly Lys
        275                 280                 285

Glu Trp Tyr Ile Pro Leu Pro His His Ile Met Thr Lys Gly Ala Phe
    290                 295                 300

Leu Gly Gly Ala Asp Ile Lys Glu Cys Ile Glu Ser Phe Ser Asn Tyr
305                 310                 315                 320
```

Ile Cys Pro Ser Asp Pro Gly Phe Ile Leu Asn His Glu Leu Glu Asn
325 330 335

Cys Leu Ser Gly Asn Ile Thr Gln Cys Pro Lys Thr Ile Val Thr Ser
340 345 350

Asp Ile Val Pro Arg Tyr Ala Phe Val Asp Gly Gly Val Ile Ala Asn
355 360 365

Cys Ile Pro Thr Thr Cys Thr Cys Asn Gly Ile Asp Asn Arg Ile Asn
370 375 380

Gln Ser Pro Asp Gln Gly Ile Lys Ile Ile Thr Tyr Lys Glu Cys Gln
385 390 395 400

Ile Val Gly Ile Asn Gly Met Leu Phe Lys Thr Asn Gln Glu Gly Thr
405 410 415

Leu Ala Lys Tyr Thr Phe Asp Asp Ile Lys Leu Asn Asn Ser Val Ala
420 425 430

Leu Asn Pro Ile Asp Ile Ser Leu Glu Leu Asn Lys Ala Lys Ser Glu
435 440 445

Leu Glu Glu Ser Lys Arg Trp Tyr Glu Lys Ser Asn His Lys Leu Asp
450 455 460

Ser Ile Gly Ser Trp Tyr Gln Ser Ser Ala Thr Ile Ile Ile Ile Ile
465 470 475 480

Val Met Ile Val Val Leu Leu Ile Ile Asn Ala Ile Ile Ile Met Ile
485 490 495

Thr Ile Lys His Leu Arg Ala Arg Asn Arg His Pro Asn Asn Lys Asp
500 505 510

Ser Glu Pro Tyr Val Leu Thr Asn Arg Gln
515 520

<210> SEQ ID NO 77
<211> LENGTH: 523
<212> TYPE: PRT
<213> ORGANISM: Artificial Sequence
<220> FEATURE:
<223> OTHER INFORMATION: Recombinant parainfluenza virus F sequence

<400> SEQUENCE: 77

Gln Val Asp Ile Ile Lys Leu Gln Arg Val Gly Ile Leu Val Ser Lys
1 5 10 15

Pro Lys Ser Ile Lys Ile Ser Gln Asn Phe Glu Thr Arg Tyr Leu Val
20 25 30

Leu Asn Leu Ile Pro Asn Ile Glu Asn Ala Gln Ser Cys Gly Asp Gln
35 40 45

Gln Ile Lys Gln Tyr Lys Lys Leu Leu Asp Arg Leu Ile Ile Pro Leu
50 55 60

Tyr Asp Gly Leu Arg Leu Gln Gln Asp Ile Ile Val Val Asp Asn Asn
65 70 75 80

Leu Lys Asn Asn Thr Asn His Arg Ala Lys Arg Phe Phe Gly Glu Ile
85 90 95

Ile Gly Thr Ile Ala Leu Gly Val Ala Thr Ser Ala Gln Ile Thr Ala
100 105 110

Ala Val Ala Leu Val Glu Ala Lys Gln Ala Arg Ser Asp Ile Glu Arg
115 120 125

Val Lys Asn Ala Val Arg Asp Thr Asn Lys Ala Val Gln Ser Ile Gln
130 135 140

Gly Ser Val Gly Asn Leu Ile Val Ala Cys Lys Ser Val Gln Asp Tyr
145 150 155 160

Val Asn Asn Glu Ile Val Pro Ser Ile Lys Arg Leu Gly Cys Glu Ala
165 170 175

Ala Gly Leu Gln Leu Gly Ile Ala Leu Thr Gln His Tyr Ser Glu Leu
180 185 190

Thr Asn Ile Phe Gly Asp Asn Ile Gly Thr Leu Lys Glu Lys Gly Ile
195 200 205

Lys Leu Gln Gly Ile Ala Ser Leu Tyr His Thr Cys Ile Thr Glu Ile
210 215 220

Phe Thr Thr Ser Thr Val Asp Gln Tyr Asp Ile Tyr Asp Leu Leu Phe
225 230 235 240

Thr Glu Ser Ile Lys Met Arg Val Ile Asp Val Asp Leu Asn Asp Tyr
245 250 255

Ser Ile Thr Leu Gln Val Arg Leu Pro Leu Leu Thr Lys Ile Ser Asp
260 265 270

Ala Gln Ile Tyr Asn Val Asp Ser Val Ser Tyr Asn Ile Gly Gly Thr
275 280 285

Glu Trp Tyr Ile Pro Leu Pro Arg Asn Ile Met Thr Lys Gly Ala Phe
290 295 300

Leu Gly Gly Ala Asn Leu Gln Asp Cys Ile Glu Ser Phe Ser Asp Tyr
305 310 315 320

Ile Cys Pro Ser Asp Pro Gly Phe Ile Leu Asn Arg Asp Ile Glu Asn
325 330 335

Cys Leu Ser Gly Asn Ile Thr Gln Cys Pro Lys Thr Leu Val Ile Ser
340 345 350

Asp Ile Val Pro Arg Tyr Ala Phe Val Asp Gly Gly Val Ile Ala Asn
355 360 365

Cys Leu Ser Thr Thr Cys Thr Cys Asn Gly Ile Asp Asn Arg Ile Asn
370 375 380

Gln Ala Pro Asp Gln Gly Ile Lys Ile Ile Thr Tyr Lys Asp Cys Gln
385 390 395 400

Thr Ile Gly Ile Asn Gly Met Leu Phe Lys Thr Asn Gln Glu Gly Thr
405 410 415

Leu Ala Ala Tyr Thr Pro Val Asp Ile Thr Leu Asn Asn Ser Val Asn
420 425 430

Leu Asp Pro Ile Asp Leu Ser Ile Glu Leu Asn Arg Ala Arg Ser Asp
435 440 445

Leu Ala Glu Ser Lys Glu Trp Tyr Lys Arg Ser Glu Ala Lys Leu Asp
450 455 460

Ser Val Gly Ser Trp Tyr Gln Ser Ser Thr Thr Glu Ile Ile Gln Ile
465 470 475 480

Val Met Ile Ile Val Leu Phe Ile Ile Asn Ile Ile Val Leu Ile Val
485 490 495

Leu Ile Lys Tyr Ser Arg Ser Gln Asn Gln Ser Met Asn Asn His Met
500 505 510

Asn Glu Pro Tyr Ile Leu Thr Asn Lys Val Gln
515 520

<210> SEQ ID NO 78
<211> LENGTH: 522
<212> TYPE: PRT
<213> ORGANISM: Artificial Sequence
<220> FEATURE:
<223> OTHER INFORMATION: Recombinant parainfluenza virus F sequence

<400> SEQUENCE: 78

-continued

```
Gln Ile Asp Ile Thr Lys Leu Gln Ser Val Gly Val Leu Val Asn Ser
1               5                   10                  15

Pro Lys Gly Ile Lys Ile Ser Gln Asn Phe Glu Thr Arg Tyr Leu Ile
            20                  25                  30

Leu Ser Leu Ile Pro Lys Ile Glu Asp Ser His Ser Cys Gly Asn Gln
        35                  40                  45

Gln Ile Asp Gln Tyr Lys Lys Leu Leu Asp Arg Leu Ile Ile Pro Leu
    50                  55                  60

Tyr Asp Gly Leu Lys Leu Gln Lys Asp Val Ile Val Val Asn His Glu
65                  70                  75                  80

Ser His Asn Asn Thr Asn Leu Arg Thr Lys Arg Phe Phe Gly Glu Ile
                85                  90                  95

Ile Gly Thr Ile Ala Ile Gly Ile Ala Thr Ser Ala Gln Ile Thr Ala
            100                 105                 110

Ala Val Ala Leu Val Glu Ala Lys Gln Ala Arg Ser Asp Ile Asp Lys
        115                 120                 125

Leu Lys Glu Ala Ile Lys Asp Thr Asn Lys Ala Val Gln Ser Ile Gln
    130                 135                 140

Ser Ser Val Gly Asn Leu Ile Val Ala Cys Lys Ser Val Gln Asp Tyr
145                 150                 155                 160

Val Asn Asn Glu Ile Val Pro Ser Ile Thr Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Gly Glu Lys Gly Val
        195                 200                 205

Lys Leu Gln Gly Ile Ala Ser Leu Tyr Arg Thr Cys Ile Thr Glu Val
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Ser Asp Tyr
                245                 250                 255

Ser Ile Thr Leu Gln Val Arg Leu Pro Leu Leu Thr Lys Val Ser Asn
            260                 265                 270

Thr Gln Ile Tyr Lys Val Asp Ser Ile Ser Tyr Asn Ile Gln Gly Lys
        275                 280                 285

Glu Trp Tyr Ile Pro Leu Pro His His Ile Met Thr Lys Gly Ala Phe
    290                 295                 300

Leu Gly Gly Ala Asp Ile Lys Glu Cys Ile Glu Ser Phe Ser Asn Tyr
305                 310                 315                 320

Ile Cys Pro Ser Asp Pro Gly Phe Ile Leu Asn His Glu Met Glu Asn
                325                 330                 335

Cys Leu Ser Gly Asn Ile Thr Gln Cys Pro Lys Thr Ile Val Thr Ser
            340                 345                 350

Asp Ile Val Pro Arg Tyr Ala Phe Val Asp Gly Gly Val Ile Ala Asn
        355                 360                 365

Cys Ile Pro Thr Thr Cys Thr Cys Asn Gly Ile Asp Asn Arg Ile Asn
    370                 375                 380

Gln Ser Pro Asp Gln Gly Ile Lys Ile Ile Thr Tyr Lys Glu Cys Gln
385                 390                 395                 400

Ile Val Gly Ile Asn Gly Met Leu Phe Lys Thr Asn Gln Glu Gly Thr
                405                 410                 415

Leu Ala Lys Tyr Thr Phe Asp Asn Ile Lys Leu Asn Asn Ser Val Ala
```

```
            420                 425                 430

Leu Asn Pro Ile Asp Ile Ser Leu Glu Leu Asn Lys Val Lys Ser Asp
        435                 440                 445

Leu Glu Glu Ser Lys Arg Trp Ile Glu Lys Ser Asn Gln Lys Leu Asp
    450                 455                 460

Ser Ile Gly Ser Trp His Gln Ser Ser Val Thr Ile Ile Ile Ile Ile
465                 470                 475                 480

Val Met Ile Val Val Leu Leu Ile Ile Asn Ala Ile Ile Ile Met Ile
                485                 490                 495

Met Ile Arg Tyr Leu Arg Asp Arg Asn Arg His Leu Asn Asn Lys Asp
            500                 505                 510

Ser Glu Pro Tyr Val Leu Thr Asn Arg Gln
        515                 520


<210> SEQ ID NO 79
<211> LENGTH: 522
<212> TYPE: PRT
<213> ORGANISM: Artificial Sequence
<220> FEATURE:
<223> OTHER INFORMATION: Recombinant parainfluenza virus F sequence

<400> SEQUENCE: 79

Gln Ile Asp Ile Thr Lys Leu Gln Asn Val Gly Val Leu Val Asn Ser
1               5                   10                  15

Pro Lys Gly Ile Lys Ile Ser Gln Asn Phe Glu Thr Arg Tyr Leu Ile
            20                  25                  30

Leu Ser Leu Ile Pro Lys Ile Asp Asp Ser His Ser Cys Gly Asn Gln
        35                  40                  45

Gln Ile Asp Gln Tyr Lys Lys Leu Leu Asp Arg Leu Ile Ile Pro Leu
    50                  55                  60

Tyr Asp Gly Leu Lys Leu Gln Arg Asp Val Ile Val Val Asn His Glu
65                  70                  75                  80

Ser His Asn Asn Thr Asn Leu Arg Thr Lys Arg Phe Phe Gly Glu Ile
                85                  90                  95

Ile Gly Thr Ile Ala Ile Gly Ile Ala Thr Ser Ala Gln Ile Thr Ala
            100                 105                 110

Ala Val Ala Leu Val Glu Ala Lys Gln Ala Arg Ser Asp Ile Asp Lys
        115                 120                 125

Leu Lys Glu Ala Ile Lys Asp Thr Asn Lys Ala Val Gln Ser Ile Gln
    130                 135                 140

Ser Ser Val Gly Asn Leu Ile Val Ala Cys Lys Ser Val Gln Asp Tyr
145                 150                 155                 160

Val Asn Asn Glu Ile Val Pro Ser Ile Thr Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Arg Glu Lys Gly Val
        195                 200                 205

Lys Leu Gln Gly Ile Ala Ser Leu Tyr Arg Thr Cys Ile Thr Glu Val
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Ser Asp Tyr
                245                 250                 255

Ser Ile Thr Leu Gln Val Arg Leu Pro Leu Leu Thr Lys Val Ser Asn
```

260                 265                 270

Thr Gln Ile Tyr Lys Val Asp Ser Ile Ser Tyr Asn Ile Gln Gly Lys
        275                 280                 285

Glu Trp Tyr Ile Pro Leu Pro His His Ile Met Thr Lys Gly Ala Phe
    290                 295                 300

Leu Gly Gly Ala Asp Ile Lys Glu Cys Ile Glu Ser Phe Ser Asn Tyr
305                 310                 315                 320

Ile Cys Pro Ser Asp Pro Gly Phe Ile Leu Asn His Glu Leu Glu Asn
                325                 330                 335

Cys Leu Ser Gly Asn Ile Thr Gln Cys Pro Lys Thr Ile Val Thr Ser
            340                 345                 350

Asp Ile Val Pro Arg Tyr Ala Phe Val Asp Gly Gly Val Ile Ala Asn
        355                 360                 365

Cys Ile Pro Thr Thr Cys Thr Cys Asn Gly Ile Asp Asn Arg Ile Asn
    370                 375                 380

Gln Ser Pro Asp Gln Gly Ile Lys Ile Ile Thr Tyr Lys Glu Cys Gln
385                 390                 395                 400

Ile Val Gly Ile Asn Gly Met Leu Phe Lys Thr Asn Gln Glu Gly Thr
                405                 410                 415

Leu Ala Lys Tyr Thr Phe Asp Asp Ile Lys Leu Asn Asn Ser Val Ala
            420                 425                 430

Leu Asn Pro Ile Asp Ile Ser Leu Glu Leu Asn Lys Val Lys Ser Glu
        435                 440                 445

Leu Glu Glu Ser Lys Arg Trp Ile Glu Lys Ser Asn His Lys Leu Asp
    450                 455                 460

Ser Ile Gly Ser Trp Tyr Gln Ser Ser Ala Thr Ile Ile Ile Ile Ile
465                 470                 475                 480

Val Met Ile Val Val Leu Leu Ile Ile Asn Ala Ile Ile Ile Met Ile
                485                 490                 495

Thr Ile Lys His Leu Arg Ala Arg Asn Arg His Pro Asn Asn Lys Asp
            500                 505                 510

Ser Glu Pro Tyr Val Leu Thr Asn Arg Gln
        515                 520

<210> SEQ ID NO 80
<211> LENGTH: 523
<212> TYPE: PRT
<213> ORGANISM: Artificial Sequence
<220> FEATURE:
<223> OTHER INFORMATION: Recombinant parainfluenza virus F sequence

<400> SEQUENCE: 80

Gln Val Asp Ile Ile Lys Leu Gln Arg Val Gly Ile Leu Val Ser Lys
1               5                   10                  15

Pro Lys Ser Ile Lys Ile Ser Gln Asn Phe Glu Thr Arg Tyr Leu Val
            20                  25                  30

Leu Asn Leu Ile Pro Asn Ile Glu Asn Ala Gln Ser Cys Gly Asp Gln
        35                  40                  45

Gln Ile Lys Gln Tyr Lys Lys Leu Leu Asp Arg Leu Ile Ile Pro Leu
    50                  55                  60

Tyr Asp Gly Leu Arg Leu Gln Gln Asp Ile Ile Val Val Asp Asn Asn
65                  70                  75                  80

Leu Lys Asn Asn Thr Asn His Arg Ala Lys Arg Phe Phe Gly Glu Ile
                85                  90                  95

Ile Gly Thr Ile Ala Leu Gly Val Ala Thr Ser Ala Gln Ile Thr Ala

-continued

```
            100                 105                 110

Ala Val Ala Leu Val Glu Ala Lys Gln Ala Arg Ser Asp Ile Glu Arg
        115                 120                 125

Val Lys Asn Ala Val Arg Asp Thr Asn Lys Ala Val Gln Ser Ile Gln
    130                 135                 140

Gly Ser Val Gly Asn Leu Ile Val Ala Cys Lys Ser Val Gln Asp Tyr
145                 150                 155                 160

Val Asn Asn Glu Ile Val Pro Ser Ile Lys Arg Leu Gly Cys Glu Ala
                165                 170                 175

Ala Gly Leu Gln Leu Gly Ile Ala Leu Thr Gln His Tyr Ser Glu Leu
            180                 185                 190

Thr Asn Ile Phe Gly Asp Asn Ile Gly Thr Leu Lys Glu Lys Gly Ile
        195                 200                 205

Lys Leu Gln Gly Ile Ala Ser Leu Tyr His Thr Cys Ile Thr Glu Ile
    210                 215                 220

Phe Thr Thr Ser Thr Val Asp Gln Tyr Asp Ile Tyr Asp Leu Leu Phe
225                 230                 235                 240

Thr Glu Ser Ile Lys Met Arg Val Ile Asp Val Asp Leu Asn Asp Tyr
                245                 250                 255

Ser Ile Thr Leu Gln Val Arg Leu Pro Leu Leu Thr Lys Ile Ser Asp
            260                 265                 270

Ala Gln Ile Tyr Asn Val Asp Ser Val Ser Tyr Asn Ile Gly Gly Thr
        275                 280                 285

Glu Trp Tyr Ile Pro Leu Pro Arg Asn Ile Met Thr Lys Gly Ala Phe
    290                 295                 300

Leu Gly Gly Ala Asn Leu Gln Asp Cys Ile Glu Ser Phe Ser Asp Tyr
305                 310                 315                 320

Ile Cys Pro Ser Asp Pro Gly Phe Ile Leu Asn Arg Asp Ile Glu Asn
                325                 330                 335

Cys Leu Ser Gly Asn Ile Thr Gln Cys Pro Lys Thr Leu Val Ile Ser
            340                 345                 350

Asp Ile Val Pro Arg Tyr Ala Phe Val Asp Gly Gly Val Ile Ala Asn
        355                 360                 365

Cys Leu Ser Thr Thr Cys Thr Cys Asn Gly Ile Asp Asn Arg Ile Asn
    370                 375                 380

Gln Ala Pro Asp Gln Gly Ile Lys Ile Ile Thr Tyr Lys Asp Cys Gln
385                 390                 395                 400

Thr Ile Gly Ile Asn Gly Met Leu Phe Lys Thr Asn Gln Glu Gly Thr
                405                 410                 415

Leu Ala Ala Tyr Thr Pro Val Asp Ile Thr Leu Asn Asn Ser Val Asn
            420                 425                 430

Leu Asp Pro Ile Asp Leu Ser Ile Glu Leu Asn Arg Val Arg Ser Asp
        435                 440                 445

Leu Ala Glu Ser Lys Glu Trp Ile Lys Arg Ser Glu Ala Lys Leu Asp
    450                 455                 460

Ser Val Gly Ser Trp Tyr Gln Ser Ser Thr Thr Glu Ile Ile Gln Ile
465                 470                 475                 480

Val Met Ile Ile Val Leu Phe Ile Ile Asn Ile Ile Val Leu Ile Val
                485                 490                 495

Leu Ile Lys Tyr Ser Arg Ser Gln Asn Gln Ser Met Asn Asn His Met
            500                 505                 510

Asn Glu Pro Tyr Ile Leu Thr Asn Lys Val Gln
        515                 520
```

<210> SEQ ID NO 81
<211> LENGTH: 1746
<212> TYPE: DNA
<213> ORGANISM: Artificial Sequence
<220> FEATURE:
<223> OTHER INFORMATION: Recombinant parainfluenza virus F sequence

<400> SEQUENCE: 81
atgcccatgg gcagcctgca gcccctggcc accctgtacc tgctgggcat gctggtggcc 60
tccgtgctgg ccggatccca gatccctgtg gataagctga gcaacgtggg cgtgatcatc 120
aatgagggca agctgctgaa gatcgccggc tcttacgaga gccggtatat cgtgctgtcc 180
ctggtgccat ctatcgacct gcaggatggc tgcggcacca cacagatcat ccagtacaag 240
aacctgctga atagactgct gatcccactg aaggacgccc tggatctgca ggagagcctg 300
atcaccatca caaatgatac cacagtgacc aacgacaatc cacagacaag ggctccgga 360 gccgtgatcg gaaccatcgc cctgggagtg gcaaccgcag cacagatcac agcaggaatc 420
gccctggccg aggcaaggga ggcccgcaag gatatcgccc tgatcaagga ctctatcgtg 480
aagacccaca atagcgtgga gttcatccag cggggcatcg gcgagcagat catcgccctg 540
aagacactgc aggattttgt gaacgacgag atccggcctg ccatcggcga gctgagatgt 600
gagacaacag ccctgaagct gggcatcaag ctgacccagc actactccga gctggccaca 660
gccttcagct ccaatctggg caccatcggc gagaagagcc tgacactgca ggccctgtct 720
agcctgtatt ccgccaacat caccgagatc ctgtccacaa tcaagaagga caagtctgat 780
atctacgaca tcatctatac cgagcaggtg aagggcacag tgatcgacgt ggatctggag 840
aagtatatgg tgaccctgct ggtgaagatc ccaatcctgt ctgagatccc aggcgtgctg 900
atctacaggg cctcctctat cagctataac atcgagggag aggagtggca cgtggcaatc 960
cccaactaca tcatcaataa ggccagctcc ctgggaggag cagatgtgac caattgcatc 1020
gagtctaagc tggcctatat ctgtcccaga gatcctacac agctgatccc tgacaaccag 1080
cagaagtgca tcctgggcga cgtgagcaag tgtcccgtga ccaaagtgat caacaatctg 1140
gtgcctaagt tcgcctttat caacggcggc gtggtggcca attgcatcgc ctccacctgc 1200
acatgtggca ccaacagaat ccccgtgaat caggatcgct ctaagggcgt gacattcctg 1260
acctacacaa actgtggcct gatcggcatc aatggcatcg agctgtatgc caacaagcgg 1320
ggcagagata ccacatgggg caatcagatc atcaaggtcg gccctgccgt gtccatcagg 1380
ccagtggaca tcagcctgaa cctggcctcc atcaccaatt ttctggagga gatcaagaca 1440
gagctgatga agatcgagga caagatcgag gagatcctgt ctaaaatcta ccacatcgag 1500
aacgagatcg cccgcatcaa gaagctgatc ggcgaggccc ccgctagcgg aggaggactg 1560
gaagtgctgt tccagggccc cgggtctgat tacaaggacg atgacgataa aggcagcggc 1620
tctgcctggt cacatcccca gtttgagaag ggaggcggga gcggcggagg gagcggaggc 1680
tccgcttgga gccatcccca gtttgagaaa ggcagcgggc accaccacca ccaccaccac 1740
cactga 1746

<210> SEQ ID NO 82
<211> LENGTH: 1770
<212> TYPE: DNA
<213> ORGANISM: Artificial Sequence
<220> FEATURE:
<223> OTHER INFORMATION: Recombinant parainfluenza virus F sequence

<400> SEQUENCE: 82
atgcccatgg gcagcctgca gcccctggcc accctgtacc tgctgggcat gctggtggcc 60
tccgtgctgg ccggatccga cgccatcgct ggagatcagc tgctgaatat cggcgtgatt 120
cagtctaaga tccggagtct gatgtactat accgacggcg gggccagctt cattgtggtc 180
aaactgctgc ccaacctgcc cccttccaac gggacatgca atatcacttc tctggacgcc 240
tacaatgtga ccctgtttaa gctgctgaca cctctgatcg agaacctgag taaaatttca 300
actgtgaccg atacaggagg cgggtcagga ggagggagcg gagtggtcgt gggcctggcc 360
gctctgggcg tggctactgc agcccagatc accgctgcag tggcaattgt caaggcaaac 420
gccaatgccg ctgcaatcaa caatctggcc agctccattc agagtactaa caaggcagtg 480
tcagacgtga tcgatgccag ccggaccatt gctacagcag tgcaggctat ccaggacaga 540
attaatggcg caatcgtcaa cgggattaca tcagccagct gtagggcaca cgatgccctg 600
atcggcagca ttctgaacct gtacctgact gagctgacca caatcttcca taaccagatt 660
acaaatcccg ctctgactcc tctgtctatc caggcactgc gcattctgct gggcagtacc 720
ctgccaatcg tgattgagtc aaagctgaac accaatttca acacagccga actgctgtct 780
agtgggctgc tgaccggaca gatcatttcc atctctccca tgtatatgca gatgctgatc 840
cagattaacg tgcccacctt catcatgcag cccggcgcca aggtcattga cctgatcgct 900
attagcgcaa atcacaaact gcaggaagtc gtggtccagg tgcctaacag aatcctggag 960
tacgccaacg aactgcagaa ttatcctgct aacgattgcg tggtcacacc aaatagcgtg 1020
ttttgtcgat acaacgaggg ctcccctatc ccagaatctc agtatcagtg cctgcggggg 1080
aatctgaaca gctgtacttt caccccaatc attgggaatt ttctgaagag attcgccttt 1140
gctaatggag tgctgtacgc taactgcaaa agcctgctgt gcaggtgtgc cgacccacca 1200
cacgtggtca gccaggacga tactcagggc atctccatca ttgacattaa gaggtgttct 1260
gagatgatgc tggatacctt cagttttcgc atcacatcaa ctttcaacgc tacttatgtg 1320
accgactttt ccatgatcaa tgccaacatt gtccatctga gccccctgga tctgtccaat 1380
cagatcaact ctattaataa gagcctgaaa tccgccgagg actggatcgc tgatagtaat 1440
ttctttgcca accaggctcg caccgcaatg aagcagattg aagataagat cgaggaaatt 1500
ctgtctaaga tctatcatat cgagaacgaa atcgcacgaa ttaagaaact gatcggcgaa 1560
gcccctgcta gcggaggagg actggaagtg ctgttccagg gccccgggtc tgattacaag 1620
gacgatgacg ataaaggcag cggctctgcc tggtcacatc cccagtttga gaagggaggc 1680
gggagcggcg gagggagcgg aggctccgct tggagccatc cccagtttga gaaaggcagc 1740
gggcaccacc accaccacca ccaccactga 1770

<210> SEQ ID NO 83
<211> LENGTH: 1743
<212> TYPE: DNA
<213> ORGANISM: Artificial Sequence
<220> FEATURE:
<223> OTHER INFORMATION: Recombinant parainfluenza virus F sequence

<400> SEQUENCE: 83
atgcccatgg gcagcctgca gcccctggcc accctgtacc tgctgggcat gctggtggcc 60
tccgtgctgg ccggatccct ggatatcacc cacctgatga acctgggcac cgtgccaaca 120
gccatccggt ctctggtgta ctatacctac acaaagccta gctatctgac cgtggatctg 180
atcccaaacc tgaagaatct ggaccagaac tgcaattaca gctccctgaa ctactataat 240

```
aagacagccc tgtccctgat ccagcccatc gccgacaaca tcaatagact gacaaagcct    300
atcacctccg gaggaggctc tggaggaggc agcggagccg tgatcggaac catcgccctg    360
ggagtggcaa cagcagcaca ggtgaccgcc gccatcggcc tggccaaggc ccaggagaac    420
gccaagctga tcctgacact gaagaaggcc gccaccgaga caaatgaggc cgtgagggat    480
ctggccaaca gcaataagat cgtggtgaag atgatctccg ccatccagaa ccagatcaat    540
accatcatcc agcctgccat cgatcagatc aattgtcaga tcaaggacct gcaggtggcc    600
aacatcctga atctgtatct gaccgagatc accacagtgt tccacaacca gctgacaaat    660
ccagccctgg agtctatcag catccaggcc ctgaagtccc tgctgggctc taccctgcca    720
gaggtgctgt ctaagctgga tctgaacaat atcagcgccg cctccgtgat ggccagcgga    780
ctgatcaagg gccagatcat cgccgtggac atccctacca tgacactggt gctgatggtg    840
cagatcccat ccatctctcc cctgcggcag gccaagatca tcgatctgac ctctatcaca    900
atccacacca acagccagga ggtgcaggca gtggtgccag ccagagtgct ggagatcggc    960
tccgagatcc tgggcttcga cggcagcgtg tgccagatca caaaggatac cgtgttttgt   1020
ccatacaatg acgcctatgt gctgcccatc cagcagaagc ggtgcctgca gggccagacc   1080
agagattgcg tgttcacccc agtggcaggc accttccctc ggagatttct gaccacatac   1140
ggcacaatcg tggccaactg cagggatctg gtgtgctcct gtctgcgccc ccctcagatc   1200
atctatcagc ctgacgagaa tccagtgacc atcatcgaca aggacctgtg caccacactg   1260
acactggaca gcatcaccat cgagatccag aagtctatca acagcacatt caggcgcgag   1320
gtggtgctgg agagcacaca ggtgaggtcc ctgaccccac tggacctgag caccgacctg   1380
aaccagttta atcagctgct gaagtccgcc gaggaccaca tccagagggt gaccgattac   1440
ctgaactcca tcgaggacaa gatcgaggag atcctgtcta aaatctacca catcgagaat   1500
gagatcgccc ggatcaagaa gctgatcggc gaggcccctg ctagcggagg aggactggaa   1560
gtgctgttcc agggccccgg gtctgattac aaggacgatg acgataaagg cagcggctct   1620
gcctggtcac atccccagtt tgagaaggga ggcgggagcg gcggagggag cggaggctcc   1680
gcttggagcc atccccagtt tgagaaaggc agcgggcacc accaccacca ccaccaccac   1740
tga                                                                 1743
```

<210> SEQ ID NO 84
<211> LENGTH: 1743
<212> TYPE: DNA
<213> ORGANISM: Artificial Sequence
<220> FEATURE:
<223> OTHER INFORMATION: Recombinant parainfluenza virus F sequence

<400> SEQUENCE: 84

```
atgcccatgg gcagcctgca gcccctggcc accctgtacc tgctgggcat gctggtggcc     60
tccgtgctgg ccggatccct ggatatcacc cacctgatga acctgggcac cgtgccaaca    120
gccatccggt ctctggtgta ctatacctac acaaagccta gctatctgac cgtggatctg    180
atcccaaacc tgaagaatct ggaccagaac tgcaattaca gctccctgaa ctactataat    240
aagacagccc tgtccctgat ccagcccatc gccgacaaca tcaatagact gacaaagcct    300
atcacctccg gaggaggctc tggaggaggc agcggagccg tgatcggaac catcgccctg    360
ggagtggcaa cagcagcaca ggtgaccgcc gccatcggcc tggccaaggc ccaggagaac    420
gccaagctga tcctgacact gaagaaggcc gccaccgaga caaatgaggc cgtgagggat    480
```

-continued

```
ctggccaaca gcaataagat cgtggtgaag atgtgctccg ccatccagaa ccagatcaat    540

accatcatcc agcctgccat cgatcagatc aattgtcaga tcaaggacct gcaggtggcc    600

aacatcctga atctgtatct gaccgagatc accacagtgt tccacaacca gctgacaaat    660

ccagccctgg agtctatcag catccaggcc ctgaagtccc tgctgggctc ttgtctgcca    720

gaggtgctgt ctaagctgga tctgaacaat atcagcgccg cctccgtgat ggccagcgga    780

ctgatcaagg gccagatcat cgccgtggac atccctacca tgacactggt gctgatggtg    840

cagatcccat ccatctctcc cctgcggcag gccaagatca tcgatctgac ctctatcaca    900

atccacacca acagccagga ggtgcaggca gtggtgccag ccagagtgct ggagatcggc    960

tccgagatcc tgggcttcga cggcagcgtg tgccagatca caaaggatac cgtgttttgt   1020

ccatacaatg acgcctatgt gctgcccatc cagcagaagc ggtgcctgca gggccagacc   1080

agagattgcg tgttcacccc agtggcaggc accttccctc ggagatttct gaccacatac   1140

ggcacaatcg tggccaactg cagggatctg gtgtgctcct gtctgcgccc ccctcagatc   1200

atctatcagc ctgacgagaa tccagtgacc atcatcgaca aggacctgtg caccacactg   1260

acactggaca gcatcaccat cgagatccag aagtctatca acagcacatt caggcgcgag   1320

gtggtgctgg agagcacaca ggtgaggtcc ctgaccccac tggacctgag caccgacctg   1380

aaccagttta atcagctgct gaagtccgcc gaggaccaca tccagagggt gaccgattac   1440

ctgaactcca tcgaggacaa gatcgaggag atcctgtcta aaatctacca catcgagaat   1500

gagatcgccc ggatcaagaa gctgatcggc gaggcccctg ctagcggagg aggactggaa   1560

gtgctgttcc agggccccgg gtctgattac aaggacgatg acgataaagg cagcggctct   1620

gcctggtcac atccccagtt tgagaaggga ggcgggagcg gcggagggag cggaggctcc   1680

gcttggagcc atccccagtt tgagaaaggc agcgggcacc accaccacca ccaccaccac   1740

tga                                                                 1743
```

<210> SEQ ID NO 85
<211> LENGTH: 1644
<212> TYPE: DNA
<213> ORGANISM: Artificial Sequence
<220> FEATURE:
<223> OTHER INFORMATION: Recombinant parainfluenza virus F sequence

<400> SEQUENCE: 85

```
ggtaccgcca ccatgtactc aatgcagctg gcctcttgcg tcacactgac actggtcctg     60

ctggtcaact cacagatcga catcactaaa ctgcagcacg tcggggtgct ggtcaactcc    120

ccaaagggaa tgaaaatttc tcagaatttc gagacaagat acctgatcct gagcctgatt    180

cccaagatcg aagattcaaa cagctgcggg gaccagcaga ttaagcagta caaacgactg    240

ctggatcggc tgatcattcc tctgtatgat ggactgaagc tgcagaaaga cgtgatcgtc    300

acaaatcagg agtccaacga aaataccgac ccaaggacag agcgcttctt tggaggcgtg    360

atcggaacta tcgcactggg agtcgctact tctgcacaga tcaccgcagc tgtggctctg    420

gtcgaggcca agcaggctaa aagtgatatt gagaagctga aagaagccat ccgagacacc    480

aacaaggctg tgcagagcgt ccagagctcc gtgggcaatc tgattgtcgc catcaagtca    540

gtgcaggatt acgtcaacaa agagattgtg cccagcatcg cacgcctggg gtgtgaagca    600

gcaggactgc agctgggaat cgcactgacc cagcactact ccgagctgac aaacattttt    660

ggggacaata tcggatctct gcaggaaaag ggcatcaagc tgcagggcat cgctagtctg    720

tataggacaa atattactga gatcttcacc acatcaactg tggacaagta cgatatctat    780
```

```
gacctgctgt ttaccgaaag catcaaggtg agagtgatcg acgtggatct gaacgattat    840

tccattactc tgcaggtcag actgcctctg ctgacaaggc tgctgaatac tcagatctac    900

aaggtggact ccatttctta taacatccag aatcgggagt ggtacattcc actgccctct    960

cacatcatga ccaagggcgc attcctggga ggcgccgatg tgaaagagtg cattgaagcc   1020

ttctctagtt atatctgtcc tagcgaccca ggatttgtgc tgaaccatga gatggaaagt   1080

tgcctgtcag gcaatattag tcagtgtcca cggactaccg tgacctcaga tatcgtcccc   1140

agatacgcat ttgtgaacgg gggagtggtc gccaattgca tcacaactac ctgcacatgt   1200

aacgggattg gaaacagaat caatcagccc cctgaccagg gcgtgaagat cattacacac   1260

aaagagtgta acactatcgg cattaatggg atgctgttca acaccaataa ggaaggcaca   1320

ctggcctttt atactcctga cgatatcacc ctgaacaata gcgtggctct ggatccaatc   1380

gacatttcca tcgagctgaa caaggtgaaa tctgacctgg aagagagtaa ggaatggtat   1440

cggagatcaa atcagaaact gagcgctatt gaggacaaga tcgaggagat cctgagcaag   1500

atctaccaca tcgagaacga gatcgccaga atcaagaagc tgatcggcga ggcccccgga   1560

ggcctggtgc ctcggggcag ccaccaccac caccaccaca gtgcttggag ccacccacag   1620

tttgaaaaat gatgagcggc cgcc                                          1644
```

<210> SEQ ID NO 86
<211> LENGTH: 1644
<212> TYPE: DNA
<213> ORGANISM: Artificial Sequence
<220> FEATURE:
<223> OTHER INFORMATION: Recombinant parainfluenza virus F sequence

<400> SEQUENCE: 86

```
ggtaccgcca ccatgtactc aatgcagctg gcctcttgcg tcacactgac actggtcctg     60

ctggtcaact cacagatcga catcactaaa ctgcagcacg tcggggtgct ggtcaactcc    120

ccaaagggaa tgaaaatttc tcagaatttc gagacaagat acctgatcct gagcctgatt    180

cccaagatcg aagattcaaa cagctgcggg gaccagcaga ttaagcagta caaacgactg    240

ctggatcggc tgatcattcc tctgtatgat ggactgaagc tgcagaaaga cgtgatcgtc    300

acaaatcagg agtccaacga aaataccgac ccaaggacag agcgcttctt tggaggcgtg    360

atcggaacta tcgcactggg agtcgctact tctgcacaga tcaccgcagc tgtggctctg    420

gtcgaggcca agcaggctaa aagtgatatt gagaagctga aagaagccat ccgagacacc    480

aacaaggctg tgcagagcgt ccagagctcc gtgggcaatc tgatttgcgc catcaagtca    540

gtgcaggatt acgtcaacaa agagattgtg cccagcatcg cacgcctggg gtgtgaagca    600

gcaggactgc agctgggaat cgcactgacc cagcactact ccgagctgac aaacattttt    660

ggggacaata tcggatctct gcaggaaaag ggcatcaagc tgcagggcat cgctagtctg    720

tataggacaa atattactga gtgcttcacc acatcaactg tggacaagta cgatatctat    780

gacctgctgt ttaccgaaag catcaaggtg agagtgatcg acgtggatct gaacgattat    840

tccattactc tgcaggtcag actgcctctg ctgacaaggc tgctgaatac tcagatctac    900

aaggtggact ccatttctta taacatccag aatcgggagt ggtacattcc actgccctct    960

cacatcatga ccaagggcgc attcctggga ggcgccgatg tgaaagagtg cattgaagcc   1020

ttctctagtt atatctgtcc tagcgaccca ggatttgtgc tgaaccatga gatggaaagt   1080

tgcctgtcag gcaatattag tcagtgtcca cggactaccg tgacctcaga tatcgtcccc   1140
```

```
agatacgcat ttgtgaacgg gggagtggtc gccaattgca tcacaactac ctgcacatgt   1200

aacgggattg gaaacagaat caatcagccc cctgaccagg gcgtgaagat cattacacac   1260

aaagagtgta acactatcgg cattaatggg atgctgttca acaccaataa ggaaggcaca   1320

ctggcctttt atactcctga cgatatcacc ctgaacaata gcgtggctct ggatccaatc   1380

gacatttcca tcgagctgaa caaggtgaaa tctgacctgg aagagagtaa ggaatggtat   1440

cggagatcaa atcagaaact gagcgctatt gaggacaaga tcgaggagat cctgagcaag   1500

atctaccaca tcgagaacga gatcgccaga atcaagaagc tgatcggcga ggcccccgga   1560

ggcctggtgc ctcggggcag ccaccaccac caccaccaca gtgcttggag ccacccacag   1620

tttgaaaaat gatgagcggc cgcc                                          1644
```

<210> SEQ ID NO 87
<211> LENGTH: 1644
<212> TYPE: DNA
<213> ORGANISM: Artificial Sequence
<220> FEATURE:
<223> OTHER INFORMATION: Recombinant parainfluenza virus F sequence

<400> SEQUENCE: 87

```
ggtaccgcca ccatgtactc aatgcagctg gcctcttgcg tcacactgac actggtcctg     60

ctggtcaact cacagatcga catcactaaa ctgcagcacg tcggggtgct ggtcaactcc    120

ccaaagggaa tgaaaatttc tcagaatttc gagacaagat acctgatcct gagcctgatt    180

cccaagatcg aagattcaaa cagctgcggg gaccagcaga ttaagcagta caaacgactg    240

ctggatcggc tgatcattcc tctgtatgat ggactgaagc tgcagaaaga cgtgatcgtc    300

acaaatcagg agtccaacga aaataccgac ccaaggacag agcgcttctt tggaggcgtg    360

atcggaacta tcgcactggg agtcgctact tctgcacaga tcaccgcagc tgtggctctg    420

gtcgaggcca agcaggctaa aagtgatatt gagaagctga aagaagccat ccgagacacc    480

aacaaggctg tgcagagcgt ccagagctcc gtgggcaatc tgattgtcgc catcaagtca    540

gtgcaggatt acgtcaacaa agagattgtg cccagcatcg cacgcctggg gtgtgaagca    600

gcaggactgc agctgggaat cgcactgacc cagcactact ccgagctgac aaactgtttt    660

ggggacaata tcggatctct gcaggaaaag ggcatcaagc tgcagtgcat cgctagtctg    720

tataggacaa atattactga gatcttcacc acatcaactg tggacaagta cgatatctat    780

gacctgctgt ttaccgaaag catcaaggtg agagtgatcg acgtggatct gaacgattat    840

tccattactc tgcaggtcag actgcctctg ctgacaaggc tgctgaatac tcagatctac    900

aaggtggact ccatttctta taacatccag aatcgggagt ggtacattcc actgccctct    960

cacatcatga ccaagggcgc attcctggga ggcgccgatg tgaaagagtg cattgaagcc   1020

ttctctagtt atatctgtcc tagcgaccca ggatttgtgc tgaaccatga gatggaaagt   1080

tgcctgtcag gcaatattag tcagtgtcca cggactaccg tgacctcaga tatcgtcccc   1140

agatacgcat ttgtgaacgg gggagtggtc gccaattgca tcacaactac ctgcacatgt   1200

aacgggattg gaaacagaat caatcagccc cctgaccagg gcgtgaagat cattacacac   1260

aaagagtgta acactatcgg cattaatggg atgctgttca acaccaataa ggaaggcaca   1320

ctggcctttt atactcctga cgatatcacc ctgaacaata gcgtggctct ggatccaatc   1380

gacatttcca tcgagctgaa caaggtgaaa tctgacctgg aagagagtaa ggaatggtat   1440

cggagatcaa atcagaaact gagcgctatt gaggacaaga tcgaggagat cctgagcaag   1500

atctaccaca tcgagaacga gatcgccaga atcaagaagc tgatcggcga ggcccccgga   1560
```

ggcctggtgc ctcggggcag ccaccaccac caccaccaca gtgcttggag ccacccacag 1620
tttgaaaaat gatgagcggc cgcc 1644

<210> SEQ ID NO 88
<211> LENGTH: 1640
<212> TYPE: DNA
<213> ORGANISM: Artificial Sequence
<220> FEATURE:
<223> OTHER INFORMATION: Recombinant parainfluenza virus F sequence

<400> SEQUENCE: 88
tctagaccac catgtactca atgcagctgg cctcttgcgt cacactgaca ctggtcctgc 60
tggtcaactc acagatcgac atcactaaac tgcagcacgt cggggtgctg gtcaactccc 120
caaagggaat gaaaatttct cagaatttcg agacaagata cctgatcctg agcctgattc 180
ccaagatcga agattcaaac agctgcgggg accagcagat taagcagtac aaacgactgc 240
tggatcggct gatcattcct ctgtatgatt gcctgaagct gcagaaagac gtgatcgtca 300
caaatcagga gtccaacgaa aataccgacc caaggacaga gcgcttcttt ggaggcgtga 360
tcggaactat cgcactggga gtcgctactt ctgcacagat caccgcagct gtggctctgg 420
tcgaggccaa gcaggctaaa agtgatattg agaagctgaa agaagccatc cgagacacca 480
acaaggctgt gcagagcgtc cagagctccg tgggcaatct gattgtcgcc atcaagtcag 540
tgcaggatta cgtcaacaaa gagattgtgc ccagcatcgc acgcctgggg tgtgaagcag 600
caggactgca gctgggaatc gcactgaccc agcactactc cgagctgaca aacatttttg 660
gggacaatat cggatctctg tgcgaaaagg gcatcaagct gcagggcatc gctagtctgt 720
ataggacaaa tattactgag atcttcacca catcaactgt ggacaagtac gatatctatg 780
acctgctgtt taccgaaagc atcaaggtga gagtgatcga cgtggatctg aacgattatt 840
ccattactct gcaggtcaga ctgcctctgc tgacaaggct gctgaatact cagatctaca 900
aggtggactc catttcttat aacatccaga atcgggagtg gtacattcca ctgccctctc 960
acatcatgac caagggcgca ttcctgggag gcgccgatgt gaaagagtgc attgaagcct 1020
tctctagtta tatctgtcct agcgacccag gatttgtgct gaaccatgag atggaaagtt 1080
gcctgtcagg caatattagt cagtgtccac ggactaccgt gacctcagat atcgtcccca 1140
gatacgcatt tgtgaacggg ggagtggtcg ccaattgcat cacaactacc tgcacatgta 1200
acgggattgg aaacagaatc aatcagcccc ctgaccaggg cgtgaagatc attacacaca 1260
aagagtgtaa cactatcggc attaatggga tgctgttcaa caccaataag gaaggcacac 1320
tggcctttta tactcctgac gatatcaccc tgaacaatag cgtggctctg gatccaatcg 1380
acatttccat cgagctgaac aaggtgaaat ctgacctgga agagagtaag gaatggtatc 1440
ggagatcaaa tcagaaactg agcgctattg aggacaagat cgaggagatc ctgagcaaga 1500
tctaccacat cgagaacgag atcgccagaa tcaagaagct gatcggcgag gcccccggag 1560
gcctggtgcc tcggggcagc caccaccacc accaccacag tgcttggagc cacccacagt 1620
ttgaaaaatg atgaccgcgg 1640

<210> SEQ ID NO 89
<211> LENGTH: 1640
<212> TYPE: DNA
<213> ORGANISM: Artificial Sequence
<220> FEATURE:
<223> OTHER INFORMATION: Recombinant parainfluenza virus F sequence

<400> SEQUENCE: 89
tctagaccac catgtactca atgcagctgg cctcttgcgt cacactgaca ctggtcctgc 60
tggtcaactc acagatcgac atcactaaac tgcagcacgt cggggtgctg gtcaactccc 120
caaagggaat gaaaatttct cagaatttcg agacaagata cctgatcctg agcctgattc 180
ccaagatcga agattcaaac agctgcgggg accagcagat taagcagtac aaacgactgc 240
tggatcggct gatcattcct ctgtatgatg gactgaagct gcagaaagac gtgatcgtca 300
caaatcagga gtccaacgaa aataccgacc caaggacaga gcgcttcttt ggaggcgtga 360
tcggaactat cgcactggga gtcgctactt ctgcacagat caccgcagct gtggctctgg 420
tcgaggccaa gcaggctaaa agtgatattg agaagctgaa agaagccatc cgagacacca 480
acaaggctgt gcagagcgtc cagagctccg tgggcaatct gattgtcgcc atcaagtcag 540
tgcaggatta cgtcaacaaa gagattgtgc ccagcatcgc acgcctgggg tgtgaagcag 600
caggactgca gctgggaatc gcactgaccc agcactactc cgagctgaca aacatttttg 660
ggtgcaatat cggatcttgc caggaaaagg gcatcaagct gcagggcatc gctagtctgt 720
ataggacaaa tattactgag atcttcacca catcaactgt ggacaagtac gatatctatg 780
acctgctgtt taccgaaagc atcaaggtga gagtgatcga cgtggatctg aacgattatt 840
ccattactct gcaggtcaga ctgcctctgc tgacaaggct gctgaatact cagatctaca 900
aggtggactc catttcttat aacatccaga atcgggagtg gtacattcca ctgccctctc 960
acatcatgac caagggcgca ttcctgggag gcgccgatgt gaaagagtgc attgaagcct 1020
tctctagtta tatctgtcct agcgacccag gatttgtgct gaaccatgag atggaaagtt 1080
gcctgtcagg caatattagt cagtgtccac ggactaccgt gacctcagat atcgtcccca 1140
gatacgcatt tgtgaacggg ggagtggtcg ccaattgcat cacaactacc tgcacatgta 1200
acgggattgg aaacagaatc aatcagcccc ctgaccaggg cgtgaagatc attacacaca 1260
aagagtgtaa cactatcggc attaatggga tgctgttcaa caccaataag gaaggcacac 1320
tggcctttta tactcctgac gatatcaccc tgaacaatag cgtggctctg gatccaatcg 1380
acatttccat cgagctgaac aaggtgaaat ctgacctgga agagagtaag gaatggtatc 1440
ggagatcaaa tcagaaactg agcgctattg aggacaagat cgaggagatc ctgagcaaga 1500
tctaccacat cgagaacgag atcgccagaa tcaagaagct gatcggcgag gcccccggag 1560
gcctggtgcc tcggggcagc caccaccacc accaccacag tgcttggagc cacccacagt 1620
ttgaaaaatg atgaccgcgg 1640

<210> SEQ ID NO 90
<211> LENGTH: 1640
<212> TYPE: DNA
<213> ORGANISM: Artificial Sequence
<220> FEATURE:
<223> OTHER INFORMATION: Recombinant parainfluenza virus F sequence

<400> SEQUENCE: 90
tctagaccac catgtactca atgcagctgg cctcttgcgt cacactgaca ctggtcctgc 60
tggtcaactc acagatcgac atcactaaac tgcagcacgt cggggtgctg gtcaactccc 120
caaagggaat gaaaatttct cagaatttcg agacaagata cctgatcctg agcctgattc 180
ccaagatcga agattcaaac agctgcgggg accagcagat taagcagtac aaacgactgc 240
tggatcggct gatcattcct ctgtatgatg gactgaagct gcagaaagac gtgatcgtca 300
caaatcagga gtccaacgaa aataccgacc caaggacaga gcgcttcttt ggaggcgtga 360

```
tcggaactat cgcactggga gtcgctactt ctgcacagat caccgcagct gtggctctgg    420
tcgaggccaa gcaggctaaa agtgatattg agaagctgaa agaagccatc cgagacacca    480
acaaggctgt gcagagcgtc tgcagctccg tgggcaattg cattgtcgcc atcaagtcag    540
tgcaggatta cgtcaacaaa gagattgtgc ccagcatcgc acgcctgggg tgtgaagcag    600
caggactgca gctgggaatc gcactgaccc agcactactc cgagctgaca aacatttttg    660
gggacaatat cggatctctg caggaaaagg gcatcaagct gcagggcatc gctagtctgt    720
ataggacaaa tattactgag atcttcacca catcaactgt ggacaagtac gatatctatg    780
acctgctgtt taccgaaagc atcaaggtga gagtgatcga cgtggatctg aacgattatt    840
ccattactct gcaggtcaga ctgcctctgc tgacaaggct gctgaatact cagatctaca    900
aggtggactc catttcttat aacatccaga atcgggagtg gtacattcca ctgccctctc    960
acatcatgac caagggcgca ttcctgggag gcgccgatgt gaaagagtgc attgaagcct   1020
tctctagtta tatctgtcct agcgacccag gatttgtgct gaaccatgag atggaaagtt   1080
gcctgtcagg caatattagt cagtgtccac ggactaccgt gacctcagat atcgtcccca   1140
gatacgcatt tgtgaacggg ggagtggtcg ccaattgcat cacaactacc tgcacatgta   1200
acgggattgg aaacagaatc aatcagcccc ctgaccaggg cgtgaagatc attacacaca   1260
aagagtgtaa cactatcggc attaatggga tgctgttcaa caccaataag gaaggcacac   1320
tggcctttta tactcctgac gatatcaccc tgaacaatag cgtggctctg gatccaatcg   1380
acatttccat cgagctgaac aaggtgaaat ctgacctgga agagagtaag gaatggtatc   1440
ggagatcaaa tcagaaactg agcgctattg aggacaagat cgaggagatc ctgagcaaga   1500
tctaccacat cgagaacgag atcgccagaa tcaagaagct gatcggcgag gcccccggag   1560
gcctggtgcc tcggggcagc caccaccacc accaccacag tgcttggagc cacccacagt   1620
ttgaaaaatg atgaccgcgg                                               1640
```

<210> SEQ ID NO 91
<211> LENGTH: 1644
<212> TYPE: DNA
<213> ORGANISM: Artificial Sequence
<220> FEATURE:
<223> OTHER INFORMATION: Recombinant parainfluenza virus F sequence

<400> SEQUENCE: 91

```
ggtaccgcca ccatgtactc aatgcagctg gcctcttgcg tcacactgac actggtcctg     60
ctggtcaact cacagatcga catcactaaa ctgcagcacg tcggggtgct ggtcaactcc    120
ccaaagggaa tgaaaatttc tcagaatttc gagacaagat acctgatcct gagcctgatt    180
cccaagatcg aagattcaaa cagctgcggg gaccagcaga ttaagcagta caaacgactg    240
ctggatcggc tgatcattcc tctgtatgat ggactgaagc tgcagaaaga cgtgatcgtc    300
acaaatcagg agtccaacga aaataccgac ccaaggacag agcgcttctt tggaggcgtg    360
atcggaacta tcgcactggg agtcgctact tctgcacaga tcaccgcagc tgtggctctg    420
gtcgaggcca agcaggctaa aagtgatatt gagaagctga aagaagccat ccgagacacc    480
aacaaggctg tgcagagcgt ctgcagctcc gtgggcaatt gcattgtcgc catcaagtca    540
gtgcaggatt acgtcaacaa agagattgtg cccagcatcg cacgcctggg gtgtgaagca    600
gcaggactgc agctgggaat cgcactgacc cagcactact ccgagctgac aaactgtttt    660
ggggacaata tcggatctct gcaggaaaag ggcatcaagc tgcagtgcat cgctagtctg    720
```

-continued

```
tataggacaa atattactga gatcttcacc acatcaactg tggacaagta cgatatctat    780

gacctgctgt ttaccgaaag catcaaggtg agagtgatcg acgtggatct gaacgattat    840

tccattactc tgcaggtcag actgcctctg ctgacaaggc tgctgaatac tcagatctac    900

aaggtggact ccatttctta taacatccag aatcgggagt ggtacattcc actgccctct    960

cacatcatga ccaagggcgc attcctggga ggcgccgatg tgaaagagtg cattgaagcc   1020

ttctctagtt atatctgtcc tagcgaccca ggatttgtgc tgaaccatga gatggaaagt   1080

tgcctgtcag gcaatattag tcagtgtcca cggactaccg tgacctcaga tatcgtcccc   1140

agatacgcat ttgtgaacgg gggagtggtc gccaattgca tcacaactac ctgcacatgt   1200

aacgggattg gaaacagaat caatcagccc cctgaccagg gcgtgaagat cattacacac   1260

aaagagtgta acactatcgg cattaatggg atgctgttca acaccaataa ggaaggcaca   1320

ctggcctttt atactcctga cgatatcacc ctgaacaata gcgtggctct ggatccaatc   1380

gacatttcca tcgagctgaa caaggtgaaa tctgacctgg aagagagtaa ggaatggtat   1440

cggagatcaa atcagaaact gagcgctatt gaggacaaga tcgaggagat cctgagcaag   1500

atctaccaca tcgagaacga gatcgccaga atcaagaagc tgatcggcga ggcccccgga   1560

ggcctggtgc ctcggggcag ccaccaccac caccaccaca gtgcttggag ccacccacag   1620

tttgaaaaat gatgagcggc cgcc                                          1644
```

<210> SEQ ID NO 92
<211> LENGTH: 1644
<212> TYPE: DNA
<213> ORGANISM: Artificial Sequence
<220> FEATURE:
<223> OTHER INFORMATION: Recombinant parainfluenza virus F sequence

<400> SEQUENCE: 92

```
ggtaccgcca ccatgtactc aatgcagctg gcctcttgcg tcacactgac actggtcctg     60

ctggtcaact cacagatcga catcactaaa ctgcagcacg tcggggtgct ggtcaactcc    120

ccaaagggaa tgaaaatttc tcagaatttc gagacaagat acctgatcct gagcctgatt    180

cccaagatcg aagattcaaa cagctgcggg gaccagcaga ttaagcagta caaacgactg    240

ctggatcggc tgatcattcc tctgtatgat ggactgaagc tgcagaaaga cgtgatcgtc    300

acaaatcagg agtccaacga aaataccgac ccaaggacag agcgcttctt tggaggcgtg    360

atcggaacta tcgcactggg agtcgctact tctgcacaga tcaccgcagc tgtggctctg    420

gtcgaggcca agcaggctaa aagtgatatt gagaagctga aagaagccat ccgagacacc    480

aacaaggctg tgcagagcgt ccagagctcc gtgggcaatc tgattgtcgc ctgcaagtca    540

gtgcaggatt acgtcaacaa agagattgtg cccagcatcg cacgcctggg gtgtgaagca    600

gcaggactgc agctgggaat cgcactgacc cagcactact ccgagctgac aaacattttt    660

ggggacaata tcggatctct gcaggaaaag ggcatcaagc tgcagggcat cgctagtctg    720

tataggacat gtattactga gatcttcacc acatcaactg tggacaagta cgatatctat    780

gacctgctgt ttaccgaaag catcaaggtg agagtgatcg acgtggatct gaacgattat    840

tccattactc tgcaggtcag actgcctctg ctgacaaggc tgctgaatac tcagatctac    900

aaggtggact ccatttctta taacatccag aatcgggagt ggtacattcc actgccctct    960

cacatcatga ccaagggcgc attcctggga ggcgccgatg tgaaagagtg cattgaagcc   1020

ttctctagtt atatctgtcc tagcgaccca ggatttgtgc tgaaccatga gatggaaagt   1080

tgcctgtcag gcaatattag tcagtgtcca cggactaccg tgacctcaga tatcgtcccc   1140
```

agatacgcat ttgtgaacgg gggagtggtc gccaattgca tcacaactac ctgcacatgt 1200
aacgggattg gaaacagaat caatcagccc cctgaccagg gcgtgaagat cattacacac 1260
aaagagtgta acactatcgg cattaatggg atgctgttca acaccaataa ggaaggcaca 1320
ctggcctttt atactcctga cgatatcacc ctgaacaata gcgtggctct ggatccaatc 1380
gacatttcca tcgagctgaa caaggtgaaa tctgacctgg aagagagtaa ggaatggtat 1440
cggagatcaa atcagaaact gagcgctatt gaggacaaga tcgaggagat cctgagcaag 1500
atctaccaca tcgagaacga gatcgccaga atcaagaagc tgatcggcga ggcccccgga 1560
ggcctggtgc ctcggggcag ccaccaccac caccaccaca gtgcttggag ccacccacag 1620
tttgaaaaat gatgagcggc cgcc 1644

<210> SEQ ID NO 93
<211> LENGTH: 551
<212> TYPE: PRT
<213> ORGANISM: parainfluenza virus 5

<400> SEQUENCE: 93

Met Gly Thr Ile Ile Gln Phe Leu Val Val Ser Cys Leu Leu Ala Gly
1               5                   10                  15

Thr Gly Ser Ile Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Val Glu Leu Pro Thr Leu Thr Val Gln Pro Ala Thr Gln Ile Ile Asp

```
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asp Phe Val Tyr His
        515                 520                 525

Asn Gln Ala Phe Tyr His Ser Gln Ser Asp Leu Ser Glu Lys Asn Arg
    530                 535                 540

Pro Ala Thr Leu Gly Thr Arg
545                 550


<210> SEQ ID NO 94
<211> LENGTH: 539
<212> TYPE: PRT
<213> ORGANISM: human metapneumovirus

<400> SEQUENCE: 94

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95
```

```
Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Phe Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510

Ile Ile Lys Lys Thr Lys Lys Pro Thr Gly Ala Pro Pro Glu Leu Ser
```

```
        515                 520                 525

Gly Val Thr Asn Asn Gly Phe Ile Pro His Asn
    530                 535


<210> SEQ ID NO 95
<211> LENGTH: 574
<212> TYPE: PRT
<213> ORGANISM: Human respiratory syncytial virus

<400> SEQUENCE: 95

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

-continued

```
Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```